US012534451B2

(12) United States Patent
Tangallapally et al.

(10) Patent No.: US 12,534,451 B2
(45) Date of Patent: Jan. 27, 2026

(54) SMALL MOLECULE MODULATORS OF PanK

(71) Applicant: St. Jude Children's Research Hospital, Memphis, TN (US)

(72) Inventors: Rajendra P. Tangallapally, Collierville, TN (US); Richard E. Lee, Cordova, TN (US); Anne V. Edwards, Memphis, TN (US); Charles O. Rock, Bartlett, TN (US); Suzanne Jackowski, Bartlett, TN (US); Mi Kyung Yun, Collierville, TN (US); Chitra Subramanian, Cordova, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1084 days.

(21) Appl. No.: 17/598,163

(22) PCT Filed: Mar. 26, 2020

(86) PCT No.: PCT/US2020/025058

§ 371 (c)(1),
(2) Date: Sep. 24, 2021

(87) PCT Pub. No.: WO2020/198526

PCT Pub. Date: Oct. 1, 2020

(65) Prior Publication Data

US 2022/0185796 A1 Jun. 16, 2022

Related U.S. Application Data

(60) Provisional application No. 62/824,872, filed on Mar. 27, 2019.

(51) Int. Cl.

| | |
|---|---|
| ***C07D 403/04*** | (2006.01) |
| ***C07D 403/08*** | (2006.01) |
| ***C07D 413/04*** | (2006.01) |
| ***C07D 417/04*** | (2006.01) |
| ***C07D 495/04*** | (2006.01) |
| ***C07D 498/04*** | (2006.01) |
| ***C07D 513/04*** | (2006.01) |

(52) U.S. Cl.

CPC ......... *C07D 403/04* (2013.01); *C07D 403/08* (2013.01); *C07D 413/04* (2013.01); *C07D 417/04* (2013.01); *C07D 495/04* (2013.01); *C07D 498/04* (2013.01); *C07D 513/04* (2013.01)

(58) Field of Classification Search

CPC .. C07D 403/04; C07D 403/08; C07D 413/04; C07D 417/04; C07D 495/04; C07D 498/04; C07D 513/04; C07D 401/04; C07D 498/02; A61P 25/00

See application file for complete search history.

(56) References Cited

U.S. PATENT DOCUMENTS

| | | | | |
|---|---|---|---|---|
| 4,216,212 | A * | 8/1980 | Flora | A61K 31/66 514/121 |
| 5,939,462 | A * | 8/1999 | Connell | C07D 213/56 514/665 |
| 7,238,693 | B2 | 7/2007 | Nicolai et al. | |
| 7,754,724 | B2 | 7/2010 | Lorsbach et al. | |
| 8,153,633 | B2 | 4/2012 | Austin et al. | |
| 8,227,467 | B2 | 7/2012 | Kyle et al. | |
| 8,618,097 | B2 * | 12/2013 | Bencsik | A61P 9/10 514/252.16 |
| 8,975,398 | B2 | 3/2015 | Hansen et al. | |
| 2003/0114517 | A1 | 6/2003 | Greenlee et al. | |
| 2006/0035884 | A1 | 2/2006 | Neitzel et al. | |
| 2006/0160819 | A1 | 7/2006 | Hansen et al. | |
| 2007/0004750 | A1 * | 1/2007 | Lorsbach | C07D 403/14 514/254.01 |
| 2009/0306100 | A1 | 12/2009 | Barbosa et al. | |
| 2010/0004254 | A1 | 1/2010 | Sun et al. | |
| 2010/0041663 | A1 | 2/2010 | He et al. | |
| 2010/0210594 | A1 | 8/2010 | Wagner et al. | |
| 2010/0240663 | A1 * | 9/2010 | Christos | A61P 27/00 435/375 |
| 2011/0021530 | A1 | 1/2011 | Billich et al. | |
| 2012/0083476 | A1 | 4/2012 | Breitenbucher et al. | |
| 2013/0072497 | A1 | 3/2013 | Lorsbach et al. | |
| 2014/0275095 | A1 | 9/2014 | Dvorak et al. | |

(Continued)

FOREIGN PATENT DOCUMENTS

| | | |
|---|---|---|
| WO | WO-2004/011441 | 2/2004 |
| WO | WO2004/058754 | 7/2004 |
| WO | WO-2016/168619 | 10/2016 |

(Continued)

OTHER PUBLICATIONS

Holden-Dye, L. et al. Anthelmintic drugs and nematicides: studies in Caenorhabditis elegans. WormBook : the online review of C. elegans biology, 2014: 1-29. (Year: 2014).*

(Continued)

*Primary Examiner* — Jean P Cornet

*Assistant Examiner* — Chihyi Lee

(74) *Attorney, Agent, or Firm* — Ballard Spahr LLP

(57) ABSTRACT

The present disclosure relates to chemical compounds that modulate pantothenate kinase (PanK) activity for the treatment of metabolic disorders (such as diabetes mellitus type II), neurologic disorders (such as pantothenate kinase-associated neurodegeneration), pharmaceutical compositions containing such compounds, and their use in treatment.

18 Claims, 2 Drawing Sheets

(56) References Cited

U.S. PATENT DOCUMENTS

2022/0363667 A1* 11/2022 Tanaka ................. C07D 403/14

FOREIGN PATENT DOCUMENTS

| | | | | |
|---|---|---|---|---|
| WO | WO-2017/223474 | | 12/2017 | |
| WO | WO-2017223474 | A1 * | 12/2017 | ........... A61K 31/501 |
| WO | WO2019/133632 | | 7/2019 | |
| WO | WO2019/133634 | | 7/2019 | |
| WO | WO2019/133635 | | 7/2019 | |

OTHER PUBLICATIONS

Bhat A. R. Biological Activity of Pyrimidine Derivativies: A Review. Organic & Medicinal Chem IJ, 2017. vol. 2(2): 555581. (Year: 2017).*

Bassyouni, F.A. et al. Synthesis and anticancer activity of some new pyridine derivatives. Res Chem Intermed, 2012. vol. 38: 1291-1310. (Year: 2012).*

Elmeligie, S., et al. Design and Synthesis of Pyridazine Containing Compounds with Promising Anticancer Activity. Chemical & pharmaceutical bulletin, 2017. vol. 65(3): 236-247. (Year: 2017).*

Ali, E. M. H., et al. Thieno[2,3-d]pyrimidine as a promising scaffold in medicinal chemistry: Recent advances. Bioorganic & medicinal chemistry, 2019. vol. 27(7): 1159-1194. Published online on Feb. 21, 2019. (Year: 2019).*

Henderson, E. D. et al. Design, Synthesis and Evaluation of Novel N-Substituted-[Benzoylamino]-5-Ethyl-1,2,3,6-Tetrahydropyridines as Potential Anti-Cancer Agents. Madridge journal of pharmaceutical research, 2019. vol. 3(1): 52-59. Published online Mar. 4, 2019. (Year: 2019).*

Koshio, H., et al. Synthesis and biological activity of novel 1,4-diazepane derivatives as factor Xa inhibitor with potent anticoagulant and antithrombotic activity. Bioorganic & medicinal chemistry, 2004. vol. 12(9): 2179-2191. (Year: 2004).*

CAS Registry No. 1357881-66-3 (Entered STN Registry Feb. 28, 2012). (Year: 2012).*

Patani, G. A. et al. Bioisosterism: A Rational Approach in Drug Design. Chemical reviews, 1996, vol. 96, 8: 3147-3176. (Year: 1996).*

Sharma, L.K. et al. A high-throughput screen reveals new small-molecule activators and inhibitors of pantothenate kinases. J Med Chem, 2015. vol. 58(3): 1563-1568. (Year: 2015).*

U.S. Appl. No. 62/354,012, filed Jun. 23, 2016, Lalit Kumar Sharma.

U.S. Appl. No. 16/307,473 (U.S. Pat. No. 10,899,734), filed Dec. 5, 2018 (Jan. 26, 2021), Lalit Kumar Sharma.

U.S. Appl. No. 17/120,800 (2021/0246113), filed Dec. 14, 2020 (Aug. 12, 2021), Lalit Kumar Sharma.

U.S. Appl. No. 62/610,839, filed Dec. 27, 2017, Suzanne Jackowski.

U.S. Appl. No. 62/751,210, filed Oct. 26, 2018, Suzanne Jackowski.

U.S. Appl. No. 16/957,996 (2021/0023081), filed Jun. 25, 2020, Suzanne Jackowski.

U.S. Appl. No. 62/610,831, filed Dec. 27, 2017, Richard E. Lee.

U.S. Appl. No. 62/610,835, filed Dec. 27, 2017, Richard E. Lee.

U.S. Appl. No. 16/958,022, filed Jun. 25, 2020, Richard E. Lee.

U.S. Appl. No. 62/824,872, filed Mar. 27, 2019, Rajendra P.

PCT, PCT/US2017/039037 (WO 2017/223474), Jun. 23, 2017 (Dec. 28, 2017), St. Jude Children's Research Hospital.

PCT, PCT/US2018/067536 (WO 2019/133632), Dec. 26, 2018 (Jul. 4, 2019), St. Jude Children's Research Hospital.

PCT, PCT/US2018/067538 (WO 2019/133634), Dec. 26, 2018 (Jul. 4, 2019), St. Jude Children's Research Hospital.

PCT, PCT/US2018/067539 (WO 2019/133635), Dec. 26, 2018 (Jul. 4, 2019), St. Jude Children's Research Hospital.

PCT, PCT/US2020/25058, Mar. 26, 2020, St. Jude Children's Research Hospital.

Sharma et al. (2018) "A therapeutic approach to pantothenate kinase associated neurodegeneration," *Nature Communications* 9(1), https://www.nature.com/articles/s41467-018-06703-2.pdf.

Cecil Textbook of Medicine(1996), Edited by Bennet, JD, and Plum, 20$^{th}$ Edition vol. 1: 1004-1010.

Cohen, ett al. (1999) Current Opinion in Chemical Biology, 3, 459-465.

Dansie et al. (2014) Physiological roles of the pantothenate kinases, Biochem. Soc. Trans. 42:1033-1036.

Garcia et al. (2012) Germline deletion of pantothenate kinases 1 and 2 reveals the key roles for CoA in postnatal metabolism, PLoS one 7: e40871.

Jackowski and Rock (1981) Regulation of coenzyme A biosynthesis. J. Bacteriol. 148: 926-932.

Johnson et al. (2004) Mitochondrial localization of human PANK2 and hypotheses of secondary iron accumulation in pantothenate kinase-associated neurodegeneration, Ann. N Y. Acad. Sci. 1012: 282-298.

Kotzbauer et al. (2005) Altered neuronal mitochondrial coenzyme A synthesis in neurodegeneration with brain iron accumulation caused by abnormal processing, stability, and catalytic activity of mutant pantothenate kinase 2, Neurosci. 25: 689-698.

Kuo et al. Deficiency of pantothenate kinase 2 (Pank2) in mice leads to retinal degeneration and azoospermia. Hum. Mol. Genet. (2005), 14, 49-57.

Leonardi et al. (2007) Localization and Regulation of Mouse Pantothenate Kinase 2, FEBS Lett. 581:4639-4644.

Leonardi et al. (2010) Pantothenate Kinase 1 is required to support the metabolic transition from the fed to the fasted state, PloS one 5: el1107.

Leonardi et al. (2014) Pank 1 deletion in leptin-deficient mice reduces hyperglycaemia and hyperinsulinaemia and modifies global metabolism without affecting insulin resistance, Diabetologia 57: 1466-1475.

Mitchell et al. (2008) "Hereditary and acquired diseases of acyl-coenzyme A metabolism" *Mol. Genet. Metab.* 9 pp.:4-15.

Pubmed Compound Summary for CID 110727414, 'AKOS027640281', U.S. National Library of Medicine, (2016), (https://pubchem.ncbi.nlm.nih.gov/compound/110727414); p. 3.

Pubmed Compound Summary for CID 53621124, 'MolPort-020-021-215', U.S. National Library of Medicine, (2011),(https://pubchem.ncbi.nlm.nih.gov/compound/53621124); p. 3.

PubChem Compound Summary for CID 75373203 Create Date: Jul. 12, 2014 (Jul. 12, 2014) Date Accessed: Feb. 20, 2019 (Feb. 20, 2019); p. 4, compound listed.

PubChem Compound Summary for CID 121060331 deposited on Jun. 17, 2016 (17.06.2016) pp. 1-10. p. 3.

Rock et al. (2002) "The murine pantothenate kinase (Pank1) gene encodes two differentially regulated pantothenate kinase isozymes" *Gene* 291: 35-43.

Sabatti et al., Genome-wide association analysis of metabolic traits in a birth cohort from a founder population. Nature Genet. (2009), 41, 35-46.

Sharma et al. (2015) A High-Throughput Screen Reveals New Small-Molecule Activators and Inhibitors of Pantothenate Kinases, Med. Chem. 58: 1563-1568.

Tafesse et al. 'Synthesis and evaluation of pyridazinylpiperazines as vanilloid receptor 1 antagonists' Bioorganic & Medicinal Chemistry Letters, (2004) vol. 14, p. 5513-5519; p. 5515.

Zano et al. (2015) "Correction of a genetic deficiency in pantothenate kinase 1 using phosphopantothenate replacement therapy" *Mol. Genet. Metab.* 116:281-288.

Zhang et al. (2005) "Feedback regulation of murine pantothenate kinase 3 by coenzyme A and coenzyme A thioesters." *J. Biol. Chem.* 280: 32594-32601.

Zhang et al. (2006) Biochemical Properties of Human Pantothenate Kinase 2 Isoforms and Mutations Linked to Pantothenate Kinase-associated Neurodegeneration, J. Biol. Chem. 281:107-114.

Zhou et al. (2001) A novel pantothenate kinase gene (PANK2) is defective in Hallervorden-Spatz syndrome, Nat. Genet. 28: 345-349.

Freshney, et al. (1983) Culture of Animal Cells, Manual of Basic Technique, Alan R. Liss, Inc. p. 4.

(56) References Cited

OTHER PUBLICATIONS

Guenzel et al. (2013) "Generation of a hypomorphic model of propionic acidemia amenable to gene therapy testing" *Mol. Ther.* 21(7): 1316-23.

* cited by examiner

SMALL MOLECULE MODULATORS OF PanK

CROSS-REFERENCE TO RELATED APPLICATIONS

This Application is a national phase application under 35 U.S.C. § 371 of International Application No. PCT/US2020/025058, filed on Mar. 26, 2020, which claims the benefit of U.S. Application No. 62/824,872, filed on Mar. 27, 2019, the contents of which are hereby incorporated by reference in their entireties.

BACKGROUND

Pantothenate Kinase (PanK, EC 2.7.1.33) catalyzes the biochemical conversion of pantothenate (vitamin B5) to phosphopantothenate and thereby initiates the biosynthesis of coenzyme A (CoA). In most organisms the activities of the PanK enzymes regulate the CoA intracellular concentration (Leonardi et al. (2005) *Prog. Lipid Res.* 44: 125-153; Jackowski and Rock (1981) *J Bacteriol.* 148: 926-932; Zano et al. (2015) *Mol. Genet. Metab.* 116:281-288). CoA is an essential cofactor that functions as a carboxylic acid substrate carrier in various synthetic and oxidative metabolic pathways, such as the tricarboxylic acid cycle, sterol biosynthesis, heme biosynthesis, fatty acid and complex lipid synthesis and metabolism, and epigenetic modification of chromatin. Four closely related active PanK isoforms are identified in mammals: PanK1α, PanK1β, PanK2, and PanK3, which are encoded by three genes (Zhou et al. (2001) *Nat. Genet.* 28: 345-349; Zhang et al. (2005) *J Biol. Chem.* 280: 32594-32601; Rock et al. (2002) *Gene* 291: 35-43). The PanKs regulate cellular CoA through feedback inhibition of the enzyme activity by CoA or CoA thioesters and each isoform responds to inhibition with a different sensitivity (Leonardi et al. (2005) *Prog. Lipid Res.* 44: 125-153). The PanK isoform expression profiles differ among individual cell types, tissues and organs and the relative abundance of one or more isoforms determines the respective CoA levels (Dansie et al. (2014) *Biochem. Soc. Trans.* 42:1033-1036).

Mutations in the human PANK2 gene result in a rare and life-threatening neurological disorder known as PanK-associated neurodegeneration (PKAN) (Zhou et al. (2001) *Nat. Genet.* 28: 345-349; Johnson et al. (2004) *Ann. N. Y. Acad. Sci.* 1012: 282-298; Kotzbauer et al. (2005) *J Neurosci.* 25: 689-698). PKAN is an inherited autosomal recessive disorder that leads to progressive dystonia, dysarthria, parkinsonism, and pigmentary retinopathy. Classic PKAN develops in the first 10 years of life, starting around age 3; and patients are at risk for early death. The PANK2 gene is highly expressed in human neuronal tissues and many of the mutations associated with PKAN result in truncated or inactivated PanK2 protein expression, or severely reduced activity (Zhang et al. (2006) *J. Biol. Chem.* 281:107-114). The PANK2 mutations are predicted to result in significantly lower CoA levels, thereby reducing neuronal metabolism and function in PKAN patients. Tools are lacking for investigation of the relationship(s) between CoA levels and neurodegeneration. Activation of the PanK1 or PanK3 proteins that are also expressed in neuronal tissues (Leonardi et al. (2007) *FEBS Lett.* 581:4639-4644) could compensate for the reduction in PanK2 activity because functional redundancy among the isoforms is demonstrated in the Pank1$^{-/-}$ and Pank2$^{-/-}$ mouse models (Leonardi et al. (2010).

Limitation of the CoA supply by genetic deletion of Pank1 in mice blunts the increase in hepatic CoA in response to fasting. This, in turn, decreases fatty acid oxidation and glucose production by the liver resulting in fasting hypoglycemia (Leonardi et al. (2010) *PloS one* 5: e11107). Hypoglycemia and a significant reduction in fatty acid and ketone oxidation are the main causes for the early death of the Pank1$^{-/-}$ Pank2$^{-/-}$ mice in which both genes are deleted (Garcia et al. (2012) *PLoS one* 7: e40871). The ob/ob leptin-deficient mouse is a model of obesity-associated type II diabetes that exhibits abnormally high hepatic CoA (Leonardi et al. (2014) *Diabetologia* 57: 1466-1475). Consistent with the connection between hepatic CoA levels and glucose homeostasis, deletion of Pank1 in the ob/ob mouse reduces hepatic CoA and results in normalization of the diabetic hyperglycemia and associated hyperinsulinemia characteristic of this strain (Leonardi et al. (2014) *Diabetologia* 57: 1466-1475). A genome-wide association study (Sabatti et al. (2009) *Nature Genet.* 41: 35-46) indicates a significant correlation between PANK1 gene variants and insulin levels in humans, supporting the concept that PanK inhibitors may be useful therapeutics for diabetes. Taken together, these data demonstrate the impact of altering the intracellular level of CoA on oxidative metabolism and glucose homeostasis.

The associations of PanK with diseases like PKAN and diabetes led us to identify and develop PanK activators and inhibitors capable of modulating CoA levels and to assess the feasibility of such compounds as therapeutics in these diseases. We recently disclosed our initial high throughput screening effort towards this goal (Sharma et. al. (2015) *J. Med. Chem.* 58: 1563-1568; Sharma et. al. (2018) *Nature Communications* 9:4399). Our subsequent re-examination, careful filteration of hits and medicinal chemistry efforts identified new chemotypes capable of modulating PanK activity.

Despite the documented association of PanK with diseases like PKAN and diabetes, the feasibility of PanK antagonists capable of modulating CoA levels as disease therapeutics is uncertain. Thus, there remains a need for potent modulators of PanK to investigate the role of CoA in disease. The following disclosure describes a group of such compounds, as well as methods for making and using them.

SUMMARY

In accordance with the purpose(s) of the invention, as embodied and broadly described herein, the invention, in one aspect, relates to compositions and methods for use in the prevention and treatment of disorders associated with pantothenate kinase activity such as, for example, PKAN and diabetes.

Disclosed are compounds having a structure represented by a formula:

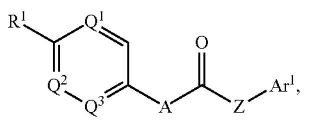

wherein A is selected from —O—, —$CH_2$—, —$CF_2$—, —NH—, —N($CH_3$)—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

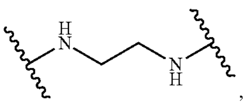,
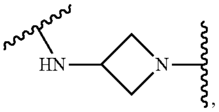,
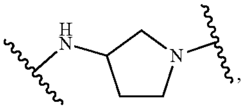,
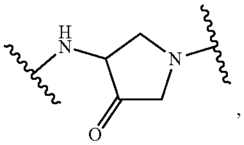,
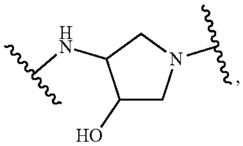,
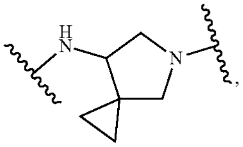,
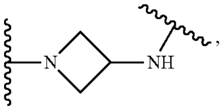,
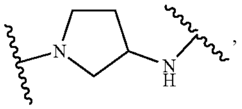,
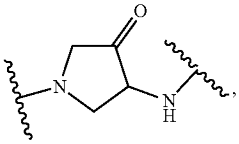,
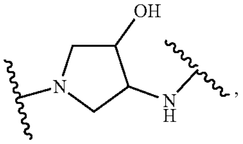,
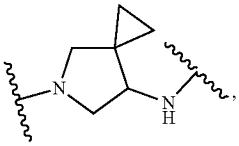,
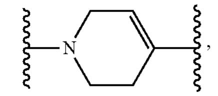,
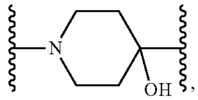,
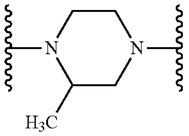,
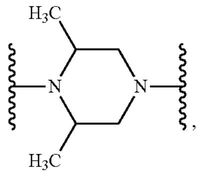,
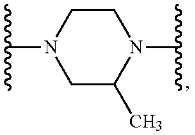,
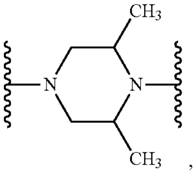,
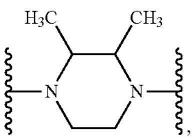,
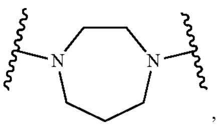,
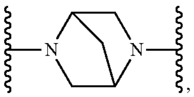,
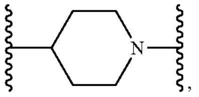,
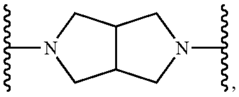, -continued

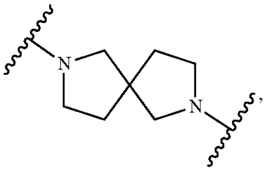,
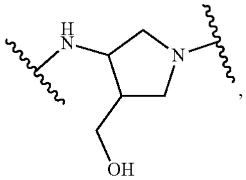,
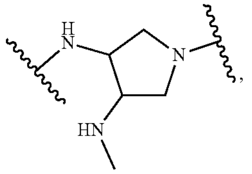,
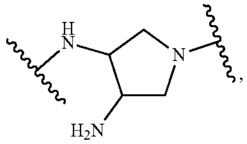,
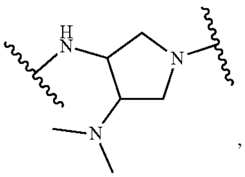,
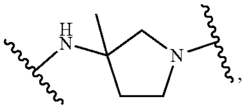,
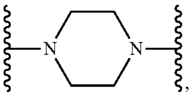,
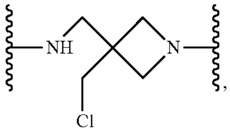,
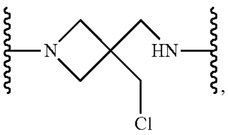,
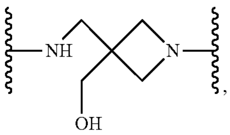,
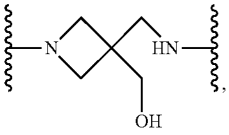,
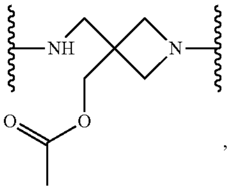, and
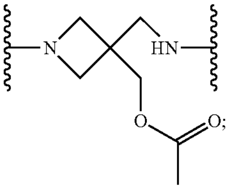;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

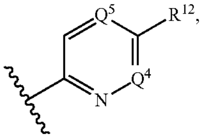,
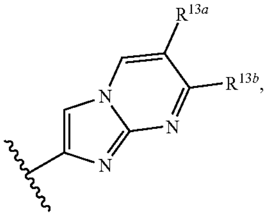,
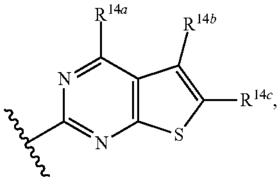,
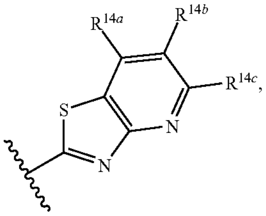 and
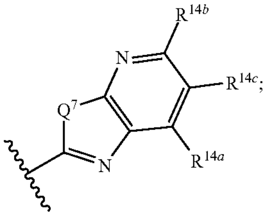;

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from 0, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

Also disclosed are compounds having a structure represented by a formula:

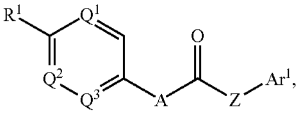, wherein A is selected from —O—, —$CH_2$—, —$CF_2$—, —NH—, —$N(CH_3)$—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

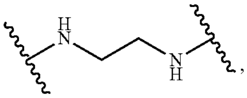,
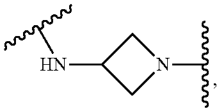,
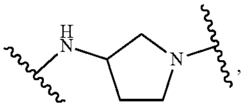,
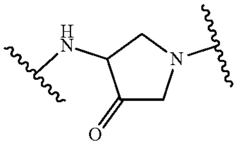,
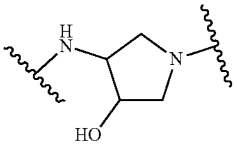,
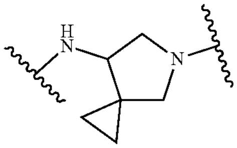,
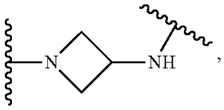,
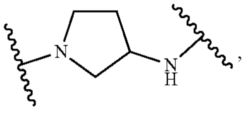,
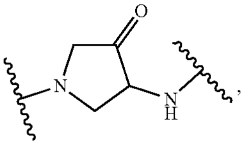,
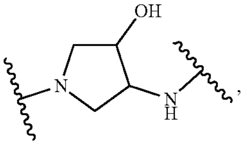,
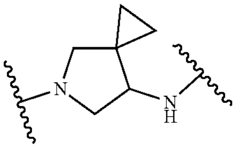,
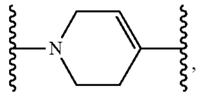,
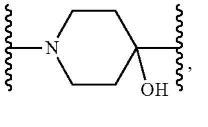,
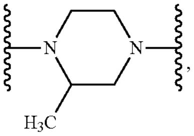,
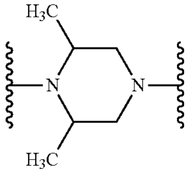,
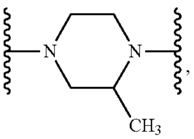, -continued

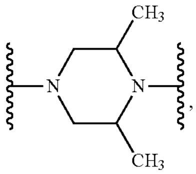, 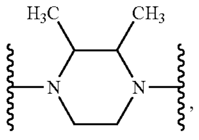,

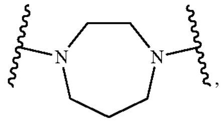, 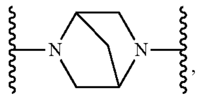,

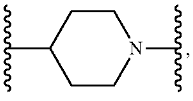, 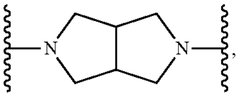,

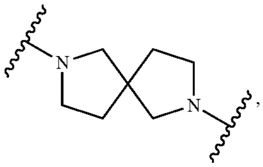, 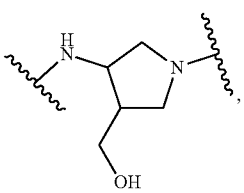,

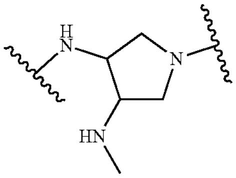, 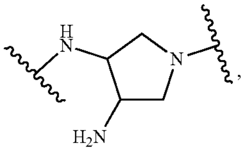,

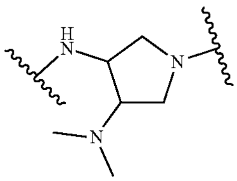, 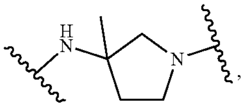, and

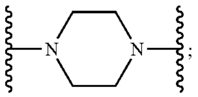;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

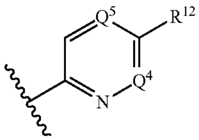 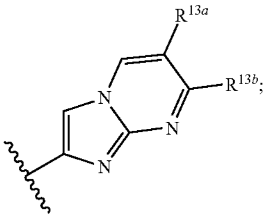;

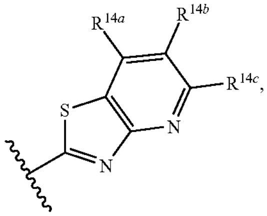, and

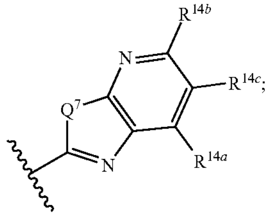;

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from 0, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

Also disclosed are compounds having a structure represented by a formula:

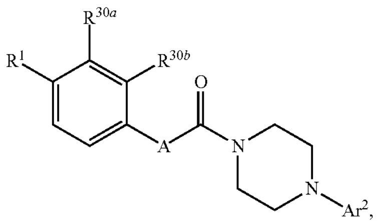

wherein A is selected from —O— and —$CH_2$—; wherein $R^1$ is selected from C1-C4 alkyl, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^1$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from

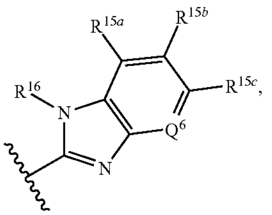

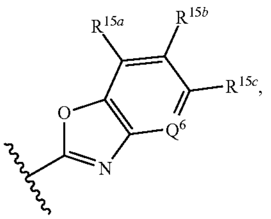

and

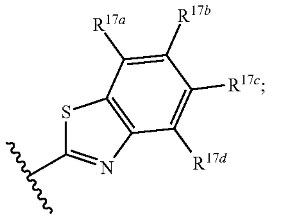

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein each of $R^{30a}$ and $R^{30b}$ is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

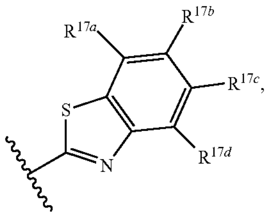

then A is —$CH_2$— and $R^1$ is selected from —$NR^{10}SO_2R^{11}$ and $Cy^1$, and provided that when $Ar^2$ is

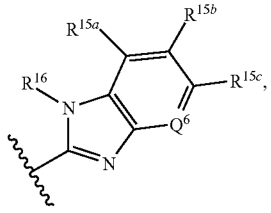

then A is —$CH_2$—, or a pharmaceutically acceptable salt thereof.

Also disclosed are compounds having a structure represented by a formula:

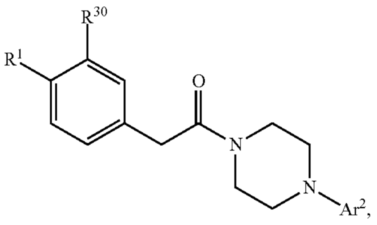

wherein $R^1$ is selected from C1-C4 alkyl, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

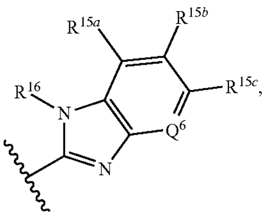

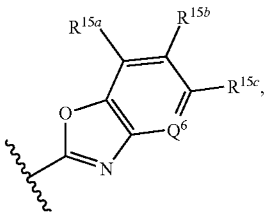

and

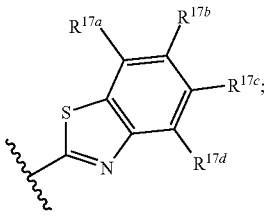

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{11c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

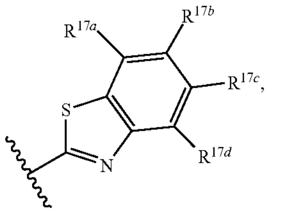

then $R^1$ is selected from —$NR^{10}SO_2R^{11}$ and $Cy^1$, or a pharmaceutically acceptable salt thereof.

Also disclosed are compounds having a structure selected from:

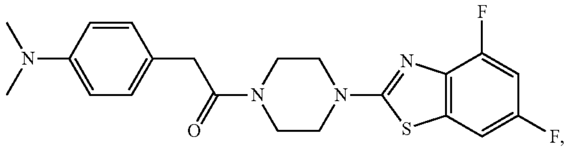

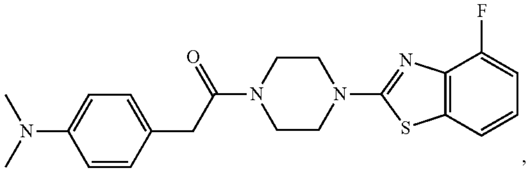

,

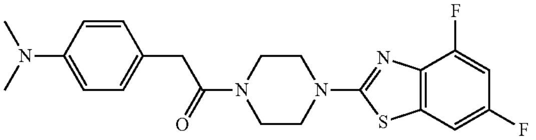

and

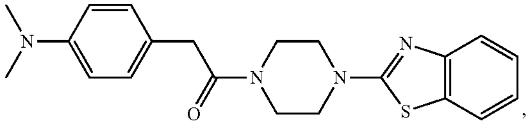

, or a pharmaceutically acceptable salt thereof.

Also disclosed are methods of making a disclosed compound.

Also disclosed are pharmaceutical compositions comprising a therapeutically effective amount of at least one disclosed compound and a pharmaceutically acceptable carrier.

Also disclosed are methods of modulating pantothenate kinase activity in at least one cell, the method comprising the step of contacting at least one cell with an effective amount of at least one disclosed compound, or a pharmaceutically acceptable salt thereof.

Also disclosed are methods of treating a disorder associated with pantothenate kinase activity in a subject, the method comprising administering to the subject an effective amount of at least one disclosed compound, or a pharmaceutically acceptable salt thereof.

Also disclosed are kits comprising at least one disclosed compound and one or more In one aspect, disclosed are kits comprising a disclosed compound and one or more of: (a) at least one agent known to treat PKAN; (b) at least one agent known to treat diabetes; (c) at least one agent known to treat metabolic acidemias; (d) instructions for treating PKAN; and (d) instructions for treating diabetes, metabolic syndrome, metabolic acidemias, and/or side effects of aging.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1A:
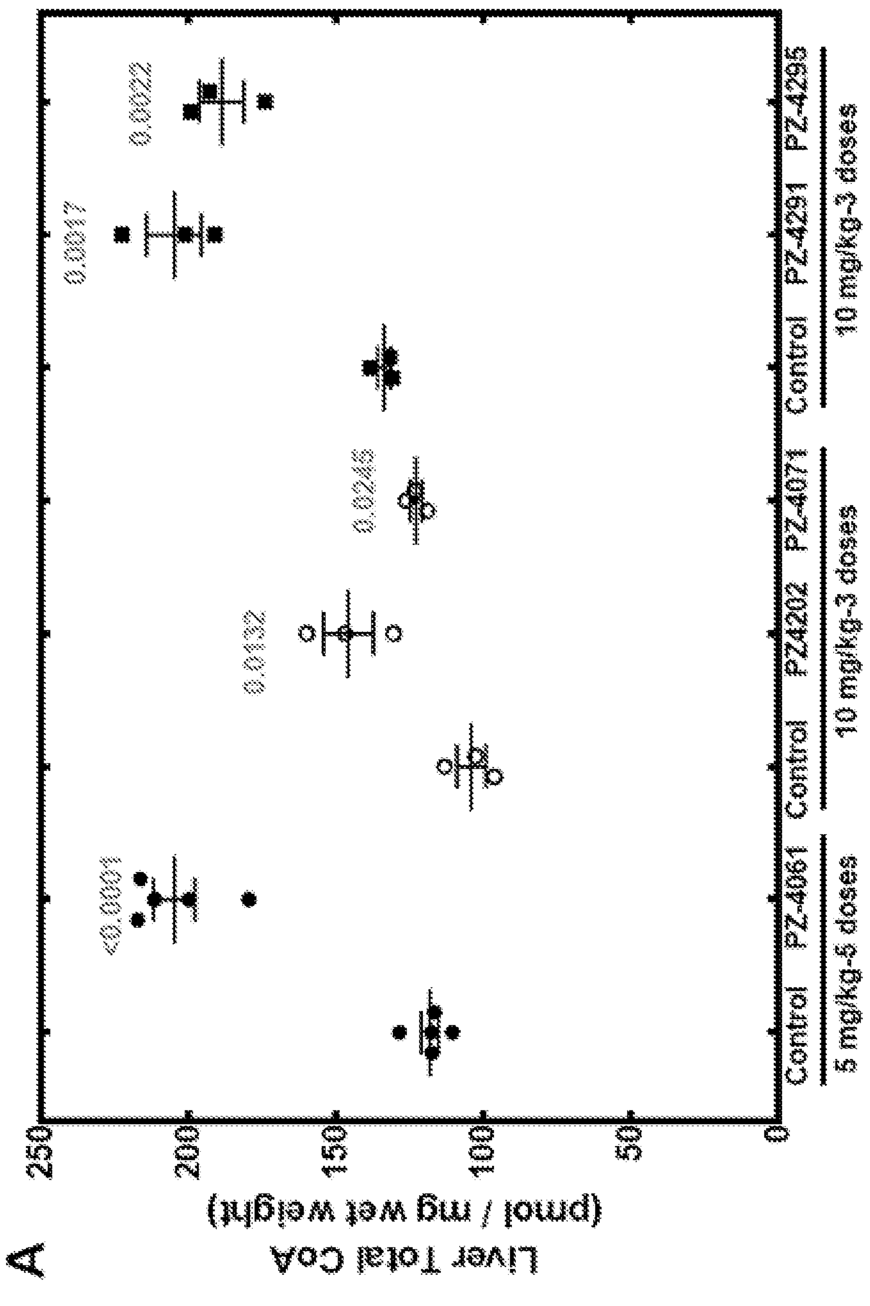
FIG. 1A and FIG. 1B show representative data illustrating the total CoA from tissues of C57B16 mice were on chow containing 1000 ppm Pantothenate and treated with the compounds either once a day (3 doses) or twice a day (5 doses) for 3 days. Specifically, liver total CoA (FIG. 1A) and forebrain total CoA (FIG. 1B) are shown. There were either 5 or 3 mice used in the study as indicated in the figure. The CoA values are mean±SEM. The data for each set is compared to its control and the p value was calculated using unpaired t-test which is given in grey.
Figure 1B:
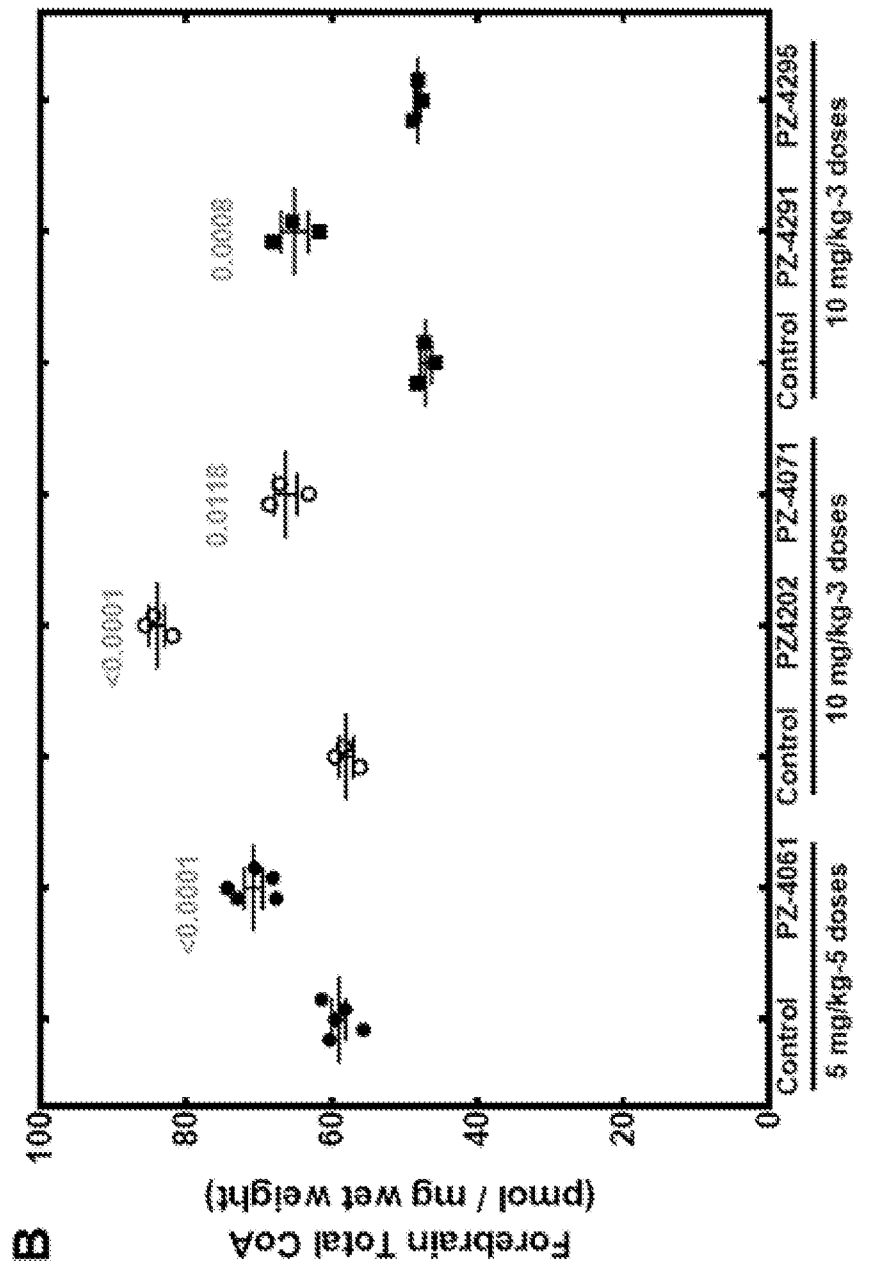

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, $—NH_2$, (C1-C4) alkylamino, (C1-C4)(C1-C4) dialkylamino, ether, halogen, —OH, C1-C4 hydroxyalkyl, $—NO_2$, silyl, sulfo-oxo, —SH, and C1-C4 thioalkyl, as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldeyhyde, —$NH_2$, (C1-C4) alkylamino, (C1-C4)(C1-C4) dialkylamino, carboxylic acid, ester, ether, halogen, —OH, C1-C4 hydroxyalkyl, ketone, azide, —$NO_2$, silyl, sulfo-oxo, —SH, and C1-C4 thioalkyl, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)_a$— or $-(A^1O(O)C\text{-}A^2\text{-}OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen," and "pseudohalo" as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl" as used herein can be used interchangeably and refer to single and multicyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN or —C≡N.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "R," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene$)O—N(R^\circ)_2$; or $—(C_{1-4}$ straight or branched alkylene$)C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; —O(halo$R^\bullet$), $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene$)C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), $—OH$, $—OR^\bullet$, —O(halo$R^\bullet$), $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, -(halo$R^\bullet$), $—OH$, $—OR^\bullet$, —O(halo$R^\bullet$), $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

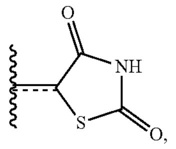

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−)

or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

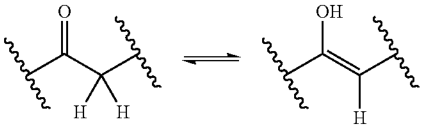

keto form enol form

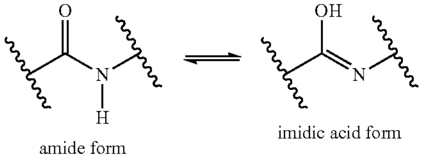

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

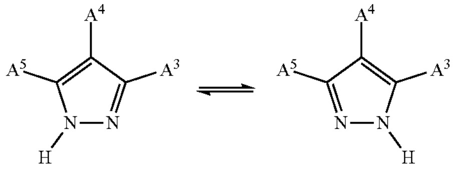

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

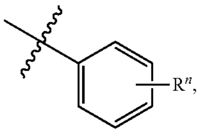

which is understood to be equivalent to a formula:

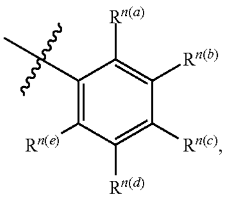

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are compounds useful in treating or preventing a disorder associated with PanK activity such as, for example, PKAN, diabetes, metabolic syndrome, and metabolic acidemias. In a further aspect, the disclosed compounds exhibit modulation of PanK activity. In a still further aspect, the disclosed compounds exhibit inhibition of PanK activity. In yet a further aspect, the disclosed compounds exhibit activation of PanK activity.

In one aspect, the compounds of the invention are useful in the treatment or prevention of disorders associated with PanK dysfunction and other diseases in which PanKs or altered levels of CoA and CoA esters are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

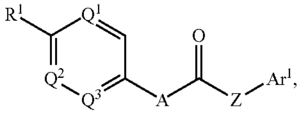

wherein A is selected from —O—, —$CH_2$—, —$CF_2$—, —NH—, —N($CH_3$)—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

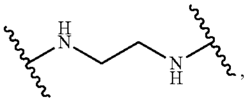,
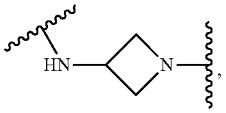,
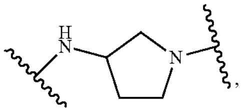,
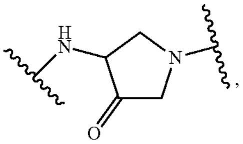,
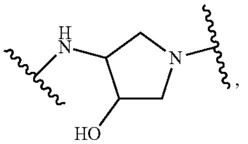,
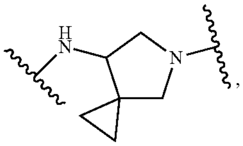,
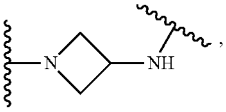,
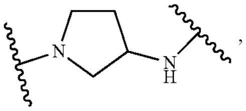,
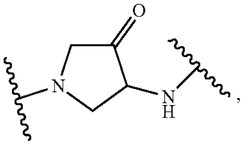,
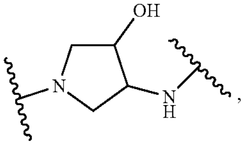,
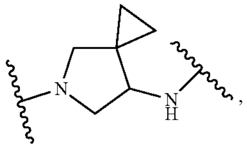,
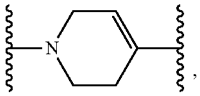,
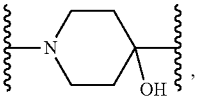,
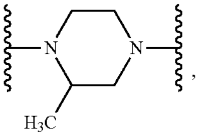,
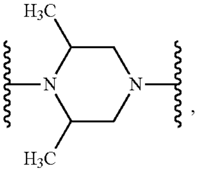,
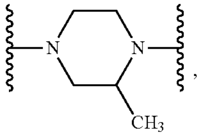,
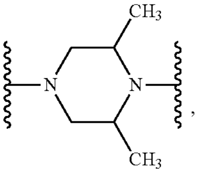,
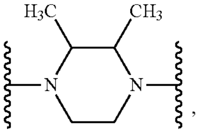,
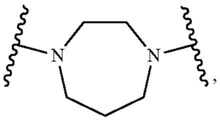,
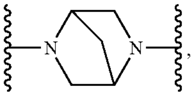,
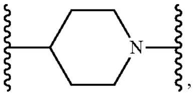,
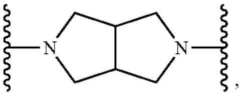,
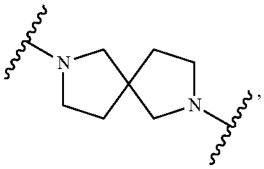, -continued

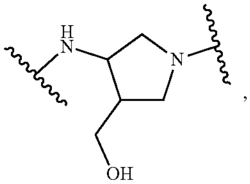,
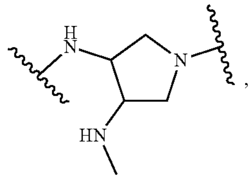,
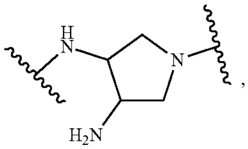,
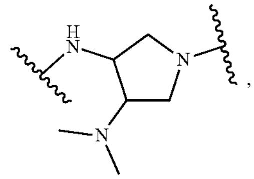,
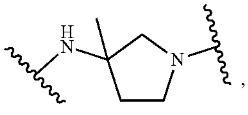,
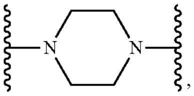,
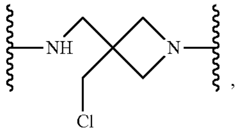,
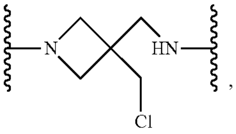,
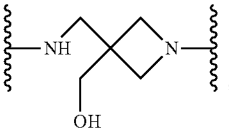,
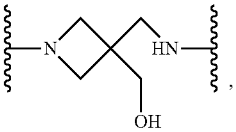,
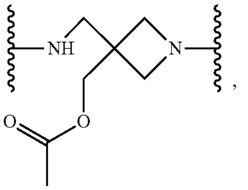, and
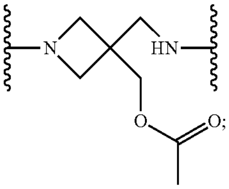;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

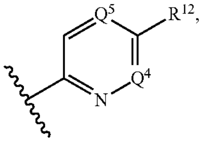,
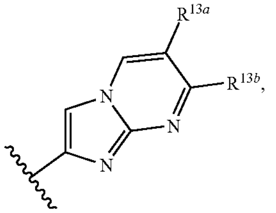,
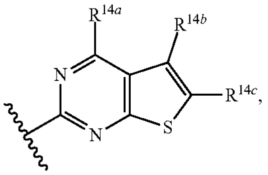,
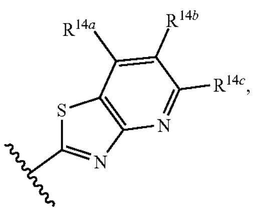, and
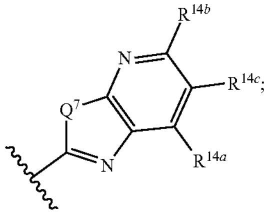;

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxy-alkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from O, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

In one aspect, disclosed are compounds having a structure represented by a formula:

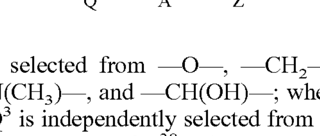, wherein A is selected from —O—, —$CH_2$—, —$CF_2$—, —NH—, —N($CH_3$)—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

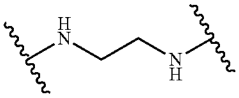, 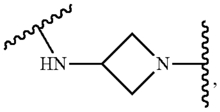,
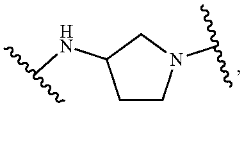, 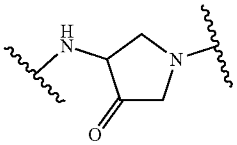,
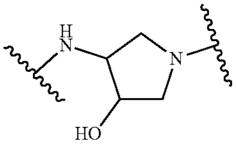, 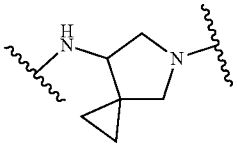,
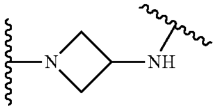, 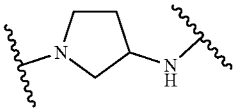,
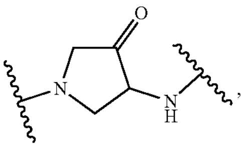, 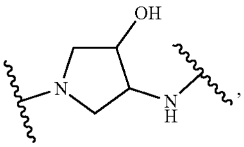,
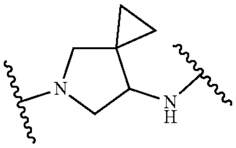, 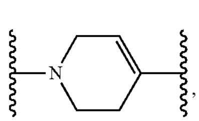,
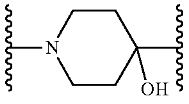, 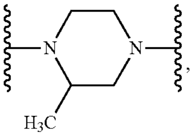,
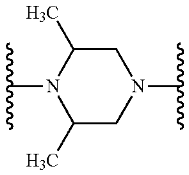, 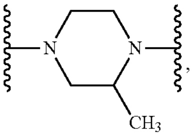,
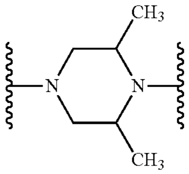, 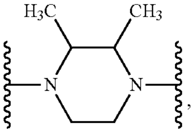,
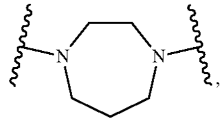, 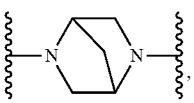,
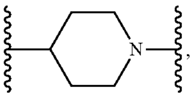, 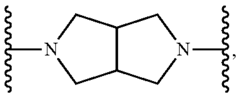, -continued

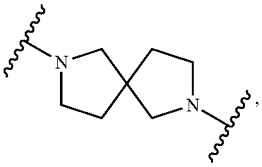,
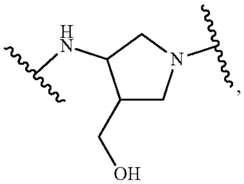,
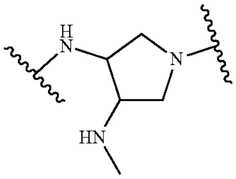,
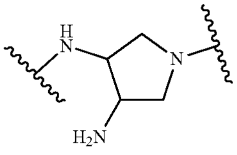,
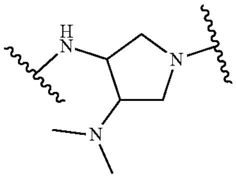,
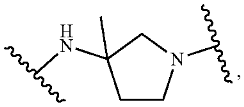, and
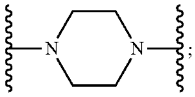;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from

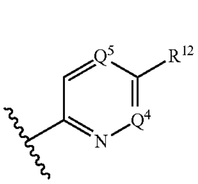
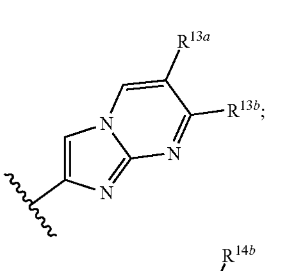
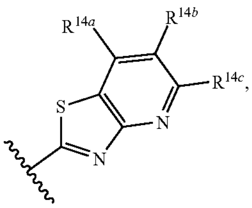, and
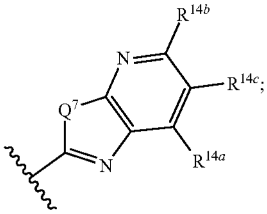

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from O, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

In one aspect, disclosed are compounds having a structure represented by a formula:

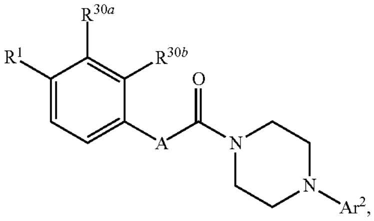

wherein A is selected from —O— and —$CH_2$—; wherein $R^1$ is selected from C1-C4 alkyl, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^1$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

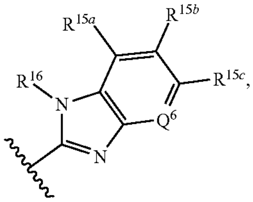,
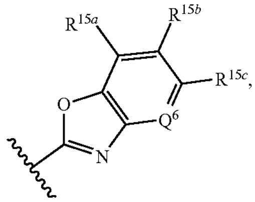, and

-continued

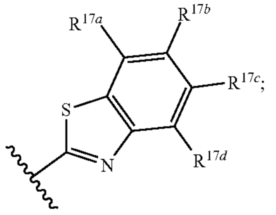

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein each of $R^{30a}$ and $R^{30b}$ is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

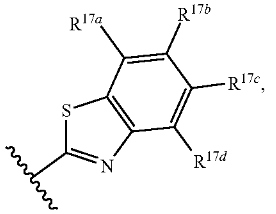

then A is —$CH_2$— and $R^1$ is selected from —$NR^{10}SO_2R^{11}$ and $Cy^1$, and provided that when $Ar^2$ is

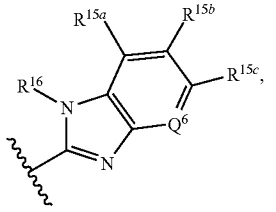

then A is —$CH_2$—, or a pharmaceutically acceptable salt thereof.

In one aspect, disclosed are compounds having a structure represented by a formula:

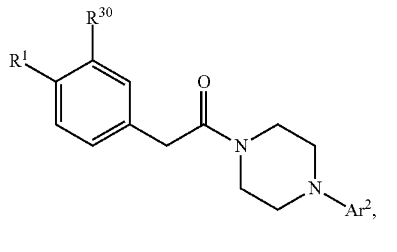

wherein $R^1$ is selected from C1-C4 alkyl, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

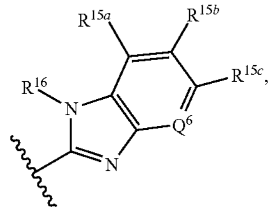

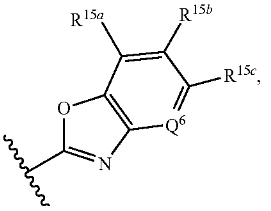

and

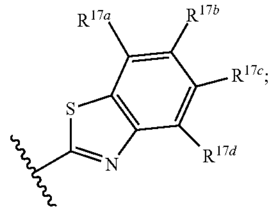

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

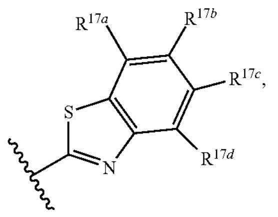

then $R^1$ is selected from —$NR^{10}SO_2R^{11}$ and $Cy^1$, or a pharmaceutically acceptable salt thereof.

In one aspect, disclosed are compounds having a structure selected from:

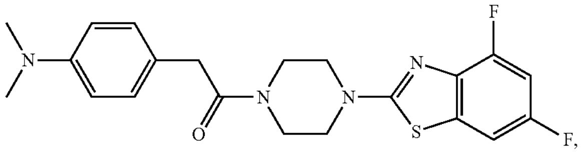

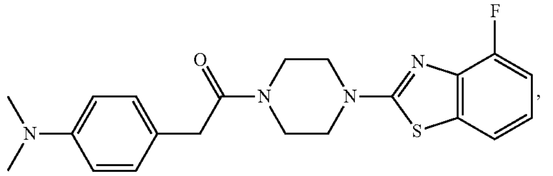

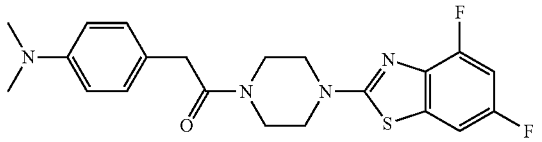

and

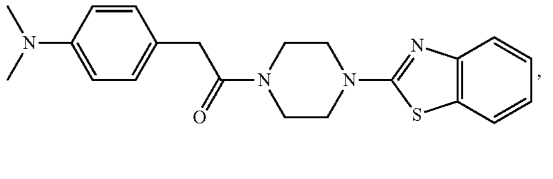

or a pharmaceutically acceptable salt thereof.

In a further aspect, the compound has a structure represented by a formula:

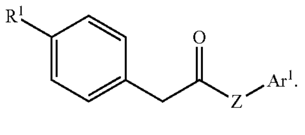

In a further aspect, the compound has a structure re resented by a formula:

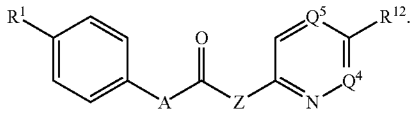

In a further aspect, the compound has a structure represented by a formula:

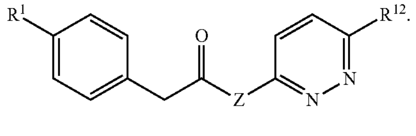

In a further aspect, the compound has a structure represented by a formula:

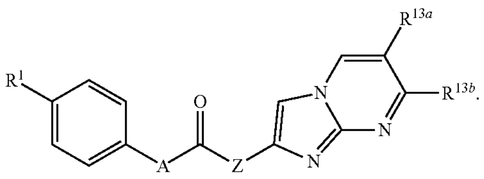

In a further aspect the compound has a structure represented by a formula:

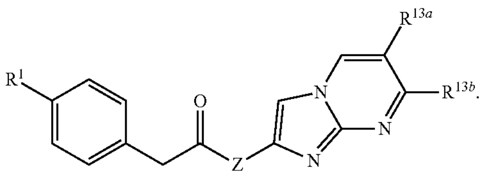

In a further aspect, the compound has a structure represented by a formula:

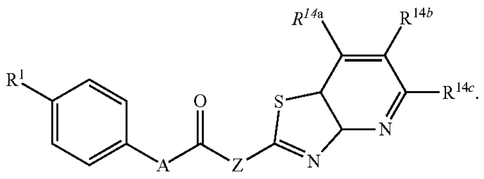

In a further aspect, the compound has a structure represented by a formula:

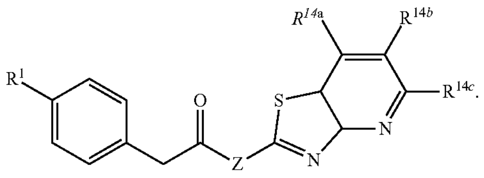

In a further aspect, the compound has a structure represented by a formula:
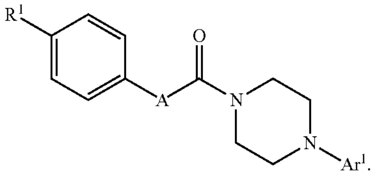
In a further aspect, the compound has a structure represented by a formula:
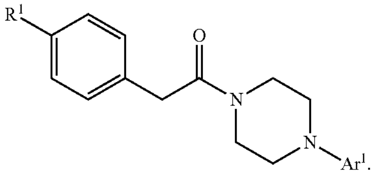
In a further aspect, the compound is selected from:
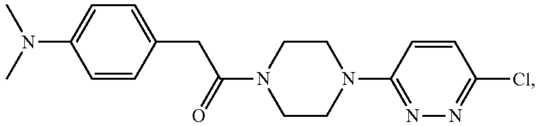
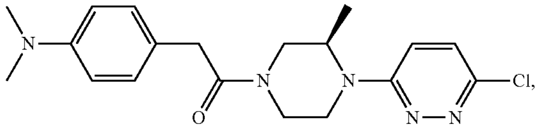
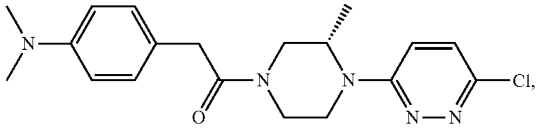
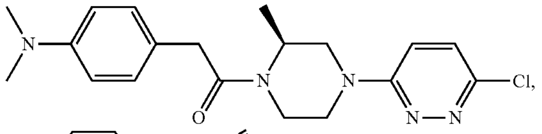
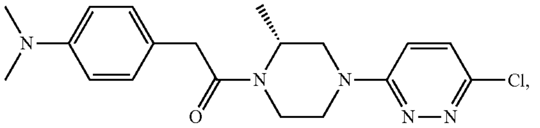
and
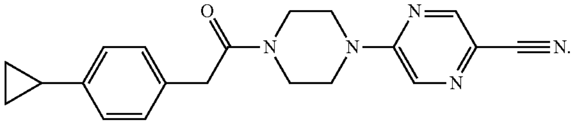
In a further aspect, the compound is selected from:
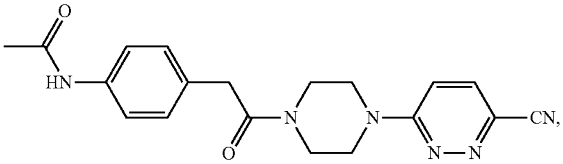
-continued
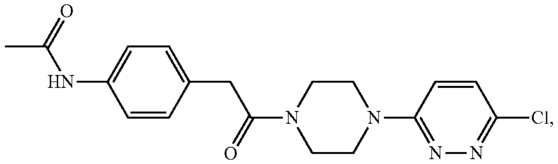
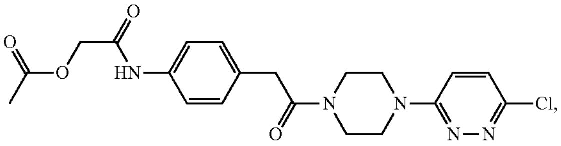
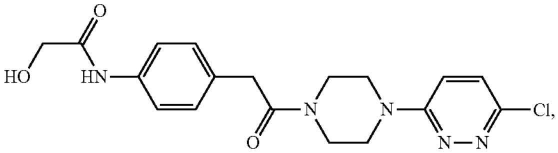
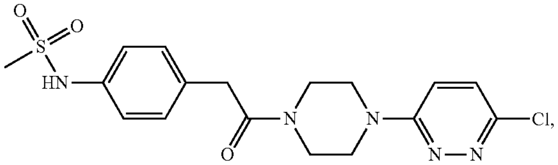
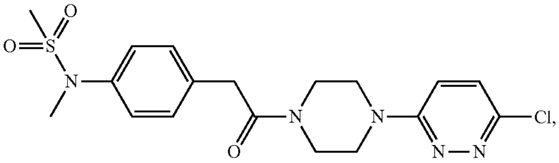
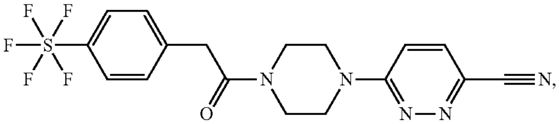
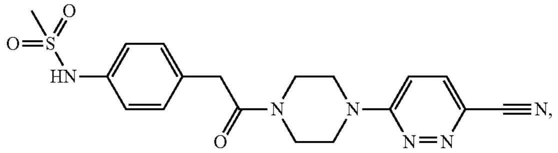
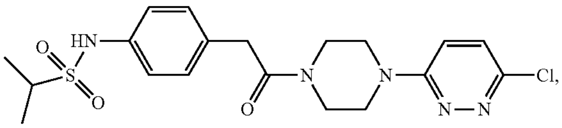
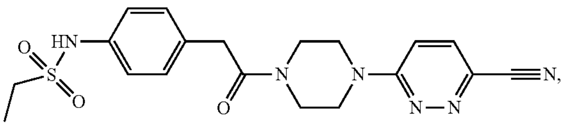
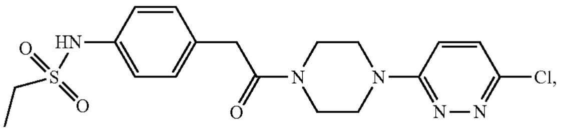
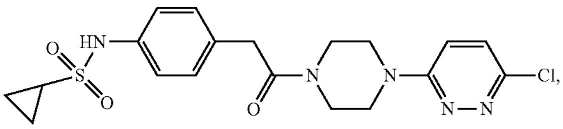
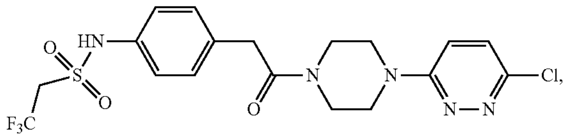

-continued
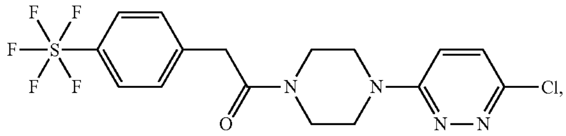
,
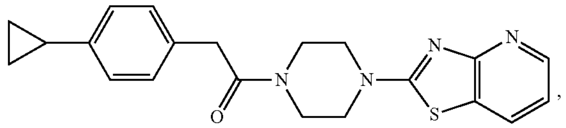
,
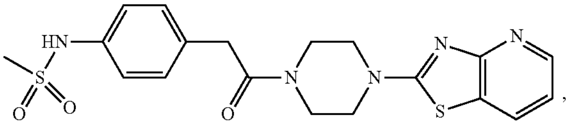
,
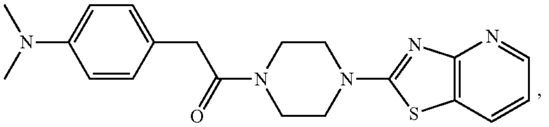
,
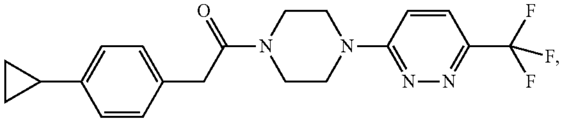
,
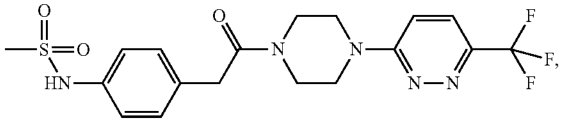
,
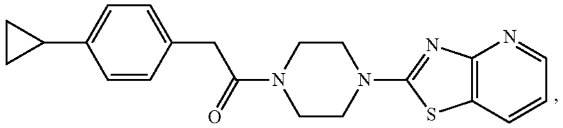
,
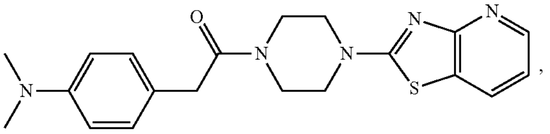
,
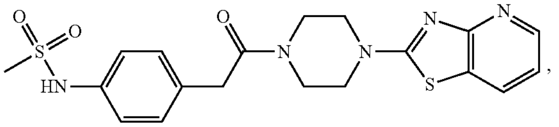
,
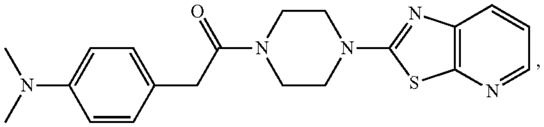
,
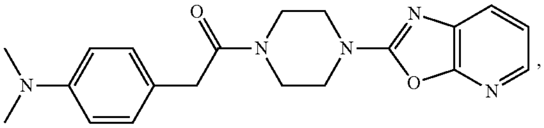
,
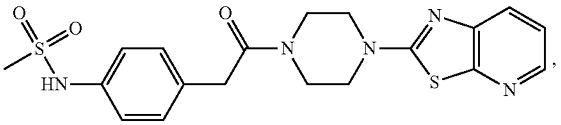
,
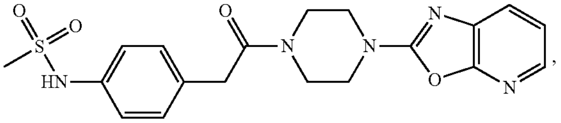
,
-continued
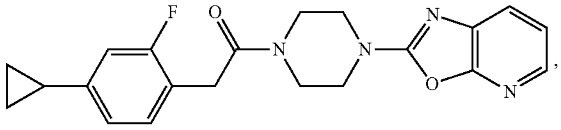
,
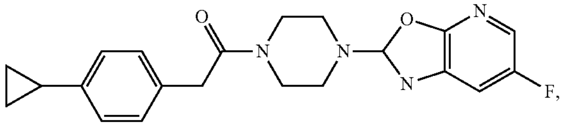
,
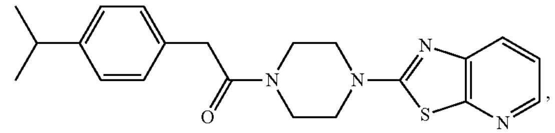
,
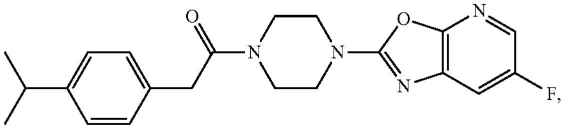
,
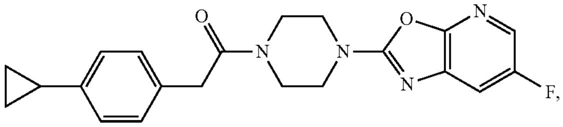
,
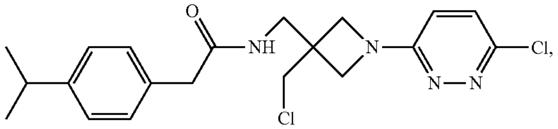
,
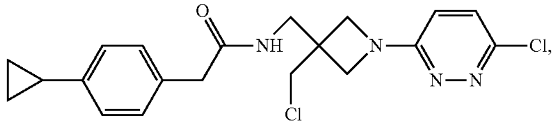
,
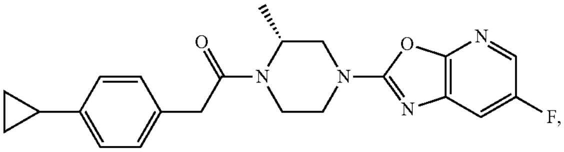
,
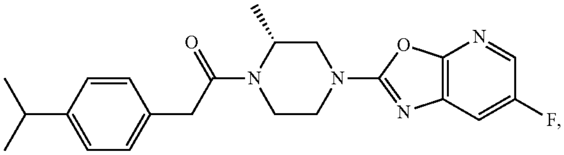
,
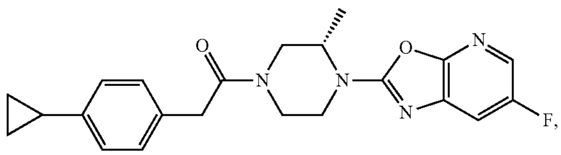
,
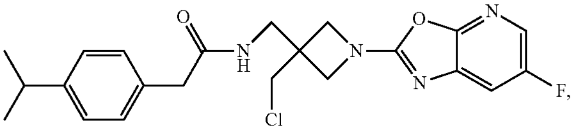
,
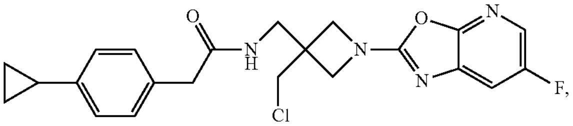
, -continued
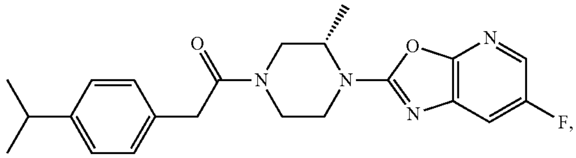
,
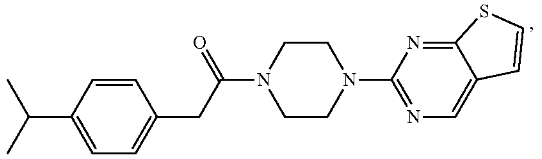
,
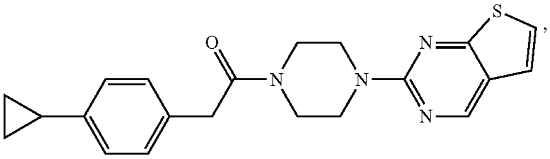
,
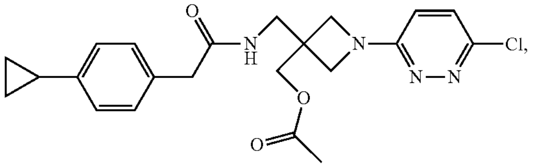
, and
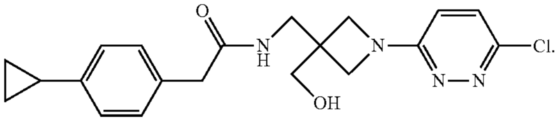
.
In a further aspect, the compound has a structure represented by a formula:
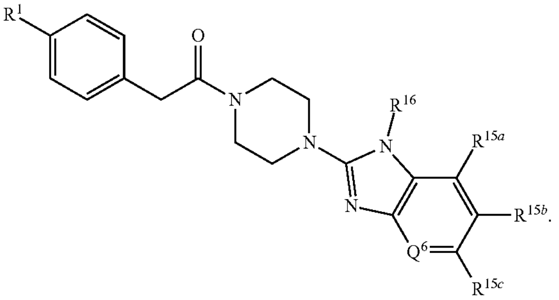
.
In a further aspect, the compound has a structure represented by a formula:
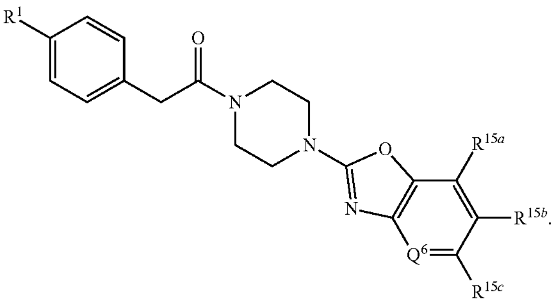
.
In a further aspect, the compound has a structure represented by a formula:
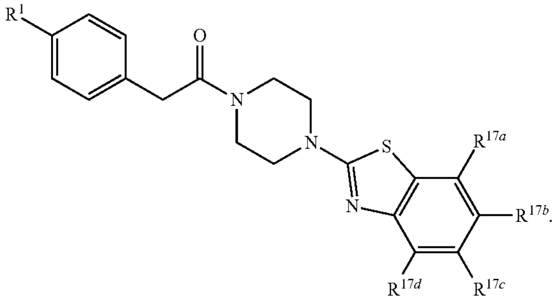
.
In a further aspect, the compound has a structure selected from:
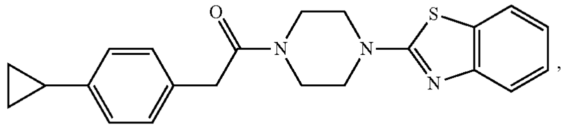
,
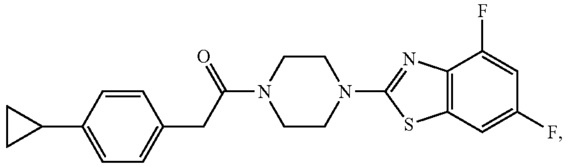
,
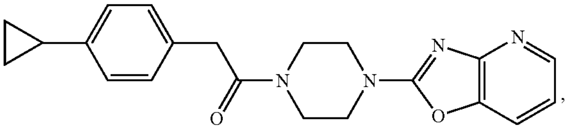
,
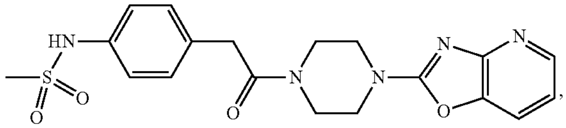
,
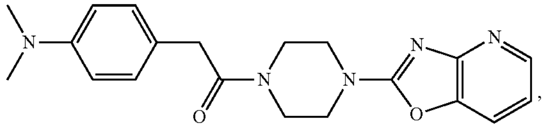
,
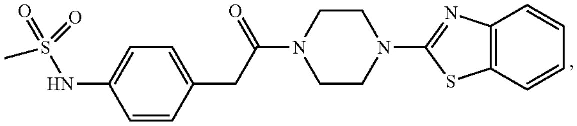
,
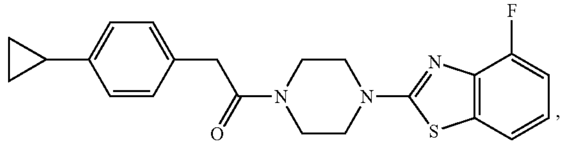
,
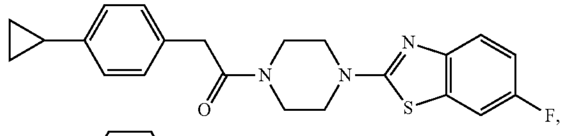
,
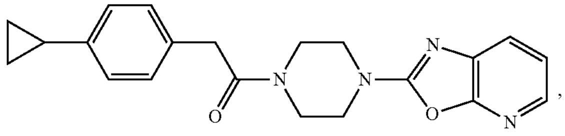
, -continued
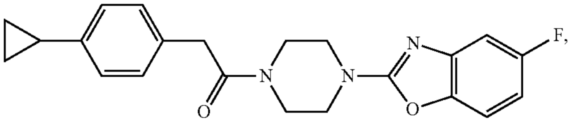
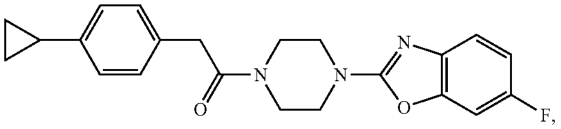
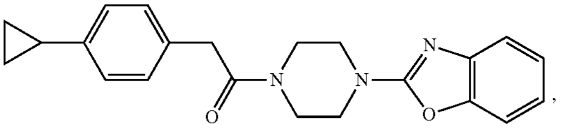
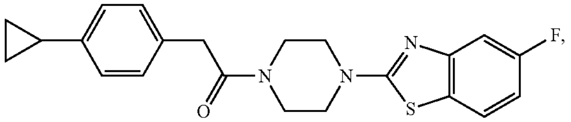
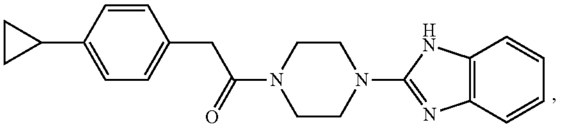
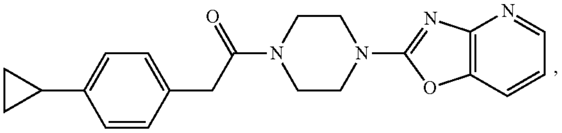
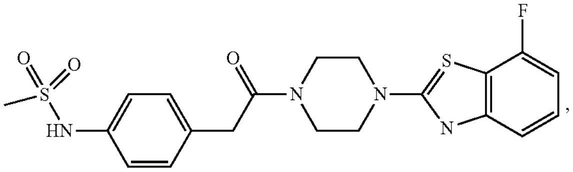
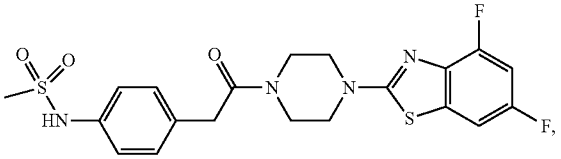
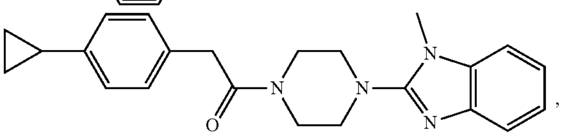
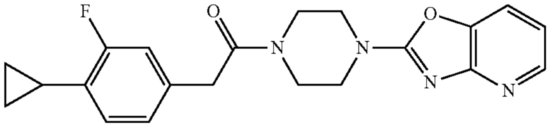
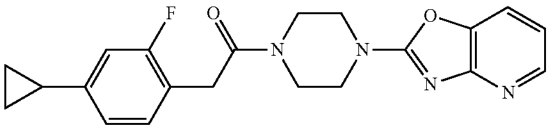
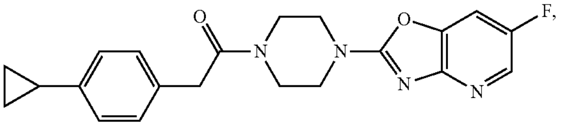
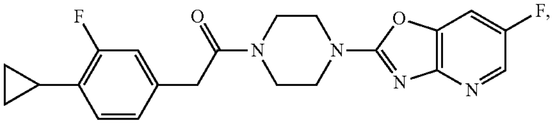
-continued
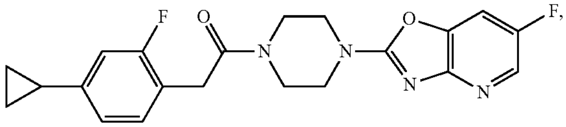
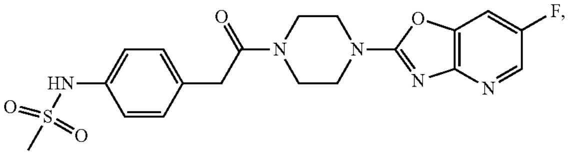
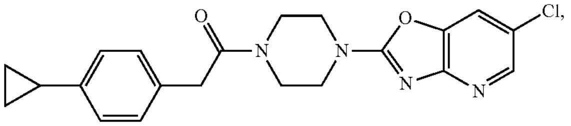
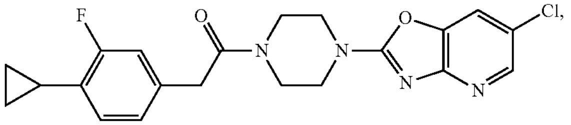
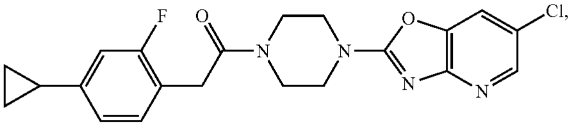
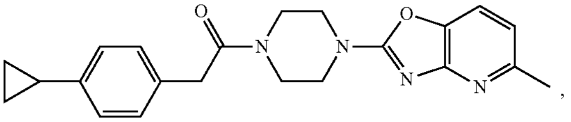
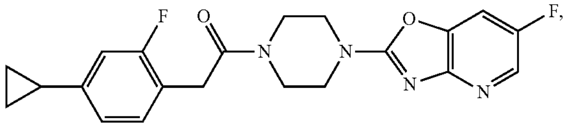
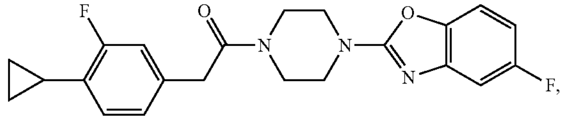
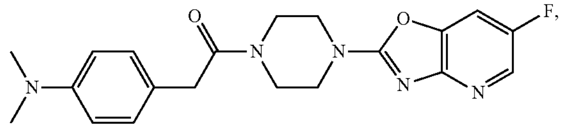
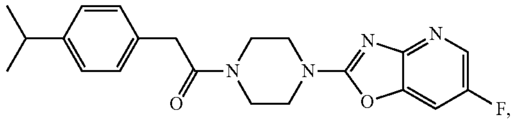
and
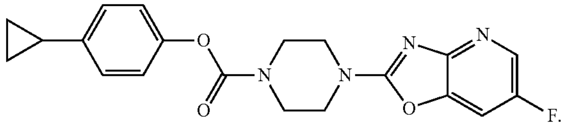
In a further aspect, the compound has a structure selected from:
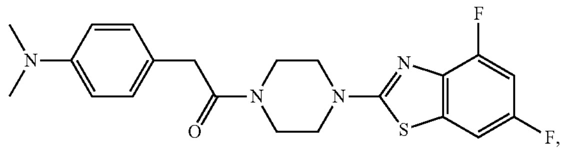

-continued

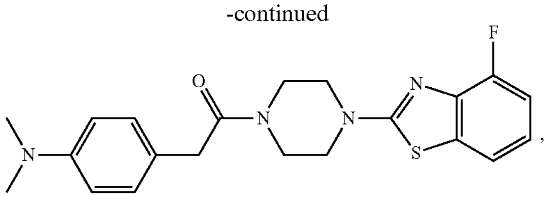,

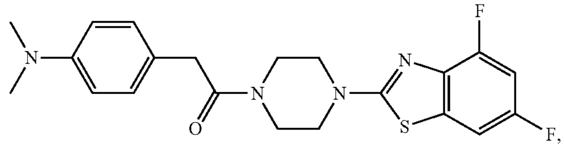,

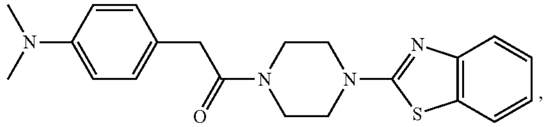,

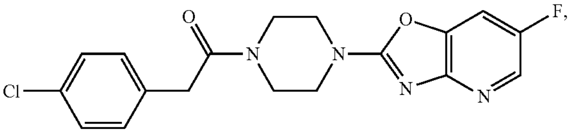,

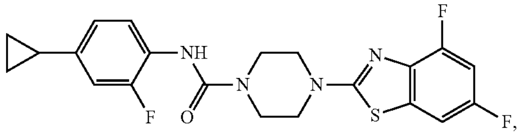, and

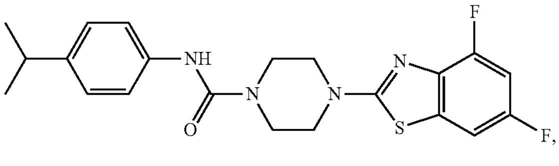, or a pharmaceutically acceptable salt thereof.

a. A GROUPS

In one aspect, A is selected from O, CO, $CH_2$, $CF_2$, NH, $N(CH_3)$, and CH(OH). In one aspect, A is selected from O, CO, $CH_2$, $CF_2$, NH, and CH(OH). In one aspect, O, CO, $CH_2$, $CF_2$, $N(CH_3)$, and CH(OH). In one aspect, A is selected from O, CO, $CH_2$, $CF_2$, and CH(OH).

In one aspect, A is selected from —O— and —$CH_2$—. In a further aspect, A is —O—. In a still further aspect, A is —$CH_2$—.

In a further aspect, A is selected from O, CO, $CH_2$, and $CF_2$. In a still further aspect, A is selected from O, CO, and $CH_2$. In yet a further aspect, A is selected from O and CO. In an even further aspect, A is O. In a still further aspect, A is CO. In yet a further aspect, A is $CH_2$. In an even further aspect, A is $CF_2$.

In a further aspect, A is selected from NH and $N(CH_3)$. In a still further aspect, A is NH. In yet a further aspect, A is $N(CH_3)$.

In a further aspect, A is selected from NH and $CH_2$.

In a further aspect, A is CH(OH).

b. $Q^1$, $Q^2$, and $Q^3$ Groups

In one aspect, each of $Q^1$, $Q^2$, and $Q^3$ is independently selected from N and $CR^{30}$. In a further aspect, each of $Q^1$, $Q^2$, and $Q^3$ is $CR^{30}$.

In various aspects, each of $Q^1$, $Q^2$, and $Q^3$ is independently selected from N and CH. In a further aspect, each of $Q^1$, $Q^2$, and $Q^3$ is CH.

In a further aspect, $Q^1$ is N and $Q^2$ and $Q^3$ are $CR^{30}$. In a still further aspect, $Q^2$ is N and $Q^1$ and $Q^3$ are $CR^{30}$. In yet a further aspect, $Q^3$ is N and $Q^1$ and $Q^2$ are $CR^{30}$.

In a further aspect, $Q^1$ is N and $Q^2$ and $Q^3$ are CH. In a still further aspect, $Q^2$ is N and $Q^1$ and $Q^3$ are CH. In yet a further aspect, $Q^3$ is N and $Q^1$ and $Q^2$ are CH.

In a further aspect, $Q^1$ is CH and $Q^2$ and $Q^3$ are N. In a still further aspect, $Q^2$ is CH and $Q^1$ and $Q^3$ are N. In yet a further aspect, $Q^3$ is CH and $Q^1$ and $Q^2$ are N.

c. $Q^4$ and $Q^5$ Groups

In one aspect, one of $Q^4$ and $Q^5$, when present, is N and one of $Q^4$ and $Q^5$, when present, is CH. In a further aspect, $Q^4$, when present, is N and $Q^5$, when present, is CH. In a still further aspect, $Q^4$, when present, is CH and $Q^5$, when present, is N.

d. $Q^6$ Groups

In one aspect, $Q^6$, when present, is selected from N and $CR^{21}$. In a further aspect, $Q^6$, when present, is $CR^{21}$. In a still further aspect, $Q^6$, when present, is N.

e. $Q^7$ Groups

In one aspect, $Q^7$, when present, is selected from O, S, and $NR^{16}$. In a further aspect, $Q^7$, when present, is selected from O and S. In a still further aspect, $Q^7$, when present, is selected from O and $NR^{16}$. In yet a further aspect, $Q^7$, when present, is selected from S and $NR^{16}$. In an even further aspect, $Q^7$, when present, is O. In a still further aspect, $Q^7$, when present, is S. In yet a further aspect, $Q^7$, when present, is $NR^{16}$.

f. Z Groups

In one aspect, Z is a structure selected from:

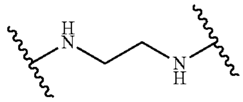, 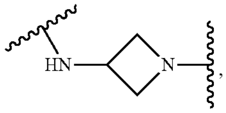,

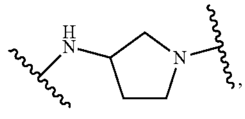, 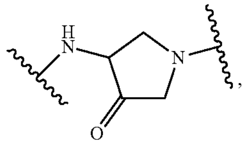,

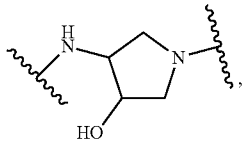, 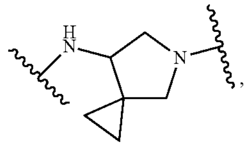,

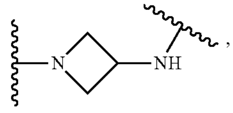, 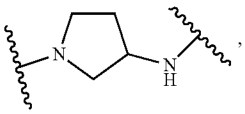,

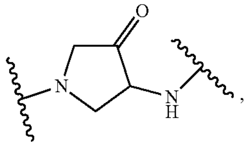, 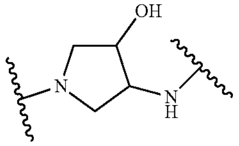,

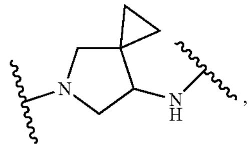, 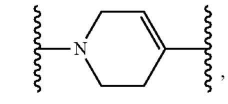,

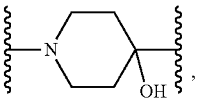, 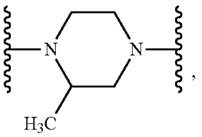,

-continued
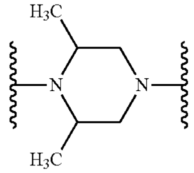,
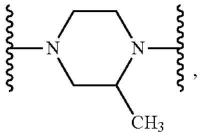,
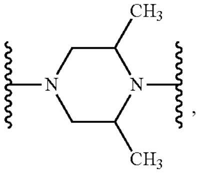,
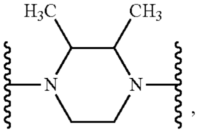,
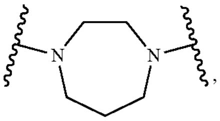,
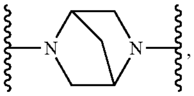,
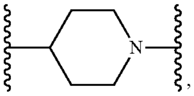,
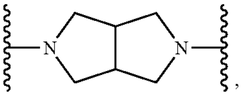,
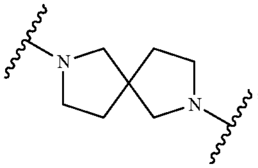,
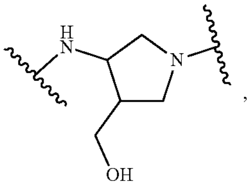,
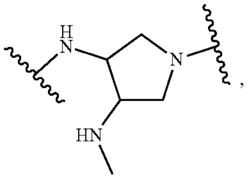,
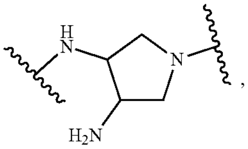,
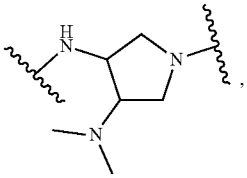,
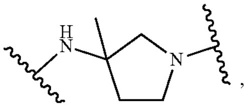,
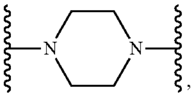,
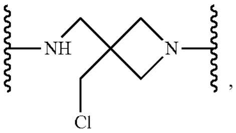,
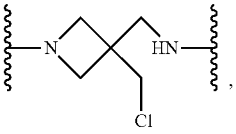,
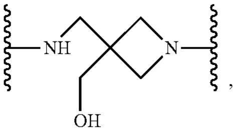,
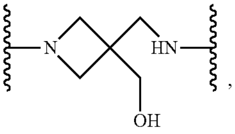,
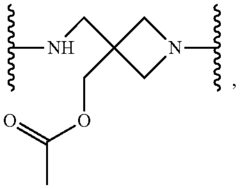, and
-continued
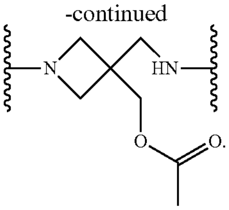
In one aspect, Z is a structure selected from:
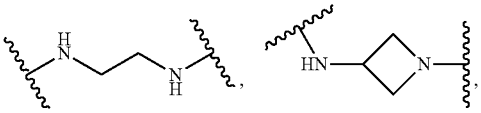,
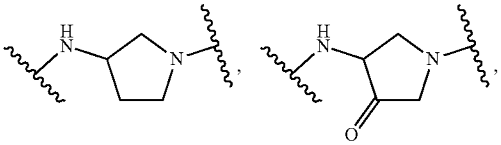,
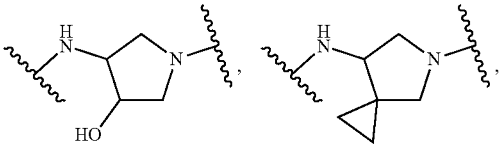,
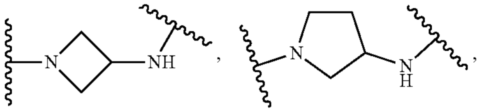,
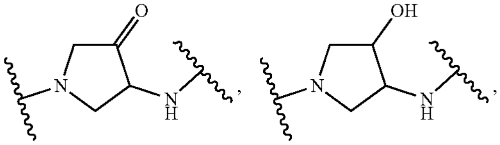,
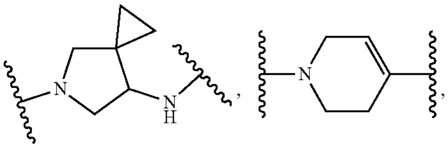,
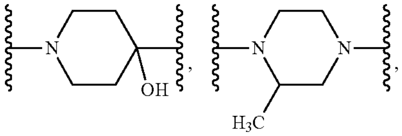,
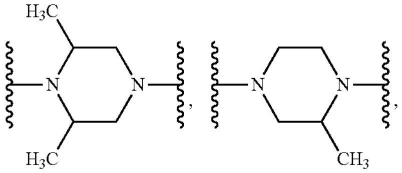,
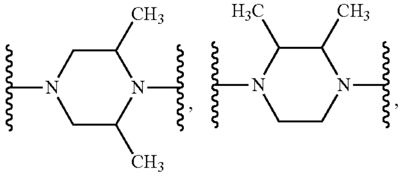,
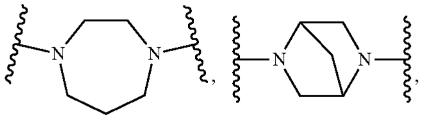, -continued
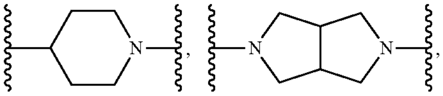,
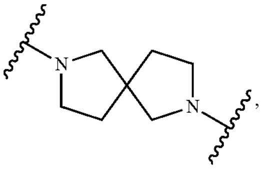, 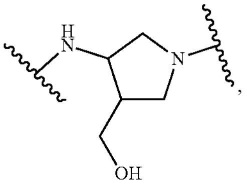,
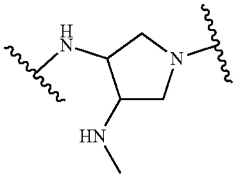, 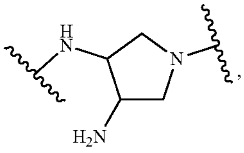,
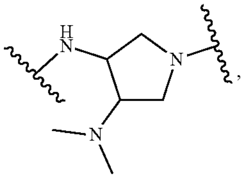, 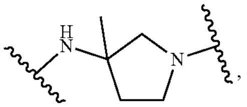, and
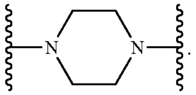.
In one aspect, Z is a structure selected from:
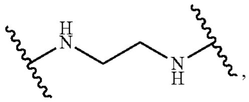, 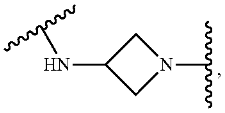,
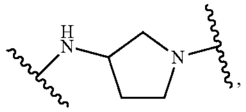, 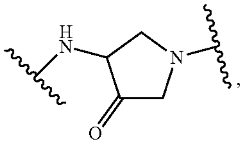,
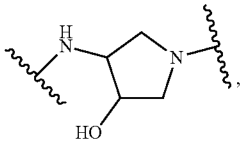, 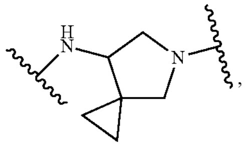,
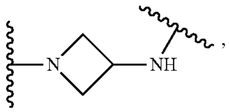, 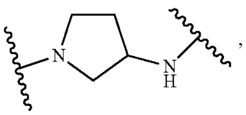,
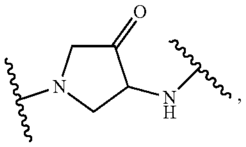, 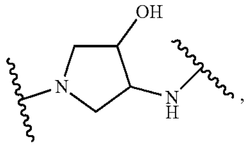,
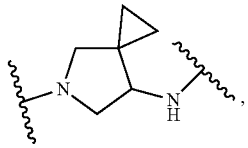, 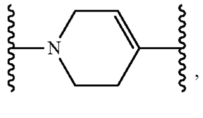,
-continued
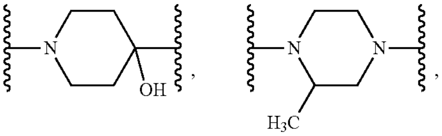,
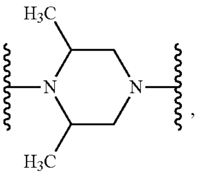, 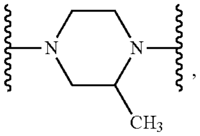,
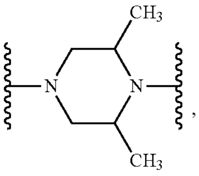, 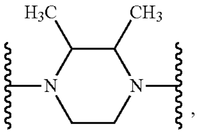,
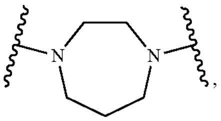, 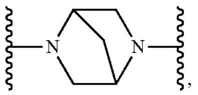,
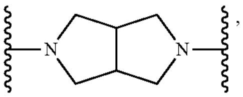, 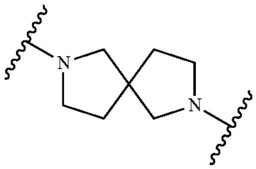,
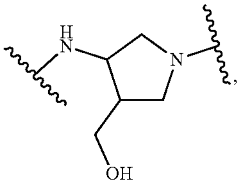, 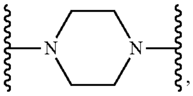,
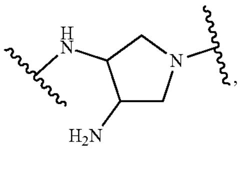, 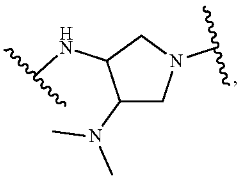, and
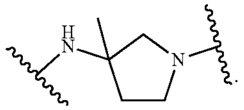.
In a further aspect, Z is a structure selected from:
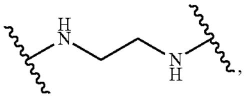, 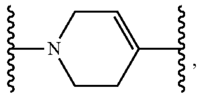,
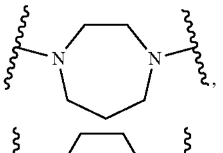, 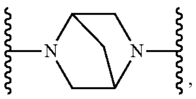,
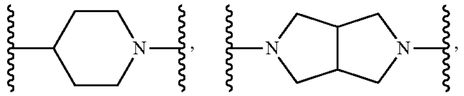, -continued
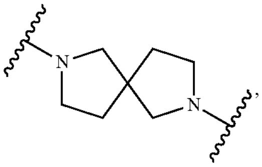
and
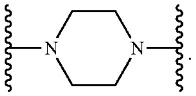
In a still further aspect Z is:
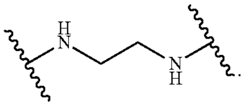 [SMILES: *NCCN*]
In yet a further aspect, Z is a structure selected from:
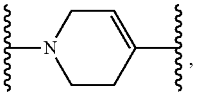
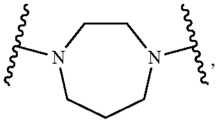
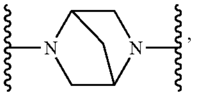
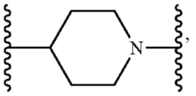
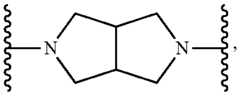
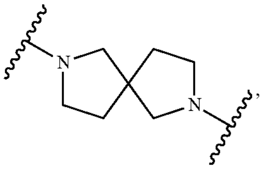
and
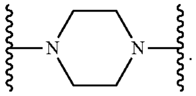
In an even further aspect, Z is a structure selected from:
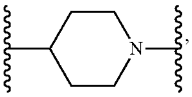
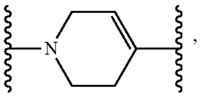
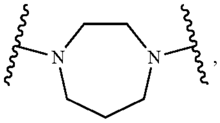
and
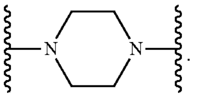
In a still further aspect, Z is a structure selected from:
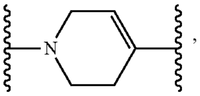
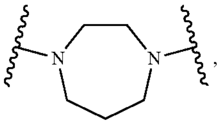
and
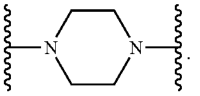
In yet a further aspect, Z is a structure selected from:
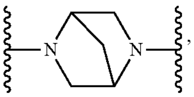
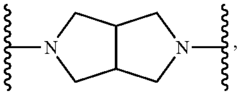
and
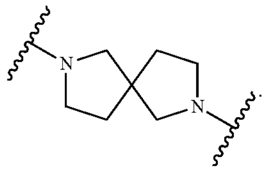
In a further aspect, Z is a structure selected from:
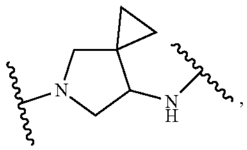
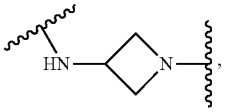
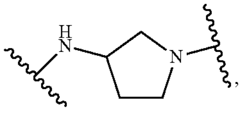
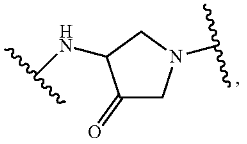
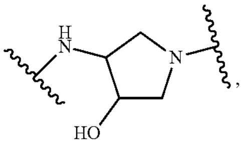
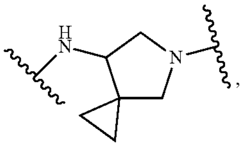
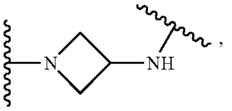
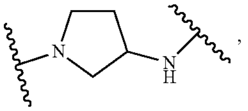
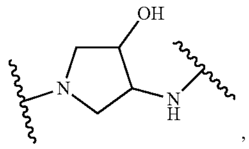
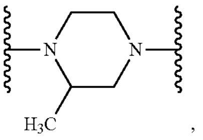
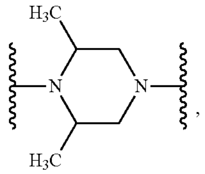
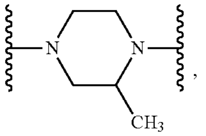
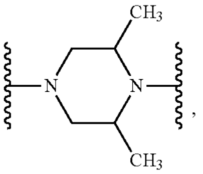
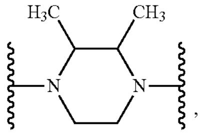
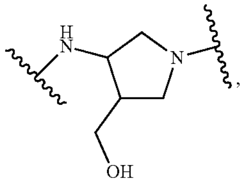
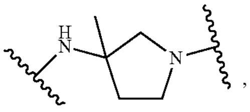

-continued
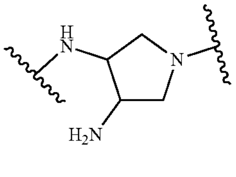
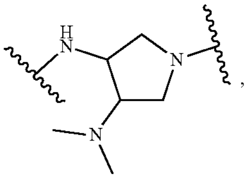
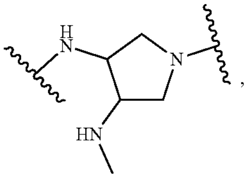
and
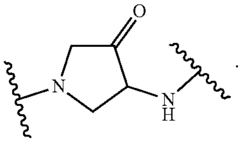
In a still further aspect, Z is a structure selected from:
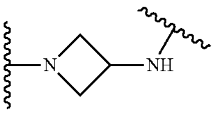
and
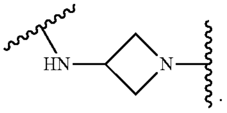
In yet a further aspect, Z is a structure selected from:
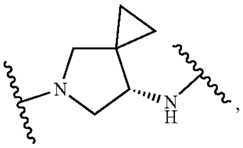
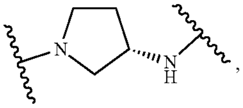
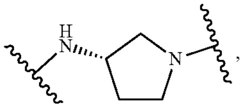
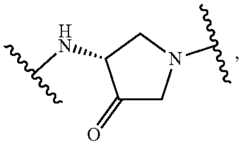
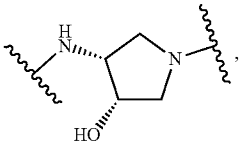
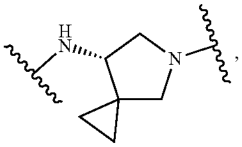
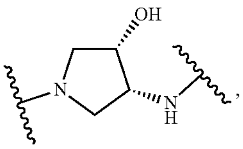
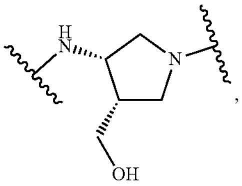
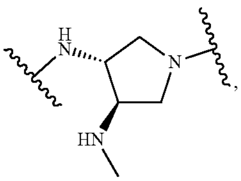
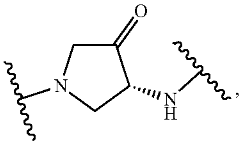
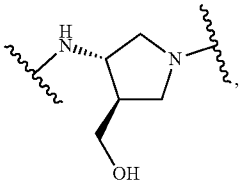
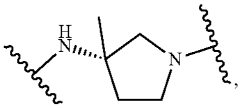
-continued
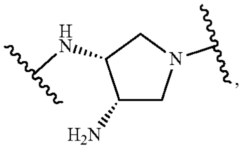
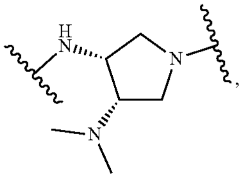
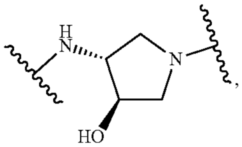
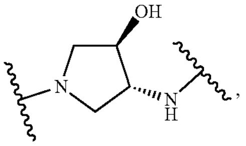
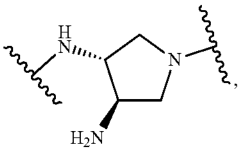
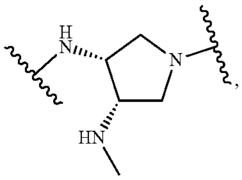
and
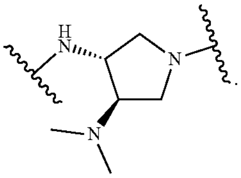
In an even further aspect, Z is a structure selected front
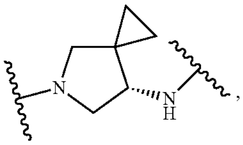
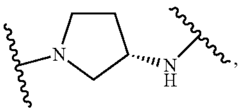
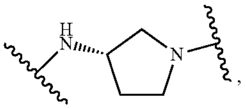
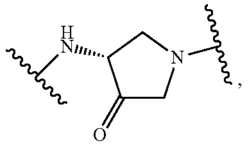
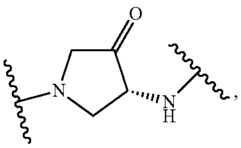
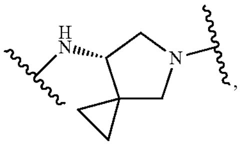
and
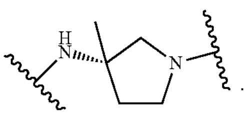
In a still further aspect, Z is a structure selected from:
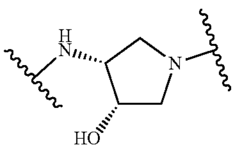
, -continued
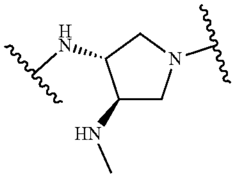
,
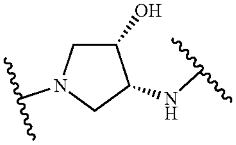
,
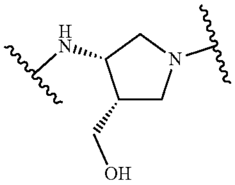
,
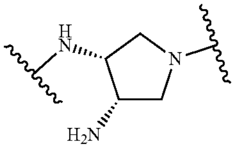
,
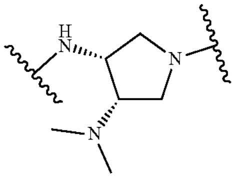
,
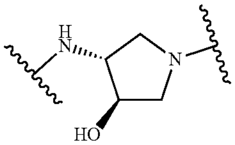
,
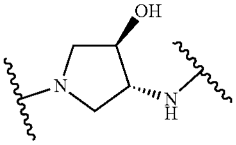
,
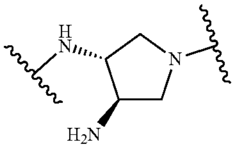
,
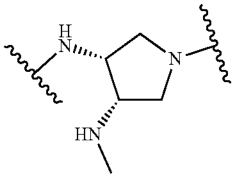
,
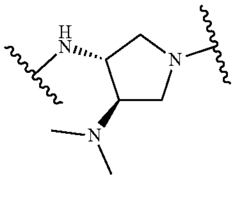
, and
-continued
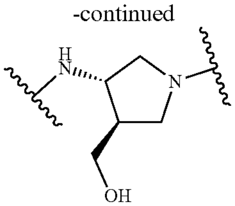
.
In yet a further aspect, Z is a structure selected from:
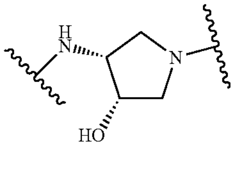
,
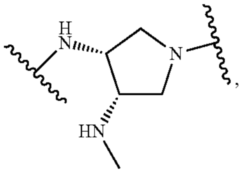
,
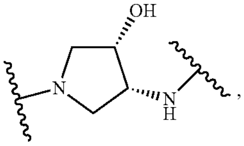
,
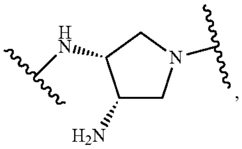
,
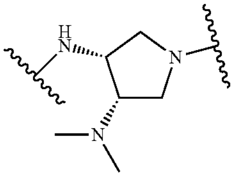
, and
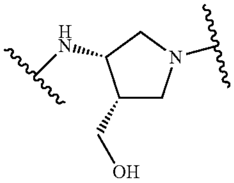
.
In an even further aspect, Z is a structure selected from:
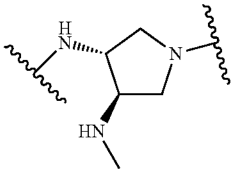
,
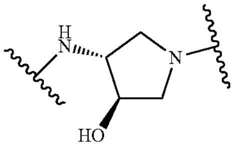
,
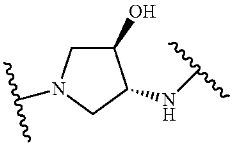
,
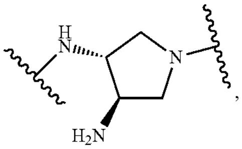
,
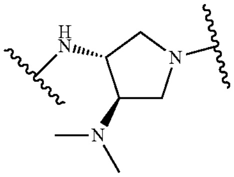
, and
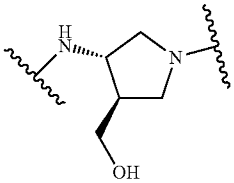
.
In a still further aspect, Z is a structure selected from:
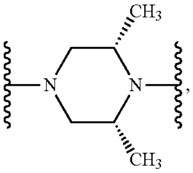
,
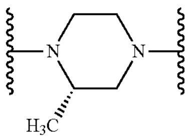
, -continued
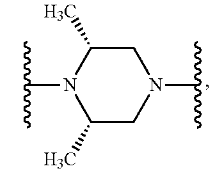,
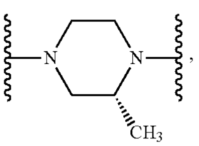,
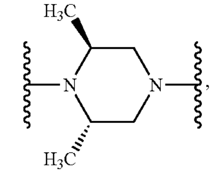,
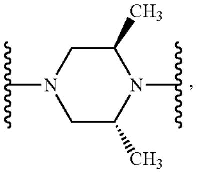,
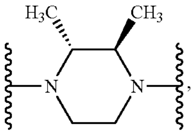, and 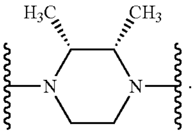.
In yet a further aspect, Z is a structure selected from:
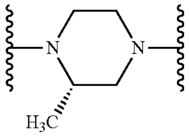 and 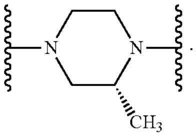.
In an even further aspect, Z is a structure selected from:
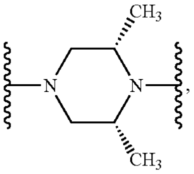,
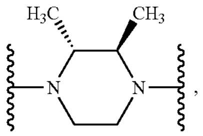,
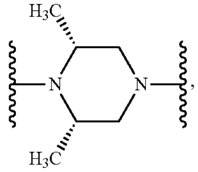,
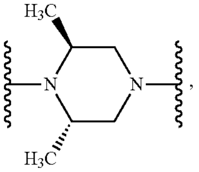,
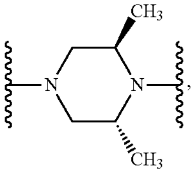, and 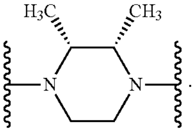.
In a still further aspect, Z is a structure selected from:
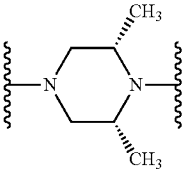,
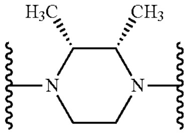, and
-continued
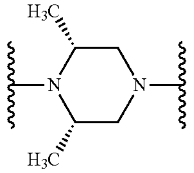.
In yet a further aspect, Z is a structure selected from:
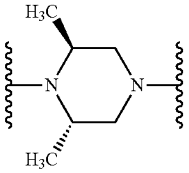,
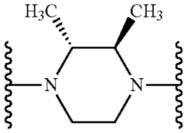, and
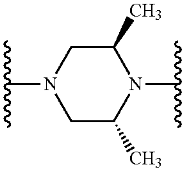.
In a further aspect, Z is a structure selected from:
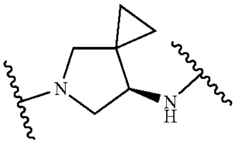,
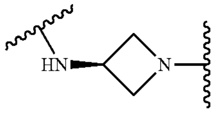,
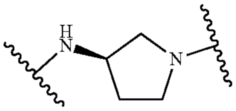,
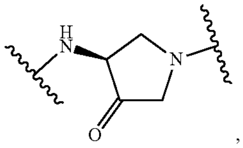,
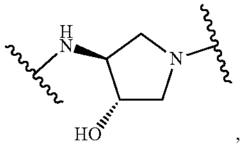,
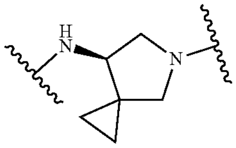,
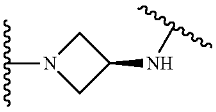, -continued
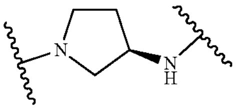
,
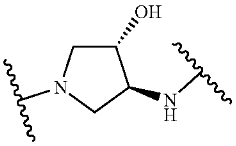
,
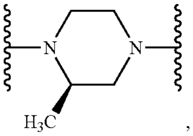
,
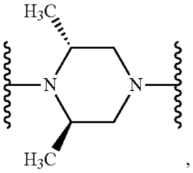
,
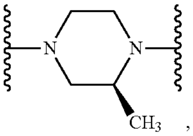
,
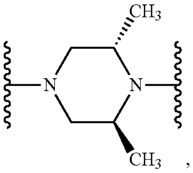
,
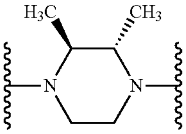
,
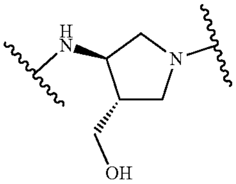
,
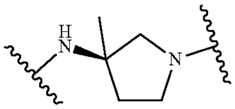
,
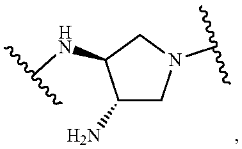
,
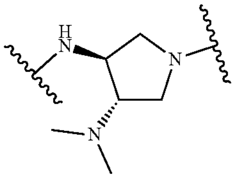
,
-continued
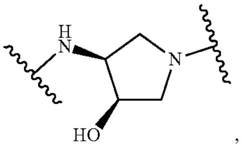
,
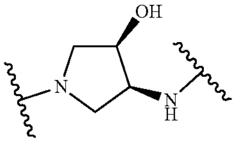
,
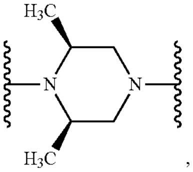
,
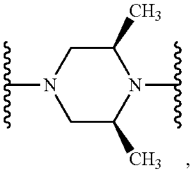
,
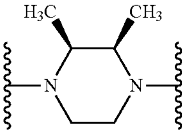
,
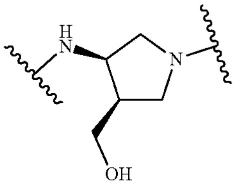
,
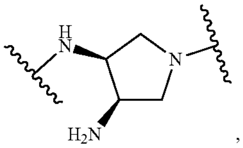
,
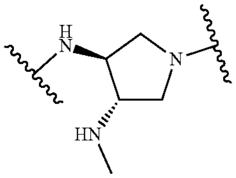
,
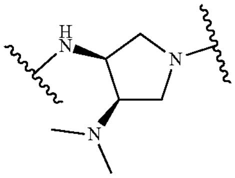
,
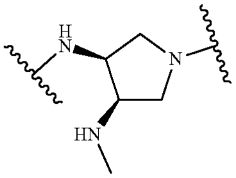
, and -continued
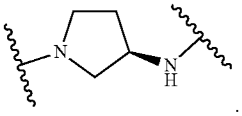
.
In a still further aspect, Z is a structure from:
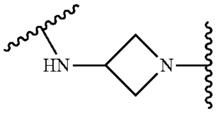
and
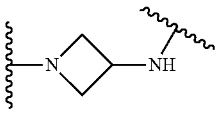
.
In a still further aspect, Z is a structure from:
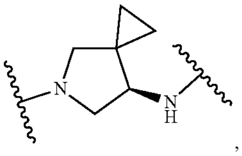
,
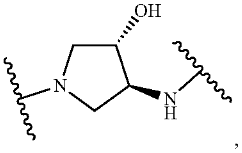
,
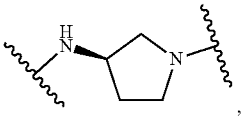
,
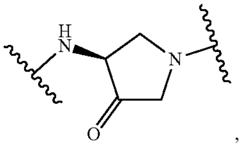
,
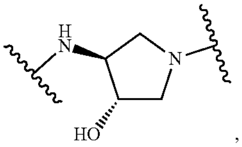
,
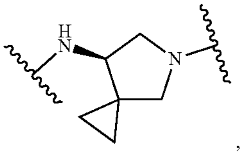
,
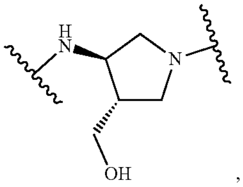
,
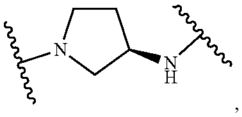
,
-continued
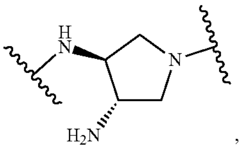
,
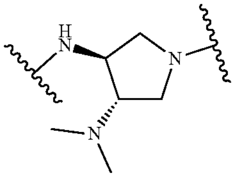
,
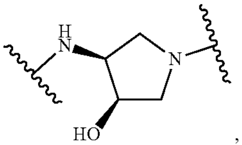
,
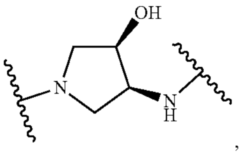
,
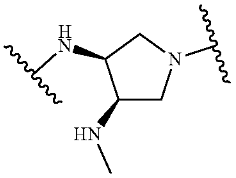
,
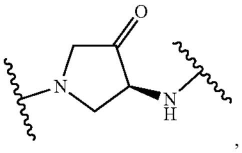
,
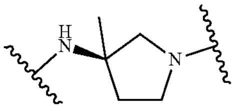
,
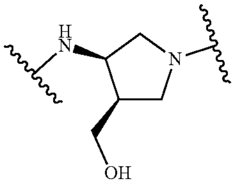
,
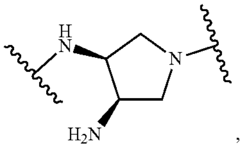
,
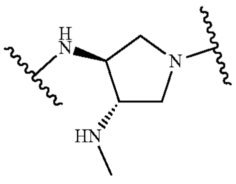
, and -continued
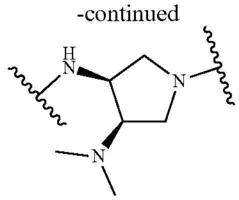
.
In an even further aspect, Z is a structure selected from:
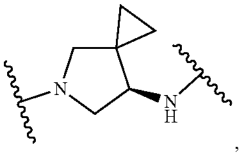
,
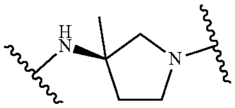
,
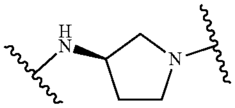
,
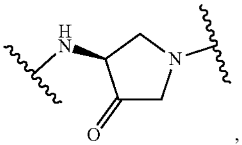
,
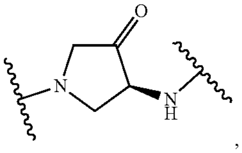
,
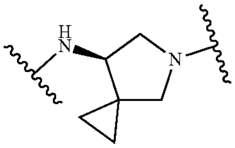
, and
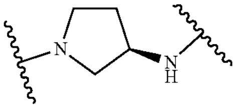
.
In a still further aspect, Z is a structure selected from:
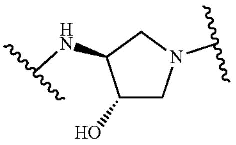
,
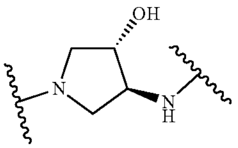
,
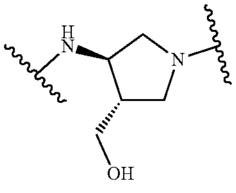
,
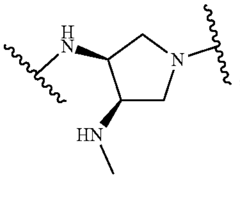
,
-continued
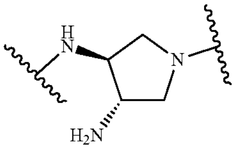
,
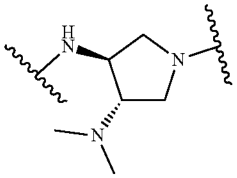
,
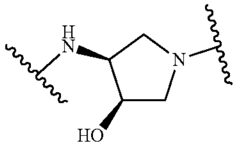
,
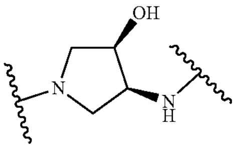
,
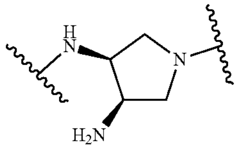
,
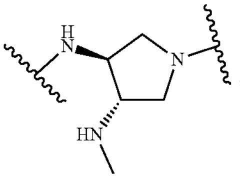
,
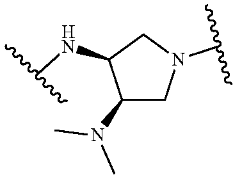
, and
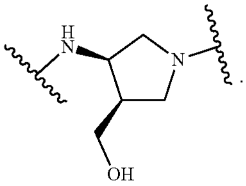
.
In yet a further aspect, Z is a structure selected from:
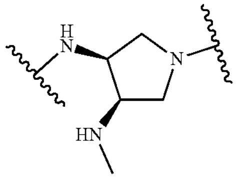
,
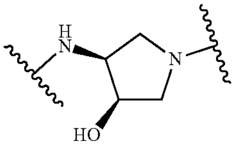
,
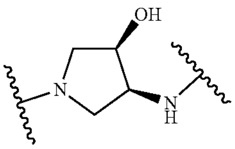
,
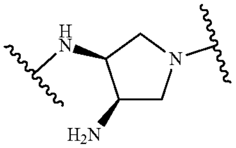
,
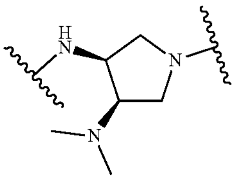
, and
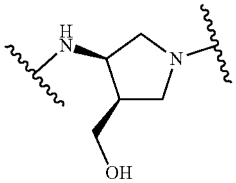
.
In an even further aspect, Z is a structure selected from:
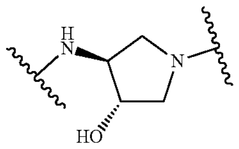
,
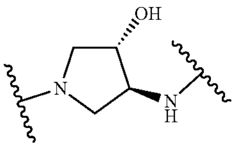
, -continued

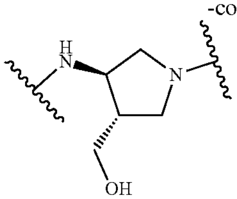,

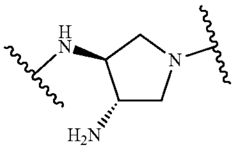,

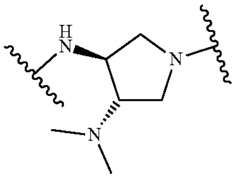, and

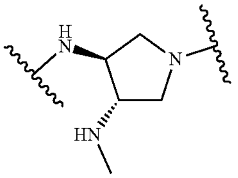.

In a still further aspect, Z is a structure selected from:

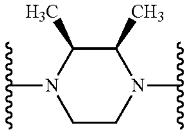,

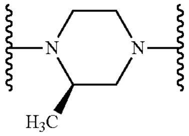,

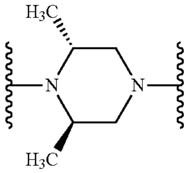,

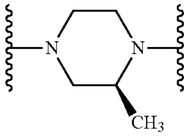,

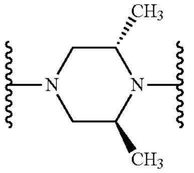,

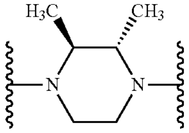,

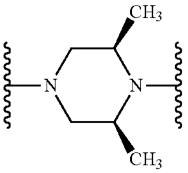, and

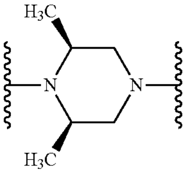.

In yet a further aspect, Z is a structure selected from:

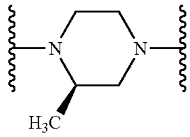 and

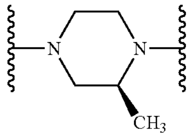.

In an even further aspect, Z is a structure selected from:

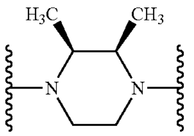,

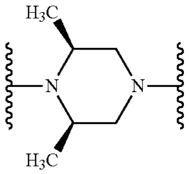,

-continued

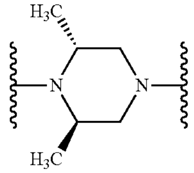,

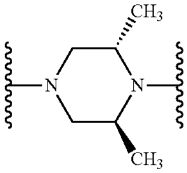,

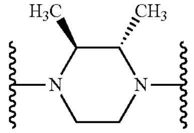, and

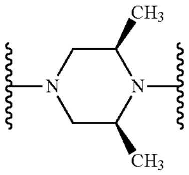.

In a still further aspect, Z is a structure selected from:

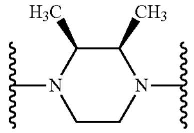,

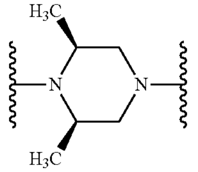, and

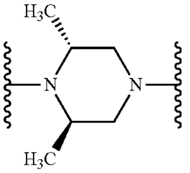,

In yet a further aspect, Z is a structure selected from:

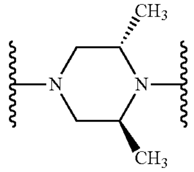,

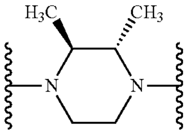, and

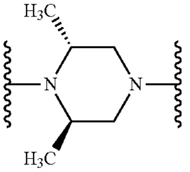.

In a further aspect, Z is a structure:

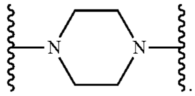 [SMILES: *N1CCN(*)CC1].

g. $R^1$ Groups

In one aspect, $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^1$, and $Cy^1$. In a further aspect, $R^1$ is selected from —$NH_2$, methyl, ethyl, n-propyl, isopropyl, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_3)CH_2CH_2CH_3$, —$N(CH_3)CH(CH_3)_2$, —$NR^{10}C(O)R^{11}$, —$NR^{10}SO_2R^{11}$, and $Cy^1$. In a still further aspect, $R^1$ is selected from —$NH_2$, methyl, ethyl, —$NHCH_3$, —$NHCH_2CH_3$, —$N(CH_3)_2$, —$N(CH_3)CH_2CH_3$, —$NR^{10}C(O)R^{11}$, —$NR^{10}SO_2R^{11}$, and $Cy^1$. In yet a further aspect, $R^1$ is selected from —$NH_2$, methyl, —$NHCH_3$, —$N(CH_3)_2$, —$NR^{10}C(O)R^{11}$, —$NR^{10}SO_2R^{11}$, and $Cy^1$.

In one aspect, $R^1$ is selected from C1-C4 alkyl, —$NR^{10}C(O)R^{11}$, —$NR^{10}SO_2R^{11}$, and $Cy^1$. In a further aspect, $R^1$ is selected from methyl, ethyl, n-propyl, isopropyl, —$NR^{10}C(O)R^{11}$, —$NR^{10}SO_2R^{11}$, and $Cy^1$. In a still further aspect, $R^1$ is selected from methyl, ethyl, —$NR^{10}C(O)R^{11}$, —$NR^{10}SO_2R^{11}$, and $Cy^1$. In yet a further aspect, $R^1$ is selected from methyl, —$NR^{10}C(O)R^{11}$, —$NR^{10}SO_2R^{11}$, and $Cy^1$.

In one aspect, $R^1$ is selected from C1-C4 alkyl, (C1-C4)(C1-C4) dialkylamino, —$NR^{10}C(O)R^{11}$, —$NR^{10}SO_2R^{11}$, and $Cy^1$. In a further aspect, $R^1$ is selected from methyl, ethyl, n-propyl, isopropyl, —$N(CH_3)_2$, —$N(CH_3)CH_2CH_3$, —$N(CH_3)CH_2CH_2CH_3$, —$N(CH_3)CH(CH_3)_2$, —$NR^{10}C(O)R^{11}$, —$NR^{10}SO_2R^{11}$, and $Cy^1$. In a still further aspect, $R^1$ is selected from methyl, ethyl, —$N(CH_3)_2$, —$N(CH_3)CH_2CH_3$, —$NR^{10}C(O)R^{11}$, —$NR^{10}SO_2R^{11}$, and $Cy^1$. In yet a further aspect, $R^1$ is selected from methyl, —$N(CH_3)_2$, —$NR^{10}C(O)R^{11}$, —$NR^{10}SO_2R^{11}$, and $Cy^1$.

In a further aspect, $R^1$ is selected from —$NH_2$, (C1-C4) alkylamino, (C1-C4)(C1-C4) dialkylamino, —$NR^{10}C(O)R^{11}$, —$NR^{10}SO_2R^{11}$. In a still further aspect, $R^1$ is selected from —$NH_2$, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_3)CH_2CH_2CH_3$, —$N(CH_3)CH(CH_3)_2$, —$NR^{10}C(O)R^{11}$, —$NR^{10}SO_2R^{11}$, and $Cy^1$. In yet a further aspect, $R^1$ is selected from —$NH_2$, —$NHCH_3$, —$NHCH_2CH_3$, —$N(CH_3)_2$, —$N(CH_3)CH_2CH_3$, —$NR^{10}C(O)R^{11}$, —$NR^{10}SO_2R^{11}$, and $Cy^1$. In an even further aspect, $R^1$ is selected from —$NH_2$, —$NHCH_3$, —$N(CH_3)_2$, —$NR^{10}C(O)R^{11}$, —$NR^{10}SO_2R^{11}$, and $Cy^1$.

In a further aspect, $R^1$ is selected from —$NR^{10}C(O)R^{11}$ and —$NR^{10}SO_2R^{11}$. In a still further aspect, $R^1$ is —$NR^{10}C(O)R^{11}$. In yet a further aspect, $R^1$ is —$NR^{10}SO_2R^{11}$.

In a further aspect, $R^1$ is selected from (C1-C4) alkylamino and (C1-C4)(C1-C4) dialkylamino. In a still further aspect, $R^1$ is selected from —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_3)CH_2CH_2CH_3$, and —$N(CH_3)CH(CH_3)_2$. In yet a further aspect, $R^1$ is selected from —$NHCH_3$, —$NHCH_2CH_3$, —$N(CH_3)_2$, and —$N(CH_3)CH_2CH_3$. In an even further aspect, $R^1$ is selected from —$NHCH_3$ and —$N(CH_3)_2$. In a still further aspect, $R^1$ is —$NHCH_3$. In yet a further aspect, $R^1$ is —$N(CH_3)_2$.

In a further aspect, $R^1$ is C1-C4 alkyl. In a still further aspect, $R^1$ is selected from methyl, ethyl, n-propyl, isopropyl. In yet a further aspect, $R^1$ is selected from methyl and ethyl. In an even further aspect, $R^1$ is ethyl. In a still further aspect, $R^1$ is methyl.

In a further aspect, $R^1$ is selected from n-propyl and isopropyl. In a still further aspect, $R^1$ is n-propyl. In yet a further aspect, $R^1$ is isopropyl.

In a further aspect, $R^1$ is selected from —$NH_2$ and $Cy^1$. In a still further aspect, $R^1$ is —$NH_2$. In yet a further aspect, $R^1$ is $Cy^1$.

h. $R^{10}$ Groups

In one aspect, $R^{10}$, when present, is selected from hydrogen and C1-C4 alkyl. In a further aspect, $R^{10}$, when present, is hydrogen.

In a further aspect, $R^{10}$, when present, is selected from hydrogen, methyl, ethyl, n-propyl, and isopropyl. In a still further aspect, $R^{10}$, when present, is selected from hydrogen, methyl, and ethyl. In yet a further aspect, $R^{10}$, when present, is selected from hydrogen and ethyl. In an even further aspect, $R^{10}$, when present, is selected from hydrogen and methyl.

In a further aspect, $R^{10}$, when present, is C1-C4 alkyl. In a still further aspect, $R^{10}$, when present, is selected from methyl, ethyl, n-propyl, and isopropyl. In yet a further aspect, $R^{10}$, when present, is selected from methyl and ethyl. In an even further aspect, $R^{10}$, when present, is ethyl. In a still further aspect, $R^{10}$, when present, is methyl.

i. $R^{11}$ Groups

In one aspect, $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$. In a further aspect, $R^{11}$, when present, is selected from hydrogen, methyl, ethyl, n-propyl, isopropyl, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$CH_2OH$, —$CH_2CH_2OH$, —$CH_2CH_2CH_2OH$, —$CH(CH_3)CH_2OH$, —$CH_2OC(O)CH_3$, —$CH_2OC(O)CH_2CH_3$, —$CH_2CH_2OC(O)CH_3$, —$CH_2OC(O)CH_2CH_2CH_3$, —$CH_2CH_2CH_2OC(O)CH_3$, and $Cy^2$. In a still further aspect, $R^{11}$, when present, is selected from hydrogen, methyl, ethyl, —$CF_3$, —$CHF_2$, —$CH_2F$, —$CH_2CH_2F$, —$CCl_3$, —$CHCl_2$, —$CH_2Cl$, —$CH_2CH_2Cl$, —$CH_2OH$, —$CH_2CH_2OH$, —$CH_2OC(O)CH_3$, —$CH_2OC(O)CH_2CH_3$, —$CH_2CH_2OC(O)CH_3$, and $Cy^2$. In yet a further aspect, $R^{11}$, when present, is selected from hydrogen, methyl, —$CF_3$, —$CHF_2$, —$CH_2F$, —$CCl_3$, —$CHCl_2$, —$CH_2Cl$, —$CH_2OH$, —$CH_2OC(O)CH_3$, and $Cy^2$.

In various aspects, $R^{11}$, when present, is selected from hydrogen and $Cy^2$. In a further aspect, $R^{11}$, when present, is $Cy^2$. In a still further aspect, $R^{11}$, when present, is hydrogen.

In various aspects, $R^1$, when present, is selected from C1-C4 alkyl and C1-C4 haloalkyl. In a further aspect, $R^{11}$, when present, is selected from methyl, ethyl, n-propyl, isopropyl, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{11}$, when present, is selected from methyl, ethyl, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{11}$, when present, is selected from methyl, —$CF_3$, —$CHF_2$, —$CH_2F$, —$CCl_3$, —$CHCl_2$, and —$CH_2Cl$.

In various aspects, $R^{11}$, when present, is C1-C4 alkyl. In a further aspect, $R^{11}$, when present, is selected from methyl, ethyl, n-propyl, and isopropyl. In a still further aspect, $R^{11}$, when present, is selected from methyl and ethyl. In yet a further aspect, $R^{11}$, when present, is ethyl. In an even further aspect, $R^{11}$, when present, is methyl.

In various aspects, $R^{11}$, when present, is selected C1-C4 haloalkyl. In a further aspect, $R^{11}$, when present, is selected from —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{11}$, when present, is selected from —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{11}$, when present, is selected from —$CF_3$, —$CHF_2$, —$CH_2F$, —$CCl_3$, —$CHCl_2$, and —$CH_2Cl$.

In various aspects, $R^{11}$, when present, is selected from C1-C4 hydroxyalkyl and —(C1-C4 alkyl)-OC(O)—(C1-C4 alkyl). In a further aspect, $R^{11}$, when present, is selected from —$CH_2OH$, —$CH_2CH_2OH$, —$CH_2CH_2CH_2OH$, —CH (CH$_3$)CH$_2$OH, —CH$_2$OC(O)CH$_3$, —CH$_2$OC(O)CH$_2$CH$_3$, —CH$_2$CH$_2$OC(O)CH$_3$, —CH$_2$OC(O)CH$_2$CH$_2$CH$_3$, and —CH$_2$CH$_2$CH$_2$OC(O)CH$_3$. In a still further aspect, $R^{11}$, when present, is selected from —CH$_2$OH, —CH$_2$CH$_2$OH, —CH$_2$OC(O)CH$_3$, —CH$_2$OC(O)CH$_2$CH$_3$, and —CH$_2$CH$_2$OC(O)CH$_3$. In yet a further aspect, $R^{11}$, when present, is selected from —CH$_2$OH and —CH$_2$OC(O)CH$_3$.

In various aspects, $R^{11}$, when present, is C1-C4 hydroxyalkyl. In a further aspect, $R^{11}$, when present, is selected from —CH$_2$OH, —CH$_2$CH$_2$OH, —CH$_2$CH$_2$CH$_2$OH, and —CH(CH$_3$)CH$_2$OH. In a still further aspect, $R^D$, when present, is selected from —CH$_2$OH and —CH$_2$CH$_2$OH. In yet a further aspect, $R^{11}$, when present, is —CH$_2$OH.

In various aspects, $R^{11}$, when present, is —(C1-C4 alkyl)-OC(O)—(C1-C4 alkyl). In a further aspect, $R^{11}$, when present, is selected from —CH$_2$OC(O)CH$_3$, —CH$_2$OC(O)CH$_2$CH$_3$, —CH$_2$CH$_2$OC(O)CH$_3$, —CH$_2$OC(O)CH$_2$CH$_2$CH$_3$, and —CH$_2$CH$_2$CH$_2$OC(O)CH$_3$. In a still further aspect, $R^{11}$, when present, is selected from —CH$_2$OC(O)CH$_3$, —CH$_2$OC(O)CH$_2$CH$_3$, and —CH$_2$CH$_2$OC(O)CH$_3$. In yet a further aspect, $R^{11}$, when present, is —CH$_2$OC(O)CH$_3$.

j. $R^{12}$ Groups

In one aspect, $R^{12}$, when present, is selected from halogen, —CN, —NO$_2$, C1-C4 polyhaloalkyl, and —SO$_2$R$^{20}$. In a further aspect, $R^{12}$, when present, is selected from —F, —Cl, —Br, —CN, —NO$_2$, —CF$_3$, —CHF$_2$, —CH$_2$CF$_3$, —CH$_2$CH$_2$CF$_3$, —CH(CH$_3$)CF$_3$, —CCl$_3$, —CHCl$_2$, —CH$_2$CCl$_3$, —CH$_2$CH$_2$CCl$_3$, —CH(CH$_3$)CCl$_3$, and —SO$_2$R$^{20}$. In a still further aspect, $R^{12}$, when present, is selected from —F, —Cl, —Br, —CN, —NO$_2$, —CF$_3$, —CHF$_2$, —CH$_2$CF$_3$, —CCl$_3$, —CHCl$_2$, —CH$_2$CCl$_3$, and —SO$_2$R$^{20}$. In yet a further aspect, $R^{12}$, when present, is selected from —F, —Cl, —Br, —CN, —NO$_2$, —CF$_3$, —CHF$_2$, —CCl$_3$, —CHCl$_2$, and —SO$_2$R$^{20}$.

In various aspects, $R^{12}$, when present, is selected from —CN, —NO$_2$, and —SO$_2$R$^{20}$. In a further aspect, $R^{12}$, when present, is selected from —CN and —NO$_2$. In a still further aspect, $R^{12}$, when present, is —CN. In yet a further aspect, $R^{12}$, when present, is —NO$_2$. In an even further aspect, $R^{12}$, when present, is —SO$_2$R$^{20}$.

In various aspects, $R^{12}$, when present, is selected from halogen and C1-C4 polyhaloalkyl. In a further aspect, $R^{12}$, when present, is selected from —F, —Cl, —Br, —CF$_3$, —CHF$_2$, —CH$_2$CF$_3$, —CH$_2$CH$_2$CF$_3$, —CH(CH$_3$)CF$_3$, —CCl$_3$, —CHCl$_2$, —CH$_2$CCl$_3$, —CH$_2$CH$_2$CCl$_3$, and —CH(CH$_3$)CCl$_3$. In a still further aspect, $R^{12}$, when present, is selected from —F, —Cl, —Br, —CF$_3$, —CHF$_2$, —CH$_2$CF$_3$, —CCl$_3$, —CHCl$_2$, and —CH$_2$CCl$_3$. In yet a further aspect, $R^{12}$, when present, is selected from —F, —Cl, —Br, —CF$_3$, —CHF$_2$, —CCl$_3$, and —CHCl$_2$.

In various aspects, $R^{12}$, when present, is halogen. In a further aspect, $R^{12}$, when present, is selected from —F, —Cl, and —Br. In a still further aspect, $R^{12}$, when present, is selected from —F and —Cl. In yet a further aspect, $R^{12}$, when present, is —F. In an even further aspect, $R^{12}$, when present, is —F. In a still further aspect, $R^{12}$, when present, is —Cl. In yet a further aspect, $R^{12}$, when present, is —Br. In an even further aspect, $R^{12}$, when present, is —I.

In various aspects, $R^{12}$, when present, is C1-C4 polyhaloalkyl. In a further aspect, $R^{12}$, when present, is selected from —CF$_3$, —CHF$_2$, —CH$_2$CF$_3$, —CH$_2$CH$_2$CF$_3$, —CH(CH$_3$)CF$_3$, —CCl$_3$, —CHCl$_2$, —CH$_2$CCl$_3$, —CH$_2$CH$_2$CCl$_3$, and —CH(CH$_3$)CCl$_3$. In a still further aspect, $R^{12}$, when present, is selected from —CF$_3$, —CHF$_2$, —CH$_2$CF$_3$, —CCl$_3$, —CHCl$_2$, and —CH$_2$CCl$_3$. In yet a further aspect, $R^{12}$, when present, is selected from —CF$_3$, —CHF$_2$, —CCl$_3$, and —CHCl$_2$. In an even further aspect, $R^{12}$, when present, is —CF$_3$.

In a further aspect, $R^{12}$, when present, is selected from —Cl and —CN.

k. $R^{13A}$ and $R^{13B}$ Groups

In one aspect, each of $R^{13a}$ and $R^{13b}$, when present, is independently selected from hydrogen, halogen, —CN, —NO$_2$, C1-C4 haloalkyl, and C1-C4 haloalkoxy. In a further aspect, each of $R^{13a}$ and $R^{13b}$, when present, is independently selected from hydrogen, fluoro, chloro, bromo, —CN, —NO$_2$, —CF$_3$, —CHF$_2$, —CH$_2$F, —CH$_2$CH$_2$F, —CH$_2$CH$_2$CH$_2$F, —CH(CH$_3$)CH$_2$F, —CCl$_3$, —CHCl$_2$, —CH$_2$Cl, —CH$_2$CH$_2$Cl, —CH$_2$CH$_2$CH$_2$Cl, —CH(CH$_3$)CH$_2$Cl, —OCF$_3$, —OCHF$_2$, —OCH$_2$F, —OCH$_2$CH$_2$F, —OCH$_2$CH$_2$CH$_2$F, —OCH(CH$_3$)CH$_2$F, —OCCl$_3$, —OCHCl$_2$, —OCH$_2$Cl, —OCH$_2$CH$_2$Cl, —OCH$_2$CH$_2$CH$_2$Cl, and —OCH(CH$_3$)CH$_2$Cl. In a still further aspect, each of $R^{13a}$ and $R^{13b}$, when present, is independently selected from hydrogen, fluoro, chloro, bromo, —CN, —NO$_2$, —CF$_3$, —CHF$_2$, —CH$_2$F, —CH$_2$CH$_2$F, —CCl$_3$, —CHCl$_2$, —CH$_2$Cl, —CH$_2$CH$_2$Cl, —OCF$_3$, —OCHF$_2$, —OCH$_2$F, —OCH$_2$CH$_2$F, —OCCl$_3$, —OCHCl$_2$, —OCH$_2$Cl, and —OCH$_2$CH$_2$Cl. In yet a further aspect, each of $R^{13a}$ and $R^{13b}$, when present, is independently selected from hydrogen, fluoro, chloro, bromo, —CN, —NO$_2$, —CF$_3$, —CHF$_2$, —CH$_2$F, —CCl$_3$, —CHCl$_2$, —CH$_2$Cl, —OCF$_3$, —OCHF$_2$, —OCH$_2$F, —OCCl$_3$, —OCHCl$_2$, and —OCH$_2$Cl.

In various aspects, each of $R^{13a}$ and $R^{13b}$, when present, is hydrogen.

In various aspects, each of $R^{13a}$ and $R^{13b}$, when present, is independently selected from hydrogen, —CN, —NO$_2$, and C1-C4 haloalkoxy. In a further aspect, each of $R^{13a}$ and $R^{13b}$, when present, is independently selected from hydrogen, —CN, —NO$_2$, —OCF$_3$, —OCHF$_2$, —OCH$_2$F, —OCH$_2$CH$_2$F, —OCH$_2$CH$_2$CH$_2$F, —OCH(CH$_3$)CH$_2$F, —OCCl$_3$, —OCHCl$_2$, —OCH$_2$Cl, —OCH$_2$CH$_2$Cl, —OCH$_2$CH$_2$CH$_2$Cl, and —OCH(CH$_3$)CH$_2$Cl. In a still further aspect, each of $R^{13a}$ and $R^{13b}$, when present, is independently selected from hydrogen, —CN, —NO$_2$, —OCF$_3$, —OCHF$_2$, —OCH$_2$F, —OCH$_2$CH$_2$F, —OCCl$_3$, —OCHCl$_2$, —OCH$_2$Cl, and —OCH$_2$CH$_2$Cl. In yet a further aspect, each of $R^{13a}$ and $R^{13b}$, when present, is independently selected from hydrogen, —CN, —NO$_2$, —OCF$_3$, —OCHF$_2$, —OCH$_2$F, —OCCl$_3$, —OCHCl$_2$, and —OCH$_2$Cl.

In various aspects, each of $R^{13a}$ and $R^{13b}$, when present, is independently selected from hydrogen and C1-C4 haloalkoxy. In a further aspect, each of $R^{13a}$ and $R^{13b}$, when present, is independently selected from hydrogen, —OCF$_3$, —OCHF$_2$, —OCH$_2$F, —OCH$_2$CH$_2$F, —OCH$_2$CH$_2$CH$_2$F, —OCH(CH$_3$)CH$_2$F, —OCCl$_3$, —OCHCl$_2$, —OCH$_2$Cl, —OCH$_2$CH$_2$Cl, —OCH$_2$CH$_2$CH$_2$Cl, and —OCH(CH$_3$)CH$_2$Cl. In a still further aspect, each of $R^{13a}$ and $R^{13b}$, when present, is independently selected from hydrogen, —OCF$_3$, —OCHF$_2$, —OCH$_2$F, —OCH$_2$CH$_2$F, —OCCl$_3$, —OCHCl$_2$, —OCH$_2$Cl, and —OCH$_2$CH$_2$Cl. In yet a further aspect, each of $R^{13a}$ and $R^{13b}$, when present, is independently selected from hydrogen, —OCF$_3$, —OCHF$_2$, —OCH$_2$F, —OCCl$_3$, —OCHCl$_2$, and —OCH$_2$Cl.

In various aspects, each of $R^{13a}$ and $R^{13b}$, when present, is independently selected from hydrogen, halogen, C1-C4 haloalkyl, and C1-C4 haloalkoxy. In a further aspect, each of $R^{13a}$ and $R^{13b}$, when present, is independently selected from hydrogen, fluoro, chloro, bromo, —CF$_3$, —CHF$_2$, —CH$_2$F, —CH$_2$CH$_2$F, —CH$_2$CH$_2$CH$_2$F, —CH(CH$_3$)CH$_2$F, —CCl$_3$, —CHCl$_2$, —CH$_2$Cl, —CH$_2$CH$_2$Cl, —CH$_2$CH$_2$CH$_2$Cl, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{13a}$ and $R^{13b}$, when present, is independently selected from hydrogen, fluoro, chloro, bromo, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{13a}$ and $R^{13b}$, when present, is independently selected from hydrogen, fluoro, chloro, bromo, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, each of $R^{13a}$ and $R^{13b}$, when present, is independently selected from hydrogen and C1-C4 haloalkyl. In a further aspect, each of $R^{13a}$ and $R^{13b}$, when present, is independently selected from hydrogen, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, each of $R^{13a}$ and $R^{13b}$, when present, is independently selected from hydrogen, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, each of $R^{13a}$ and $R^{13b}$, when present, is independently selected from hydrogen, —$CF_3$, —$CHF_2$, —$CH_2F$, —$CCl_3$, —$CHCl_2$, and —$CH_2Cl$.

In various aspects, each of $R^{13a}$ and $R^{13b}$, when present, is independently selected from hydrogen and C1-C4 haloalkoxy. In a further aspect, each of $R^{13a}$ and $R^{13b}$, when present, is independently selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{13a}$ and $R^{13b}$, when present, is independently selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{13a}$ and $R^{13b}$, when present, is independently selected from hydrogen, —$OCF_3$, —$OCHF_2$, —$OCH_2F$, —$OCCl_3$, —$OCHCl_2$, and —$OCH_2Cl$.

In various aspects, each of $R^{13a}$ and $R^{13b}$, when present, is independently selected from hydrogen and halogen. In a further aspect, each of $R^{13a}$ and $R^{13b}$, when present, is independently selected from hydrogen, fluoro, chloro, and bromo. In a still further aspect, each of $R^{13a}$ and $R^{13b}$, when present, is independently selected from hydrogen, fluoro, and chloro. In yet a further aspect, each of $R^{13a}$ and $R^{13b}$, when present, is independently selected from hydrogen and fluoro. In an even further aspect, each of $R^{13a}$ and $R^{13b}$, when present, is independently selected from hydrogen and chloro.

a. $R^{14a}$, $R^{14b}$, and $R^{14c}$ Groups

In one aspect, each of $R^{14a}$, $R^{14b}$, and $R^{14c}$, when present, is independently selected from hydrogen, halogen, —CN, —$NO_2$, C1-C4 haloalkyl, and C1-C4 haloalkoxy. In a further aspect, each of $R^{14a}$, $R^{14b}$, and $R^{14c}$, when present, is independently selected from hydrogen, fluoro, chloro, bromo, —CN, —$NO_2$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{14a}$, $R^{14b}$, and $R^{14c}$, when present, is independently selected from hydrogen, fluoro, chloro, bromo, —CN, —$NO_2$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{14a}$, $R^{14b}$, and $R^{14c}$, when present, is independently selected from hydrogen, fluoro, chloro, bromo, —CN, —$NO_2$, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, each of $R^{14a}$, $R^{14b}$, and $R^{14c}$, when present, is hydrogen.

In various aspects, each of $R^{14a}$, $R^{14b}$, and $R^{14c}$, when present, is independently selected from hydrogen, —CN, —$NO_2$, and C1-C4 haloalkoxy. In a further aspect, each of $R^{14a}$, $R^{14b}$, and $R^{14c}$, when present, is independently selected from hydrogen, —CN, —$NO_2$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{14a}$, $R^{14b}$, and $R^{14c}$, when present, is independently selected from hydrogen, —CN, —$NO_2$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{14a}$, $R^{14b}$, and $R^{14c}$, when present, is independently selected from hydrogen, —CN, —$NO_2$, —$OCF_3$, —$OCHF_2$, —$OCH_2F$, —$OCCl_3$, —$OCHCl_2$, and —$OCH_2Cl$.

In various aspects, each of $R^{14a}$, $R^{14b}$, and $R^{14c}$, when present, is independently selected from hydrogen and C1-C4 haloalkoxy. In a further aspect, each of $R^{14a}$, $R^{14b}$, and $R^{14c}$, when present, is independently selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{14a}$, $R^{14b}$, and $R^{14c}$, when present, is independently selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{14a}$, $R^{14b}$, and $R^{14c}$, when present, is independently selected from hydrogen, —$OCF_3$, —$OCHF_2$, —$OCH_2F$, —$OCCl_3$, —$OCHCl_2$, and —$OCH_2Cl$.

In various aspects, each of $R^{14a}$, $R^{14b}$, and $R^{14c}$, when present, is independently selected from hydrogen, halogen, C1-C4 haloalkyl, and C1-C4 haloalkoxy. In a further aspect, each of $R^{14a}$, $R^{14b}$, and $R^{14c}$, when present, is independently selected from hydrogen, fluoro, chloro, bromo, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{14a}$, $R^{14b}$, and $R^{14c}$, when present, is independently selected from hydrogen, fluoro, chloro, bromo, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{14a}$, $R^{14b}$, and $R^{14c}$, when present, is independently selected from hydrogen, fluoro, chloro, bromo, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, each of $R^{14a}$, $R^{14b}$, and $R^{14c}$, when present, is independently selected from hydrogen and C1-C4 haloalkyl. In a further aspect, each of $R^{14a}$, $R^{14b}$, and $R^{14c}$, when present, is independently selected from hydrogen, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, and $—CH(CH_3)CH_2Cl$. In a still further aspect, each of $R^{14a}$, $R^{14b}$, and $R^{14c}$, when present, is independently selected from hydrogen, $—CF_3$, $—CHF_2$, $—CH_2F$, $—CH_2CH_2F$, $—CCl_3$, $—CHCl_2$, $—CH_2Cl$, and $—CH_2CH_2Cl$. In yet a further aspect, each of $R^{14a}$, $R^{14b}$, and $R^{14c}$, when present, is independently selected from hydrogen, $—CF_3$, $—CHF_2$, $—CH_2F$, $—CCl_3$, $—CHCl_2$, and $—CH_2Cl$.

In various aspects, each of $R^{14a}$, $R^{14b}$, and $R^{14c}$, when present, is independently selected from hydrogen and C1-C4 haloalkoxy. In a further aspect, each of $R^{14a}$, $R^{14b}$, and $R^{14c}$, when present, is independently selected from hydrogen, $—OCF_3$, $—OCHF_2$, $—OCH_2F$, $—OCH_2CH_2F$, $—OCH_2CH_2CH_2F$, $—OCH(CH_3)CH_2F$, $—OCCl_3$, $—OCHCl_2$, $—OCH_2Cl$, $—OCH_2CH_2Cl$, $—OCH_2CH_2CH_2Cl$, and $—OCH(CH_3)CH_2Cl$. In a still further aspect, each of $R^{14a}$, $R^{14b}$, and $R^{14c}$, when present, is independently selected from hydrogen, $—OCF_3$, $—OCHF_2$, $—OCH_2F$, $—OCH_2CH_2F$, $—OCCl_3$, $—OCHCl_2$, $—OCH_2Cl$, and $—OCH_2CH_2Cl$. In yet a further aspect, each of $R^{14a}$, $R^{14b}$, and $R^{14c}$, when present, is independently selected from hydrogen, $—OCF_3$, $—OCHF_2$, $—OCH_2F$, $—OCCl_3$, $—OCHCl_2$, and $—OCH_2Cl$.

In various aspects, each of $R^{14a}$, $R^{14b}$, and $R^{14c}$, when present, is independently selected from hydrogen and halogen. In a further aspect, each of $R^{14a}$, $R^{14b}$, and $R^{14c}$, when present, is independently selected from hydrogen, fluoro, chloro, and bromo. In a still further aspect, each of $R^{14a}$, $R^{14b}$, and $R^{14c}$, when present, is independently selected from hydrogen, fluoro, and chloro. In yet a further aspect, each of $R^{14a}$, $R^{14b}$, and $R^{14c}$, when present, is independently selected from hydrogen and fluoro. In an even further aspect, each of $R^{14a}$, $R^{14b}$, and $R^{14c}$, when present, is independently selected from hydrogen and chloro.

b. $R^{15a}$, $R^{15b}$, and $R^{15c}$ Groups

In one aspect, each of $R^{15a}$, $R^{15b}$, and $R^{15c}$, when present, is independently selected from hydrogen, halogen, —CN, $—NO_2$, C1-C4 haloalkyl, and C1-C4 haloalkoxy. In a further aspect, each of $R^{15a}$, $R^{15b}$, and $R^{15c}$, when present, is independently selected from hydrogen, fluoro, chloro, bromo, —CN, $—NO_2$, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, $—CH(CH_3)CH_2Cl$, $—OCF_3$, $—OCHF_2$, $—OCH_2F$, $—OCH_2CH_2F$, $—OCH_2CH_2CH_2F$, $—OCH(CH_3)CH_2F$, $—OCCl_3$, $—OCHCl_2$, $—OCH_2Cl$, $—OCH_2CH_2Cl$, $—OCH_2CH_2CH_2Cl$, and $—OCH(CH_3)CH_2Cl$. In a still further aspect, each of $R^{15a}$, $R^{15b}$, and $R^{15c}$, when present, is independently selected from hydrogen, fluoro, chloro, bromo, —CN, $—NO_2$, $—CF_3$, $—CHF_2$, $—CH_2F$, $—CH_2CH_2F$, $—CCl_3$, $—CHCl_2$, $—CH_2Cl$, $—CH_2CH_2Cl$, $—OCF_3$, $—OCHF_2$, $—OCH_2F$, $—OCH_2CH_2F$, $—OCCl_3$, $—OCHCl_2$, $—OCH_2Cl$, and $—OCH_2CH_2Cl$. In yet a further aspect, each of $R^{15a}$, $R^{15b}$, and $R^{15c}$, when present, is independently selected from hydrogen, fluoro, chloro, bromo, —CN, $—NO_2$, $—CF_3$, $—CHF_2$, $—CH_2F$, $—CCl_3$, $—CHCl_2$, $—CH_2Cl$, $—OCF_3$, $—OCHF_2$, $—OCH_2F$, $—OCCl_3$, $—OCHCl_2$, and $—OCH_2Cl$.

In various aspects, each of $R^{15a}$, $R^{15b}$, and $R^{15c}$, when present, is hydrogen.

In various aspects, each of $R^{15a}$, $R^{15b}$, and $R^{15c}$, when present, is independently selected from hydrogen, —CN, $—NO_2$, and C1-C4 haloalkoxy. In a further aspect, each of $R^{15a}$, $R^{15b}$, and $R^{15c}$, when present, is independently selected from hydrogen, —CN, $—NO_2$, $—OCF_3$, $—OCHF_2$, $—OCH_2F$, $—OCH_2CH_2F$, $—OCH_2CH_2CH_2F$, $—OCH(CH_3)CH_2F$, $—OCCl_3$, $—OCHCl_2$, $—OCH_2Cl$, $—OCH_2CH_2Cl$, $—OCH_2CH_2CH_2Cl$, and $—OCH(CH_3)CH_2Cl$. In a still further aspect, each of $R^{15a}$, $R^{15b}$, and $R^{15c}$, when present, is independently selected from hydrogen, —CN, $—NO_2$, $—OCF_3$, $—OCHF_2$, $—OCH_2F$, $—OCH_2CH_2F$, $—OCCl_3$, $—OCHCl_2$, $—OCH_2Cl$, and $—OCH_2CH_2Cl$. In yet a further aspect, each of $R^{15a}$, $R^{15b}$, and $R^{15c}$, when present, is independently selected from hydrogen, —CN, $—NO_2$, $—OCF_3$, $—OCHF_2$, $—OCH_2F$, $—OCCl_3$, $—OCHCl_2$, and $—OCH_2Cl$.

In various aspects, each of $R^{15a}$, $R^{15b}$, and $R^{15c}$, when present, is independently selected from hydrogen and C1-C4 haloalkoxy. In a further aspect, each of $R^{15a}$, $R^{15b}$, and $R^{15c}$, when present, is independently selected from hydrogen, $—OCF_3$, $—OCHF_2$, $—OCH_2F$, $—OCH_2CH_2F$, $—OCH_2CH_2CH_2F$, $—OCH(CH_3)CH_2F$, $—OCCl_3$, $—OCHCl_2$, $—OCH_2Cl$, $—OCH_2CH_2Cl$, $—OCH_2CH_2CH_2Cl$, and $—OCH(CH_3)CH_2Cl$. In a still further aspect, each of $R^{15a}$, $R^{15b}$, and $R^{15c}$, when present, is independently selected from hydrogen, $—OCF_3$, $—OCHF_2$, $—OCH_2F$, $—OCH_2CH_2F$, $—OCCl_3$, $—OCHCl_2$, $—OCH_2Cl$, and $—OCH_2CH_2Cl$. In yet a further aspect, each of $R^{15a}$, $R^{15b}$, and $R^{15c}$, when present, is independently selected from hydrogen, $—OCF_3$, $—OCHF_2$, $—OCH_2F$, $—OCCl_3$, $—OCHCl_2$, and $—OCH_2Cl$.

In various aspects, each of $R^{15a}$, $R^{15b}$, and $R^{15c}$, when present, is independently selected from hydrogen, halogen, C1-C4 haloalkyl, and C1-C4 haloalkoxy. In a further aspect, each of $R^{15a}$, $R^{15b}$, and $R^{15c}$, when present, is independently selected from hydrogen, fluoro, chloro, bromo, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, $—CH(CH_3)CH_2Cl$, $—OCF_3$, $—OCHF_2$, $—OCH_2F$, $—OCH_2CH_2F$, $—OCH_2CH_2CH_2F$, $—OCH(CH_3)CH_2F$, $—OCCl_3$, $—OCHCl_2$, $—OCH_2Cl$, $—OCH_2CH_2Cl$, $—OCH_2CH_2CH_2Cl$, and $—OCH(CH_3)CH_2Cl$. In a still further aspect, each of $R^{15a}$, $R^{15b}$, and $R^{15c}$, when present, is independently selected from hydrogen, fluoro, chloro, bromo, $—CF_3$, $—CHF_2$, $—CH_2F$, $—CH_2CH_2F$, $—CCl_3$, $—CHCl_2$, $—CH_2Cl$, $—CH_2CH_2Cl$, $—OCF_3$, $—OCHF_2$, $—OCH_2F$, $—OCH_2CH_2F$, $—OCCl_3$, $—OCHCl_2$, $—OCH_2Cl$, and $—OCH_2CH_2Cl$. In yet a further aspect, each of $R^{15a}$, $R^{15b}$, and $R^{15c}$, when present, is independently selected from hydrogen, fluoro, chloro, bromo, $—CF_3$, $—CHF_2$, $—CH_2F$, $—CCl_3$, $—CHCl_2$, $—CH_2Cl$, $—OCF_3$, $—OCHF_2$, $—OCH_2F$, $—OCCl_3$, $—OCHCl_2$, and $—OCH_2Cl$.

In various aspects, each of $R^{15a}$, $R^{15b}$, and $R^{15c}$, when present, is independently selected from hydrogen and C1-C4 haloalkyl. In a further aspect, each of $R^{15a}$, $R^{15b}$, and $R^{15c}$, when present, is independently selected from hydrogen, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, and $—CH(CH_3)CH_2Cl$. In a still further aspect, each of $R^{15a}$, $R^{15b}$, and $R^{15c}$, when present, is independently selected from hydrogen, $—CF_3$, $—CHF_2$, $—CH_2F$, $—CH_2CH_2F$, $—CCl_3$, $—CHCl_2$, $—CH_2Cl$, and $—CH_2CH_2Cl$. In yet a further aspect, each of $R^{15a}$, $R^{15b}$, and $R^{15c}$, when present, is independently selected from hydrogen, $—CF_3$, $—CHF_2$, $—CH_2F$, $—CCl_3$, $—CHCl_2$, and $—CH_2Cl$.

In various aspects, each of $R^{15a}$, $R^{15b}$, and $R^{15c}$, when present, is independently selected from hydrogen and C1-C4 haloalkoxy. In a further aspect, each of $R^{15a}$, $R^{15b}$, and $R^{15c}$, when present, is independently selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{15a}$, $R^{15b}$, and $R^{15c}$, when present, is independently selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{15a}$, $R^{15b}$, and $R^{15c}$, when present, is independently selected from hydrogen, —$OCF_3$, —$OCHF_2$, —$OCH_2F$, —$OCCl_3$, —$OCHCl_2$, and —$OCH_2Cl$.

In various aspects, each of $R^{15a}$, $R^{15b}$, and $R^{15c}$, when present, is independently selected from hydrogen and halogen. In a further aspect, each of $R^{15a}$, $R^{15b}$, and $R^{15c}$, when present, is independently selected from hydrogen, fluoro, chloro, and bromo. In a still further aspect, each of $R^{15a}$, $R^{15b}$, and $R^{15c}$, when present, is independently selected from hydrogen, fluoro, and chloro. In yet a further aspect, each of $R^{15a}$, $R^{15b}$, and $R^{15c}$, when present, is independently selected from hydrogen and fluoro. In an even further aspect, each of $R^{15a}$, $R^{15b}$, and $R^{15c}$, when present, is independently selected from hydrogen and chloro.

c. $R^{16}$ Groups

In one aspect, $R^{16}$, when present, is selected from hydrogen, halogen, —CN, —$NO_2$, C1-C4 alkyl, C1-C4 haloalkyl, and C1-C4 haloalkoxy. In a further aspect, $R^{16}$, when present, is selected from hydrogen, fluoro, chloro, bromo, —CN, —$NO_2$, methyl, ethyl, n-propyl, isopropyl, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{16}$, when present, is selected from hydrogen, fluoro, chloro, bromo, —CN, —$NO_2$, methyl, ethyl, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{16}$, when present, is selected from hydrogen, fluoro, chloro, bromo, —CN, —$NO_2$, methyl, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, $R^{16}$, when present, is hydrogen.

In one aspect, $R^{16}$, when present, is selected from hydrogen and C1-C4 alkyl. In a further aspect, $R^{16}$, when present, is selected from hydrogen, methyl, ethyl, n-propyl, and isopropyl. In a still further aspect, $R^{16}$, when present, is selected from hydrogen, methyl, and ethyl. In yet a further aspect, $R^{16}$, when present, is selected from hydrogen and methyl.

In various aspects, $R^{16}$, when present, is selected from hydrogen, —CN, —$NO_2$, and C1-C4 haloalkoxy. In a further aspect, $R^{16}$, when present, is selected from hydrogen, —CN, —$NO_2$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{16}$, when present, is selected from hydrogen, —CN, —$NO_2$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{16}$, when present, is selected from hydrogen, —CN, —$NO_2$, —$OCF_3$, —$OCHF_2$, —$OCH_2F$, —$OCCl_3$, —$OCHCl_2$, and —$OCH_2Cl$.

In various aspects, $R^{16}$, when present, is selected from hydrogen and C1-C4 haloalkoxy. In a further aspect, $R^{16}$, when present, is selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{16}$, when present, is selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{16}$, when present, is selected from hydrogen, —$OCF_3$, —$OCHF_2$, —$OCH_2F$, —$OCCl_3$, —$OCHCl_2$, and —$OCH_2Cl$.

In various aspects, $R^{16}$, when present, is selected from hydrogen, halogen, C1-C4 haloalkyl, and C1-C4 haloalkoxy. In a further aspect, $R^{16}$, when present, is selected from hydrogen, fluoro, chloro, bromo, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{16}$, when present, is selected from hydrogen, fluoro, chloro, bromo, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{16}$, when present, is selected from hydrogen, fluoro, chloro, bromo, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, $R^{16}$, when present, is selected from hydrogen and C1-C4 haloalkyl. In a further aspect, $R^{16}$, when present, is selected from hydrogen, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{16}$, when present, is selected from hydrogen, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{16}$, when present, is selected from hydrogen, —$CF_3$, —$CHF_2$, —$CH_2F$, —$CCl_3$, —$CHCl_2$, and —$CH_2Cl$.

In various aspects, $R^{16}$, when present, is selected from hydrogen and C1-C4 haloalkoxy. In a further aspect, $R^{16}$, when present, is selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{16}$, when present, is selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{16}$, when present, is selected from hydrogen, —$OCF_3$, —$OCHF_2$, —$OCH_2F$, —$OCCl_3$, —$OCHCl_2$, and —$OCH_2Cl$.

In various aspects, $R^{16}$, when present, is selected from hydrogen and halogen. In a further aspect, $R^{16}$, when present, is selected from hydrogen, fluoro, chloro, and bromo. In a still further aspect, $R^{16}$, when present, is selected from hydrogen, fluoro, and chloro. In yet a further aspect, $R^{16}$, when present, is selected from hydrogen and fluoro. In an even further aspect, $R^{16}$, when present, is selected from hydrogen and chloro.

d. $R^{17a}$, $R^{17b}$, and $R^{17c}$ Groups

In one aspect, each of $R^{17a}$, $R^{17b}$, and $R^{17c}$, when present, is independently selected from hydrogen, halogen, —CN, —$NO_2$, C1-C4 haloalkyl, and C1-C4 haloalkoxy. In a further aspect, each of $R^{17a}$, $R^{17b}$, and $R^{17c}$, when present, is independently selected from hydrogen, fluoro, chloro, bromo, —CN, —$NO_2$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{17a}$, $R^{17b}$, and $R^{17c}$, when present, is independently selected from hydrogen, fluoro, chloro, bromo, —CN, —$NO_2$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{17a}$, $R^{17b}$, and $R^{17c}$, when present, is independently selected from hydrogen, fluoro, chloro, bromo, —CN, —$NO_2$, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, each of $R^{17a}$, $R^{17b}$, and $R^{17c}$, when present, is hydrogen.

In various aspects, each of $R^{17a}$, $R^{17b}$, and $R^{17c}$, when present, is independently selected from hydrogen, —CN, —$NO_2$, and C1-C4 haloalkoxy. In a further aspect, each of $R^{17a}$, $R^{17b}$, and $R^{17c}$, when present, is independently selected from hydrogen, —CN, —$NO_2$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{17a}$, $R^{17b}$, and $R^{17c}$, when present, is independently selected from hydrogen, —CN, —$NO_2$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{17a}$, $R^{17b}$, and $R^{17c}$, when present, is independently selected from hydrogen, —CN, —$NO_2$, —$OCF_3$, —$OCHF_2$, —$OCH_2F$, —$OCCl_3$, —$OCHCl_2$, and —$OCH_2Cl$.

In various aspects, each of $R^{17a}$, $R^{17b}$, and $R^{17c}$, when present, is independently selected from hydrogen and C1-C4 haloalkoxy. In a further aspect, each of $R^{17a}$, $R^{17b}$, and $R^{17c}$, when present, is independently selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{17a}$, $R^{17b}$, and $R^{17c}$, when present, is independently selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{17a}$, $R^{17b}$, and $R^{17c}$, when present, is independently selected from hydrogen, —$OCF_3$, —$OCHF_2$, —$OCH_2F$, —$OCCl_3$, —$OCHCl_2$, and —$OCH_2Cl$.

In various aspects, each of $R^{17a}$, $R^{17b}$, and $R^{17c}$, when present, is independently selected from hydrogen, halogen, C1-C4 haloalkyl, and C1-C4 haloalkoxy. In a further aspect, each of $R^{17a}$, $R^{17b}$, and $R^{17c}$, when present, is independently selected from hydrogen, fluoro, chloro, bromo, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{17a}$, $R^{17b}$, and $R^{17c}$, when present, is independently selected from hydrogen, fluoro, chloro, bromo, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{17a}$, $R^{17b}$, and $R^{17c}$, when present, is independently selected from hydrogen, fluoro, chloro, bromo, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, each of $R^{17a}$, $R^{17b}$, and $R^{17c}$, when present, is independently selected from hydrogen and C1-C4 haloalkyl. In a further aspect, each of $R^{17a}$, $R^{17b}$, and $R^{17c}$, when present, is independently selected from hydrogen, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, each of $R^{17}$, $R^{17b}$, and $R^{17c}$, when present, is independently selected from hydrogen, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, each of $R^{17a}$, $R^{17b}$, and $R^{17c}$, when present, is independently selected from hydrogen, —$CF_3$, —$CHF_2$, —$CH_2F$, —$CCl_3$, —$CHCl_2$, and —$CH_2Cl$.

In various aspects, each of $R^{17}$, $R^{17b}$, and $R^{17c}$, when present, is independently selected from hydrogen and C1-C4 haloalkoxy. In a further aspect, each of $R^{17a}$, $R^{17b}$, and $R^{17c}$, when present, is independently selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, each of $R^{17a}$, $R^{17b}$, and $R^{17c}$, when present, is independently selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, each of $R^{17a}$, $R^{17b}$, and $R^{17c}$, when present, is independently selected from hydrogen, —$OCF_3$, —$OCHF_2$, —$OCH_2F$, —$OCCl_3$, —$OCHCl_2$, and —$OCH_2Cl$.

In various aspects, each of $R^{17a}$, $R^{17b}$, and $R^{17c}$, when present, is independently selected from hydrogen and halogen. In a further aspect, each of $R^{17a}$, $R^{17b}$, and $R^{17c}$, when present, is independently selected from hydrogen, fluoro, chloro, and bromo. In a still further aspect, each of $R^{17a}$, $R^{17b}$, and $R^{17c}$, when present, is independently selected from hydrogen, fluoro, and chloro. In yet a further aspect, each of $R^{17a}$, $R^{17b}$, and $R^{17c}$, when present, is independently selected from hydrogen and fluoro. In an even further aspect, each of $R^{17a}$, $R^{17b}$, and $R^{17c}$, when present, is independently selected from hydrogen and chloro.

e. $R^{20}$ Groups

In one aspect, $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$. In a further aspect, $R^{20}$, when present, is selected from hydrogen, methyl, ethyl, n-propyl, isopropyl, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$CH_2OH$, —$CH_2CH_2OH$, —$CH_2CH_2CH_2OH$, —$CH(CH_3)CH_2OH$, —$CH_2OC(O)CH_3$, —$CH_2OC(O)CH_2CH_3$, —$CH_2CH_2OC(O)CH_3$, —$CH_2OC(O)CH_2CH_2CH_3$, —$CH_2CH_2CH_2OC(O)CH_3$, and $Cy^3$. In a still further aspect, $R^{20}$, when present, is selected from hydrogen, methyl, ethyl, —$CF_3$, —$CHF_2$, —$CH_2F$, —$CH_2CH_2F$, —$CCl_3$, —$CHCl_2$, —$CH_2Cl$, —$CH_2CH_2Cl$, —$CH_2OH$, —$CH_2CH_2OH$, —$CH_2OC(O)CH_3$, —$CH_2OC(O)CH_2CH_3$, —$CH_2CH_2OC(O)CH_3$, and $Cy^3$. In yet a further aspect, $R^{20}$, when present, is selected from hydrogen, methyl, —$CF_3$, —$CHF_2$, —$CH_2F$, —$CCl_3$, —$CHCl_2$, —$CH_2Cl$, —$CH_2OH$, —$CH_2OC(O)CH_3$, and $Cy^3$.

In various aspects, $R^{20}$, when present, is selected from hydrogen and $Cy^3$. In a further aspect, $R^{20}$, when present, is $Cy^3$. In a still further aspect, $R^{20}$, when present, is hydrogen.

In various aspects, $R^{20}$, when present, is selected from C1-C4 alkyl and C1-C4 haloalkyl. In a further aspect, $R^{20}$, when present, is selected from methyl, ethyl, n-propyl, isopropyl, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{20}$, when present, is selected from methyl, ethyl, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{20}$, when present, is selected from methyl, —$CF_3$, —$CHF_2$, —$CH_2F$, —$CCl_3$, —$CHCl_2$, and —$CH_2Cl$.

In various aspects, $R^{20}$, when present, is C1-C4 alkyl. In a further aspect, $R^{20}$, when present, is selected from methyl, ethyl, n-propyl, and isopropyl. In a still further aspect, $R^{20}$, when present, is selected from methyl and ethyl. In yet a further aspect, $R^{20}$, when present, is ethyl. In an even further aspect, $R^{20}$, when present, is methyl.

In various aspects, $R^{20}$, when present, is selected C1-C4 haloalkyl. In a further aspect, $R^{20}$, when present, is selected from —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{20}$, when present, is selected from —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{20}$, when present, is selected from —$CF_3$, —$CHF_2$, —$CH_2F$, —$CCl_3$, —$CHCl_2$, and —$CH_2Cl$.

In various aspects, $R^{20}$, when present, is selected from C1-C4 hydroxyalkyl and —(C1-C4 alkyl)-OC(O)—(C1-C4 alkyl). In a further aspect, $R^{20}$, when present, is selected from —$CH_2OH$, —$CH_2CH_2OH$, —$CH_2CH_2CH_2OH$, —$CH(CH_3)CH_2OH$, —$CH_2OC(O)CH_3$, —$CH_2OC(O)CH_2CH_3$, —$CH_2CH_2OC(O)CH_3$, —$CH_2OC(O)CH_2CH_2CH_3$, and —$CH_2CH_2CH_2OC(O)CH_3$. In a still further aspect, $R^{20}$, when present, is selected from —$CH_2OH$, —$CH_2CH_2OH$, —$CH_2OC(O)CH_3$, —$CH_2OC(O)CH_2CH_3$, and —$CH_2CH_2OC(O)CH_3$. In yet a further aspect, $R^{20}$, when present, is selected from —$CH_2OH$ and —$CH_2OC(O)CH_3$.

In various aspects, $R^{20}$, when present, is C1-C4 hydroxyalkyl. In a further aspect, $R^{20}$, when present, is selected from —$CH_2OH$, —$CH_2CH_2OH$, —$CH_2CH_2CH_2OH$, and —$CH(CH_3)CH_2OH$. In a still further aspect, $R^{20}$, when present, is selected from —$CH_2OH$ and —$CH_2CH_2OH$. In yet a further aspect, $R^{20}$, when present, is —$CH_2OH$.

In various aspects, $R^{20}$, when present, is —(C1-C4 alkyl)-OC(O)—(C1-C4 alkyl). In a further aspect, $R^{20}$, when present, is selected from —$CH_2OC(O)CH_3$, —$CH_2OC(O)CH_2CH_3$, —$CH_2CH_2OC(O)CH_3$, —$CH_2OC(O)CH_2CH_2CH_3$, and —$CH_2CH_2CH_2OC(O)CH_3$. In a still further aspect, $R^{20}$, when present, is selected from —$CH_2OC(O)CH_3$, —$CH_2OC(O)CH_2CH_3$, and —$CH_2CH_2OC(O)CH_3$. In yet a further aspect, $R^{20}$, when present, is —$CH_2OC(O)CH_3$.

f. $R^{21}$ Groups

In one aspect, $R^{21}$, when present, is selected from hydrogen, halogen, —CN, —$NO_2$, C1-C4 haloalkyl, and C1-C4 haloalkoxy. In a further aspect, $R^{21}$, when present, is selected from hydrogen, fluoro, chloro, bromo, —CN, —$NO_2$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{21}$, when present, is selected from hydrogen, fluoro, chloro, bromo, —CN, —$NO_2$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{21}$, when present, is selected from hydrogen, fluoro, chloro, bromo, —CN, —$NO_2$, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, $R^{21}$, when present, is hydrogen.

In various aspects, $R^{21}$, when present, is selected from hydrogen, —CN, —$NO_2$, and C1-C4 haloalkoxy. In a further aspect, $R^{21}$, when present, is selected from hydrogen, —CN, —$NO_2$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{21}$, when present, is selected from hydrogen, —CN, —$NO_2$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{21}$, when present, is selected from hydrogen, —CN, —$NO_2$, —$OCF_3$, —$OCHF_2$, —$OCH_2F$, —$OCCl_3$, —$OCHCl_2$, and —$OCH_2Cl$.

In various aspects, $R^{21}$, when present, is selected from hydrogen and C1-C4 haloalkoxy. In a further aspect, $R^{21}$, when present, is selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{21}$, when present, is selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{21}$, when present, is selected from hydrogen, —$OCF_3$, —$OCHF_2$, —$OCH_2F$, —$OCCl_3$, —$OCHCl_2$, and —$OCH_2Cl$.

In various aspects, $R^{21}$, when present, is selected from hydrogen, halogen, C1-C4 haloalkyl, and C1-C4 haloalkoxy. In a further aspect, $R^{21}$, when present, is selected from hydrogen, fluoro, chloro, bromo, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{21}$, when present, is selected from hydrogen, fluoro, chloro, bromo, —$CF_3$, —$CHF_2$, —$CH_2F$, —$CH_2CH_2F$, —$CCl_3$, —$CHCl_2$, —$CH_2Cl$, —$CH_2CH_2Cl$, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{21}$, when present, is selected from hydrogen, fluoro, chloro, bromo, —$CF_3$, —$CHF_2$, —$CH_2F$, —$CCl_3$, —$CHCl_2$, —$CH_2Cl$, —$OCF_3$, —$OCHF_2$, —$OCH_2F$, —$OCCl_3$, —$OCHCl_2$, and —$OCH_2Cl$.

In various aspects, $R^{21}$, when present, is selected from hydrogen and C1-C4 haloalkyl. In a further aspect, $R^{21}$, when present, is selected from hydrogen, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, and —$CH(CH_3)CH_2Cl$. In a still further aspect, $R^{21}$, when present, is selected from hydrogen, —$CF_3$, —$CHF_2$, —$CH_2F$, —$CH_2CH_2F$, —$CCl_3$, —$CHCl_2$, —$CH_2Cl$, and —$CH_2CH_2Cl$. In yet a further aspect, $R^{21}$, when present, is selected from hydrogen, —$CF_3$, —$CHF_2$, —$CH_2F$, —$CCl_3$, —$CHCl_2$, and —$CH_2Cl$.

In various aspects, $R^{21}$, when present, is selected from hydrogen and C1-C4 haloalkoxy. In a further aspect, $R^{21}$, when present, is selected from hydrogen, —$OCF_3$, —$OCHF_2$, —$OCH_2F$, —$OCH_2CH_2F$, —$OCH_2CH_2CH_2F$, —$OCH(CH_3)CH_2F$, —$OCCl_3$, —$OCHCl_2$, —$OCH_2Cl$, —$OCH_2CH_2Cl$, —$OCH_2CH_2CH_2Cl$, and —$OCH(CH_3)CH_2Cl$. In a still further aspect, $R^{21}$, when present, is selected from hydrogen, —$OCF_3$, —$OCHF_2$, —$OCH_2F$, —$OCH_2CH_2F$, —$OCCl_3$, —$OCHCl_2$, —$OCH_2Cl$, and —$OCH_2CH_2Cl$. In yet a further aspect, $R^{21}$, when present, is selected from hydrogen, —$OCF_3$, —$OCHF_2$, —$OCH_2F$, —$OCCl_3$, —$OCHCl_2$, and —$OCH_2Cl$.

In various aspects, $R^{21}$, when present, is selected from hydrogen and halogen. In a further aspect, $R^{21}$, when present, is selected from hydrogen, fluoro, chloro, and bromo. In a still further aspect, $R^{21}$, when present, is selected from hydrogen, fluoro, and chloro. In yet a further aspect, $R^{21}$, when present, is selected from hydrogen and fluoro. In an even further aspect, $R^{21}$, when present, is selected from hydrogen and chloro.

g. $R^{30}$ Groups

In one aspect, each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, each occurrence of $R^{30}$, when present, is independently selected from hydrogen, bromo, chloro, fluoro, —$NO_2$, —CN, —OH, —SH, —$NH_2$, methyl, ethyl, n-propyl, isopropyl, —$CH_2OH$, —$CH_2CH_2OH$, —$CH_2CH_2CH_2OH$, —$CH(CH_3)CH_2OH$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCH_3$, —$OCH_2CH_3$, —$OCH_2CH_2CH_3$, —$OCH(CH_3)_2$, —$OCF_3$, —$OCHF_2$, —$OCH_2F$, —$OCH_2CH_2F$, —$OCH_2CH_2CH_2F$, —$OCH(CH_3)CH_2F$, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_3)CH_2CH_2CH_3$, and —$N(CH_3)CH(CH_3)_2$. In a still further aspect, each occurrence of $R^{30}$, when present, is independently selected from hydrogen, bromo, chloro, fluoro, —$NO_2$, —CN, —OH, —SH, —$NH_2$, methyl, ethyl, —$CH_2OH$, —$CH_2CH_2OH$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCH_3$, —$OCH_2CH_3$, —$OCF_3$, —$OCHF_2$, —$OCH_2F$, —$OCH_2CH_2F$, —$NHCH_3$, —$NHCH_2CH_3$, —$N(CH_3)_2$, and —$N(CH_3)CH_2CH_3$. In yet a further aspect, each occurrence of $R^{30}$, when present, is independently selected from hydrogen, bromo, chloro, fluoro, —$NO_2$, —CN, —OH, —SH, —$NH_2$, methyl, —$CH_2OH$, —$CF_3$, —$CHF_2$, —$CH_2F$, —$CCl_3$, —$CHCl_2$, —$CH_2Cl$, —$OCH_3$, —$OCF_3$, —$OCHF_2$, —$OCH_2F$, —$NHCH_3$, and —$N(CH_3)_2$.

In one aspect, $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $R^{30}$ is selected from hydrogen, bromo, chloro, fluoro, —$NO_2$, —CN, —OH, —SH, —$NH_2$, methyl, ethyl, n-propyl, isopropyl, —$CH_2OH$, —$CH_2CH_2OH$, —$CH_2CH_2CH_2OH$, —$CH(CH_3)CH_2OH$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCH_3$, —$OCH_2CH_3$, —$OCH_2CH_2CH_3$, —$OCH(CH_3)_2$, —$OCF_3$, —$OCHF_2$, —$OCH_2F$, —$OCH_2CH_2F$, —$OCH_2CH_2CH_2F$, —$OCH(CH_3)CH_2F$, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_3)CH_2CH_2CH_3$, and —$N(CH_3)CH(CH_3)_2$. In a still further aspect, $R^{30}$ is selected from hydrogen, bromo, chloro, fluoro, —$NO_2$, —CN, —OH, —SH, —$NH_2$, methyl, ethyl, —$CH_2OH$, —$CH_2CH_2OH$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCH_3$, —$OCH_2CH_3$, —$OCF_3$, —$OCHF_2$, —$OCH_2F$, —$OCH_2CH_2F$, —$NHCH_3$, —$NHCH_2CH_3$, —$N(CH_3)_2$, and —$N(CH_3)CH_2CH_3$. In yet a further aspect, each occurrence of $R^{30}$, when present, is independently selected from hydrogen, bromo, chloro, fluoro, —$NO_2$, —CN, —OH, —SH, —$NH_2$, methyl, —$CH_2OH$, —$CF_3$, —$CHF_2$, —$CH_2F$, —$CCl_3$, —$CHCl_2$, —$CH_2Cl$, —$OCH_3$, —$OCF_3$, —$OCHF_2$, —$OCH_2F$, —$NHCH_3$, and —$N(CH_3)_2$.

In various aspects, each occurrence of $R^{30}$, when present, is independently selected from hydrogen, halogen, C1-C4 alkyl, C1-C4 hydroxyalkyl, C1-C4 haloalkyl, and C1-C4 alkoxy. In a further aspect, each occurrence of $R^{30}$, when present, is independently selected from hydrogen, bromo, chloro, fluoro, methyl, ethyl, n-propyl, isopropyl, —$CH_2OH$, —$CH_2CH_2OH$, —$CH_2CH_2CH_2OH$, —$CH(CH_3)CH_2OH$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCH_3$, —$OCH_2CH_3$, —$OCH_2CH_2CH_3$, and —$OCH(CH_3)_2$. In a still further aspect, each occurrence of $R^{30}$, when present, is independently selected from hydrogen, bromo, chloro, fluoro, methyl, ethyl, —$CH_2OH$, —$CH_2CH_2OH$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCH_3$, and —$OCH_2CH_3$. In yet a further aspect, each occurrence of $R^{30}$, when present, is independently selected from hydrogen, bromo, chloro, fluoro, methyl, —$CH_2OH$, —$CF_3$, —$CHF_2$, —$CH_2F$, —$CCl_3$, —$CHCl_2$, —$CH_2Cl$, and —$OCH_3$.

In various aspects, $R^{30}$ is selected from hydrogen, halogen, C1-C4 alkyl, C1-C4 hydroxyalkyl, C1-C4 haloalkyl, and C1-C4 alkoxy. In a further aspect, $R^{30}$ is selected from hydrogen, bromo, chloro, fluoro, methyl, ethyl, n-propyl, isopropyl, —$CH_2OH$, —$CH_2CH_2OH$, —$CH_2CH_2CH_2OH$, —$CH(CH_3)CH_2OH$, —$CF_3$, —$CHF_2$, —$CH_2F$, —$CH_2CH_2F$, —$CH_2CH_2CH_2F$, —$CH(CH_3)CH_2F$, —$CCl_3$, —$CHCl_2$, —$CH_2Cl$, —$CH_2CH_2Cl$, —$CH_2CH_2CH_2Cl$, —$CH(CH_3)CH_2Cl$, —$OCH_3$, —$OCH_2CH_3$, —$OCH_2CH_2CH_3$, and —$OCH(CH_3)_2$. In a still further aspect, $R^{30}$ is selected from hydrogen, bromo, chloro, fluoro, methyl, ethyl, —$CH_2OH$, —$CH_2CH_2OH$, —$CF_3$, —$CHF_2$, —$CH_2F$, —$CH_2CH_2F$, —$CCl_3$, —$CHCl_2$, —$CH_2Cl$, —$CH_2CH_2Cl$, —$OCH_3$, and —$OCH_2CH_3$. In yet a further aspect, each occurrence of $R^{30}$, when present, is independently selected from hydrogen, bromo, chloro, fluoro, methyl, —$CH_2OH$, —$CF_3$, —$CHF_2$, —$CH_2F$, —$CCl_3$, —$CHCl_2$, —$CH_2Cl$, and —$OCH_3$.

In various aspects, each occurrence of $R^{30}$, when present, is independently selected from hydrogen and halogen. In a further aspect, each occurrence of $R^{30}$, when present, is independently selected from hydrogen, bromo, chloro, and fluoro. In a still further aspect, each occurrence of $R^{30}$, when present, is independently selected from hydrogen, chloro, and fluoro. In yet a further aspect, each occurrence of $R^{30}$, when present, is independently selected from hydrogen and fluoro.

In various aspects, $R^{30}$ is selected from hydrogen and halogen. In a further aspect, $R^{30}$ is selected from hydrogen, bromo, chloro, and fluoro. In a still further aspect, $R^{30}$ is selected from hydrogen, chloro, and fluoro. In yet a further aspect, $R^{30}$ is selected from hydrogen and fluoro.

In a further aspect, each occurrence of $R^{30}$, when present, is hydrogen. In a still further aspect, $R^{30}$ is hydrogen.

h. $R^{30a}$ and $R^{30b}$ Groups

In one aspect, each of $R^{30a}$ and $R^{30b}$ is independently selected from hydrogen, halogen, $—NO_2$, —CN, —OH, —SH, $—NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, each of $R^{30a}$ and $R^{30b}$ is independently selected from hydrogen, bromo, chloro, fluoro, $—NO_2$, —CN, —OH, —SH, $—NH_2$, methyl, ethyl, n-propyl, isopropyl, $—CH_2OH$, $—CH_2CH_2OH$, $—CH_2CH_2CH_2OH$, $—CH(CH_3)CH_2OH$, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, $—CH(CH_3)CH_2Cl$, $—OCH_3$, $—OCH_2CH_3$, $—OCH_2CH_2CH_3$, $—OCH(CH_3)_2$, $—OCF_3$, $—OCHF_2$, $—OCH_2F$, $—OCH_2CH_2F$, $—OCH_2CH_2CH_2F$, $—OCH(CH_3)CH_2F$, $—NHCH_3$, $—NHCH_2CH_3$, $—NHCH_2CH_2CH_3$, $—NHCH(CH_3)_2$, $—N(CH_3)_2$, $—N(CH_3)CH_2CH_3$, $—N(CH_3)CH_2CH_2CH_3$, and $—N(CH_3)CH(CH_3)_2$. In a still further aspect, each of $R^{30a}$ and $R^{30b}$ is independently selected from hydrogen, bromo, chloro, fluoro, $—NO_2$, —CN, —OH, —SH, $—NH_2$, methyl, ethyl, $—CH_2OH$, $—CH_2CH_2OH$, $—CF_3$, $—CHF_2$, $—CH_2F$, $—CH_2CH_2F$, $—CCl_3$, $—CHCl_2$, $—CH_2Cl$, $—CH_2CH_2Cl$, $—OCH_3$, $—OCH_2CH_3$, $—OCF_3$, $—OCHF_2$, $—OCH_2F$, $—OCH_2CH_2F$, $—NHCH_3$, $—NHCH_2CH_3$, $—N(CH_3)_2$, and $—N(CH_3)CH_2CH_3$. In yet a further aspect, each of $R^{30a}$ and $R^{30b}$ is independently selected from hydrogen, bromo, chloro, fluoro, $—NO_2$, —CN, —OH, —SH, $—NH_2$, methyl, $—CH_2OH$, $—CF_3$, $—CHF_2$, $—CH_2F$, $—CCl_3$, $—CHCl_2$, $—CH_2Cl$, $—OCH_3$, $—OCF_3$, $—OCHF_2$, $—OCH_2F$, $—NHCH_3$, and $—N(CH_3)_2$.

In various aspects, each of $R^{30a}$ and $R^{30b}$ is independently selected from hydrogen, halogen, C1-C4 alkyl, C1-C4 hydroxyalkyl, C1-C4 haloalkyl, and C1-C4 alkoxy. In a further aspect, each of $R^{30a}$ and $R^{30b}$ is independently selected from hydrogen, bromo, chloro, fluoro, methyl, ethyl, n-propyl, isopropyl, $—CH_2OH$, $—CH_2CH_2OH$, $—CH_2CH_2CH_2OH$, $—CH(CH_3)CH_2OH$, $—CF_3$, $—CHF_2$, $—CH_2F$, $—CH_2CH_2F$, $—CH_2CH_2CH_2F$, $—CH(CH_3)CH_2F$, $—CCl_3$, $—CHCl_2$, $—CH_2Cl$, $—CH_2CH_2Cl$, $—CH_2CH_2CH_2Cl$, $—CH(CH_3)CH_2Cl$, $—OCH_3$, $—OCH_2CH_3$, $—OCH_2CH_2CH_3$, and $—OCH(CH_3)_2$. In a still further aspect, each of $R^{30a}$ and $R^{30b}$ is independently selected from hydrogen, bromo, chloro, fluoro, methyl, ethyl, $—CH_2OH$, $—CH_2CH_2OH$, $—CF_3$, $—CHF_2$, $—CH_2F$, $—CH_2CH_2F$, $—CCl_3$, $—CHCl_2$, $—CH_2Cl$, $—CH_2CH_2Cl$, $—OCH_3$, and $—OCH_2CH_3$. In yet a further aspect, each of $R^{30a}$ and $R^{30b}$ is independently selected from hydrogen, bromo, chloro, fluoro, methyl, $—CH_2OH$, $—CF_3$, $—CHF_2$, $—CH_2F$, $—CCl_3$, $—CHCl_2$, $—CH_2Cl$, and $—OCH_3$.

In various aspects, each of $R^{30a}$ and $R^{30b}$ is independently selected from hydrogen and halogen. In a further aspect, v selected from hydrogen, bromo, chloro, and fluoro. In a still further aspect, each of $R^{30a}$ and $R^{30b}$ is independently selected from hydrogen, chloro, and fluoro. In yet a further aspect, each of $R^{30a}$ and $R^{30b}$ is independently selected from hydrogen and fluoro.

In a further aspect, each of $R^{30a}$ and $R^{30b}$ is independently hydrogen.

i. $Ar^1$ Groups

In one aspect, $Ar^1$ is a structure represented by a formula selected from:

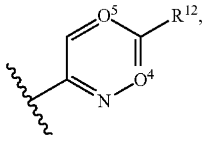

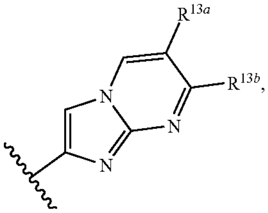

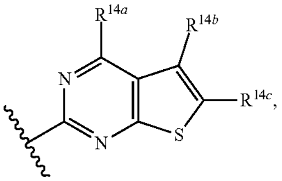

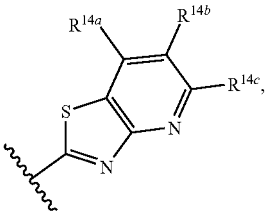

and

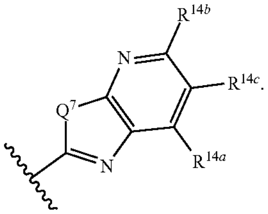

In one aspect, $Ar^1$ is a structure represented by a formula selected from:

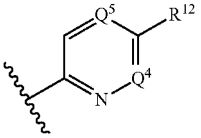

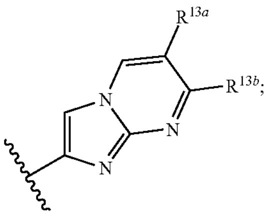

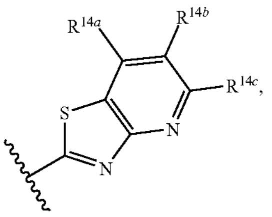

and

-continued

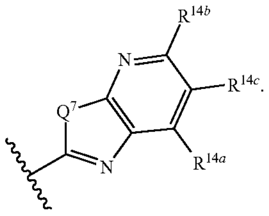

In a further aspect, $Ar^1$ is a structure represented by a formula:

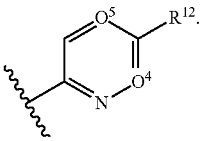

In a further aspect, $Ar^1$ is a structure represented by a formula:

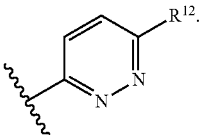

In a further aspect, $Ar^1$ is a structure represented by a formula selected from:

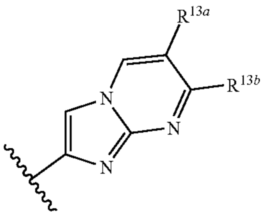

and

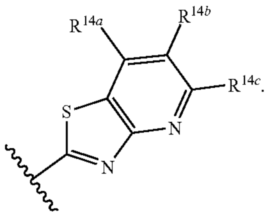

In a further aspect, $Ar^1$ is a structure represented by a formula:

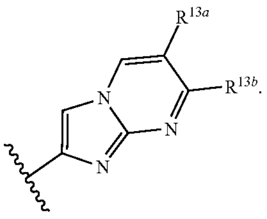

In a further aspect, $Ar^1$ is a structure represented by a formula:

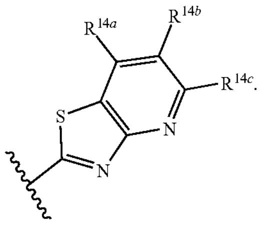

In a further aspect, $Ar^1$ is a structure represented by a formula:

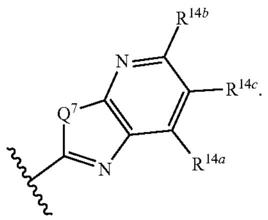

In a further aspect, $Ar^1$ is a structure represented by a formula:

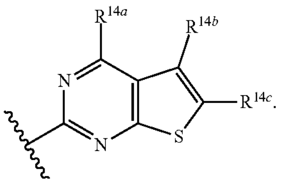

j. $Ar^2$ Groups

In one aspect, $Ar^2$ is a structure represented by a formula selected from:

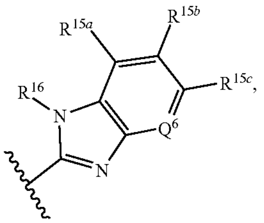

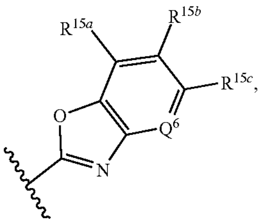

and

-continued

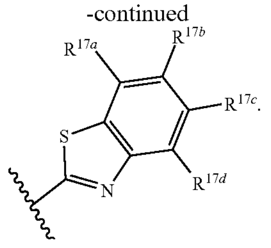

In a further aspect, $Ar^2$ is a structure represented by a formula:

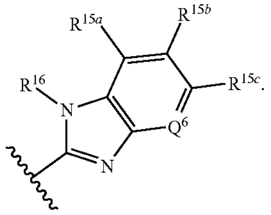

In a further aspect, $Ar^2$ is a structure represented by a formula:

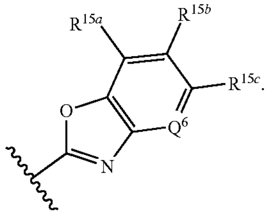

In a further aspect, $Ar^2$ is a structure represented by a formula:

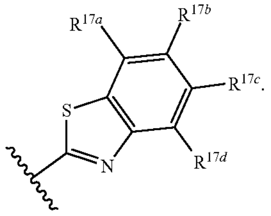

k. $Cy^1$ Groups

In one aspect, $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted cycloalkyl.

In various aspects, $Cy^1$, when present, is 3- to 6-membered cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is 3- to 6-membered cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is 3- to 6-membered cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is 3- to 6-membered cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted 3- to 6-membered cycloalkyl.

In various aspects, $Cy^1$, when present, is cyclohexyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is cyclohexyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is cyclohexyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is cyclohexyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted cyclohexyl.

In various aspects, $Cy^1$, when present, is cyclopentyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is cyclopentyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is cyclopentyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is cyclopentyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted cyclopentyl.

In various aspects, $Cy^1$, when present, is cyclobutyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is cyclobutyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is cyclobutyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is cyclobutyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted cyclobutyl.

In various aspects, $Cy^1$, when present, is cyclopropyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^1$, when present, is cyclopropyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^1$, when present, is cyclopropyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^1$, when present, is cyclopropyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^1$, when present, is unsubstituted cyclopropyl.

l. $Cy^2$ Groups

In one aspect, $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted cycloalkyl.

In various aspects, $Cy^2$, when present, is 3- to 6-membered cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is 3- to 6-membered cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is 3- to 6-membered cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is 3- to 6-membered cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted 3- to 6-membered cycloalkyl.

In various aspects, $Cy^2$, when present, is cyclohexyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is cyclohexyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is cyclohexyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is cyclohexyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted cyclohexyl.

In various aspects, $Cy^2$, when present, is cyclopentyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is cyclopentyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is cyclopentyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is cyclopentyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted cyclopentyl.

In various aspects, $Cy^2$, when present, is cyclobutyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is cyclobutyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is cyclobutyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is cyclobutyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted cyclobutyl.

In various aspects, $Cy^2$, when present, is cyclopropyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^2$, when present, is cyclopropyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^2$, when present, is cyclopropyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^2$, when present, is cyclopropyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^2$, when present, is unsubstituted cyclopropyl.

m. $Cy^3$ Groups

In one aspect, $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted cycloalkyl.

In various aspects, $Cy^3$, when present, is 3- to 6-membered cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is 3- to 6-membered cycloalkyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is 3- to 6-membered cycloalkyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is 3- to 6-membered cycloalkyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted 3- to 6-membered cycloalkyl.

In various aspects, $Cy^3$, when present, is cyclohexyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is cyclohexyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is cyclohexyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is cyclohexyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted cyclohexyl.

In various aspects, $Cy^3$, when present, is cyclopentyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is cyclopentyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is cyclopentyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is cyclopentyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted cyclopentyl.

In various aspects, $Cy^3$, when present, is cyclobutyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is cyclobutyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is cyclobutyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is cyclobutyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted cyclobutyl.

In various aspects, $Cy^3$, when present, is cyclopropyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a further aspect, $Cy^3$, when present, is cyclopropyl substituted with 0, 1, or 2 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In a still further aspect, $Cy^3$, when present, is cyclopropyl substituted with 0 or 1 group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In yet a further aspect, $Cy^3$, when present, is cyclopropyl monosubstituted with a group selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino. In an even further aspect, $Cy^3$, when present, is unsubstituted cyclopropyl.

2. Example Compounds

In one aspect, a compound can be present as one or more of the following structures:

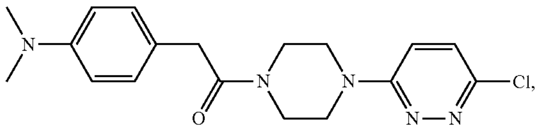

-continued

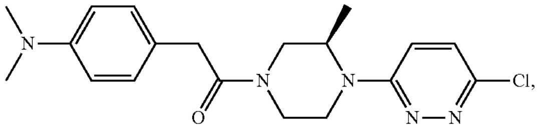

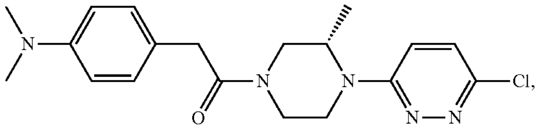

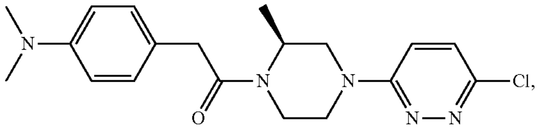

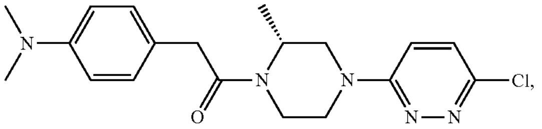

and

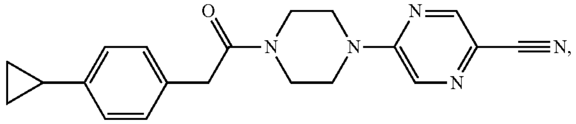

or a pharmaceutically acceptable salt thereof.

In one aspect, a compound can be present as one or more of the following structures:

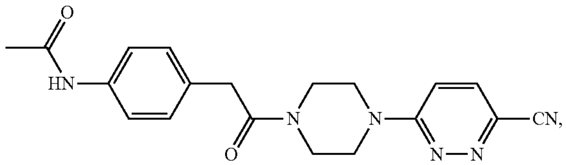

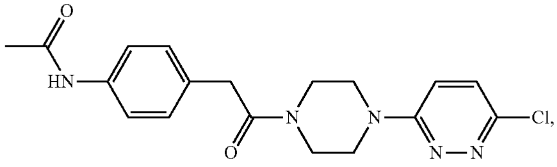

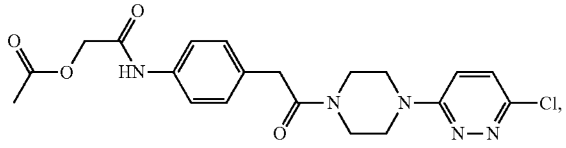

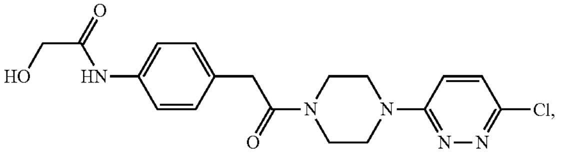

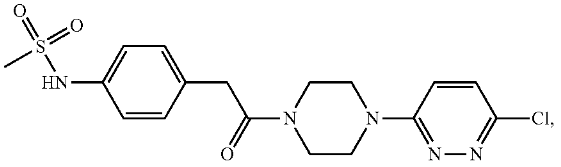

-continued
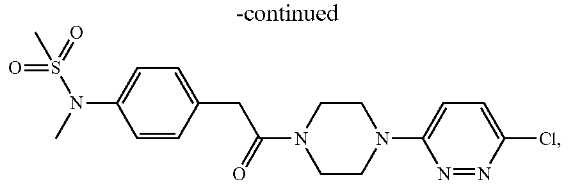
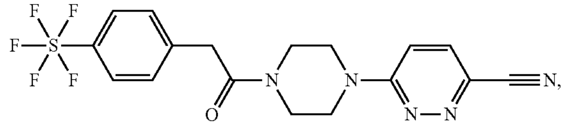
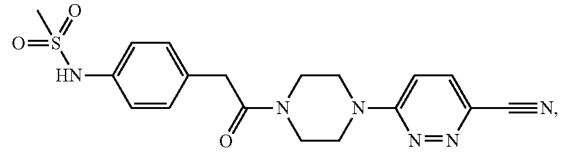
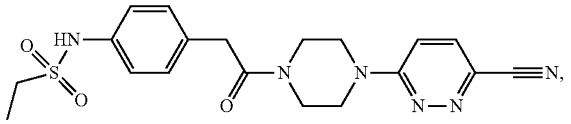
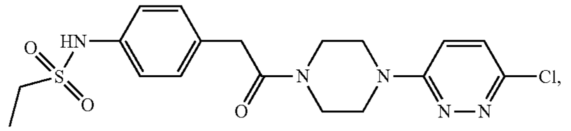
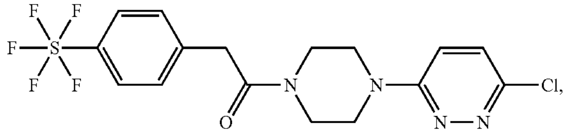
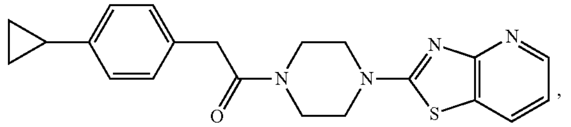
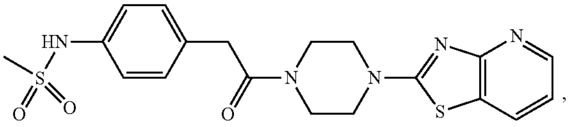
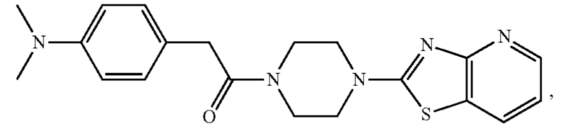
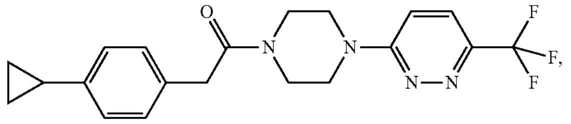
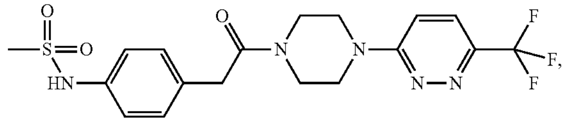
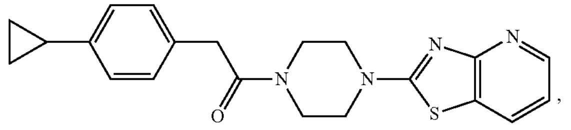
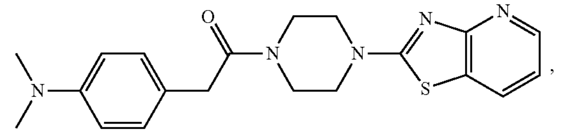
-continued
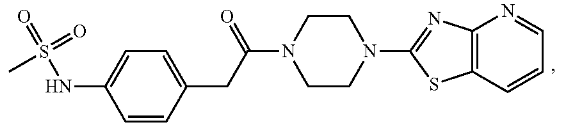
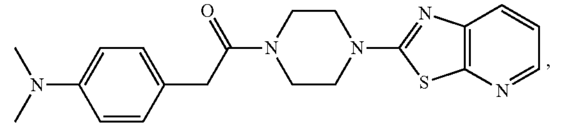
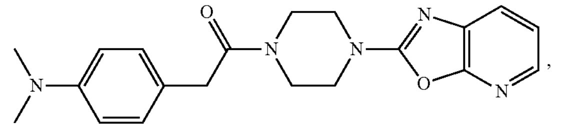
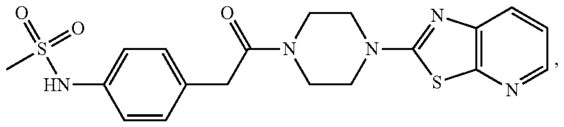
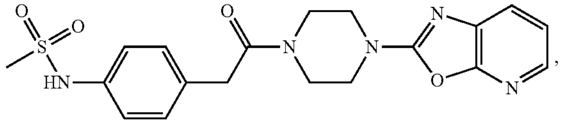
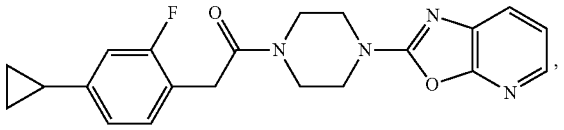
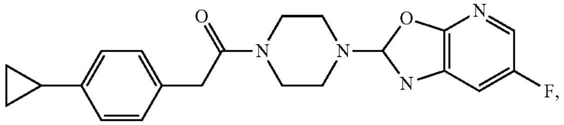
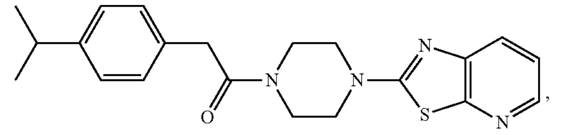
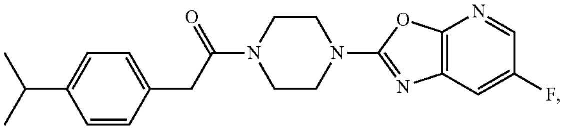
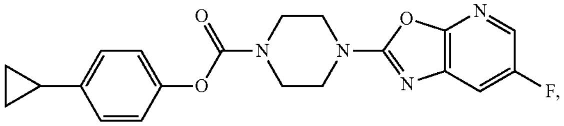
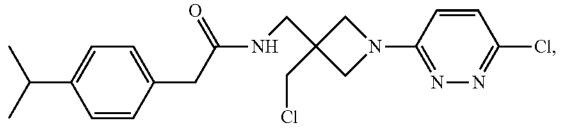
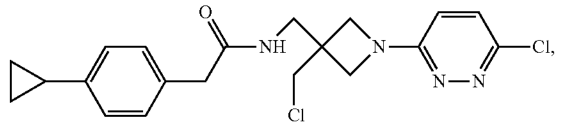
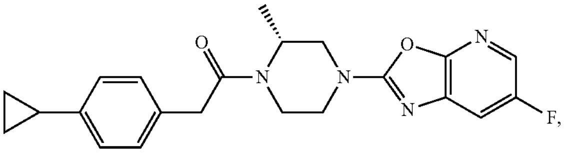

-continued
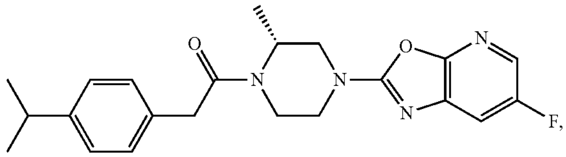,
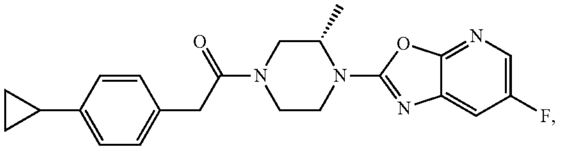,
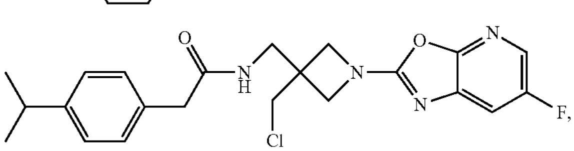,
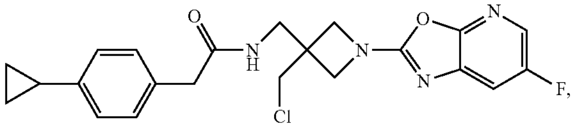,
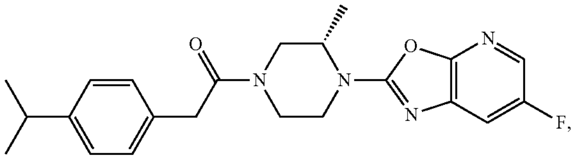,
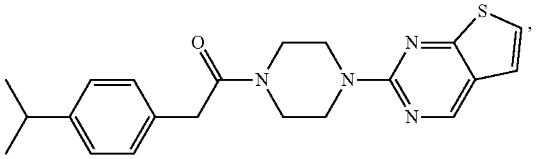,
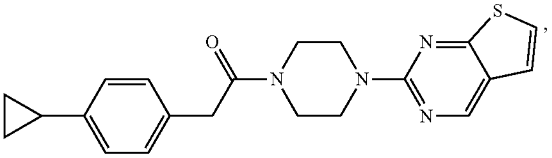,
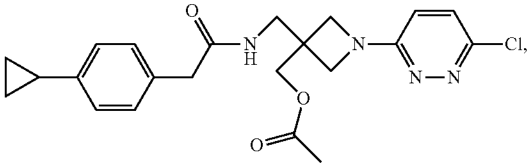, and
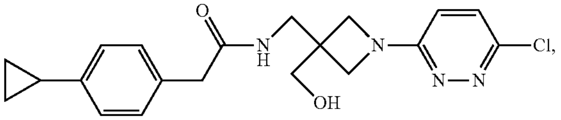,
or a pharmaceutically acceptable salt thereof.
In one aspect, a compound can be present as one or more of the following structures:
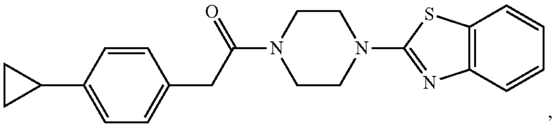,
-continued
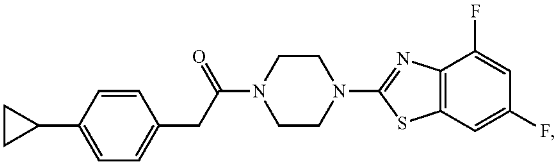,
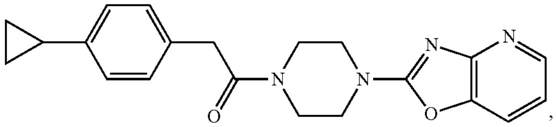,
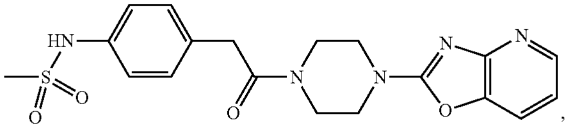,
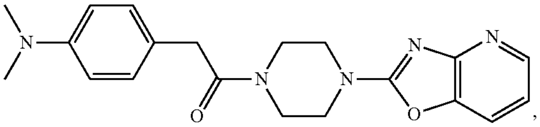,
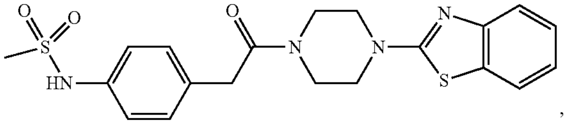,
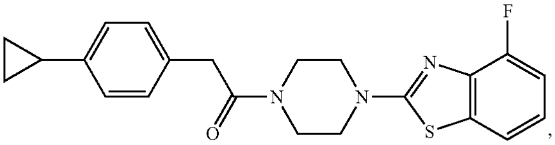,
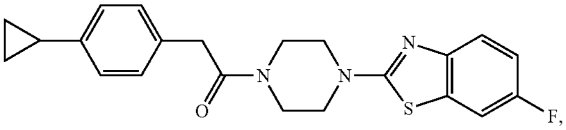,
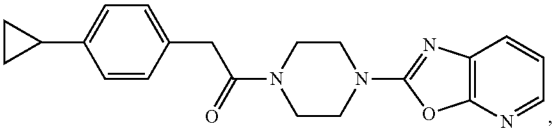,
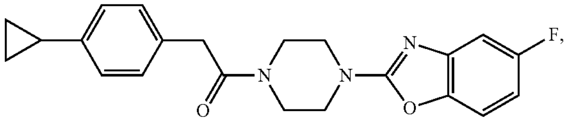,
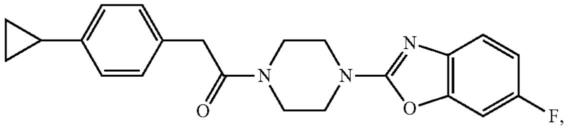,
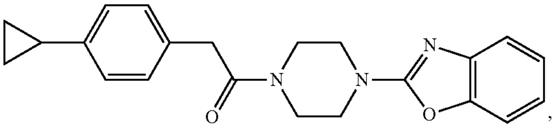,
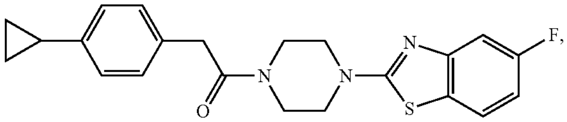,
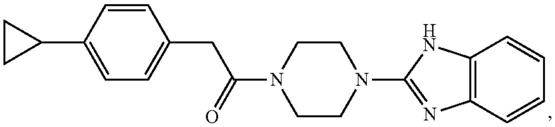, -continued
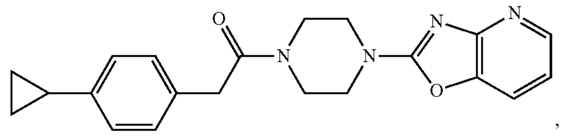
,
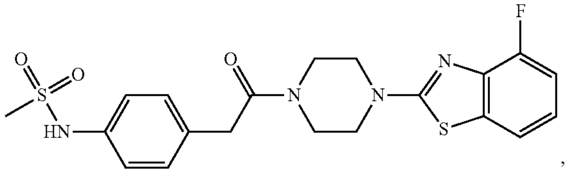
,
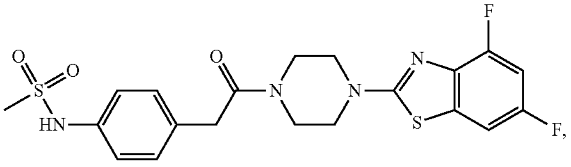
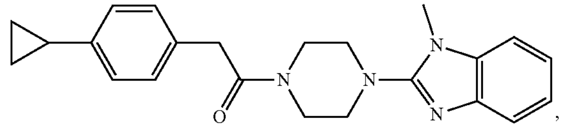
,
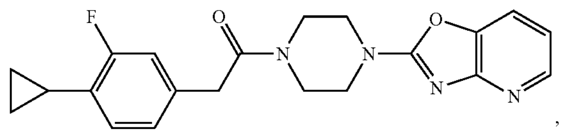
,
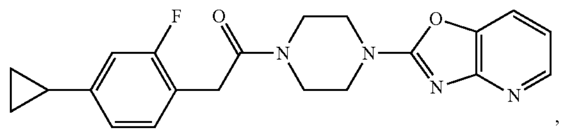
,
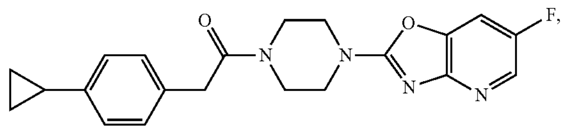
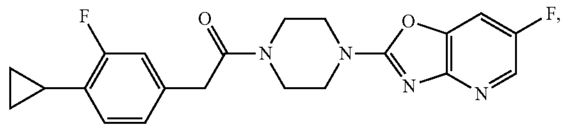
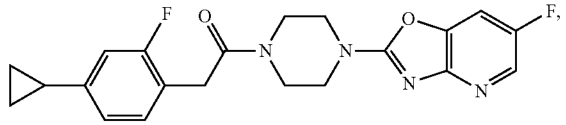
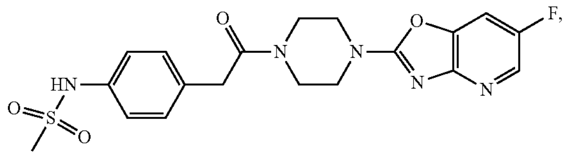
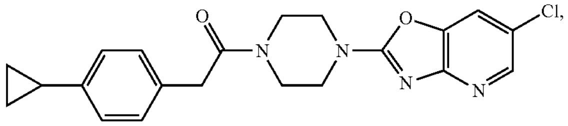
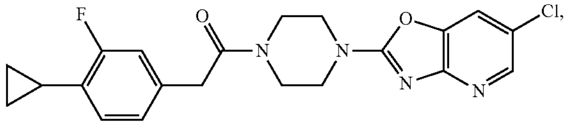
-continued
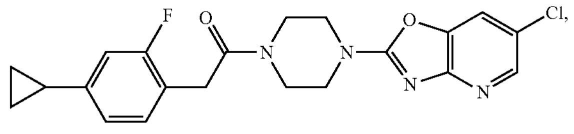
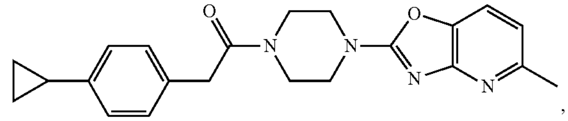
,
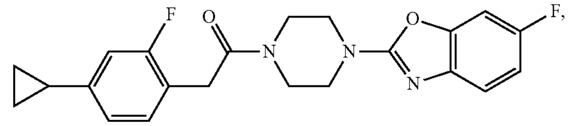
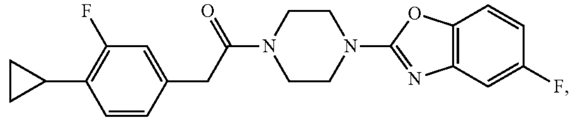
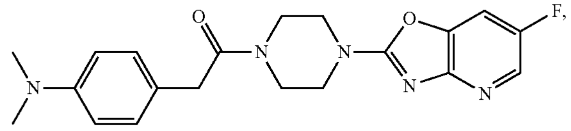
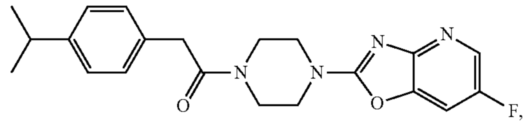
and
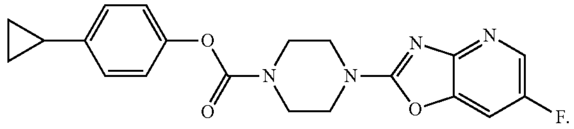
or a pharmaceutically acceptable salt thereof.
In one aspect, a compound can be present as one or more of the following structures:
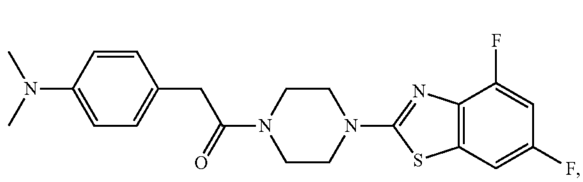
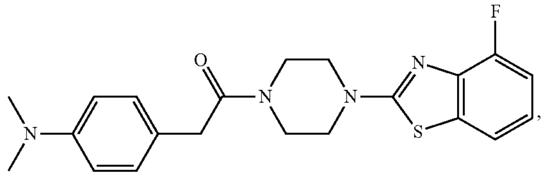
,
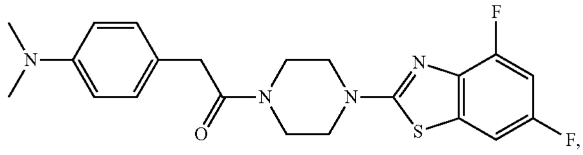
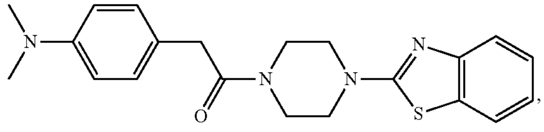
, -continued

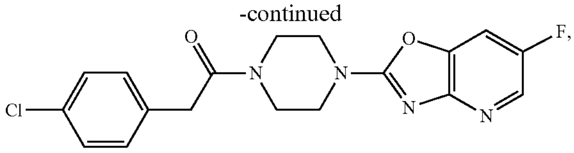
,
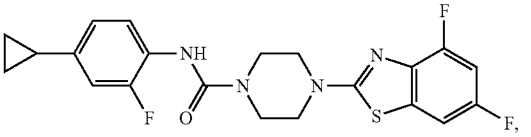
, and
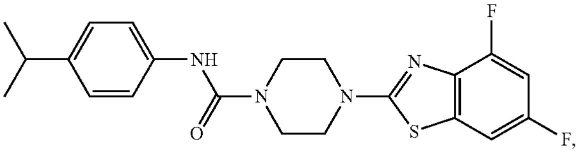
, or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as PanK antagonists, and such activity can be determined using the assay methods described herein.

In one aspect, a compound can be selected from:

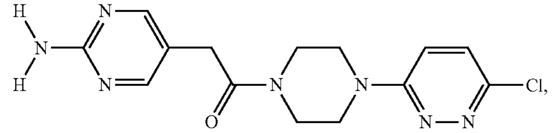
,
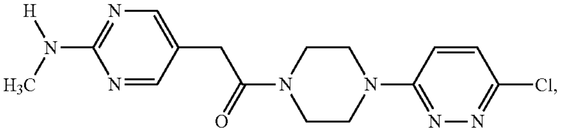
,
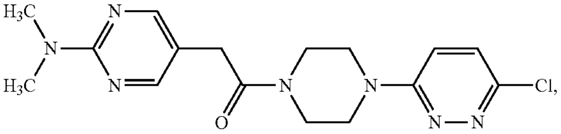
,
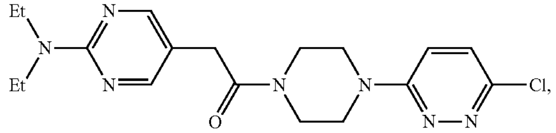
,
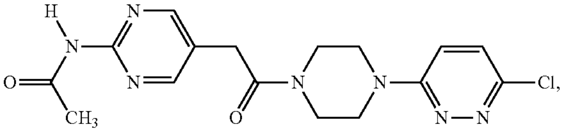
,
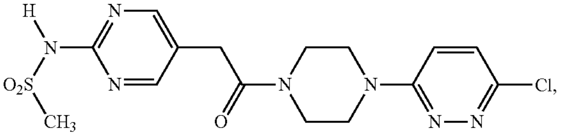
,
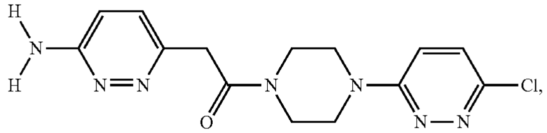
, -continued

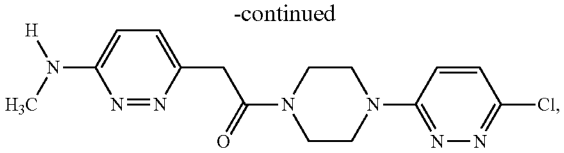
,
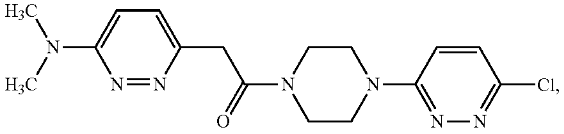
,
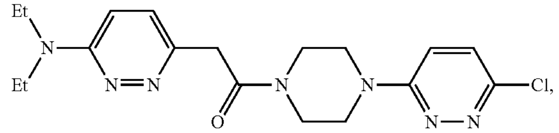
,
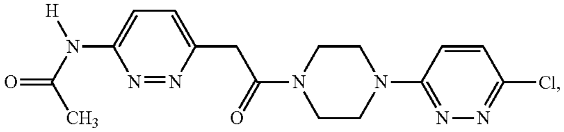
,
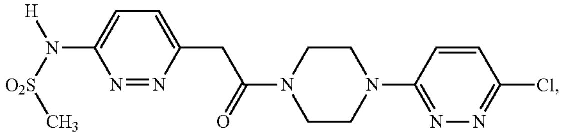
,
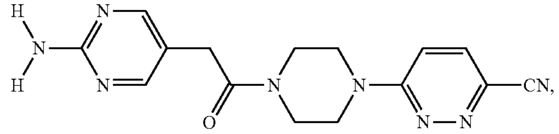
,
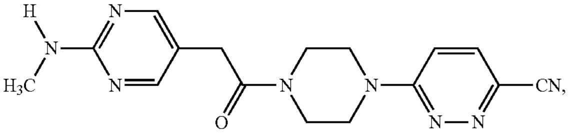
,
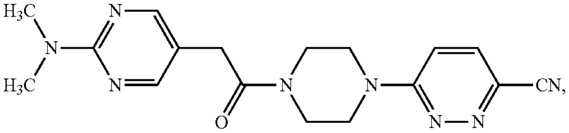
,
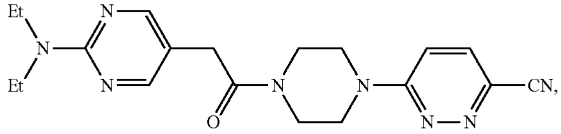
,
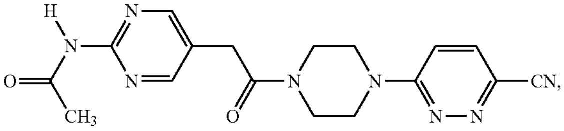
,
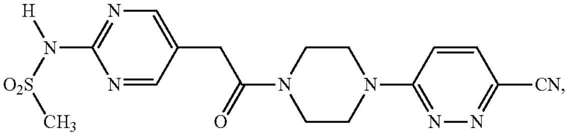
,
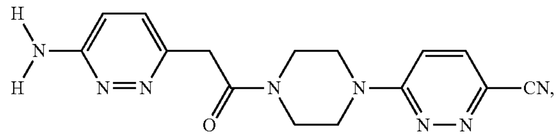
,
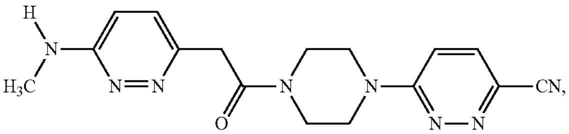
, -continued
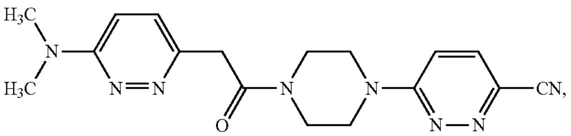
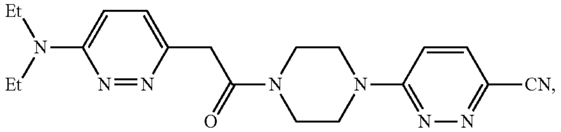
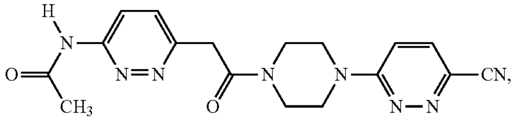
and
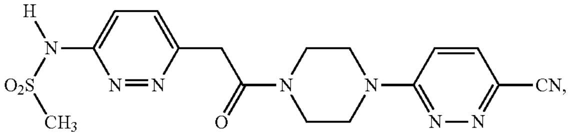
or a pharmaceutically acceptable derivative thereof.
In one aspect, a compound can be selected from:
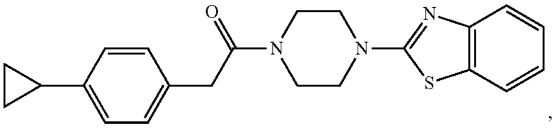
,
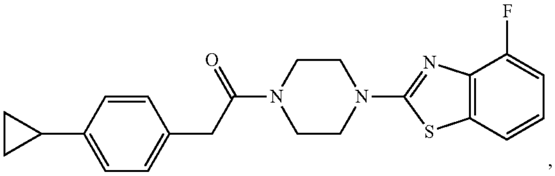
,
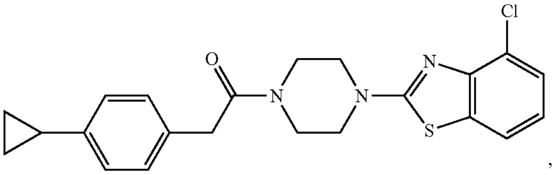
,
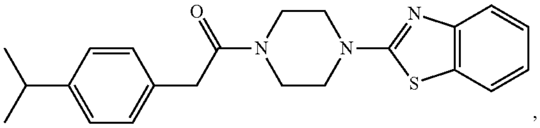
,
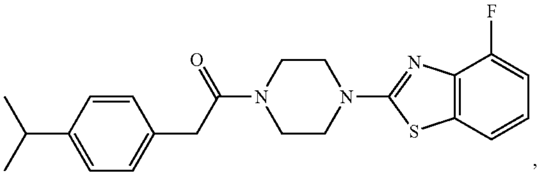
,
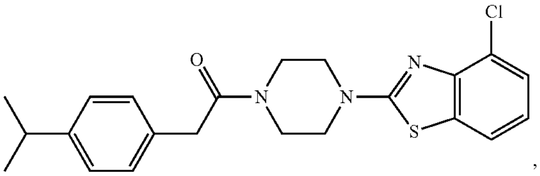
,
-continued
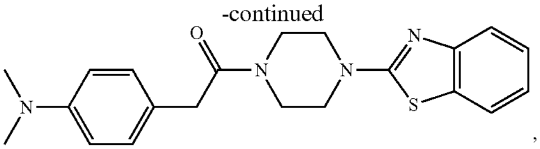
,
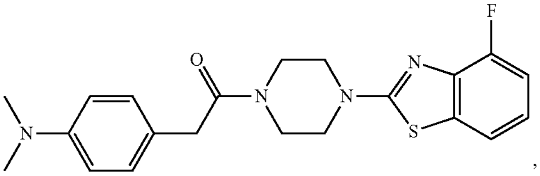
,
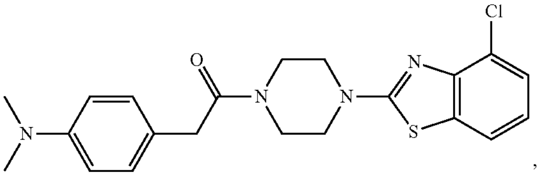
,
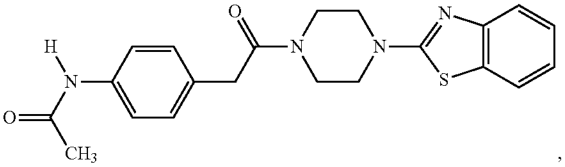
,
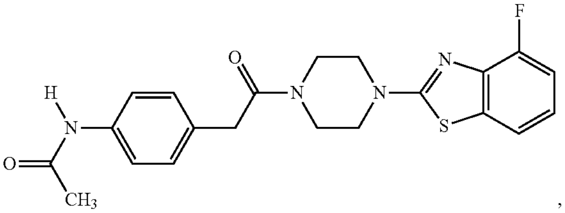
,
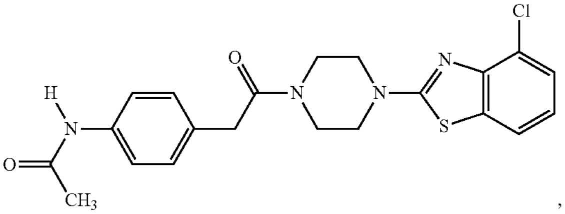
,
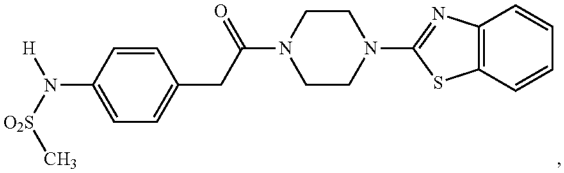
,
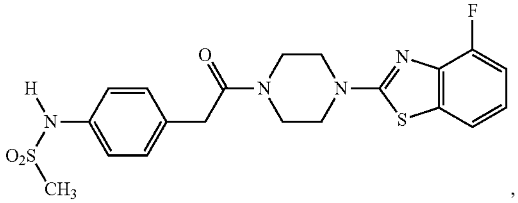
, and
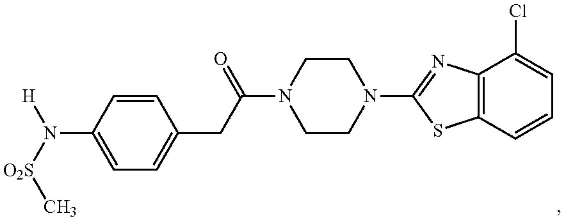
,
or a pharmaceutically acceptable derivative thereof.

In one aspect, a compound can be selected from:
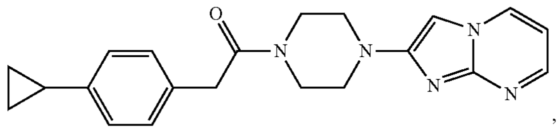
,
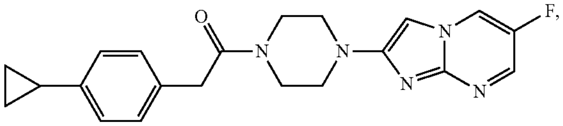
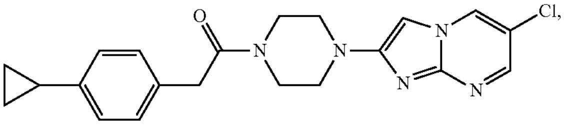
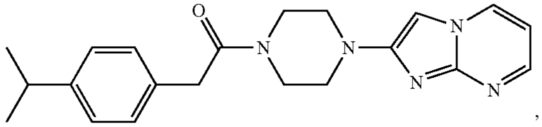
,
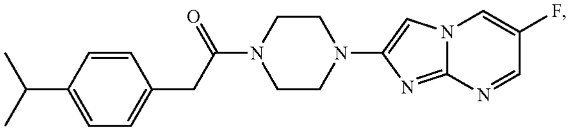
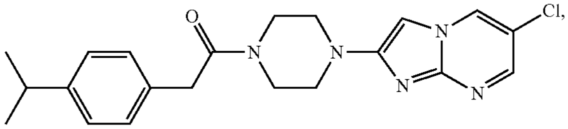
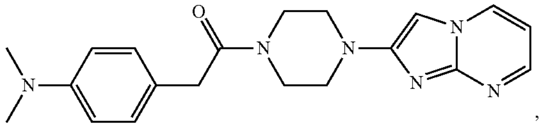
,
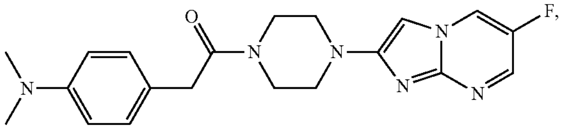
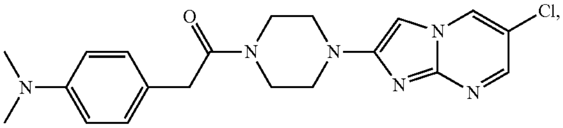
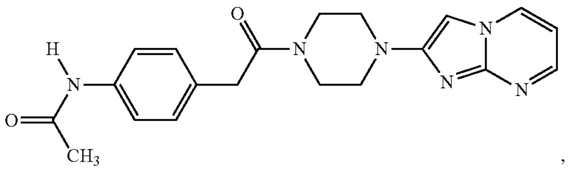
,
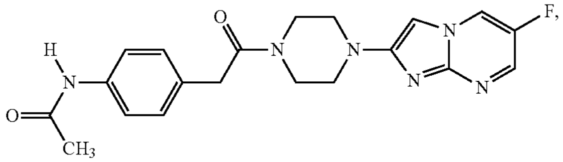
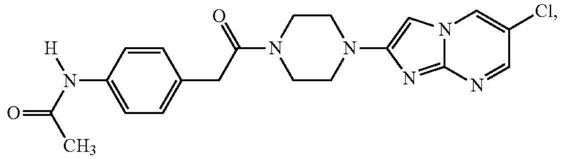
-continued
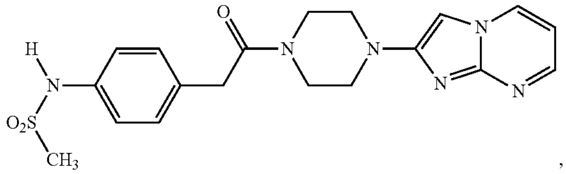
,
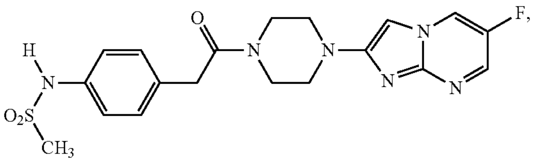
and
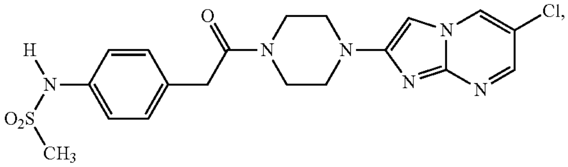
or a pharmaceutically acceptable derivative thereof.
In one aspect, a compound can be selected from:
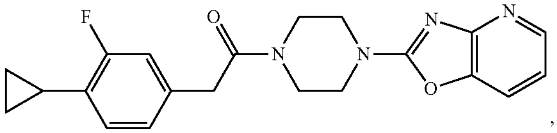
,
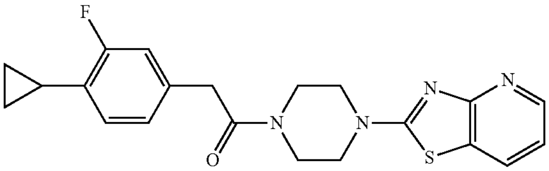
,
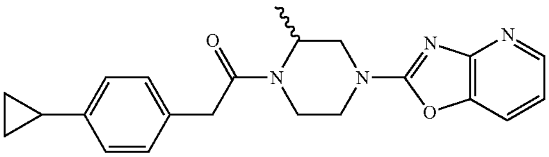
,
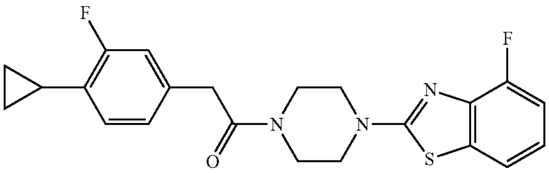
,
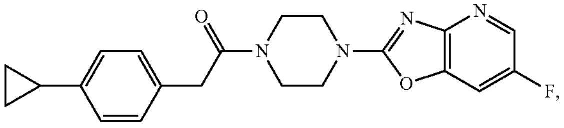
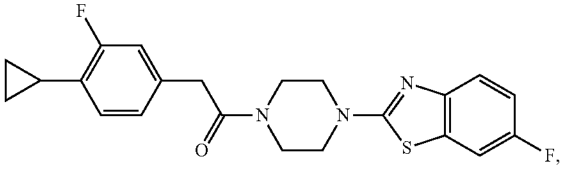

-continued
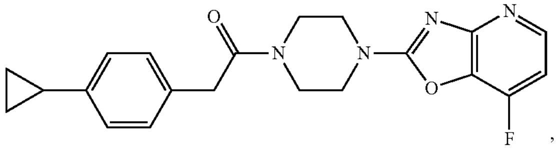,
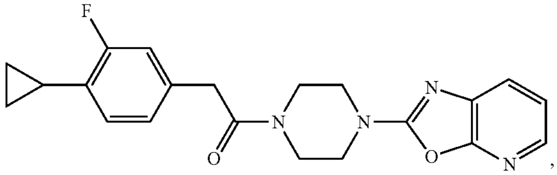,
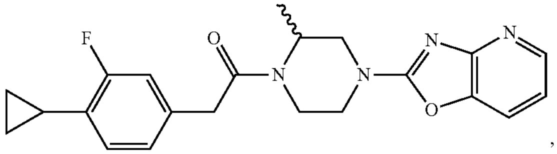,
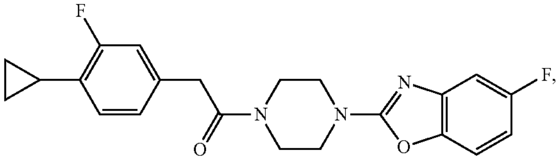,
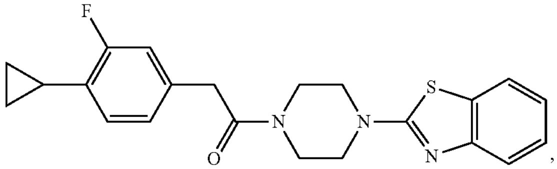,
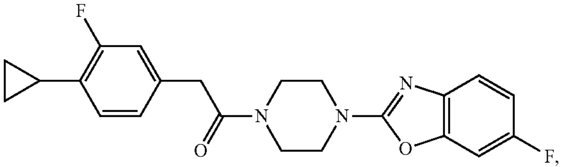,
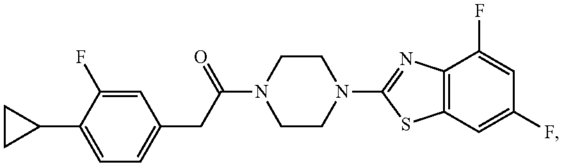,
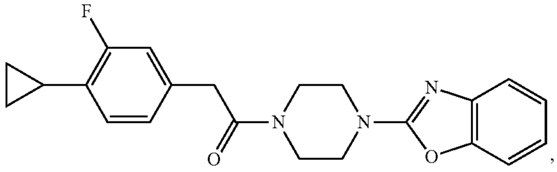,
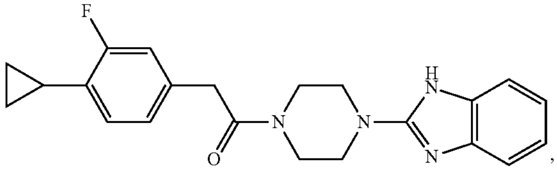,
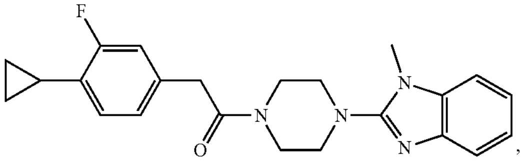, and
-continued
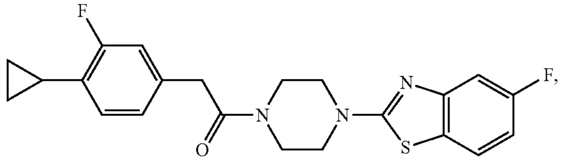,
or a pharmaceutically acceptable derivative thereof.
In one aspect, a compound can be selected from:
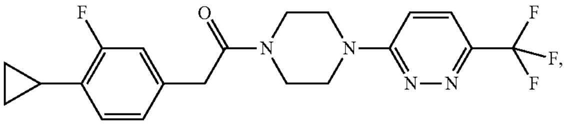,
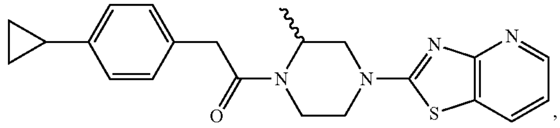,
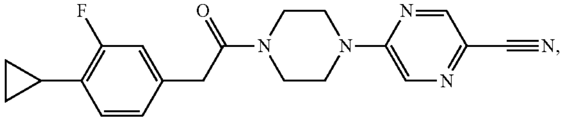,
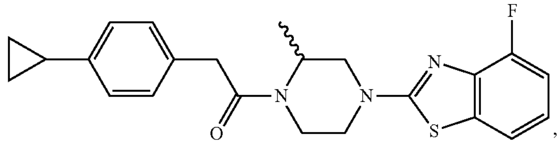,
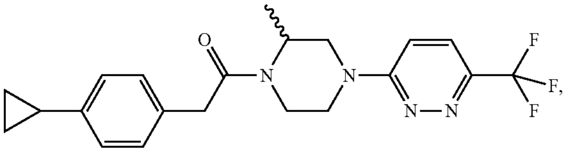,
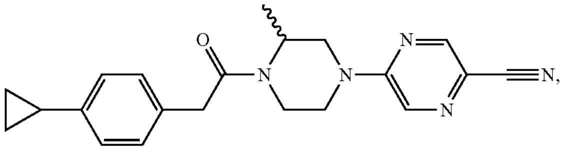,
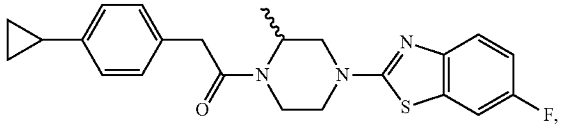,
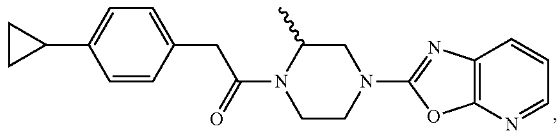,
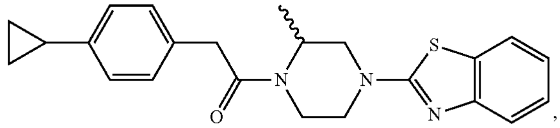,
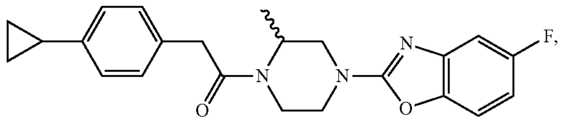, -continued

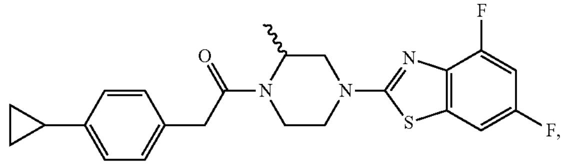

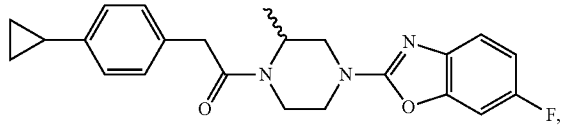

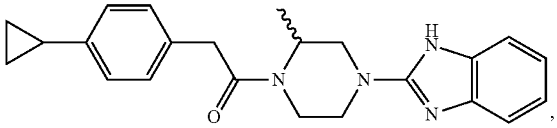

,

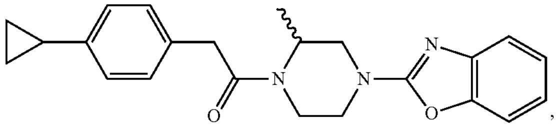

,

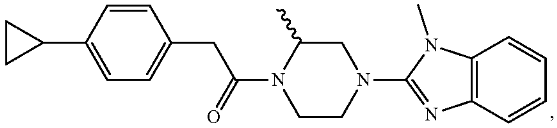

,

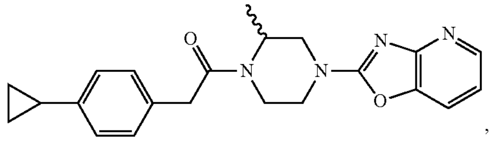

, and

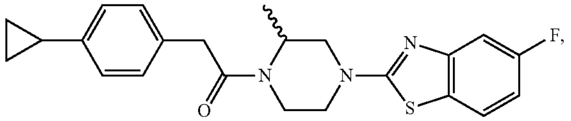

or a pharmaceutically acceptable derivative thereof.

C. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VI, as described and exemplified below. The following examples are provided so that the invention might be more fully understood, are illustrative only, and should not be construed as limiting.

1. Route I

In one aspect, substituted small molecule modulators of PanK can be prepared as shown below.

SCHEME 1A

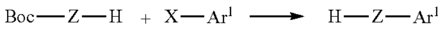

1.1 1.2 1.3

Compounds are represented in generic form, with substituents as noted in compound descriptions elsewhere herein; wherein X is halogen. As would be understood by one skilled in the art, such reaction conditions could also be used to prepare compounds in which $Ar^1$ is replaced with $Ar^2$. A more specific example is set forth below.

SCHEME 1B

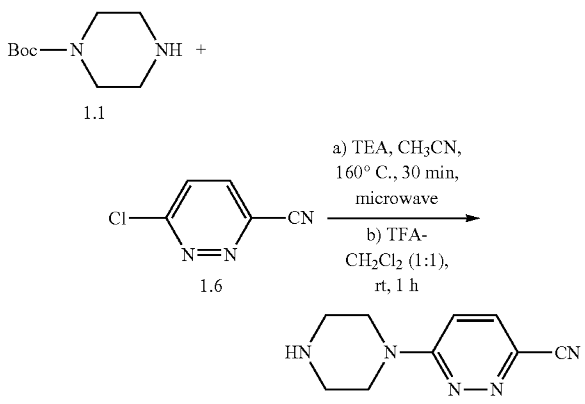

1.1

1.6

1.7

In one aspect, compounds of type 1.7, and similar compounds, can be prepared according to reaction Scheme 1B above. Thus, compounds of type 1.7 are either commercially available or can be prepared by an arylation reaction of an appropriate amine, e.g., 1.1 as shown above, and an appropriate aryl halide, e.g., 1.6 as shown above. Appropriate amines and appropriate aryl halides are commercially available or prepared by methods known to one skilled in the art. The arylation reaction is carried out in the presence of an appropriate base, e.g., triethylamine (TEA), in an appropriate solvent, e.g., acetonitrile, at an appropriate temperature, e.g., 160° C., for an appropriate period of time, e.g., 30 minutes using microwave irradiation. The arylation reaction is followed by a deprotection. The deprotection is carried out in the presence of an appropriate deprotecting agent, e.g., trifluoroacetic acid (TFA), in an appropriate solvent, e.g., dichloromethane, for an appropriate period of time, e.g., 1 hour. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted small molecule modulators of PanK similar to Formula 1.3.

2. Route II

In one aspect, substituted small molecule modulators of PanK can be prepared as shown below.

SCHEME 2A

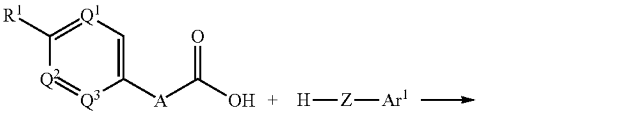

2.1 2.2

-continued

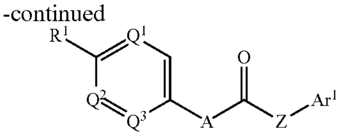

2.3

Compounds are represented in generic form, with substituents as noted in compound descriptions elsewhere herein and wherein A is selected from $CH_2$, $CF_2$, and CH(OH). As would be understood by one skilled in the art, such reaction conditions could also be used to prepare compounds in which $Ar^1$ is replaced with $Ar^2$. A more specific example is set forth below.

SCHEME 2B

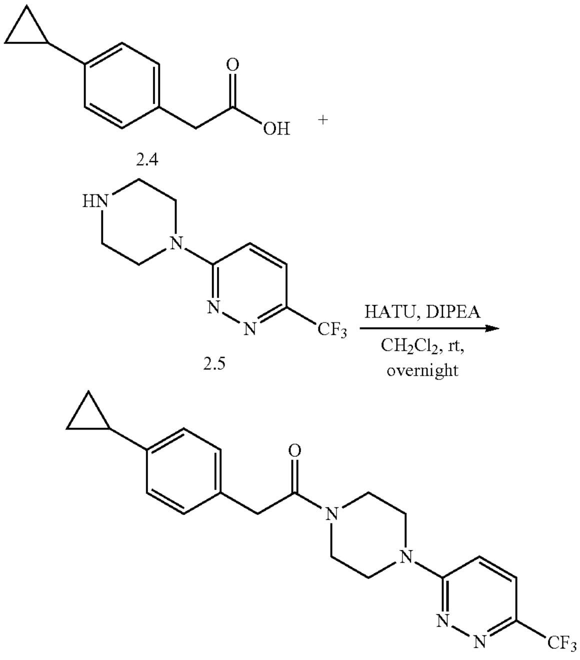

2.4 2.5 2.6

In one aspect, compounds of type 2.6, and similar compounds, can be prepared according to reaction Scheme 2B above. Thus, compounds of type 2.6 can be prepared by a coupling reaction of an appropriate carboxylic acid, e.g., 2.4 as shown above, with an appropriate amine, e.g., 2.5 as shown above. Appropriate carboxylic acids and appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dichloromethane. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted small molecule modulators of PanK similar to Formula 2.3.

3. Route III

In one aspect, substituted small molecule modulators of PanK can be prepared as shown below.

SCHEME 3A

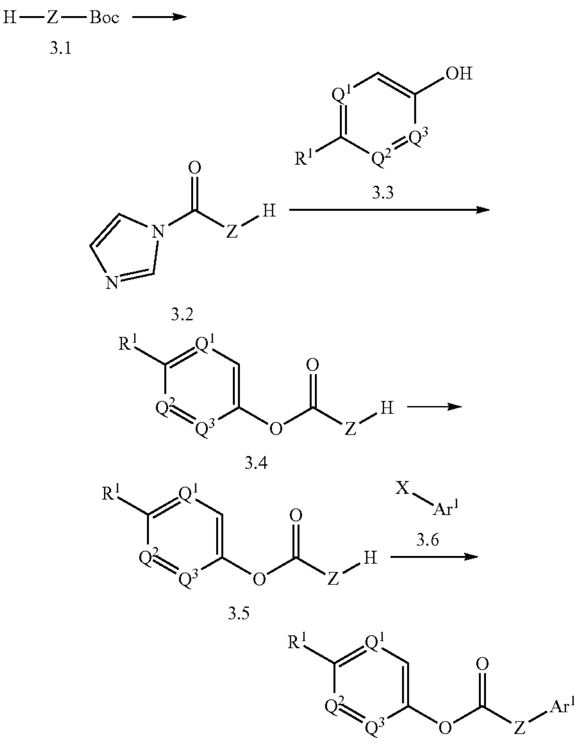

3.1 3.3 3.2 3.4 3.6 3.5 3.7

Compounds are represented in generic form, with substituents as noted in compound descriptions elsewhere herein and wherein X is halogen. A more specific example is set forth below.

SCHEME 3B

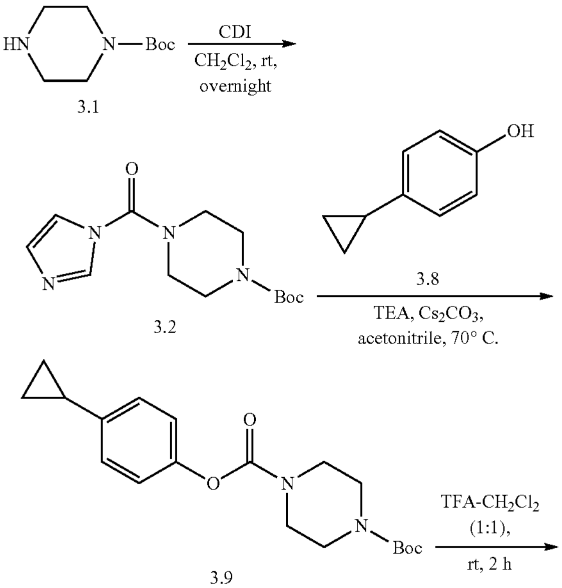

3.1 3.8 3.2 3.9

-continued

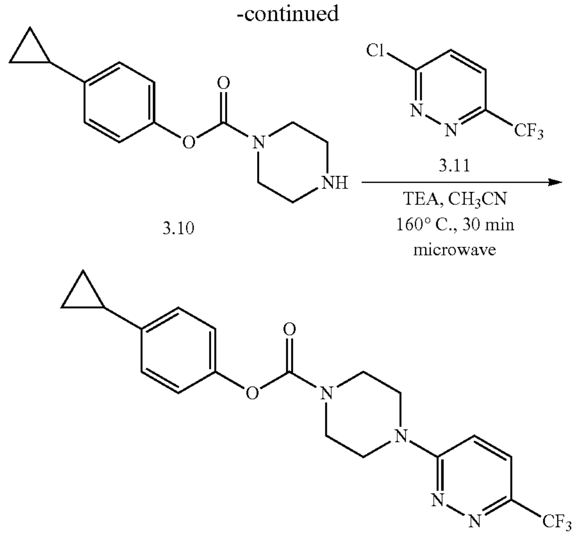

3.10

3.11

3.12

In one aspect, compounds of type 3.12, and similar compounds, can be prepared according to reaction Scheme 3B above. Thus, compounds of type 3.2 can be prepared by a coupling reaction of an appropriate amine, e.g., 3.1 as shown above. Appropriate amines are commercially available or prepared by methods known to one skilled in the art. The coupling reaction is carried out in the presence of an appropriate coupling agent, e.g., N,N-carbonyldiimidazole (CDI), in an appropriate solvent, e.g., dichloromethane. Compounds of type 3.9 can be prepared by a reaction of an appropriate activated -urea, e.g., 3.2, and an appropriate phenol, e.g., 3.8 as shown above. Appropriate phenols are commercially available or prepared by methods known to one skilled in the art. The reaction is carried out in the presence of an appropriate base, e.g., triethylamine and cesium carbonate, in an appropriate solvent, e.g., acetonitrile, at an appropriate temperature, e.g., 70° C., for an appropriate period of time, e.g., 3-4 hours or overnight. Compounds of type 3.10 can be prepared by a deprotection reaction of an appropriate piperazine, e.g., 3.9 as shown above. The deprotection reaction is carried out in the presence of an appropriate deprotecting agent, e.g., trifluoroacetic acid, and an appropriate solvent, e.g., dichloromethane, for an appropriate period of time, e.g., 2 hours. Compounds of type 3.12 can be prepared by an arylation reaction of an appropriate amine, e.g., 3.10 as shown above, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, and an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.1, 3.2, 3.3, 3.4, 3.5, and 3.6), can be substituted in the reaction to provide substituted small molecule modulators of PanK similar to Formula 3.7.

4. Route IV

In one aspect, substituted small molecule modulators of PanK can be prepared as shown below.

SCHEME 4A

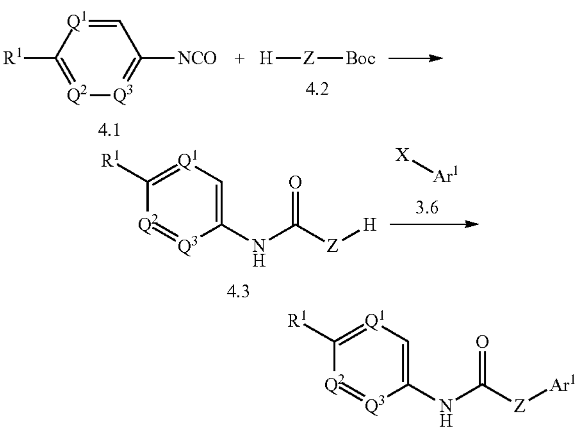

4.1

4.2

3.6

4.3

4.4

Compounds are represented in generic form, with substituents as noted in compound descriptions elsewhere herein and wherein X is halogen. A more specific example is set forth below.

SCHEME 4B

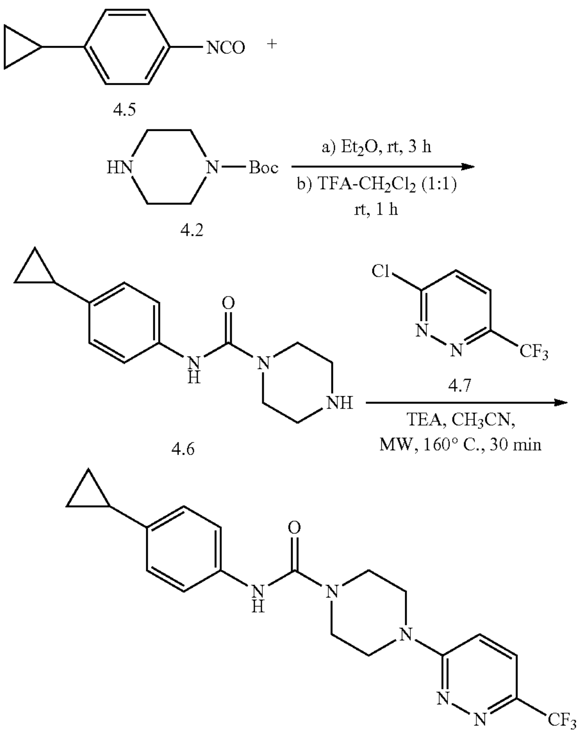

4.5

4.2

4.6

4.7

4.8

In one aspect, compounds of type 4.8, and similar compounds, can be prepared according to reaction Scheme 4B above. Thus, compounds of type 4.6 can be prepared by a urea bond formation reaction between an appropriate amine, e.g., 4.2 as shown above, and an appropriate isocyanate, e.g., 4.5 as shown above. Appropriate amines and appropriate isocyanates are commercially available or prepared by methods known to one skilled in the art. The nucleophilic substitution is carried out in the presence of an appropriate solvent, e.g., diethyl ether, for an appropriate period of time, e.g., 3 hours. The nucleophilic substitution is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 4.8 can be prepared by an arylation reaction of appropriate amine, e.g., 4.6 as shown above, and an appropriate aryl halide, e.g., 4.7 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g, 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.6, 4.1, 4.2, and 4.3), can be substituted in the reaction to provide 4-aryl-N-phenylpiperazine-1-carboxamide derivatives similar to Formula 4.4.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

5. Route V

In one aspect, substituted small molecule modulators of PanK can be prepared as shown below.

SCHEME 5A

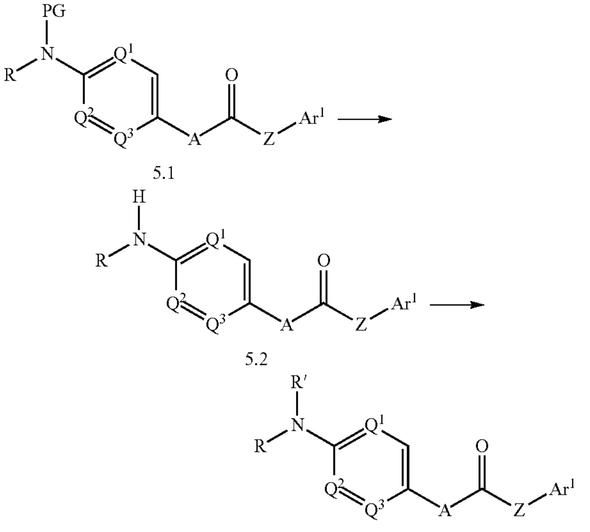

5.3

Compounds are represented in generic form, with substituents as noted in compound descriptions elsewhere herein, wherein PG is an amine protecting group, R is selected from hydrogen and C1-C4 alkyl, and $R^1$ is selected from C1-C4 alkyl, $C(O)R^{11}$, and $SO_2R^{11}$. As would be understood by one skilled in the art, such reaction conditions could also be used to prepare compounds in which $Ar^1$ is replaced with $Ar^2$. A more specific example is set forth below.

SCHEME 5B

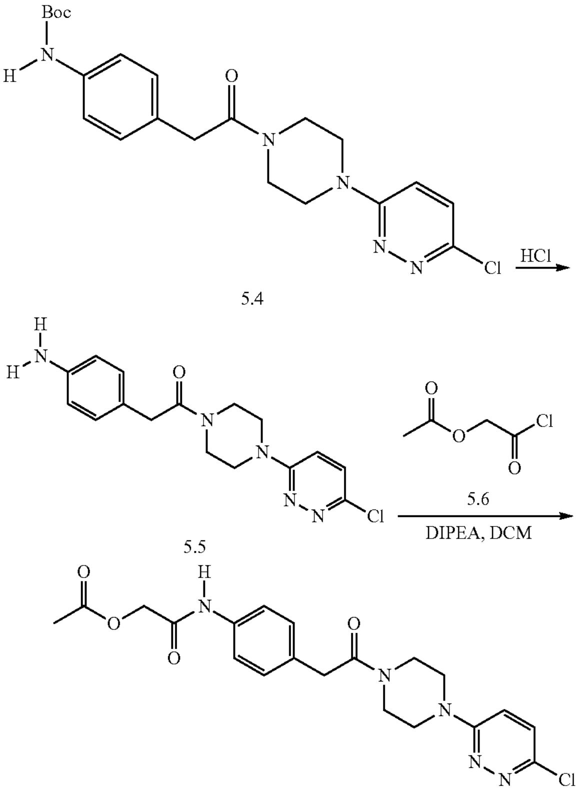

5.7

In one aspect, compounds of type 5.7, and similar compounds, can be prepared according to reaction Scheme 5B above. Thus, compounds of type 5.5 can be prepared by deprotection of an appropriate amine, e.g., 5.4 as shown above. The deprotection is carried out in the presence of an appropriate acid, e.g., hydrochloric acid. Compounds of type 5.7 can be prepared by a coupling reaction of an appropriate amine, e.g., 5.5, and an appropriate carboxylic acid or acyl halide, e.g., 5.6 as shown above. Appropriate carboxylic acids and appropriate acyl halides are commercially available or can be prepared by one of skill in the art. The coupling reaction is carried out in the presence of an appropriate base, e.g., N,N-diisopropylethylamine (DIPEA), in an appropriate solvent, e.g., dichloromethane. As can be appreciated by one skilled in the art, the above reaction provides an example of a generalized approach wherein compounds similar in structure to the specific reactants above (compounds similar to compounds of type 5.1 and 5.2), can be substituted in the reaction to provide substituted small molecule modulators of PanK similar to Formula 5.3.

D. Pharmaceutical Compositions

In one aspect, disclosed are pharmaceutical compositions comprising a disclosed compound, or a pharmaceutically acceptable salt thereof and a pharmaceutically acceptable carrier.

Thus, in one aspect, disclosed are pharmaceutical composition comprising a therapeutically effective amount of at least one compound having a structure represented by a formula:

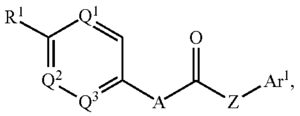

wherein A is selected from —O—, —$CH_2$—, —$CF_2$—, —NH—, —$N(CH_3)$—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

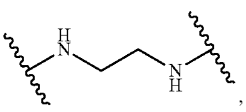 , 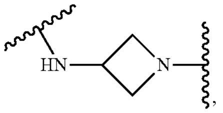 ,

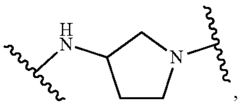 , 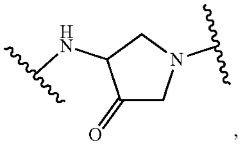 ,

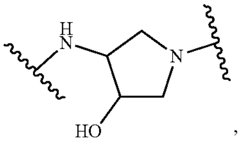 , 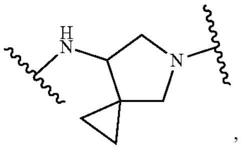 ,

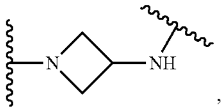 , 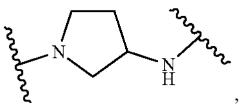 ,

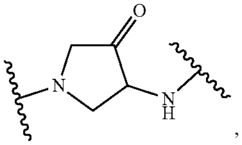 , 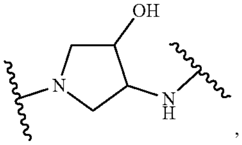 ,

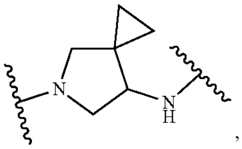 , 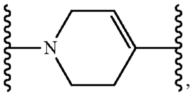 ,

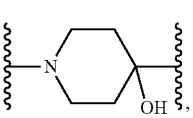 , 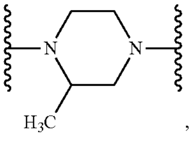 ,

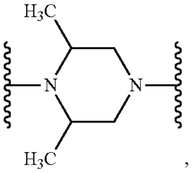 , 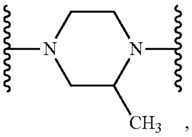 ,

-continued

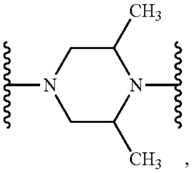 , 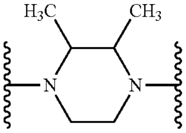 ,

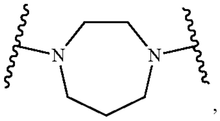 , 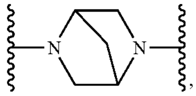 ,

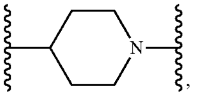 , 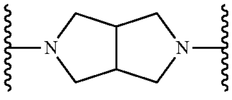 ,

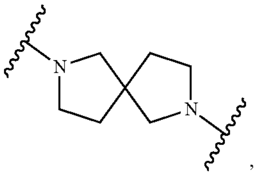 , 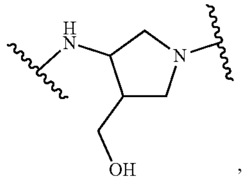 ,

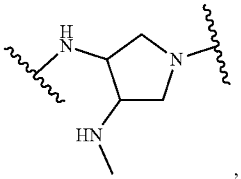 , 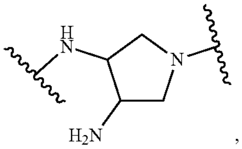 ,

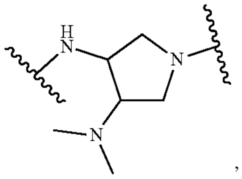 , 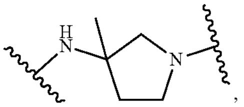 , and

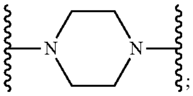 ;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

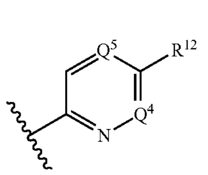

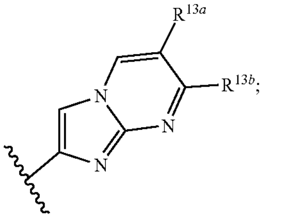

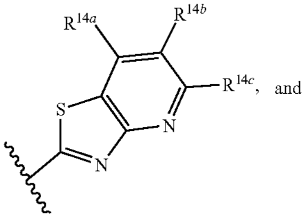

and

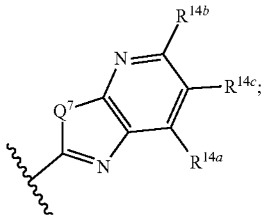

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from 0, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof, and a pharmaceutically acceptable carrier.

In one aspect, disclosed are pharmaceutical composition comprising a therapeutically effective amount of at least one compound having a structure represented by a formula:

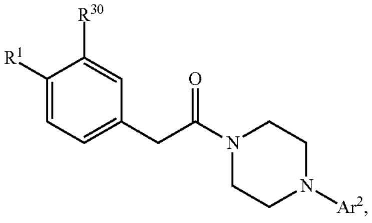

wherein $R^1$ is selected from C1-C4 alkyl, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

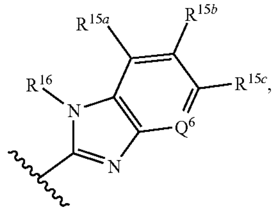

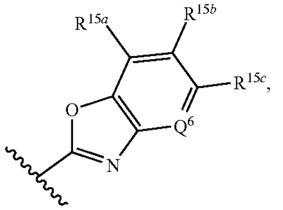

and

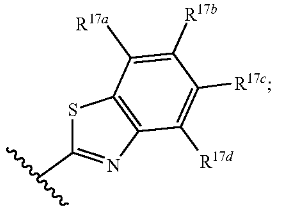

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

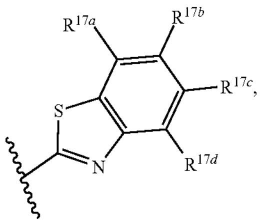

then $R^1$ is selected from $—NR^{10}SO_2R^{11}$, and $Cy^1$, or a pharmaceutically acceptable salt thereof, and a pharmaceutically acceptable carrier.

In one aspect, disclosed are pharmaceutical composition comprising a therapeutically effective amount of at least one compound having a structure selected from:

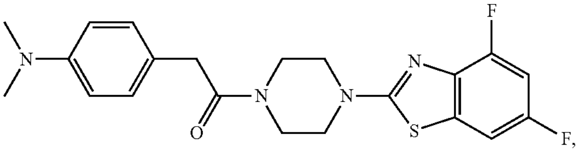

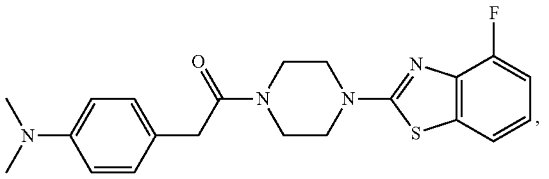

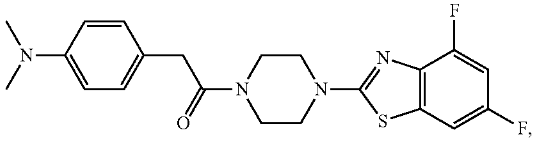

and

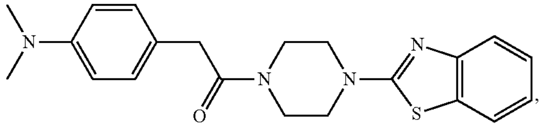

or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with pantothenate kinase activity such as, for example, PKAN, diabetes, metabolic syndrome, and metabolic acidemias.

It is understood that the disclosed compositions can be prepared from the disclosed compounds. It is also understood that the disclosed compositions can be employed in the disclosed methods of using.

E. Methods of Treating a Disorder Associated with PanK Activity

In various aspects, the compounds and compositions disclosed herein are useful for treating, preventing, ameliorating, controlling or reducing the risk of a variety of disorders associated with pantothenate kinase activity, including, for example, PKAN, aging and diabetes. Thus, in one aspect, disclosed are methods of treating a disorder associated with pantothenate kinase activity in a subject, the method comprising administering to the subject an effective amount of at least one disclosed compound or a pharmaceutically acceptable salt thereof.

Thus, in one aspect, disclosed are methods of treating a disorder associated with pantothenate kinase activity in a subject, the method comprising administering to the subject an effective amount of at least one compound having a structure represented by a formula:

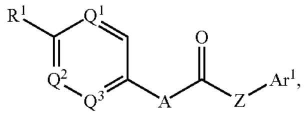

wherein A is selected from —O—, —$CH_2$—, —$CF_2$—, —NH—, —N($CH_3$)—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

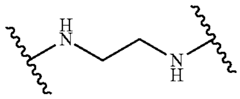

,

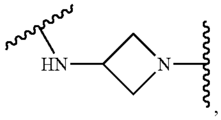

,

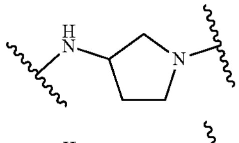

,

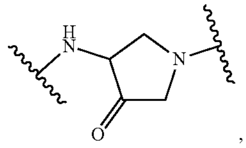

,

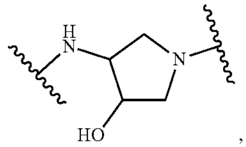

,

-continued
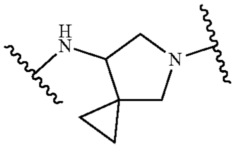
,
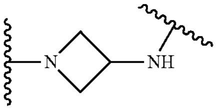
,
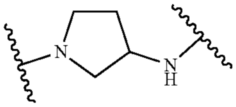
,
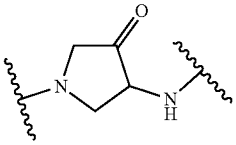
,
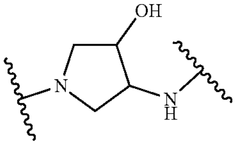
,
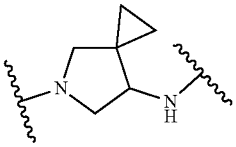
,
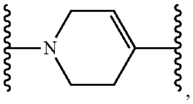
,
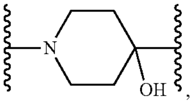
,
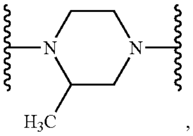
,
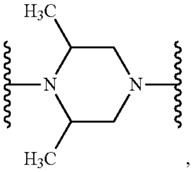
,
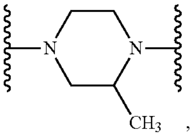
,
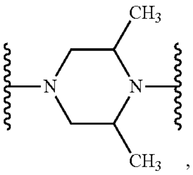
,
-continued
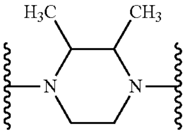
,
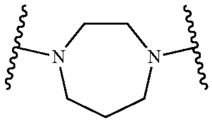
,
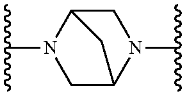
,
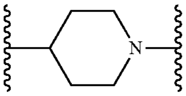
,
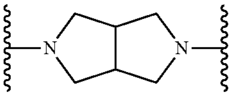
,
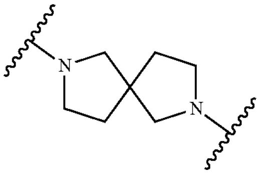
,
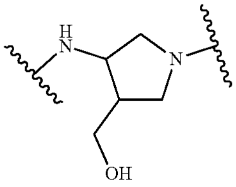
,
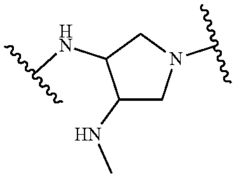
,
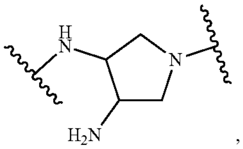
,
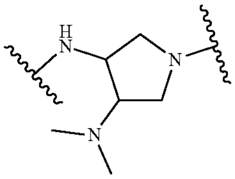
,
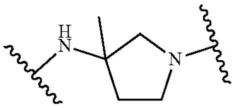
, and
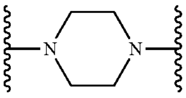
;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

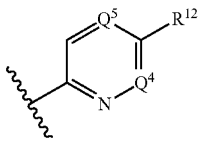

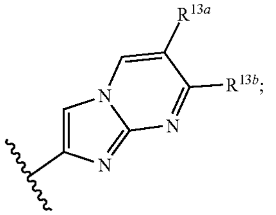

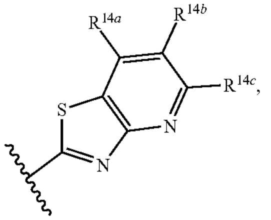

and

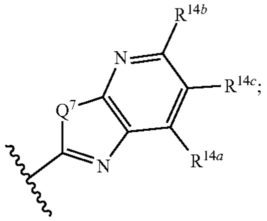

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from 0, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

In one aspect, disclosed are methods of treating a disorder associated with pantothenate kinase activity in a subject, the method comprising administering to the subject an effective amount of at least one compound having a structure represented by a formula:

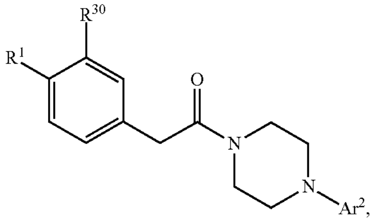

wherein $R^1$ is selected from C1-C4 alkyl, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

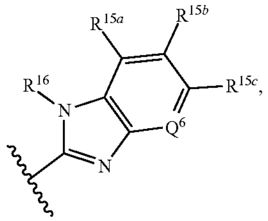

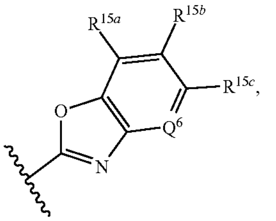

and

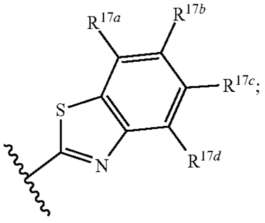

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino, provided that when $Ar^2$ is

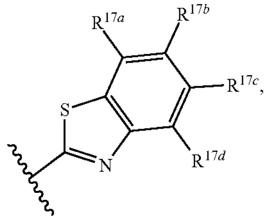

then $R^1$ is selected from —$NR^{10}SO_2R^{11}$, and $Cy^1$, or a pharmaceutically acceptable salt thereof.

In one aspect, disclosed are methods of treating a disorder associated with pantothenate kinase activity in a subject, the method comprising administering to the subject an effective amount of at least one compound having a structure selected from:

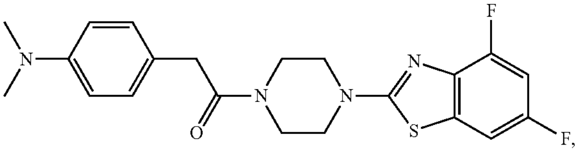

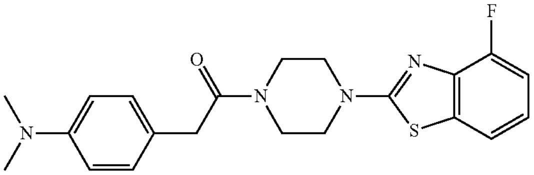

,

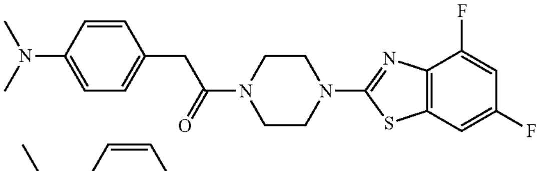

and

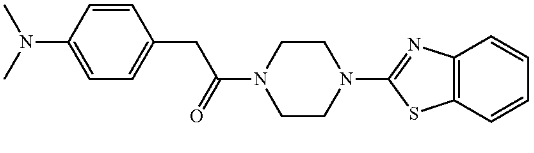

, or a pharmaceutically acceptable salt thereof.

In various aspects, the disclosed compounds can be used in combination with one or more other drugs in the treatment, prevention, control, amelioration, or reduction of risk of disorders associated with PanK activity for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of PanK activity. In a still further aspect, the compound exhibits a decrease in PanK activity.

In a further aspect, the compound exhibits inhibition of PanK activity with an $IC_{50}$ of from about 0.001 μM to about 25 μM. In a still further aspect, the compound exhibits inhibition of PanK activity with an $IC_{50}$ of from about 0.001 μM to about 15 μM. In yet a further aspect, the compound exhibits inhibition of PanK activity with an $IC_{50}$ of from about 0.001 μM to about 10 μM. In an even further aspect, the compound exhibits inhibition of PanK activity with an $IC_{50}$ of from about 0.001 μM to about 5 μM. In a still further aspect, the compound exhibits inhibition of PanK activity with an $IC_{50}$ of from about 0.001 μM to about 1 μM. In yet a further aspect, the compound exhibits inhibition of PanK activity with an $IC_{50}$ of from about 0.001 μM to about 0.5 μM. In an even further aspect, the compound exhibits inhibition of PanK activity with an $IC_{50}$ of from about 0.001 μM to about 0.1 μM. In a still further aspect, the compound exhibits inhibition of PanK activity with an $IC_{50}$ of from about 0.001 μM to about 0.05 μM. In yet a further aspect, the compound exhibits inhibition of PanK activity with an $IC_{50}$ of from about 0.001 μM to about 0.01 μM. In an even further aspect, the compound exhibits inhibition of PanK activity with an $IC_{50}$ of from about 0.001 μM to about 0.005 μM. In a still further aspect, the compound exhibits inhibition of PanK activity with an $IC_{50}$ of from about 0.005 μM to about 25 μM. In yet a further aspect, the compound exhibits inhibition of PanK activity with an $IC_{50}$ of from about 0.01 μM to about 25 μM. In an even further aspect, the compound exhibits inhibition of PanK activity with an $IC_{50}$ of from about 0.05 μM to about 25 μM. In a still further aspect, the compound exhibits inhibition of PanK activity with an $IC_{50}$ of from about 0.1 μM to about 25 μM. In yet a further aspect, the compound exhibits inhibition of PanK activity with an $IC_{50}$ of from about 0.5 μM to about 25 μM. In an even further aspect, the compound exhibits inhibition of PanK activity with an $IC_{50}$ of from about 1 μM to about 25 μM. In a still further aspect, the compound exhibits inhibition of PanK activity with an $IC_{50}$ of from about 5 μM to about 25 μM. In yet a further aspect, the compound exhibits inhibition of PanK activity with an $IC_{50}$ of from about 10 μM to about 25 μM. In an even further aspect, the compound exhibits inhibition of PanK activity with an $IC_{50}$ of from about 15 μM to about 25 μM.

In a further aspect, the subject is a mammal. In a still further aspect, the mammal is human.

In a further aspect, the subject has been diagnosed with a need for treatment of the disorder prior to the administering step. In a still further aspect, the subject is at risk for developing the disorder prior to the administering step.

In a further aspect, the method further comprises identifying a subject at risk for developing the disorder prior to the administering step.

In a further aspect, the disorder associated with pantothenate kinase activity is selected from PKAN, diabetes, metabolic syndrome, and metabolic acidemias.

F. Methods of Modulating PanK Activity in at Least One Cell

In one aspect, disclosed are methods of modulating pantothenate kinase activity in at least one cell, the method comprising the step of contacting the at least one cell with an effective amount of at least one disclosed compound, or a pharmaceutically acceptable salt thereof. In a further aspect, modulating is inhibiting.

Thus, in one aspect, disclosed are methods of modulating pantothenate kinase activity in at least one cell, the method comprising the step of contacting the at least one cell with an effective amount of at least one compound having a structure represented by a formula:

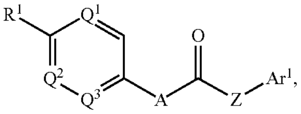

wherein A is selected from —O—, —$CH_2$—, —$CF_2$—, —NH—, —N($CH_3$)—, and —CH(OH)—; wherein each of $Q^1$, $Q^2$, and $Q^3$ is independently selected from N and $CR^{30}$; wherein each occurrence of $R^{30}$, when present, is independently selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein Z is a structure selected from:

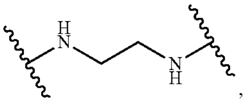 , 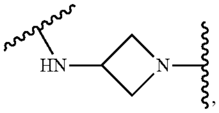 ,

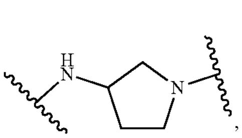 , 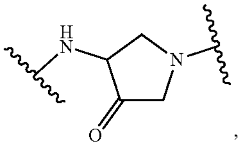 ,

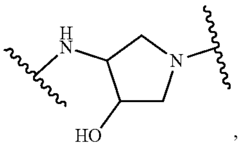 , 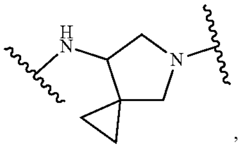 ,

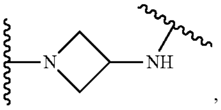 , 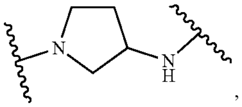 ,

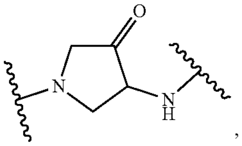 , 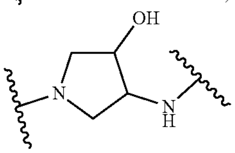 ,

-continued

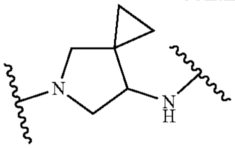 , 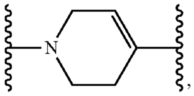 ,

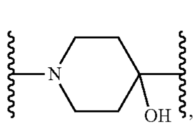 , 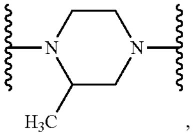 ,

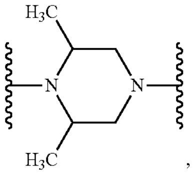 , 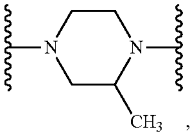 ,

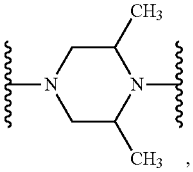 , 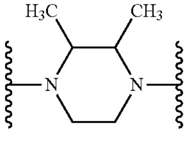 ,

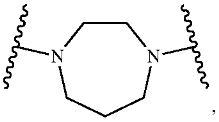 , 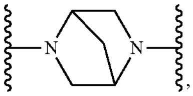 ,

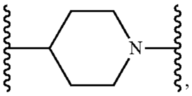 , 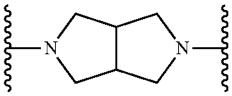 ,

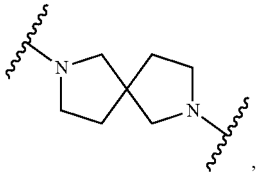 , 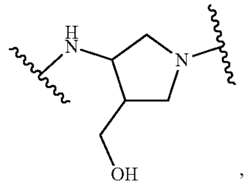 ,

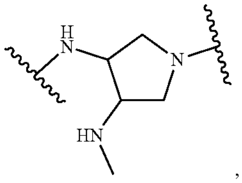 , 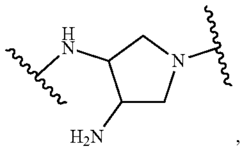 ,

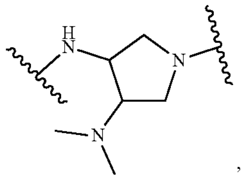 , 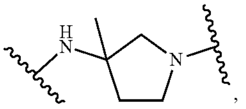 , and

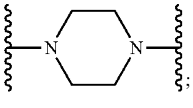 ;

wherein $R^1$ is selected from —$NH_2$, C1-C4 alkyl, (C1-C4) alkylamino, (C1-C4)(C1-C4) dialkylamino, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^1$ is a structure represented by a formula selected from:

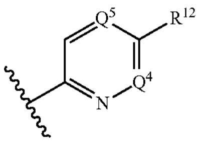

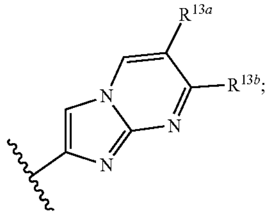
;

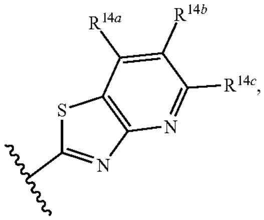
, and

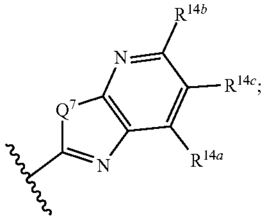
;

wherein one of $Q^4$ and $Q^5$, when present, is N and one of $Q^4$ and $Q^5$, when present, is CH; wherein $R^{12}$, when present, is selected from halogen, —CN, —$NO_2$, C1-C4 polyhaloalkyl, and —$SO_2R^{20}$; wherein $R^{20}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^3$; wherein $Cy^3$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Q^7$, when present, is selected from O, S, and $NR^{16}$; wherein $R^{16}$, when present, is selected from hydrogen, halogen, —CN, —$NO_2$, C1-C4 alkyl, C1-C4 haloalkyl, and C1-C4 haloalkoxy; wherein each of $R^{13a}$ and $R^{13b}$, when present, is selected from hydrogen, halogen, —CN, —$NO_2$, C1-C4 haloalkyl, and C1-C4 haloalkoxy; and wherein each of $R^{14a}$, $R^{14b}$, and $R^{14c}$, when present, is selected from hydrogen, halogen, —CN, —$NO_2$, C1-C4 haloalkyl, and C1-C4 haloalkoxy; provided that when $R^1$ is C1-C4 alkyl, then $Q^4$, when present, is N, $Q^5$, when present, is CH, and $R^{12}$, when present, is polyhaloalkyl, and provided that when $R^1$ is $Cy^1$, $Q^4$, when present, is N, and $Q^5$, when present, is CH, then $R^{12}$, when present, is polyhaloalkyl, or a pharmaceutically acceptable salt thereof.

In one aspect, disclosed are methods of modulating pantothenate kinase activity in at least one cell, the method comprising the step of contacting the at least one cell with an effective amount of at least one compound having a structure represented by a formula:

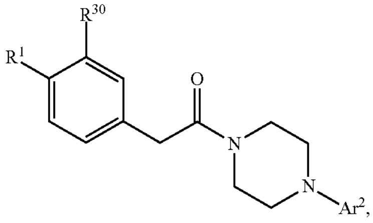
, wherein $R^1$ is selected from C1-C4 alkyl, —$NR^{10}C(O)R^{11}$, —$NR^{10}SO_2R^{11}$, and $Cy^1$; wherein X, when present, is halogen; wherein $R^{10}$, when present, is selected from hydrogen and C1-C4 alkyl; wherein $R^{11}$, when present, is selected from hydrogen, C1-C4 alkyl, C1-C4 haloalkyl, C1-C4 hydroxyalkyl, —(C1-C4 alkyl)-OC(O)—(C1-C4 alkyl), and $Cy^2$; wherein $Cy^2$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Cy^1$, when present, is cycloalkyl substituted with 0, 1, 2, or 3 groups independently selected from halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino, and (C1-C4)(C1-C4) dialkylamino; wherein $Ar^2$ is a structure represented by a formula selected from:

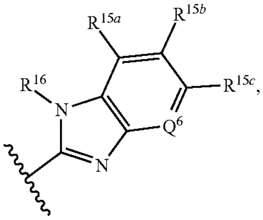
,

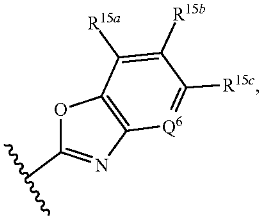
, and

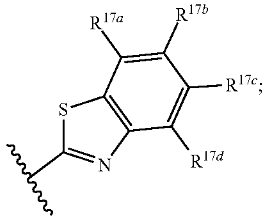
;

wherein $Q^6$, when present, is selected from N and $CR^{21}$; wherein $R^{21}$, when present, is selected from hydrogen, halogen, —CN, —$NO_2$, C1-C4 haloalkyl, and C1-C4 haloalkoxy; wherein each of $R^{15a}$, $R^{15b}$, and $R^{15c}$, when present, is independently selected from hydrogen, halogen, —CN, —$NO_2$, C1-C4 haloalkyl, and C1-C4 haloalkoxy; wherein $R^{16}$, when present, is selected from hydrogen, halogen, —CN, —$NO_2$, C1-C4 alkyl, C1-C4 haloalkyl, and C1-C4 haloalkoxy; wherein each of $R^{17a}$, $R^{17b}$, $R^{17c}$, and $R^{17d}$, when present, is independently selected from hydrogen, halogen, —CN, —$NO_2$, C1-C4 haloalkyl, and C1-C4 haloalkoxy; and wherein $R^{30}$ is selected from hydrogen, halogen, —$NO_2$, —CN, —OH, —SH, —$NH_2$, C1-C4 alkyl, C1-C4 hydroxyalkyl, C1-C4 haloalkyl, C1-C4 alkoxy, C1-C4 haloalkoxy, C1-C4 alkylamino,

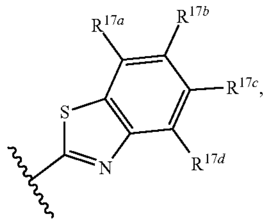

and (C1-C4)(C1-C4) dialkylamino, provided that when $Ar^2$ is, then $R^1$ is selected from —$NR^{10}SO_2R^{11}$, and $Cy^1$, or a pharmaceutically acceptable salt thereof.

In one aspect, disclosed are methods of modulating pantothenate kinase activity in at least one cell, the method comprising the step of contacting the at least one cell with an effective amount of at least one compound having a structure selected from:

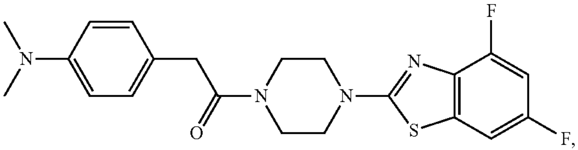

,

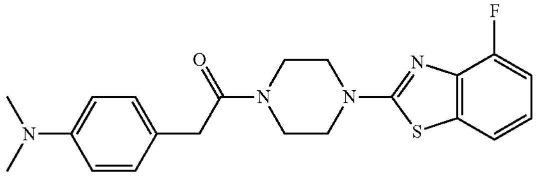

,

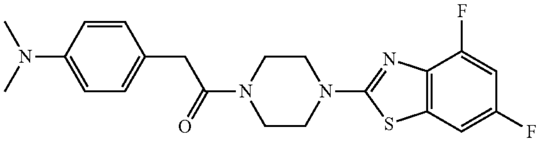

and

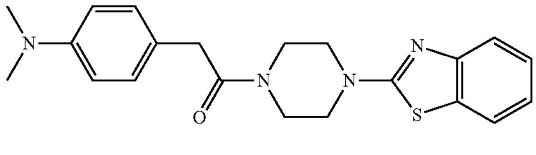

, or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

In a further aspect, the mammal has been diagnosed with a need for treatment of a disorder associated with pantothenate kinase activity prior to the administering step. In a still further aspect, the disorder associated with pantothenate kinase activity is selected from PKAN, diabetes, metabolic syndrome, and metabolic acidemias.

In a further aspect, the mammal has been diagnosed with a need for modulating pantothenate kinase activity prior to the administering step.

G. Methods of Using the Compositions

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder associated with PanK dysfunction in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of protein and especially PanK. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of modulators of PanK.

In a further aspect, the invention relates to the use of a disclosed compound or product of a disclosed method in the manufacture of a medicament for the treatment of a disorder associated with PanK activity and associated Coenzyme A levels such as, for example, PKAN, diabetes, metabolic syndrome, and metabolic acidemias.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of PKAN in a vertebrate animal. In a further aspect, the use relates to the treatment of PKAN in a human subject.

In a further aspect, the use is the treatment of diabetes. In a still further aspect, the diabetes is type II diabetes.

It is understood that the disclosed uses can be employed in connection with the disclosed compounds, methods, compositions, and kits. In a further aspect, the invention relates to the use of a disclosed compound or composition of a medicament for the treatment of a disorder associated with PanK activity in a mammal.

In a further aspect, the invention relates to the use of a disclosed compound or composition in the manufacture of a medicament for the treatment of a disorder associated with PanK activity selected from PKAN, diabetes, metabolic syndrome, and metabolic acidemias.

3. Kits

In one aspect, disclosed are kits comprising a disclosed compound and one or more of: (a) at least one agent known to treat PKAN; (b) at least one agent known to treat diabetes; (c) at least one agent known to treat metabolic acidemias; (d) instructions for treating PKAN; and (d) instructions for treating diabetes, metabolic syndrome, metabolic acidemias, and/or side effects of aging.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with PanK activity. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with PanK activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent known to treat PKAN are co-formulated. In a still further aspect, the compound and the at least one agent known to treat PKAN are co-packaged.

In a further aspect, the compound and the at least one agent known to treat diabetes are co-formulated. In a still further aspect, the compound and the at least one agent known to treat diabetes are co-packaged.

In a further aspect, the at least one agent known to treat PKAN is selected from baclofen, trihexyphenidyl, botulinum toxin, and an iron chelating agent. In a still further aspect, the iron chelating agent is deferriprone.

In a further aspect, the kit further comprises a plurality of dosage forms, the plurality comprising one or more doses; wherein each dose comprises an effective amount of the compound and the at least one agent known to treat PKAN. In a still further aspect, the effective amount is a therapeutically effective amount. In yet a further aspect, the effective amount is a prophylactically effective amount. In an even further aspect, each dose of the compound and at least one agent known to treat PKAN are co-packaged. In a still further aspect, each dose of the compound and the at least one agent known to treat PKAN are co-formulated.

In a further aspect, the at least one agent known to treat diabetes is selected from insulin, albiglutide, exenatide, liraglutide, pramlintide, dulaglutide, acarbose, alogliptin, bromocriptine mesylate, canagliflozin, chlorpropamide, colesevelam, dapagliflozin, empagliflozin, glimepiride, glipizide, glyburide, linagliptin, metformin, miglitol, nateglinide, pioglitazone, repaglinide, rosiglitazone, saxagliptin, and sitagliptin.

In a further aspect, the kit further comprises a plurality of dosage forms, the plurality comprising one or more doses; wherein each dose comprises an effective amount of the compound and at least one agent known to treat diabetes. In a still further aspect, the effective amount is a therapeutically effective amount. In yet a further aspect, the effective amount is a prophylactically effective amount. In an even further aspect, each dose of the compound and at least one agent known to treat diabetes are co-packaged. In a still further aspect, each dose of the compound and at least one agent known to treat diabetes are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder associated with PanK activity prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, PA). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, NY).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

H. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. Synthesis of PZ-4060

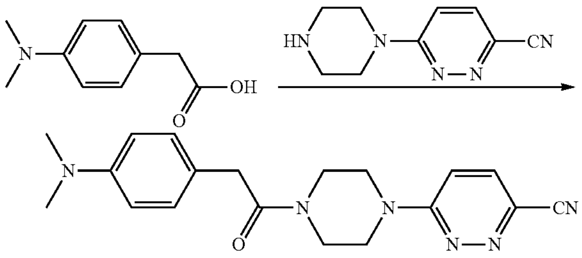

PZ-4060

To a mixture of 4-(Dimethylamino)phenylacetic acid (100 mg, 0.558 mmol) and DIPEA (292 μl, 1.674 mmol) in DMF (3 mL) at room temperature HATU (318 mg, 0.837 mmol) DIPEA (292 μl, 1.674 mmol) were added and allowed to stir for 15 min. then followed by addition of 6-(piperazin-1-yl) pyridazine-3-carbonitrile, HCl (139 mg, 0.614 mmol). The reaction mixture was stirred for 3 hrs. After completion of reaction the mixture was diluted with water (4 mL) and the separated solids were collected by filteration. The crude solid was purified by flash column chromatography using a gradient of methanol in methylene chloride (0 to 15%) as eluant to afford title compound 6-(4-(2-(4-(dimethylamino)phenyl)acetyl)piperazin-1-yl)pyridazine-3-carbonitrile. $^{1}$H NMR (500 MHz, DMSO-$d_6$) δ 7.89 (d, J=9.6 Hz, 1H), 7.34 (d, J=9.7 Hz, 1H), 7.07 (d, J=8.3 Hz, 2H), 6.68 (d, J=8.3 Hz, 2H), 3.81-3.54 (m, 10H), 2.86 (s, 6H). $^{13}$C NMR (126 MHz, DMSO) δ 170.26, 159.12, 149.60, 131.52, 129.78, 129.25, 123.30, 117.82, 113.01, 111.82, 45.05, 44.39, 44.15. ESI-MS (M+1): 352.2.

b. Synthesis of PZ-4061

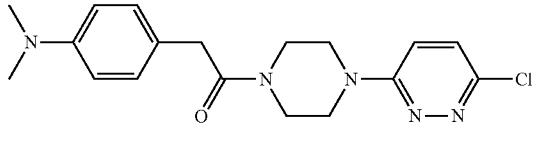 [SMILES: CN(C)c1ccc(CC(=O)N2CCN(c3ccc(Cl)nn3)CC2)cc1]

The reactants 4-(dimethylamino)phenylacetic acid (100 mg, 0.558 mmol), DIPEA (292 μl, 1.674 mmol), DMF (3 mL), HATU (318 mg, 0.837 mmol) and 3-chloro-6-(piperazin-1-yl)pyridazine, HCl (144 mg, 0.614 mmol) were reacted in similar way as explained for PZ-4060 to get 1-(4-(6-chloropyridazin-3-yl)piperazin-1-yl)-2-(4-(dimethylamino)phenyl)ethanone. $^{1}$H NMR (500 MHz, DMSO-$d_6$) δ 7.55 (d, J=9.5 Hz, 1H), 7.39 (d, J=9.6 Hz, 1H), 7.07 (d, J=8.6 Hz, 2H), 6.68 (d, J=8.6 Hz, 2H), 3.70-3.45 (m, 10H), 2.86 (s, 6H). $^{13}$C NMR (126 MHz, DMSO) δ 170.15, 159.57, 149.59, 146.79, 129.75, 129.47, 123.36, 117.39, 113.01, 45.18, 45.07, 44.82. ESI-MS (M+1): 362.3.

c. Synthesis of PZ-4069

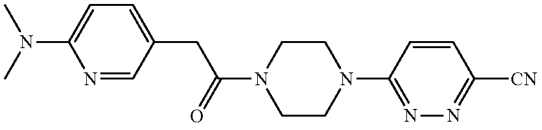

The mixture of 2-(6-(dimethylamino)pyridin-3-yl)acetic acid, Lithium (150 mg, 0.802 mmol; prepared as explained in the literature (*J Med. Chem.*, 2017, 60, 23, 9769-9789), 6-(piperazin-1-yl)pyridazine-3-carbonitrile, HCl (271 mg, 1.202 mmol), HATU (305 mg, 0.802 mmol) and DIPEA (420 μl, 2.405 mmol) in DMF (3 mL) treated as explained for example PZ-4060 to get 6-(4-(2-(6-(dimethylamino)pyridin-3-yl)acetyl)piperazin-1-yl)pyridazine-3-carbonitrile. $^{1}$H NMR (500 MHz, Chloroform-d) δ 8.03 (d, J=2.4 Hz, 1H), 7.50 (d, J=9.6 Hz, 1H), 7.44 (dd, J=8.8, 2.5 Hz, 1H), 6.85 (d, J=9.6 Hz, 1H), 6.54 (d, J=8.8 Hz, 1H), 3.93-3.59 (m, 10H), 3.10 (s, 6H). $^{13}$C NMR (126 MHz, $CDCl_3$) δ 169.95, 158.43, 158.22, 146.88, 137.98, 130.79, 129.88, 117.10, 116.58, 110.01, 106.30, 53.45, 45.13, 44.34, 43.97, 40.98, 38.26, 37.08. ESI-MS (M+1): 352.3.

d. Synthesis of PZ-4070

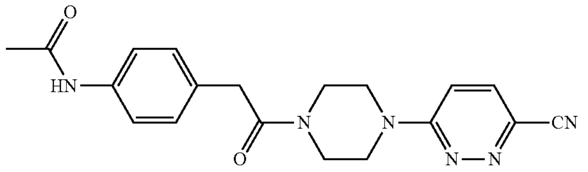 [SMILES: CC(=O)Nc1ccc(CC(=O)N2CCN(c3ccc(C#N)nn3)CC2)cc1]

The mixture of 2-(4-acetamidophenyl)acetic acid, Lithium (100 mg, 0.500 mmol), 6-(piperazin-1-yl)pyridazine-3-carbonitrile, HCl (135 mg, 0.600 mmol), HATU (190 mg, 0.500 mmol), DIPEA (262 μl, 1.499 mmol) in DMF (3 mL) treated as explained for example PZ-4060 to get N-(4-(2-(4-(6-cyanopyridazin-3-yl)piperazin-1-yl)-2-oxoethyl)phenyl)acetamide. $^{1}$H NMR (500 MHz, DMSO-$d_6$) δ 9.89 (s, 1H), 7.89 (d, J=9.6 Hz, 1H), 7.51 (d, J=8.1 Hz, 2H), 7.35 (d, J=9.7 Hz, 1H), 7.16 (d, J=8.1 Hz, 2H), 3.94-3.48 (m, 11H), 2.03 (s, 3H). $^{13}$C NMR (126 MHz, DMSO) δ 169.80, 168.60, 159.13, 138.17, 131.53, 130.57, 129.66, 129.26, 119.46, 117.82, 111.83, 45.01, 44.36, 44.12, 24.42. ESI-MS (M+1): 365.4.

e. Synthesis of PZ-4071

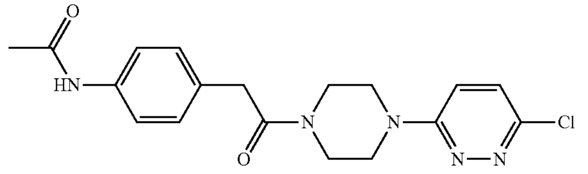 [SMILES: CC(=O)Nc1ccc(CC(=O)N2CCN(c3ccc(Cl)nn3)CC2)cc1]

The mixture of 2-(4-acetamidophenyl)acetic acid, Lithium (100 mg, 0.500 mmol), 3-chloro-6-(piperazin-1-yl)pyridazine, HCl (141 mg, 0.600 mmol), HATU (190 mg, 0.500 mmol) and DIPEA (262 μl, 1.499 mmol) in DMF (3 mL) treated as explained for example PZ-4060 to get N-(4-(2-(4-(6-chloropyridazin-3-yl)piperazin-1-yl)-2-oxoethyl)phenyl)acetamide. $^{1}$H NMR (500 MHz, DMSO-$d_6$) δ 9.89 (s, 1H), 7.56 (d, J=9.6 Hz, 1H), 7.51 (d, J=8.2 Hz, 2H), 7.39 (d, J=9.6 Hz, 1H), 7.16 (d, J=8.1 Hz, 2H), 3.81-3.46 (m, 10H), 2.03 (s, 3H). $^{13}$C NMR (126 MHz, DMSO) δ 169.68, 168.59, 159.57, 146.80, 138.16, 130.63, 129.63, 129.48, 119.46, 117.40, 45.15, 45.04, 44.80, 24.42. ESI-MS (M+1): 374.4.

f. Synthesis of PZ-4109

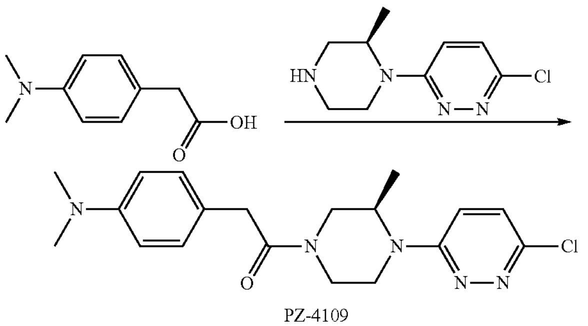

PZ-4109

The reaction was done as explained for example PZ-4060. $^{1}$H NMR (500 MHz, DMSO-$d_6$) δ 7.54 (dd, J=9.6, 5.0 Hz, 1H), 7.32 (dd, J=9.7, 2.3 Hz, 1H), 7.16-7.01 (m, 2H), 6.74-6.61 (m, 2H), 4.57-4.43 (m, 1H), 4.35-4.22 (m, 1H), 4.13-3.86 (m, 2H), 3.74-3.51 (m, 2H), 3.41 (dd, J=13.5, 3.8 Hz, 1H), 3.27-2.94 (m, 2H), 2.86 (s, 3H), 2.70 (s, 3H), 0.97 (t, J=6.3 Hz, 3H). $^{13}$C NMR (126 MHz, DMSO) δ 165.04, 158.86, 149.67, 149.59, 146.50, 146.44, 129.89, 129.66, 129.47, 123.48, 123.39, 117.01, 116.96, 113.00, 112.98, 112.96, 55.38, 49.41, 48.04, 47.91, 45.30, 45.27, 21.23, 14.03, 13.54. ESI-MS (M+1): 374.5.

g. Synthesis of PZ-4110

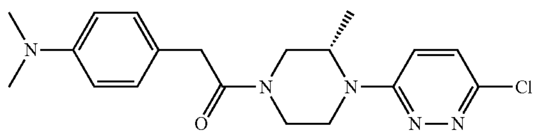 [SMILES: C[C@H]1CN(C(=O)Cc2ccc(N(C)C)cc2)CCN1c1ccc(Cl)nn1]

The reaction was done as explained for example PZ-4060. $^{1}$H NMR (500 MHz, DMSO-$d_6$) δ 7.54 (dd, J=9.6, 5.0 Hz, 1H), 7.32 (dd, J=9.7, 2.3 Hz, 1H), 7.13-7.04 (m, 2H), 6.77-6.57 (m, 2H), 4.61-4.41 (m, 1H), 4.36-4.19 (m, 1H), 4.13-3.84 (m, 2H), 3.76-3.50 (m, 2H), 3.46-2.94 (m, 3H), 2.86 (s, 3H), 2.70 (s, 3H), 0.97 (t, J=6.3 Hz, 3H). 13C NMR (126 MHz, DMSO) δ 165.05, 158.86, 149.67, 149.60, 146.50, 146.45, 129.89, 129.79, 129.66, 129.48, 123.48, 123.40, 117.02, 116.97, 112.98, 112.96, 55.38, 49.41, 48.04, 47.91, 45.30, 45.27, 14.03, 13.54. ESI-MS (M+1): 374.5.

h. Synthesis of PZ-4111

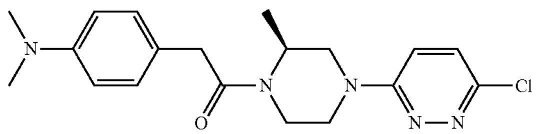 [SMILES: C[C@H]1CN(c2ccc(Cl)nn2)CCN1C(=O)Cc1ccc(N(C)C)cc1]

The reaction was done as explained for example PZ-4060. $^{1}$H NMR (500 MHz, DMSO-$d_6$) δ 7.53 (d, J=9.6 Hz, 1H), 7.37 (dd, J=14.6, 8.9 Hz, 1H), 7.12-6.98 (m, 2H), 6.67 (d, J=8.5 Hz, 2H), 4.64 (s, 1H), 4.40-4.21 (m, 1H), 4.17-4.05 (m, 2H), 3.93-3.50 (m, 3H), 3.25-3.04 (m, 1H), 3.02-2.79 (m, 4H), 2.70 (s, 3H), 1.04 (d, J=6.7 Hz, 3H). 13C NMR (126 MHz, DMSO) δ 165.05, 158.86, 149.67, 149.60, 146.50, 146.45, 129.89, 129.79, 129.66, 129.48, 123.48, 123.40, 117.02, 116.97, 112.98, 112.96, 55.38, 49.41, 48.04, 47.91, 45.30, 45.27, 14.03, 13.54. ESI-MS (M+1): 374.5.

i. Synthesis of PZ-4112

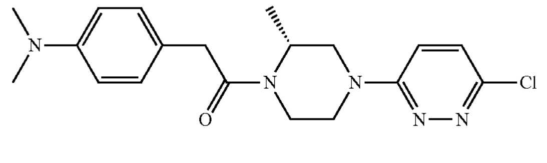 [SMILES: C[C@@H]1CN(c2ccc(Cl)nn2)CCN1C(=O)Cc1ccc(N(C)C)cc1]

The reaction was done as explained for example PZ-4060. $^{1}$H NMR (500 MHz, DMSO-$d_6$) δ 7.53 (d, J=9.6 Hz, 1H), 7.43-7.30 (m, 1H), 7.05 (d, J=8.0 Hz, 2H), 6.67 (d, J=8.5 Hz, 2H), 4.72-4.56 (m, 1H), 4.46-4.19 (m, 1H), 4.16-4.05 (m, 2H), 3.94-3.50 (m, 3H), 3.28-2.78 (m, 5H), 2.70 (s, 3H), 1.04 (d, J=6.7 Hz, 3H). ESI-MS (M+1): 374.5.

j. Synthesis of PZ-4127

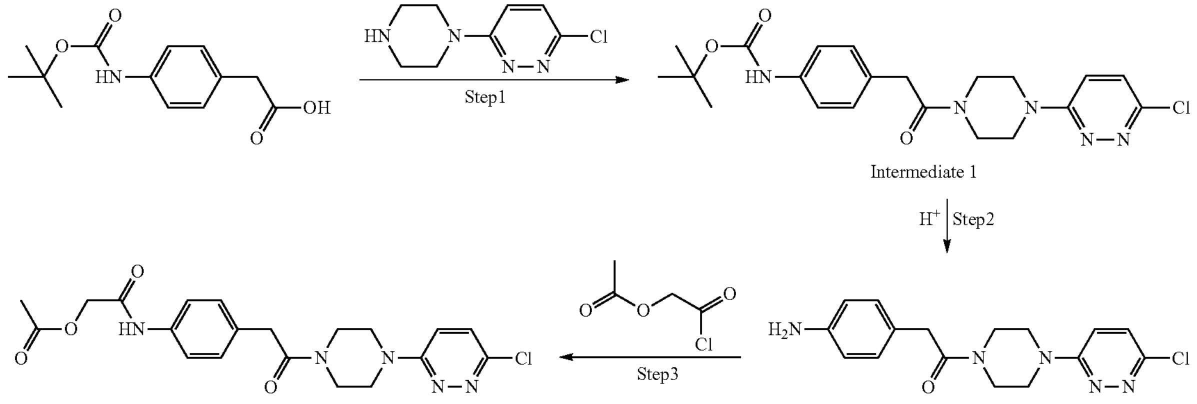

The mixture of 4-(t-Butyloxycarbonylamino)phenylacetic acid (1 g, 3.98 mmol), 3-chloro-6-(piperazin-1-yl) pyridazine, HCl (1.029 g, 4.38 mmol), HATU (2.270 g, 5.97 mmol), DIPEA (2.085 ml, 11.94 mmol), and DMF (3 mL) were treated as explained for example PZ-4060 to get intermediate 1, tert-butyl (4-(2-(4-(6-chloropyridazin-3-yl) piperazin-1-yl)-2-oxoethyl)phenyl)carbamate. ESI-MS (M+1): 432.6.

To a mixture of tert-butyl (4-(2-(4-(6-chloropyridazin-3-yl)piperazin-1-yl)-2-oxoethyl)phenyl)carbamate (0.5 g, 1.158 mmol) in DCM (10 mL) 4 N. HCl (1.447 ml, 5.79 mmol) was added and allowed to stir for 2 h and then evaporated to dryness to get intermediate 2, 2-(4-aminophenyl)-1-(4-(6-chloropyridazin-3-yl)piperazin-1-yl)ethanone. ESI-MS (M+1): 332.2.

To a mixture of 2-(4-aminophenyl)-1-(4-(6-chloropyridazin-3-yl)piperazin-1-yl)ethanone, HCl (260 mg, 0.706 mmol), DIPEA (493 μl, 2.82 mmol) in DCM (6 mL) at ice bath temperature, acetoxyacetyl chloride (91 μl, 0.847 mmol) was added and the reaction mixture was allowed to stir for 12 h. The reaction mixture was diluted with water, extracted with ethyl acetate, dried over $Na_2SO_4$, filtered and evaporated under reduced pressure to get the crude. The crude was subjected to flash column chromatography using a gradient of ethyl acetate and hexanes (0 to 100%) as eluant to afford title compound 2-((4-(2-(4-(6-chloropyridazin-3-yl)piperazin-1-yl)-2-oxoethyl)phenyl)amino)-2-oxoethyl acetate. $^1H$ NMR (500 MHz, DMSO-$d_6$) δ 10.04 (s, 1H), 7.56 (d, J=9.6 Hz, 1H), 7.51 (d, J=8.4 Hz, 2H), 7.39 (d, J=9.6 Hz, 1H), 7.19 (d, J=8.4 Hz, 2H), 4.63 (s, 2H), 3.73 (s, 2H), 3.67-3.46 (m, 8H), 2.12 (s, 3H). $^{13}C$ NMR (126 MHz, DMSO) δ 170.49, 169.62, 165.81, 159.57, 146.80, 137.24, 131.31, 129.79, 129.48, 119.83, 117.40, 62.98, 45.14, 45.05, 44.79, 20.95. ESI-MS (M+1): 432.4.

k. Synthesis of PZ-4128

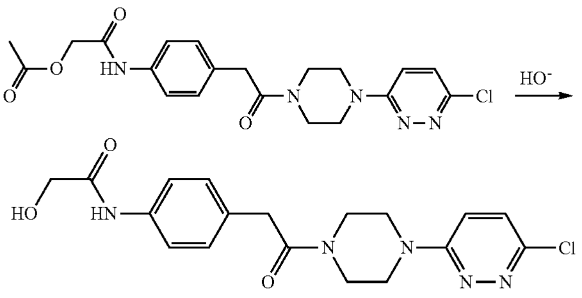

PZ-4128

The mixture of 2-((4-(2-(4-(6-chloropyridazin-3-yl)piperazin-1-yl)-2-oxoethyl)phenyl)amino)-2-oxoethyl acetate (50 mg, 0.116 mmol), lithium hydroxide (5.55 mg, 0.232 mmol) and 2:1 MeOH-Water (3 mL) stirred at room temperature for 2 h. The reaction mixture was filtered and washed with water to collect solid N-(4-(2-(4-(6-chloropyridazin-3-yl)piperazin-1-yl)-2-oxoethyl)phenyl)-2-hydroxyacetamide. $^1H$ NMR (500 MHz, DMSO-$d_6$) δ 7.60-7.51 (m, 3H), 7.38 (d, J=9.6 Hz, 1H), 7.11 (d, J=8.1 Hz, 2H), 3.86 (s, 2H), 3.70 (s, 2H), 3.65-3.45 (m, 8H). $^{13}C$ NMR (126 MHz, DMSO) δ 171.13, 169.81, 159.57, 146.78, 129.47, 129.32, 120.85, 117.38, 62.57, 45.17, 45.06, 44.78. ESI-MS (M+1): 390.3.

l. Synthesis of PZ-4140

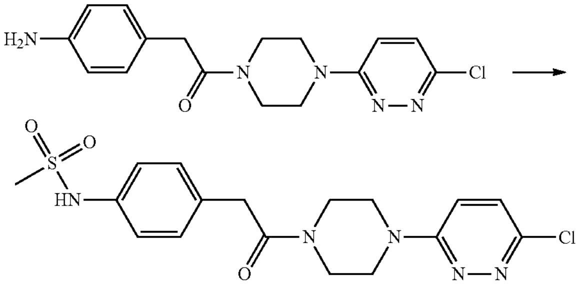

PZ-4140

The mixture of 2-(4-aminophenyl)-1-(4-(6-chloropyridazin-3-yl)piperazin-1-yl)ethanone, HCl (140 mg, 0.380 mmol) and DIPEA (266 μl, 1.521 mmol) in DCM (5 mL) was reacted with mesyl-Cl (35.5 μl, 0.456 mmol) similar to example PZ-4127 to get N-(4-(2-(4-(6-chloropyridazin-3-yl)piperazin-1-yl)-2-oxoethyl)phenyl)methanesulfonamide. $^1H$ NMR (500 MHz, DMSO-$d_6$) δ 9.66 (s, 1H), 7.56 (d, J=9.6 Hz, 1H), 7.40 (d, J=9.6 Hz, 1H), 7.21 (d, J=8.5 Hz, 2H), 7.15 (d, J=8.5 Hz, 2H), 3.74 (s, 2H), 3.68-3.50 (m, 8H), 2.96 (s, 3H). 13C NMR (126 MHz, DMSO) δ 169.57, 159.57, 146.80, 137.11, 131.85, 130.39, 129.48, 120.49, 117.39, 54.01, 45.11, 45.03, 44.79, 18.54, 17.19. ESI-MS (M+1): 410.4.

m. Synthesis of PZ-4200

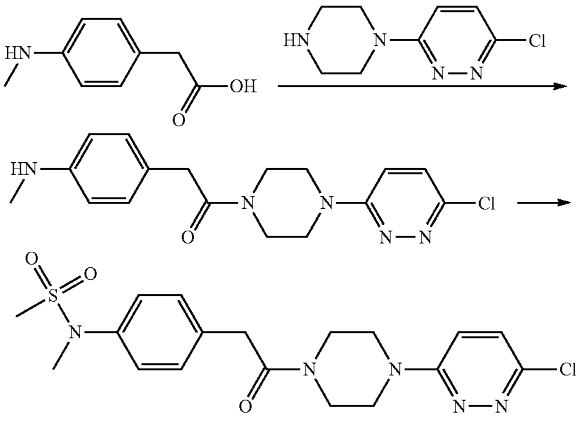

PZ-4200

$^1H$ NMR (500 MHz, DMSO-$d_6$) δ 7.57 (d, J=9.6 Hz, 1H), 7.41 (d, J=9.6 Hz, 1H), 7.35 (d, J=8.5 Hz, 2H), 7.28 (d, J=8.5 Hz, 2H), 3.80 (s, 2H), 3.72-3.54 (m, 8H), 3.22 (s, 3H), 2.93 (s, 3H). $^{13}C$ NMR (126 MHz, DMSO) δ 169.42, 159.58, 146.81, 140.43, 135.22, 130.32, 129.50, 126.60, 117.40, 45.11, 45.04, 44.80, 38.28, 35.40; ESI-MS (M+1): 424.6.

n. Synthesis of PZ-4202

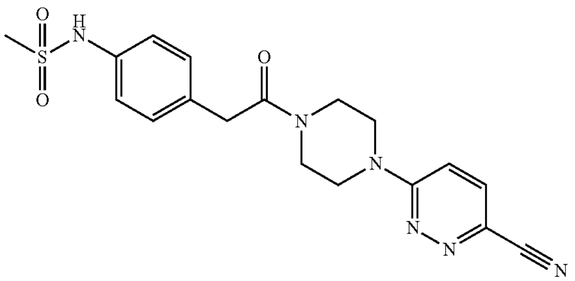 [SMILES: CS(=O)(=O)Nc1ccc(CC(=O)N2CCN(c3ccc(C#N)nn3)CC2)cc1]

The amine (50 mg, 0.155 mmol) was dissolved in $CH_2Cl_2$ (2 mL) followed by the addition of pyridine (13.80 uL, 0.171 mmol). MsCl (13.30 uL, 0.171 mmol) was added dropwise and the reaction was allowed to warm to room temperature and stirred overnight. The reaction was washed with $H_2O$ (5 mL) and the organic layer was dried over sodium sulfate. The compound was purified by flash chromatography EtOAc to 20% MeOH/EtOAc to give the product as a white powder (52 mg, 84%). $^1H$ NMR (400 MHz, DMSO-$d_6$) δ 9.65 (s, 1H), 7.90 (d, J=9.7 Hz, 1H), 7.35 (d, J=9.7 Hz, 1H), 7.25-7.10 (m, 4H), 3.75 (s, 5H), 3.66 (dd, J=16.2, 5.4 Hz, 4H), 2.96 (s, 3H). ESI-MS (M+1) 401.62.

o. Synthesis of PZ-4215

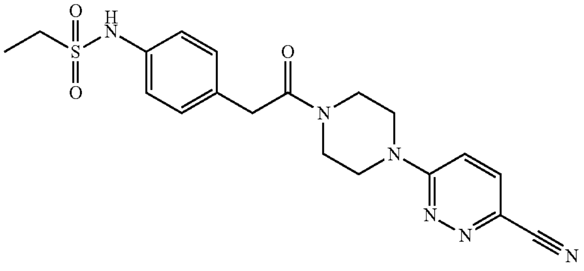 [SMILES: CCS(=O)(=O)Nc1ccc(CC(=O)N2CCN(c3ccc(C#N)nn3)CC2)cc1]

The amine (100 mg, 0.279 mmol) was dissolved in $CH_2Cl_2$ (2 mL) followed by the addition of pyridine (47.3 uL, 0.585 mmol). Ethane sulfonyl chloride (29.2 uL, 0.307 mmol) was added dropwise and the reaction was allowed to warm to room temperature and stirred overnight. The reaction was washed with $H_2O$ (5 mL) and the organic layer was dried over sodium sulfate. The compound was purified by flash chromatography EtOAc to 20% MeOH/EtOAc to give the product as a white powder (70 mg, 60.6%). $^1$H NMR (400 MHz, DMSO-$d_6$) δ 9.71 (s, 1H), 7.90 (d, J=9.7 Hz, 1H), 7.35 (d, J=9.7 Hz, 1H), 7.18 (q, J=8.7 Hz, 4H), 3.74 (s, 4H), 3.70-3.60 (m, 4H), 3.06 (q, J=7.3 Hz, 2H), 1.19 (t, J=7.4 Hz, 3H). 13C NMR (101 MHz, DMSO) δ 169.19, 158.63, 136.64, 131.03, 129.94, 119.62, 111.32, 81.22, 57.41, 44.96, 40.12, 39.91, 39.70, 39.49, 39.28, 39.19, 39.08, 38.96, 38.87, 7.97. ESI-MS (M+1) 415.42.

p. Synthesis of PZ-4216

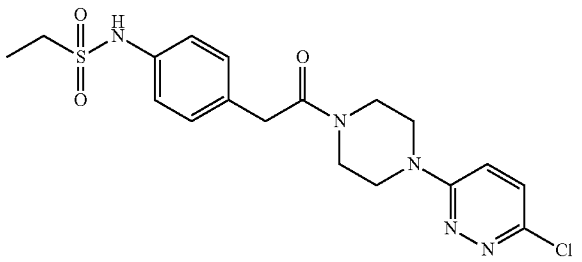 [SMILES: CCS(=O)(=O)Nc1ccc(CC(=O)N2CCN(c3ccc(Cl)nn3)CC2)cc1]

The amine (100 mg, 0.279 mmol) was dissolved in $CH_2Cl_2$ (2 mL) followed by the addition of pyridine (47.3 uL, 0.585 mmol). Ethane sulfonyl chloride (29.2 uL, 0.307 mmol) was added dropwise and then the reaction was allowed to warm to room temperature and stirred overnight. The reaction was washed with $H_2O$ (5 mL) and the organic layer was dried over sodium sulfate. The compound was purified by flash chromatography EtOAc to 20% MeOH/EtOAc to give the product as a white powder (62 mg, 53.9%). $^1$H NMR (400 MHz, DMSO-$d_6$) δ 9.71 (s, 1H), 7.56 (d, J=9.6 Hz, 1H), 7.40 (d, J=9.7 Hz, 1H), 7.18 (q, J=8.6 Hz, 4H), 3.71 (d, J=15.7 Hz, 2H), 3.67-3.52 (m, 7H), 3.05 (q, J=7.3 Hz, 2H), 1.18 (t, J=7.3 Hz, 3H). $^{13}$C NMR (101 MHz, DMSO) δ 169.08, 159.07, 136.63, 131.15, 129.91, 128.98, 119.64, 116.89, 44.95, 40.12, 39.91, 39.70, 39.49, 39.28, 39.07, 38.87, 7.97. ESI-MS (M+1) 424.52.

q. Synthesis of PZ-4283

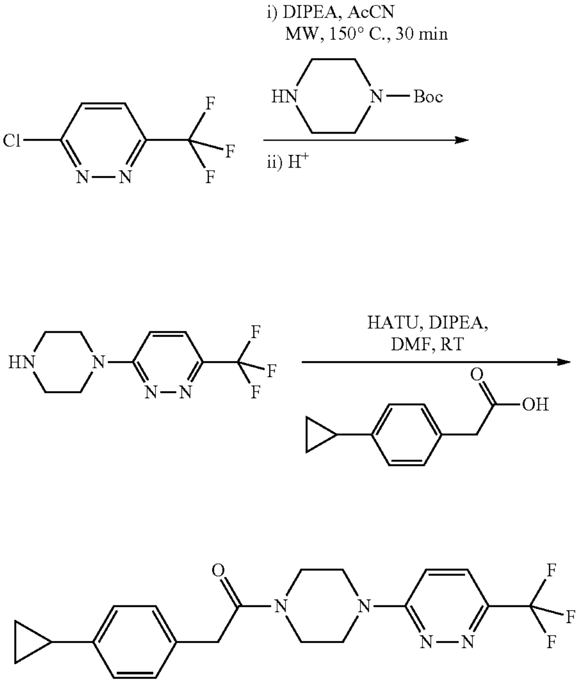

PZ-4283

The mixture of tert-butyl piperazine-1-carboxylate (250 mg, 1.342 mmol), 3-chloro-6-(trifluoromethyl)pyridazine (270 mg, 1.476 mmol) and DIPEA (0.469 ml, 2.68 mmol) in Acetonitrile (5 ml) was subjected to microwave irradiation at 150° C. for 30 min. The reaction mixture was cooled to room temperature and the solid product separated was collected by filtration and washed with water. The crude product was dried and suspended in 10 mL DCM followed by addition of 5 mL 4 N. hydrochloric acid in 1,4-dioxane and stirred for 2 hours. The reaction mixture then evaporated to dryness under reduced pressure to obtain tert-butyl 4-(6-(trifluoromethyl)pyridazin-3-yl)piperazine-1-carboxylate (300 mg) as a white solid.

To a mixture of 2-(4-cyclopropylphenyl)acetic acid (100 mg, 0.567 mmol) and DIPEA (297 μl, 1.702 mmol) in DMF (3 mL) at room temperature HATU (259 mg, 0.681 mmol) was added and stirred for 15 minutes followed by addition of 3-(piperazin-1-yl)-6-(trifluoromethyl)pyridazine, HCl (152 mg, 0.567 mmol) and the reaction mixture was allowed to stir for overnight. After completion of reaction the reaction mixture was diluted with cold water and the solids were collected by filtration followed by washing with water. The solids were dried triturated with methanol followed by filtration to get the pure 2-(4-cyclopropylphenyl)-1-(4-(6-(trifluoromethyl)pyridazin-3-yl)piperazin-1-yl)ethanone. 1H NMR (500 MHz, DMSO-d6) δ 7.83 (d, J=9.6 Hz, 1H), 7.41 (d, J=9.7 Hz, 1H), 7.13 (d, J=8.1 Hz, 2H), 7.02 (d, J=8.1 Hz, 2H), 3.83-3.55 (m, 10H), 1.88 (tt, J=8.4, 5.0 Hz, 1H), 0.99-0.86 (m, 2H), 0.69-0.58 (m, 2H). 13C NMR (126 MHz, DMSO) δ 169.80, 160.74, 142.16, 132.94, 129.31, 125.79, 113.28, 45.09, 44.55, 44.31, 15.19, 9.72. ESI-MS (M+1): 391.42 r. Synthesis of PZ-4284

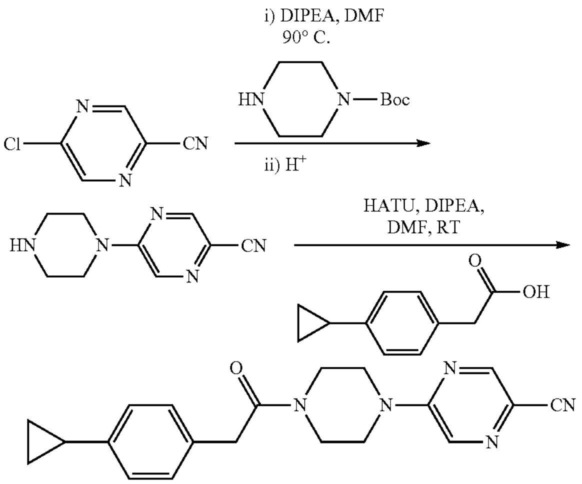

PZ-4284 was made as explained for PZ-4283 using 5-chloropyrazine-2-carbonitrile. $^1$H NMR (500 MHz, Chloroform-d) δ 8.35 (d, J=1.4 Hz, 1H), 8.10 (d, J=1.5 Hz, 1H), 7.16 (d, J=8.1 Hz, 2H), 7.05 (d, J=8.1 Hz, 2H), 3.89-3.67 (m, 6H), 3.66-3.50 (m, 4H), 1.89 (tt, J=8.4, 5.1 Hz, 1H), 1.05-0.88 (m, 2H), 0.75-0.62 (m, 2H). 13C NMR (126 MHz, CDCl3) δ 170.05, 153.72, 147.05, 143.00, 131.25, 130.90, 128.35, 126.23, 117.06, 117.00, 45.24, 43.86, 43.61, 41.02, 40.79, 15.07, 9.30. ESI-MS (M+1): 348.52.

s. Synthesis of PZ-4295

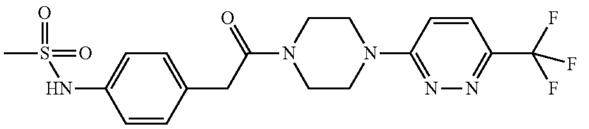 [SMILES: CS(=O)(=O)Nc1ccc(CC(=O)N2CCN(c3ccc(C(F)(F)F)nn3)CC2)cc1]

PZ-4295 was made as explained for PZ-4283 using 2-(4-(methylsulfonamido)phenyl)acetic acid. 1H NMR (400 MHz, DMSO-d6) δ 9.65 (s, 1H), 7.83 (d, J=9.7 Hz, 1H), 7.41 (d, J=9.5 Hz, 1H), 7.29-7.08 (m, 3H), 3.82-3.58 (m, 10H), 2.96 (s, 3H). ESI-MS (M+1): 444.43.

t. General Procedures to Synthesize the Piperazine Analogs i. General Procedure 1

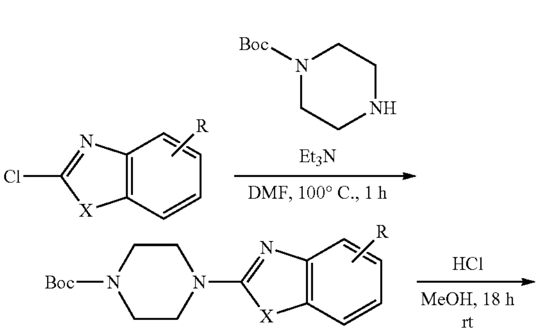

-continued

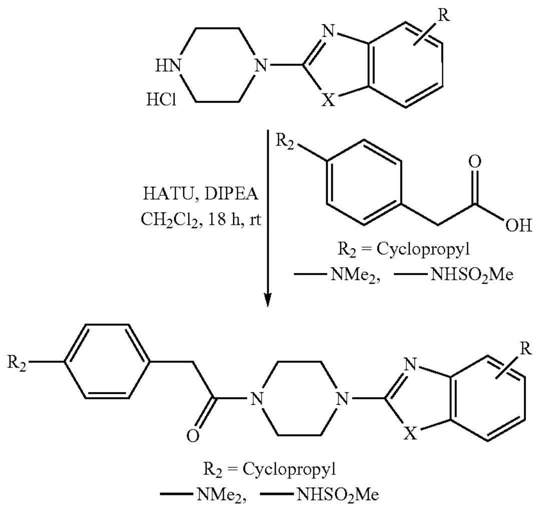

Step 1: The appropriate hetero aryl chloride (1 equiv.) was added to the mixture of 1-Boc-piperazine (1.2 equiv.) and Et3N (2.1 equiv.) in DMF. The reaction was heated to 100° C. and stirred for 12 hours. The reaction was cooled to room temperature. Following the addition of ice chips to the reaction, the product crashed out as an off white solid.

Step 2: The Boc protected benzathiazole piperazine was added to $CH_2C12$ followed by the addition of 4 M HCl in dioxane (5 equiv.) the reaction was then stirred for 3 hours. The reaction was then cooled and the solvent removed under reduced pressure to give the resultant salt as an off white solid.

Step 3: The benzathiazole piperazine (1 equiv.) was added to a pre-stirred mixture of substituted phenyl acetic acid (1.2 equiv.), HATU (1.2 equiv.) and DIPEA (2.1 equiv.) in $CH_2Cl_2$ at room temperature. The reaction was then stirred for 18 hours. Ice chips were added to the reaction, product crashed out as an off white solid, which was collected by filtration followed by washing with water. The product obtained was further purified by trituration or flash column purification.

ii. General Procedure 2

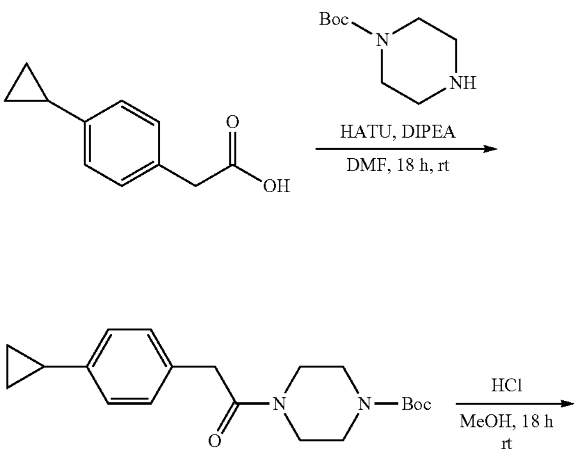

-continued

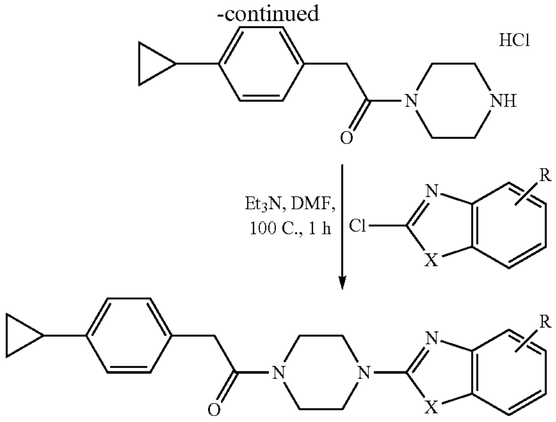

Step 1: The Boc piperazine (1 equiv.) was added to a pre-stirred mixture of cyclopropyl phenyl acetic acid (1.2 equiv.), HATU (1.2 equiv.) and DIPEA (2.1 equiv.) in $CH_2Cl_2$ at room temperature. The reaction was then stirred for 18 hours. Ice chips were then added to the reaction, if the product precipitated it was filtered and washed with $H_2O$.

Step 2: The intermediate from step 1 was added to $CH_2Cl_2$ followed by the addition of 4 M HCl in dioxane (5 equiv.) the reaction was stirred for 3 hours. The reaction was then cooled, and the solvent removed under reduced pressure to give the resultant salt as an off white solid.

Step 3: The intermediate from step 2 (1 equiv.) was added to DMF followed by $Et_3N$ (2.1 equiv.) and corresponding heteroaryl chloride (1.2 equiv.). The reaction was heated to 100° C. and stirred for 12 hours. The reaction was cooled to room temperature. Following the addition of ice chips to the reaction the product crashed out as an off white solid, which was collected by filtration followed by washing with water. The product obtained was further purified by trituration or flash column purification.

The piperazines prepared using general procedures 1 and 2 are shown below in Table 1.

TABLE 1

| No | Piperazine Intermediates | ESI-MS (M + 1) |
|---|---|---|
| 1 | 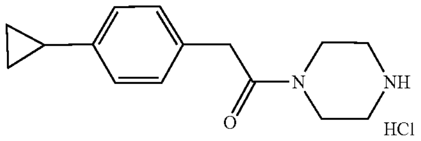 [SMILES: O=C(Cc1ccc(C2CC2)cc1)N1CCNCC1 ; Cl] | 246.31 |
| 2 | 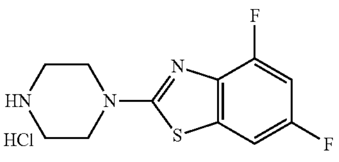 [SMILES: Cl ; Fc1cc(F)c2nc(N3CCNCC3)sc2c1] | 257.51 |
| 3 | 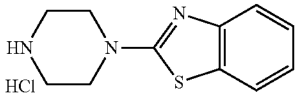 [SMILES: Cl ; c1ccc2sc(N3CCNCC3)nc2c1] | 220.11 |
| 4 | 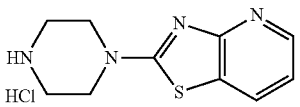 [SMILES: Cl ; c1cnc2nc(N3CCNCC3)sc2c1] | 221.01 |

TABLE 1-continued

| No | Piperazine Intermediates | ESI-MS (M + 1) |
|---|---|---|
| 5 | 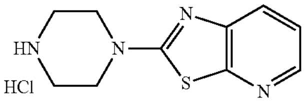 [SMILES: Cl ; c1cnc2sc(N3CCNCC3)nc2c1] | 221.21 |
| 6 | 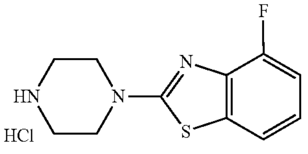 [SMILES: Cl ; Fc1cccc2sc(N3CCNCC3)nc12] | 239.31 |
| 7 | 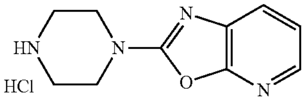 [SMILES: Cl ; c1cnc2oc(N3CCNCC3)nc2c1] | 206.41 |

(a) PZ-4291

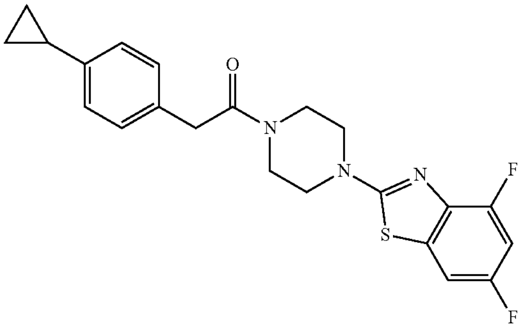

The PZ-4291 was made as explained in General Procedure 1. $^1$H NMR (400 MHz, Chloroform-d) δ 7.14-7.01 (m, 3H), 7.00-6.93 (m, 2H), 3.70 (d, J=21.9 Hz, 4H), 3.50 (td, J=12.8, 11.1, 7.7 Hz, 4H), 3.37 (dd, J=6.6, 3.8 Hz, 2H), 1.79 (tt, J=8.4, 5.1 Hz, 1H), 0.93-0.83 (m, 2H), 0.64-0.55 (m, 2H). $^{13}$C NMR (101 MHz, $CDCl_3$) δ 169.93, 167.72, 142.94, 131.36, 128.32, 126.25, 103.49, 103.44, 103.22, 102.11, 101.88, 101.83, 101.61, 99.99, 77.33, 77.21, 77.01, 76.69, 48.43, 47.87, 45.33, 41.07, 40.85, 15.06, 9.24. ESI-MS (M+1): 414.02.

(b) PZ-4285

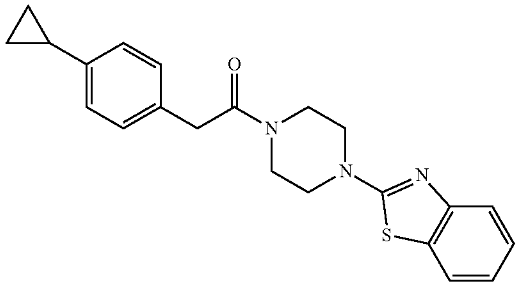

The PZ-4291 was made as explained in General Procedure 1. $^1$H NMR (400 MHz, Chloroform-d) δ 7.57-7.49 (m, 2H), 7.25 (ddd, J=8.3, 7.3, 1.3 Hz, 1H), 7.10-7.00 (m, 3H), 6.96 (d, J=8.2 Hz, 2H), 3.74 (t, J=5.3 Hz, 2H), 3.52 (d, J=5.7

Hz, 3H), 3.43 (s, 1H), 1.79 (tt, J=8.4, 5.1 Hz, 1H), 0.92-0.83 (m, 2H), 0.64-0.55 (m, 2H). ESI-MS (M+1): 378.02.

(c) PZ-4296

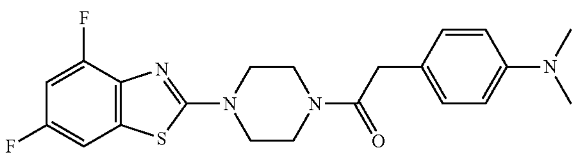

The PZ-4291 was made as explained in General Procedure 1. $^1$H NMR (400 MHz, Chloroform-d) δ 7.18-7.10 (m, 2H), 6.86 (ddd, J=10.6, 9.4, 2.4 Hz, 1H), 6.78-6.68 (m, 1H), 3.82 (t, J=5.4 Hz, 1H), 3.78-3.69 (m, 2H), 3.65-3.55 (m, 2H), 3.44 (dd, J=11.3, 6.3 Hz, 1H), 3.19 (qd, J=7.4, 4.4 Hz, 1H), 3.04-2.96 (m, 1H), 1.51 (dd, J=7.1, 3.3 Hz, 3H), 1.46 (d, J=6.6 Hz, 2H). ESI-MS (M+1): 417.02.

(d) PZ-4298

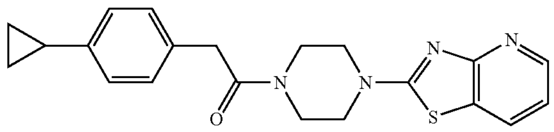

The PZ-4291 was made as explained in General Procedure 2. $^1$H NMR (400 MHz, Chloroform-d) δ 7.34-7.25 (m, 1H), 7.10-7.04 (m, 2H), 7.04-6.92 (m, 4H), 3.71 (d, J=25.0 Hz, 4H), 3.52 (d, J=5.2 Hz, 4H), 3.43 (d, J=7.1 Hz, 2H), 1.85-1.74 (m, 2H), 0.93-0.83 (m, 2H), 0.65-0.56 (m, 2H). $^{13}$C NMR (101 MHz, $CDCl_3$) δ 169.94, 142.93, 131.36, 128.33, 126.26, 122.41, 116.51, 116.47, 77.32, 77.21, 77.01, 76.69, 48.05, 45.36, 41.07, 40.84, 15.07, 9.24. ESI-MS (M+1): 379.12.

(e) PZ-4299

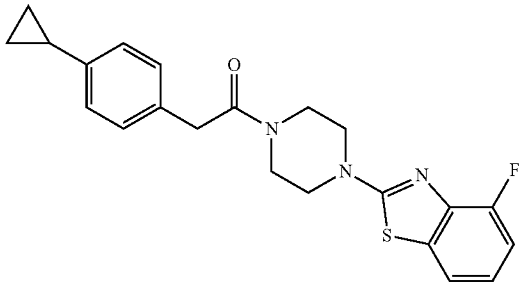

The PZ-4291 was made as explained in General Procedure 2. $^1$H NMR (400 MHz, Chloroform-d) δ 8.34 (dd, J=5.0, 1.7 Hz, 1H), 7.82 (dd, J=7.8, 1.6 Hz, 1H), 7.11-7.03 (m, 2H), 7.01-6.88 (m, 3H), 3.77-3.65 (m, 4H), 3.59-3.46 (m, 6H), 1.80 (tt, J=8.4, 5.1 Hz, 1H), 0.93-0.81 (m, 2H), 0.67-0.56 (m, 2H). $^{13}$C NMR (101 MHz, $CDCl_3$) δ 169.95, 169.67, 142.96, 131.32, 129.18, 128.35, 126.25, 116.63, 77.33, 77.21, 77.01, 76.69, 48.15, 47.66, 45.38, 41.11, 40.80, 15.06, 9.24. ESI-MS (M+1): 396.12.

(f) PZ-4300

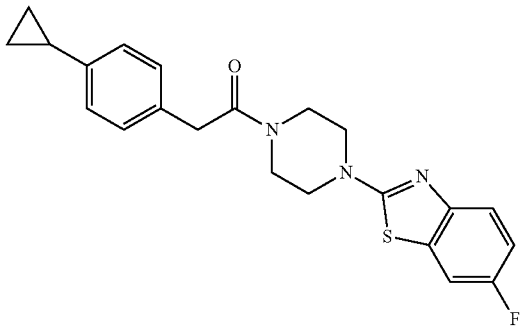

The PZ-4291 was made as explained in General Procedure 2. $^1$H NMR (400 MHz, Chloroform-d) δ 7.50-7.38 (m, 1H), 7.31-7.11 (m, 1H), 7.10-7.03 (m, 2H), 7.00-6.92 (m, 2H), 3.76-3.65 (m, 4H), 3.52-3.40 (m, 3H), 3.37 (s, 1H), 1.79 (tt, J=8.4, 5.1 Hz, 1H), 0.93-0.81 (m, 2H), 0.64-0.55 (m, 2H). $^{13}$C NMR (101 MHz, $CDCl_3$) δ 169.90, 142.92, 131.37, 128.32, 126.24, 119.78, 107.73, 107.46, 77.32, 77.21, 77.01, 76.69, 45.34, 41.05, 40.82, 15.06, 9.23. ESI-MS (M+1): 397.32.

(g) PZ-4301

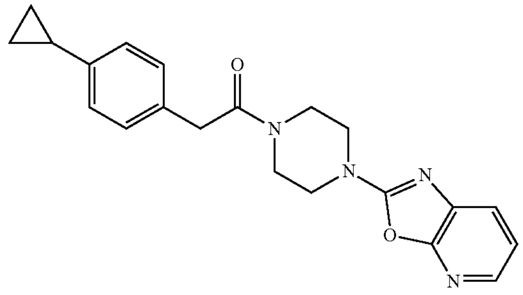

The PZ-4291 was made as explained in General Procedure 2. $^1$H NMR (400 MHz, Chloroform-d) δ 7.89 (ddd, J=16.2, 5.1, 1.5 Hz, 1H), 7.54-7.45 (m, 1H), 7.11-7.05 (m, 3H), 7.01-6.93 (m, 2H), 3.85 (s, 1H), 3.73-3.58 (m, 6H), 3.54-3.37 (m, 4H), 1.80 (tt, J=8.4, 5.1 Hz, 1H), 0.91-0.83 (m, 2H), 0.67-0.53 (m, 2H). $^{13}$C NMR (101 MHz, $CDCl_3$) δ 169.99, 160.75, 158.14, 158.08, 142.98, 139.60, 139.39, 135.38, 131.31, 128.34, 126.25, 123.69, 123.49, 120.81, 120.72, 77.34, 77.22, 77.02, 76.70, 45.40, 45.04, 44.70, 41.09, 40.81, 15.06, 9.25. ESI-MS (M+1): 364.32.

(h) PZ-4303

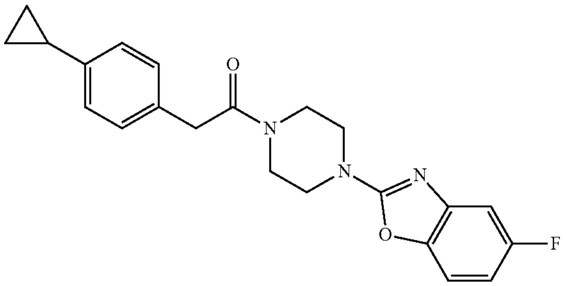

The PZ-4291 was made as explained in General Procedure 2. $^{1}H$ NMR (400 MHz, Chloroform-d) δ 7.13-7.02 (m, 3H), 7.02-6.92 (m, 3H), 6.73-6.61 (m, 1H), 3.72-3.46 (m, 8H), 3.37 (dd, J=6.6, 3.9 Hz, 2H), 1.79 (tt, J=8.4, 5.1 Hz, 1H), 0.93-0.83 (m, 2H), 0.60 (dt, J=6.5, 4.6 Hz, 2H). ESI-MS (M+1): 380.02.

(i) PZ-4304

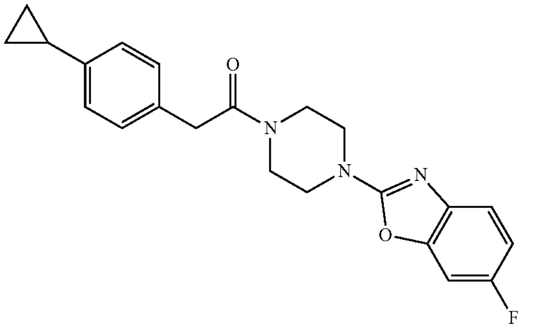

The PZ-4291 was made as explained in General Procedure 2. $^{1}H$ NMR (400 MHz, Chloroform-d) δ 7.28-7.12 (m, 1H), 7.12-7.03 (m, 2H), 7.02-6.91 (m, 3H), 6.91-6.80 (m, 1H), 3.69 (d, J=15.1 Hz, 4H), 3.63-3.53 (m, 2H), 3.50 (t, J=4.9 Hz, 2H), 3.36 (t, J=5.2 Hz, 2H), 1.79 (tt, J=8.4, 5.1 Hz, 1H), 0.94-0.81 (m, 2H), 0.67-0.53 (m, 2H). $^{13}C$ NMR (101 MHz, $CDCl_3$) δ 169.91, 142.93, 131.37, 128.33, 126.24, 116.21, 116.12, 111.35, 111.11, 97.94, 97.66, 77.33, 77.21, 77.01, 76.69, 45.56, 45.41, 41.06, 40.82, 15.06, 9.24. ESI-MS (M+1): 380.02.

(j) PZ-4305

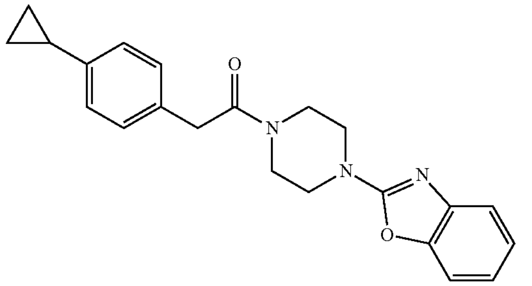

The PZ-4291 was made as explained in General Procedure 2. $^{1}H$ NMR (400 MHz, Chloroform-d) δ 7.35-7.26 (m, 1H), 7.26-7.03 (m, 4H), 7.03-6.92 (m, 3H), 3.69 (d, J=14.9 Hz, 4H), 3.59 (dd, J=6.5, 3.9 Hz, 2H), 3.50 (dd, J=6.5, 3.6 Hz, 2H), 3.38 (dd, J=6.5, 3.8 Hz, 2H), 1.79 (tt, J=8.4, 5.0 Hz, 1H), 0.92-0.83 (m, 2H), 0.64-0.55 (m, 2H). $^{13}C$ NMR (101 MHz, $CDCl_3$) δ 169.91, 161.71, 148.72, 142.89, 131.44, 128.34, 126.23, 125.47, 125.08, 124.19, 121.12, 119.74, 116.53, 110.39, 108.89, 77.33, 77.21, 77.01, 76.69, 45.50, 45.44, 45.36, 45.07, 41.13, 40.83, 15.06, 9.23. ESI-MS (M+1): 362.02.

(k) PZ-4306

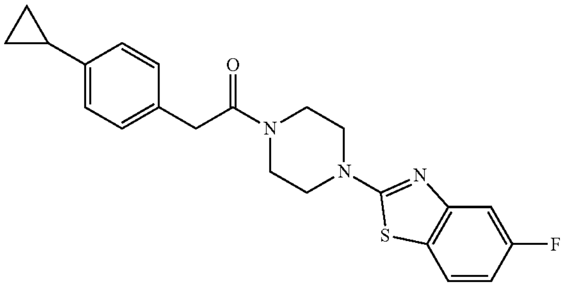

The PZ-4291 was made as explained in General Procedure 2. $^{1}H$ NMR (400 MHz, Chloroform-d) δ 7.42 (dd, J=8.7, 5.3 Hz, 1H), 7.16 (dd, J=10.0, 2.5 Hz, 1H), 7.11-7.03 (m, 2H), 7.00-6.92 (m, 2H), 6.77 (td, J=8.8, 2.5 Hz, 1H), 3.70 (d, J=21.2 Hz, 4H), 3.50 (q, J=5.9 Hz, 4H), 3.45-3.33 (m, 3H), 1.79 (tt, J=8.4, 5.1 Hz, 1H), 0.93-0.81 (m, 2H), 0.67-0.55 (m, 2H). $^{13}C$ NMR (101 MHz, $CDCl_3$) δ 170.03, 169.90, 163.36, 160.96, 142.92, 131.39, 128.32, 126.24, 121.26, 121.16, 109.70, 109.46, 106.27, 106.03, 77.33, 77.21, 77.01, 76.69, 48.28, 47.86, 45.36, 41.08, 40.84, 15.06, 9.24. ESI-MS (M+1): 396.42.

(l) PZ-4312

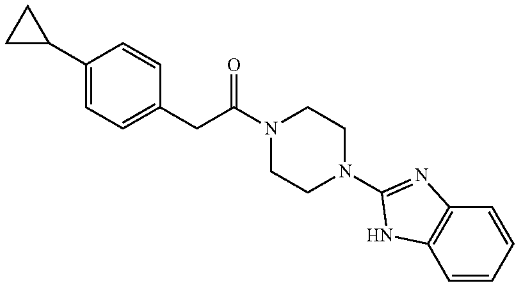

The PZ-4291 was made as explained in General Procedure 2. $^{1}H$ NMR (400 MHz, Chloroform-d) δ 7.26 (dd, J=5.8, 3.2 Hz, 1H), 7.10-6.99 (m, 3H), 7.00-6.89 (m, 2H), 3.71 (d, J=5.4 Hz, 1H), 3.66 (s, 1H), 3.52 (d, J=5.5 Hz, 1H), 3.40 (d, J=20.4 Hz, 3H), 1.78 (ddd, J=13.5, 8.5, 5.1 Hz, 1H), 0.92-0.79 (m, 2H), 0.66-0.51 (m, 2H). ESI-MS (M+1): 361.22.

(m) PZ-4313

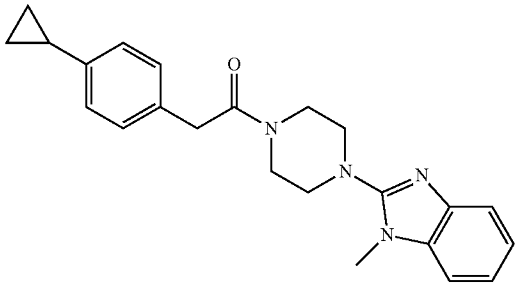

The PZ-4291 was made as explained in General Procedure 2. $^{1}H$ NMR (400 MHz, Chloroform-d) δ 7.53 (dd, J=5.6, 3.0 Hz, 1H), 7.18-7.07 (m, 3H), 7.07-6.92 (m, 3H), 3.77 (t, J=5.2 Hz, 1H), 3.68 (s, 1H), 3.54 (s, 4H), 3.19 (s, 1H), 3.11 (s, 1H), 2.89 (s, 1H), 2.81 (d, J=0.6 Hz, 1H), 1.80 (tt, J=8.4, 5.0 Hz, 1H), 0.92-0.83 (m, 2H), 0.60 (ddt, J=6.5, 4.8, 2.3 Hz, 2H). $^{13}$C NMR (101 MHz, $CDCl_3$) δ 169.94, 142.73, 131.57, 128.33, 126.20, 122.05, 108.54, 77.33, 77.21, 77.01, 76.69, 50.39, 49.89, 45.67, 41.28, 40.72, 36.47, 30.49, 15.07, 9.18. ESI-MS (M+1): 375.02.

(n) PZ-4290

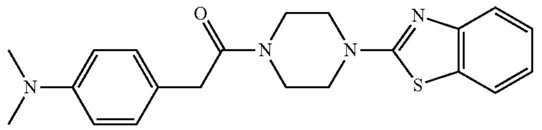

The PZ-4290 was made as explained in General Procedure 1. $^1$H NMR (400 MHz, DMSO-$d_6$) δ 7.78 (ddd, J=7.8, 1.3, 0.6 Hz, 1H), 7.47 (ddd, J=8.1, 1.2, 0.6 Hz, 1H), 7.29 (ddd, J=8.1, 7.3, 1.3 Hz, 1H), 7.14-7.02 (m, 3H), 6.68 (d, J=8.7 Hz, 2H), 3.64 (s, 4H), 3.57-3.41 (m, 4H), 2.86 (s, 6H). $^{13}$C NMR (101 MHz, DMSO) δ 169.68, 168.03, 152.21, 149.12, 130.33, 129.28, 125.98, 122.78, 121.36, 121.19, 118.66, 112.52, 47.95, 47.70, 44.68. ESI-MS (M+1): 381.42

(o) PZ-4294

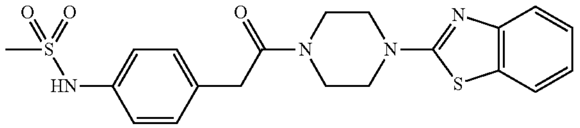

The PZ-4294 was made as explained in General Procedure 1. $^1$H NMR (400 MHz, DMSO-$d_6$) δ 9.66 (s, 1H), 7.78 (ddd, J=7.9, 1.3, 0.6 Hz, 1H), 7.51-7.45 (m, 1H), 7.33-7.25 (m, 1H), 7.24-7.14 (m, 4H), 7.13-7.06 (m, 1H), 3.80-3.46 (m, 10H), 2.96 (s, 3H). ESI-MS (M+1): 431.43.

(p) PZ-4214

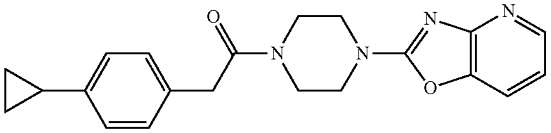

The PZ-4314 was made as explained in General Procedure 1. $^1$H NMR (500 MHz, DMSO-$d_6$) δ 8.15 (dd, J=5.1, 1.4 Hz, 1H), 7.75 (dd, J=7.8, 1.4 Hz, 1H), 7.18-7.09 (m, 2H), 7.01 (dd, J=7.9, 5.1 Hz, 3H), 3.78-3.54 (m, 9H), 1.97-1.81 (m, 1H), 0.99-0.83 (m, 2H), 0.71-0.57 (m, 2H). $^{13}$C NMR (126 MHz, DMSO) δ 169.80, 163.53, 144.65, 142.19, 141.28, 132.88, 129.34, 125.80, 116.43, 115.91, 45.56, 45.23, 45.06, 15.20, 9.73. ESI-MS (M+1): 363.32.

(p) PZ-4214

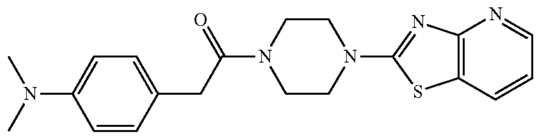

The PZ-4316 was made as explained in General Procedure 1. $^1$H NMR (500 MHz, DMSO-$d_6$) δ 8.39 (dd, J=7.8, 1.5 Hz, 1H), 8.35 (dd, J=5.3, 1.6 Hz, 1H), 7.19 (dd, J=7.8, 5.3 Hz, 1H), 7.11 (d, J=8.5 Hz, 2H), 6.78 (d, J=8.4 Hz, 2H), 3.81-3.58 (m, 10H), 2.90 (s, 6H). $^{13}$C NMR (126 MHz, DMSO) δ 171.47, 170.17, 161.92, 148.84, 143.42, 132.84, 130.00, 126.53, 116.86, 113.85, 48.40, 48.20, 44.98. ESI-MS (M+1): 382.52.

(r) PZ-4317

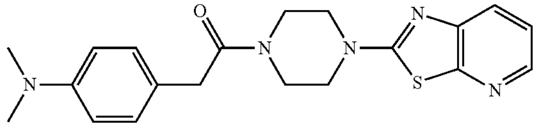

The PZ-4317 was made as explained in General Procedure 1. $^1$H NMR (500 MHz, DMSO-$d_6$) δ 8.17 (dd, J=4.7, 1.5 Hz, 1H), 7.77 (dd, J=8.1, 1.5 Hz, 1H), 7.33 (dd, J=8.1, 4.7 Hz, 1H), 7.07 (d, J=8.6 Hz, 2H), 6.69 (d, J=8.6 Hz, 2H), 3.73-3.47 (m, 10H), 2.86 (s, 6H). ESI-MS (M+1): 382.42.

(s) PZ-4318

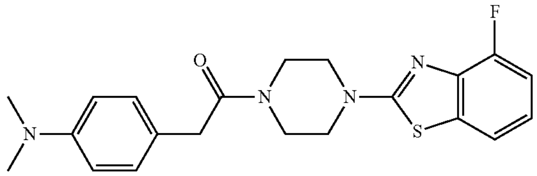

The PZ-4318 was made as explained in General Procedure 1. $^1$H NMR (500 MHz, DMSO-$d_6$) δ 7.62 (dd, J=7.8, 1.1 Hz, 1H), 7.21-7.03 (m, 4H), 6.68 (d, J=8.6 Hz, 2H), 3.65 (d, J=5.2 Hz, 6H), 3.60-3.45 (m, 4H), 2.86 (s, 6H). $^{13}$C NMR (126 MHz, DMSO) δ 170.20, 168.80, 162.77, 153.87, 151.90, 149.63, 140.82, 140.72, 133.49, 133.45, 129.79, 123.26, 122.36, 122.30, 117.85, 117.82, 113.02, 112.67, 112.52, 48.48, 48.26, 45.12. ESI-MS (M+1): 399.52.

(t) PZ-4319

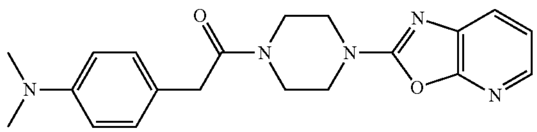

The PZ-4319 was made as explained in General Procedure 1. $^1$H NMR (500 MHz, DMSO-$d_6$) δ 7.90 (dd, J=5.1, 1.5 Hz, 1H), 7.66 (dd, J=7.7, 1.5 Hz, 1H), 7.23 (dd, J=7.7, 5.1 Hz, 1H), 7.07 (d, J=8.6 Hz, 2H), 6.68 (d, J=8.7 Hz, 2H), 3.70-3.50 (m, 10H), 2.86 (s, 6H). $^{13}$C NMR (126 MHz, DMSO) δ 170.23, 161.11, 158.25, 149.63, 138.99, 135.81, 129.80, 123.43, 123.27, 121.29, 113.02, 45.45, 45.18, 45.09. ESI-MS (M+1): 366.72.

(u) PZ-4320

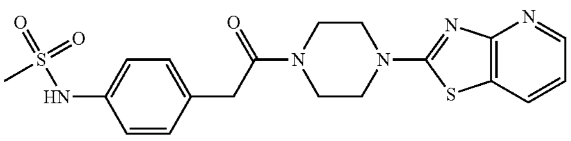

The PZ-4320 was made as explained in General Procedure 1. $^1H$ NMR (500 MHz, DMSO-$d_6$) δ 9.67 (s, 1H), 8.32 (dd, J=4.8, 1.7 Hz, 1H), 8.20 (dd, J=7.8, 1.7 Hz, 1H), 7.25-7.13 (m, 4H), 7.06 (dd, J=7.8, 4.9 Hz, 1H), 3.80-3.55 (m, 10H), 2.97 (s, 3H). $^{13}C$ NMR (126 MHz, DMSO) δ 170.02, 169.66, 164.21, 146.96, 137.15, 131.75, 130.44, 130.26, 124.96, 120.50, 116.96, 48.08, 47.88, 45.05. ESI-MS (M+1): 432.43.

(v) PZ-4321

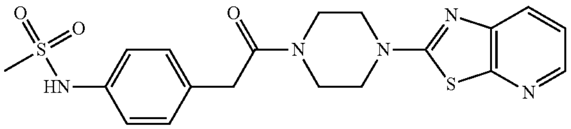

The PZ-4321 was made as explained in General Procedure 1. $^1H$ NMR (500 MHz, DMSO-$d_6$) δ 9.67 (s, 1H), 8.17 (dd, J=4.8, 1.5 Hz, 1H), 7.78 (dd, J=8.1, 1.5 Hz, 1H), 7.33 (dd, J=8.1, 4.7 Hz, 1H), 7.26-7.11 (m, 4H), 3.75 (s, 2H), 3.72-3.55 (m, 8H), 2.97 (s, 3H). $^{13}C$ NMR (126 MHz, DMSO) δ 169.64, 166.96, 155.22, 146.79, 142.70, 137.15, 131.74, 130.43, 125.12, 122.13, 120.49, 48.09, 47.84, 45.06. ESI-MS (M+1): 432.33.

(w)

PZ-4322

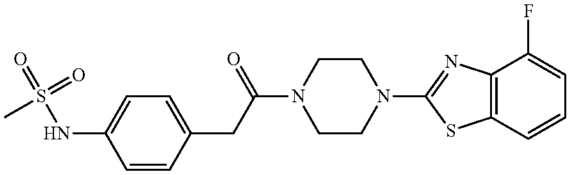

The PZ-4322 was made as explained in General Procedure 1. $^1H$ NMR (500 MHz, DMSO-$d_6$) δ 9.67 (s, 1H), 7.62 (dd, J=7.9, 1.1 Hz, 1H), 7.25-7.13 (m, 5H), 7.12-7.03 (m, 1H), 3.75 (s, 2H), 3.71-3.53 (m, 8H), 2.97 (s, 3H). $^{13}C$ NMR (126 MHz, DMSO) δ 169.62, 168.80, 153.88, 151.90, 140.83, 140.73, 137.15, 133.50, 133.46, 131.75, 130.43, 122.37, 122.31, 120.50, 117.86, 117.83, 112.68, 112.53, 48.46, 48.23, 45.05. ESI-MS (M+1): 449.33

(x)

PZ-4323

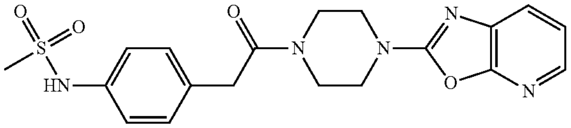

The PZ-4323 was made as explained in General Procedure 1. $^1H$ NMR (500 MHz, DMSO-$d_6$) δ 9.67 (s, 1H), 7.91 (dd, J=5.1, 1.5 Hz, 1H), 7.66 (dd, J=7.7, 1.5 Hz, 1H), 7.27-7.12 (m, 5H), 3.75 (s, 2H), 3.72-3.56 (m, 8H), 2.97 (s, 3H). $^{13}C$ NMR (126 MHz, DMSO) δ 169.64, 161.12, 158.26, 139.00, 137.14, 135.82, 131.76, 130.43, 123.44, 121.30, 120.48, 45.44, 45.16, 45.03. ESI-MS (M+1): 416.32.

(y)

PZ-4324

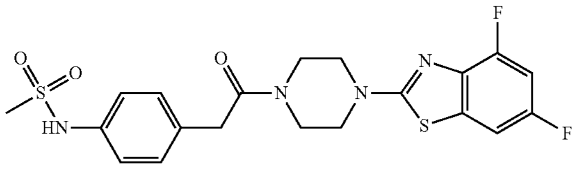

The PZ-4324 was made as explained in General Procedure 1. $^1H$ NMR (500 MHz, DMSO-$d_6$) δ 9.67 (s, 1H), 7.68-7.60 (m, 1H), 7.28-7.11 (m, 5H), 3.74 (s, 2H), 3.71-3.51 (m, 8H), 2.96 (s, 3H). $^{13}C$ NMR (126 MHz, DMSO) δ 169.62, 168.58, 157.90, 156.00, 155.91, 152.99, 152.88, 150.99, 150.88, 137.69, 137.67, 137.59, 137.57, 137.15, 133.65, 133.60, 133.55, 133.49, 131.74, 130.43, 120.49, 105.01, 104.98, 104.79, 104.76, 102.38, 102.20, 102.15, 101.98, 48.43, 48.20, 45.03. ESI-MS (M+1): 467.33.

(z)

PZ-4343

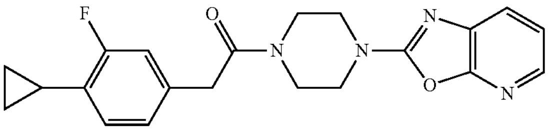

The PZ-4343 was made as explained in General Procedure 1. $^1H$ NMR (500 MHz, Chloroform-d) δ 7.98 (dd, J=5.1, 1.5 Hz, 1H), 7.60 (dd, J=7.7, 1.5 Hz, 1H), 7.17 (dd, J=7.7, 5.1 Hz, 1H), 7.00-6.82 (m, 3H), 3.88-3.52 (m, 10H), 2.07 (tt, J=8.6, 4.3 Hz, 1H), 1.04-0.92 (m, 2H), 0.76-0.63 (m, 2H). $^{13}C$ NMR (126 MHz, $CDCl_3$) δ 169.33, 162.90, 160.95, 160.75, 158.13, 139.50, 135.38, 129.69, 129.58, 126.49, 126.45, 124.08, 124.06, 123.56, 120.75, 115.30, 115.11, 77.28, 77.23, 77.03, 77.00, 76.77, 45.39, 45.13, 45.05, 41.13, 40.39, 8.54, 8.50, 7.84. ESI-MS (M+1): 381.42

(aa)

PZ-4344

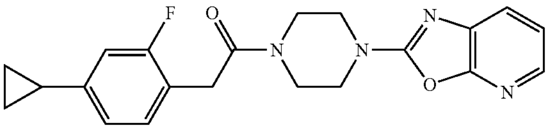

The PZ-4344 was made as explained in General Procedure 1. $^1H$ NMR (500 MHz, Chloroform-d) δ 7.98 (dt, J=5.1, 1.3 Hz, 1H), 7.60 (dt, J=7.7, 1.3 Hz, 1H), 7.25-7.11 (m, 2H), 6.87 (dd, J=7.9, 1.6 Hz, 1H), 6.78 (dd, J=11.3, 1.8 Hz, 1H), 3.86-3.59 (m, 10H), 1.93-1.82 (m, 1H), 1.06-0.93 (m, 2H), 0.75-0.63 (m, 2H). $^{13}C$ NMR (126 MHz, $CDCl_3$) δ 169.21, 161.38, 160.79, 159.44, 158.15, 146.16, 146.10, 139.47, 135.42, 130.42, 130.39, 123.53, 121.97, 121.95, 120.74, 118.36, 118.23, 112.59, 112.41, 45.27, 45.21, 45.09, 41.22, 33.19, 33.18, 15.13, 15.11, 9.56. ESI-MS (M+1): 381.42

(bb)

PZ-4348

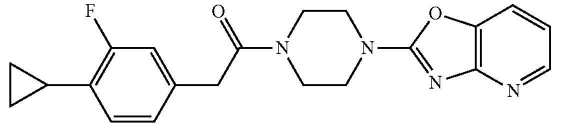

The PZ-4348 was made as explained in General Procedure 1. $^1H$ NMR (400 MHz, DMSO-$d_6$) δ 8.15 (dd, J=5.1, 1.4 Hz, 1H), 7.75 (dd, J=7.9, 1.4 Hz, 1H), 7.06-6.87 (m, 4H), 3.76 (s, 2H), 3.74-3.56 (m, 8H), 2.01 (tt, J=8.3, 5.2 Hz, 1H), 1.02-0.88 (m, 2H), 0.76-0.60 (m, 2H). ESI-MS (M+1): 381.23

(cc)

PZ-4349

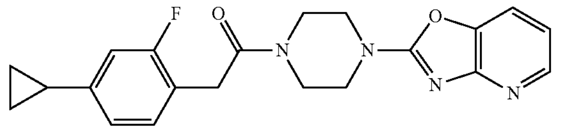

The PZ-4349 was made as explained in General Procedure 1. $^1H$ NMR (400 MHz, DMSO-$d_6$) δ 8.16 (dd, J=5.1, 1.4 Hz, 1H), 7.76 (dd, J=7.9, 1.4 Hz, 1H), 7.13 (t, J=8.2 Hz, 1H), 7.02 (dd, J=7.9, 5.1 Hz, 1H), 6.92-6.82 (m, 2H), 3.80-3.58 (m, 10H), 1.92 (tt, J=8.3, 4.9 Hz, 1H), 1.02-0.90 (m, 2H), 0.77-0.59 (m, 2H). $^{13}C$ NMR (126 MHz, DMSO) δ 168.72, 163.56, 162.24, 160.30, 158.04, 145.70, 145.64, 144.67, 141.31, 131.96, 131.92, 121.68, 121.66, 120.16, 120.03, 116.45, 115.93, 112.17, 112.00, 45.57, 45.25, 44.81, 33.17, 15.21, 15.19, 10.17, 10.11. ESI-MS (M+1): 381.23.

(dd)

PZ-4383

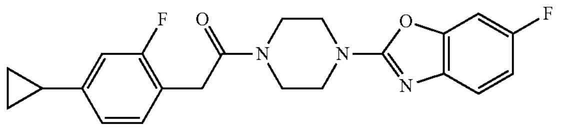

The PZ-4383 was made as explained in General Procedure 1. $^1H$ NMR (400 MHz, DMSO-$d_6$) δ 7.45 (dd, J=8.5, 2.5 Hz, 1H), 7.30 (dd, J=8.6, 4.9 Hz, 1H), 7.17-6.98 (m, 2H), 6.92-6.79 (m, 2H), 3.81-3.46 (m, 10H), 1.92 (tt, J=8.4, 5.0 Hz, 1H), 1.04-0.89 (m, 2H), 0.75-0.60 (m, 2H). ESI-MS (M+1): 396.52

(ee)

PZ-4392

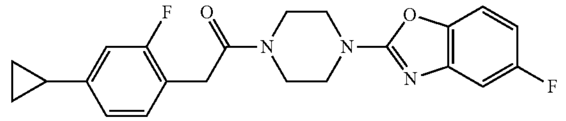

The PZ-4392 was made as explained in General Procedure 1. $^1H$ NMR (500 MHz, Chloroform-d) δ 7.19-7.16 (m, 1H), 6.95 (dd, J=7.9, 2.5 Hz, 1H), 6.89-6.75 (m, 4H), 3.71 (dd, J=6.6, 4.1 Hz, 2H), 3.66 (s, 2H), 3.60-3.55 (m, 2H), 3.50 (dd, J=6.7, 3.8 Hz, 2H), 3.42 (dd, J=6.5, 3.7 Hz, 2H), 2.03-1.93 (m, 1H), 0.93-0.85 (m, 2H), 0.66-0.60 (m, 2H). ESI-MS (M+1): 398.22 u. Oxazolopyridiens Synthesis General Procedure 1

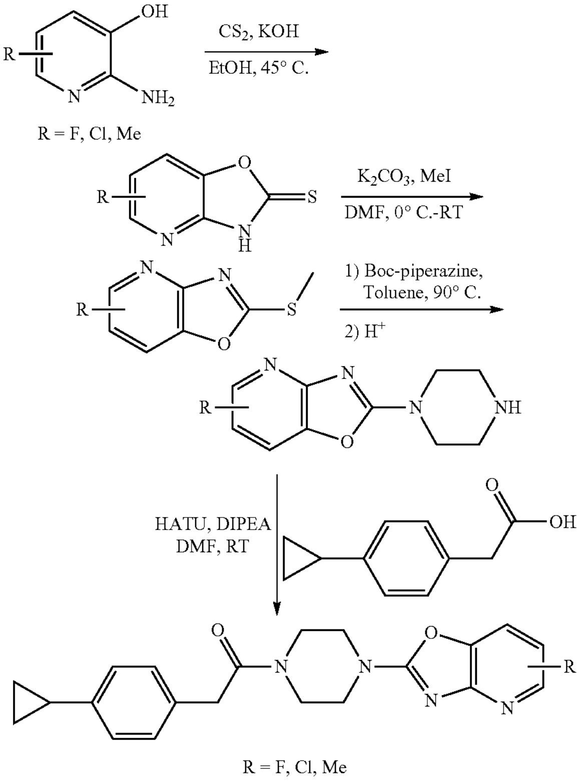

Example: Synthesis of PZ-4350

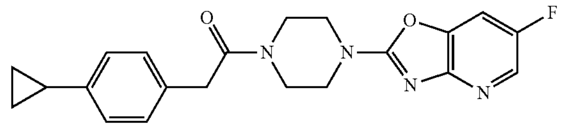 [SMILES: O=C(Cc1ccc(C2CC2)cc1)N1CCN(c2nc3ncc(F)cc3o2)CC1]

Step1: 2-Amino-3-hydroxy-5fluoropyridine (1 g, 7.81 mmol) and potassium hydroxide (526 mg, 9.37 mmol) in $CS_2$-EtOH (1:2, 25 mL) in a RB flask fitted with condenser heated to 45 degrees refluxing overnight. The reaction mixture was then cooled to RT concentrated under reduced pressure. The crude was suspended in 1 M HCl, stirred for 5 minutes, solids were collected by filtration, washed with water and dried to get the product 6-fluorooxazolo[4,5-b]pyridine-2(3H)-thione, which was used in next step without further purification.

Step 2: Iodomethane (1.829 ml, 29.4 mmol) was added to 6-fluorooxazolo[4,5-b]pyridine-2(3H)-thione (1 g, 5.88 mmol) and potassium carbonate (0.812 g, 5.88 mmol) in DMF (5 ml) at 0° C. and stirred for 2 h at ice bath temp, the RM was diluted with water, extracted with diethyl ether, the combined diethyl ether was washed with brine and dried and evaporated to get the product as an oil but crystallized over time at RT.

Step 3: 6-fluoro-2-(methylthio)oxazolo[4,5-b]pyridine (0.74 g, 4.02 mmol) and tert-butyl piperazine-1-carboxylate (0.748 g, 4.02 mmol) in toluene (10 mL) heated at 90° C. for 2 h. The reaction mixture was evaporated to dryness and purified by flash column to get tert-butyl 4-(6-fluorooxazolo[4,5-b]pyridin-2-yl)piperazine-1-carboxylate. The intermediate (523 mg, 1.718 mmol) was diluted in DCM (5 mL) and treated with 4 N. HCl in dioxane (2.5 mL) for 3 h. at room temperature. The reaction mixture was evaporated under reduced pressure to get the 2-(piperazin-1-yl)oxazolo[4,5-b]pyridine as hydrochloride salt.

Step 4: 2-(4-cyclopropylphenyl)acetic acid (100 mg, 0.567 mmol), HATU (237 mg, 0.624 mmol) and DIPEA (0.396 ml, 2.270 mmol) in DMF (2 ml) stirred for 10 min then piperazine intermediate for step 3 was added, reaction mixture was allowed to stir at room temperature for 4 h. The reaction mixture was diluted with water to crash product as solids and collected by filtration. The solids were washed with water then dried under reduced pressure. The crude product was purified by flash column chromatography to collect product 2-(4-cyclopropylphenyl)-1-(4-(6-fluorooxazolo[4,5-b]pyridin-2-yl)piperazin-1-yl)ethenone as white solid. $^1$H NMR (400 MHz, DMSO-$d_6$) δ 8.17 (dd, J=2.6, 2.1 Hz, 1H), 7.94 (dd, J=8.2, 2.6 Hz, 1H), 7.12 (d, J=8.2 Hz, 2H), 7.02 (d, J=8.2 Hz, 2H), 3.82-3.52 (m, 10H), 1.94-1.78 (m, 1H), 1.01-0.84 (m, 2H), 0.72-0.55 (m, 2H). $^{13}$C NMR (126 MHz, DMSO) δ 169.81, 164.29, 164.27, 156.02, 154.61, 154.08, 142.21, 140.84, 140.75, 132.88, 131.56, 131.35, 129.95, 129.35, 125.81, 125.76, 106.13, 105.92, 45.60, 45.28, 45.01, 15.20, 9.73. ESI-MS (M+1): 381.23 ii.

PZ-4351

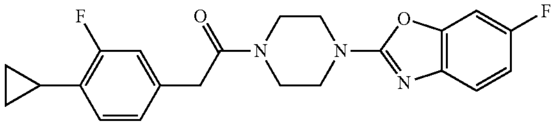

PZ-4351 was prepared from 2-(piperazin-1-yl)oxazolo[4,5-b]pyridine and 2-(4-cyclopropyl-3-fluorophenyl)acetic acid as explained for PZ-4350 in step-4. $^1$H NMR (500 MHz, DMSO-$d_6$) δ 8.18 (t, J=2.4 Hz, 1H), 7.95 (dd, J=8.2, 2.6 Hz, 1H), 7.06-6.88 (m, 3H), 3.76 (s, 2H), 3.73-3.58 (m, 8H), 2.00 (tt, J=8.5, 5.2 Hz, 1H), 1.00-0.92 (m, 2H), 0.73-0.66 (m, 2H). $^{13}$C NMR (126 MHz, DMSO) δ 169.36, 164.30, 162.29, 160.36, 156.03, 154.62, 154.09, 140.85, 140.76, 135.34, 135.28, 131.57, 131.36, 128.51, 128.40, 126.29, 126.25, 125.70, 125.67, 116.15, 115.97, 106.13, 105.93, 45.61, 45.26, 44.93, 8.66, 8.62, 8.23. ESI-MS (M+1): 399.23 iii.

PZ-4352

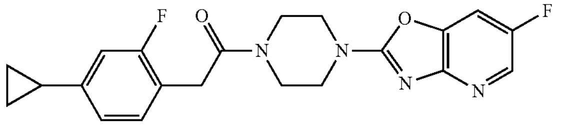

PZ-4352 was prepared from 2-(piperazin-1-yl)oxazolo[4,5-b]pyridine and 2-(4-cyclopropyl-2-fluorophenyl)acetic acid as explained for PZ-4350 in step-4. $^1$H NMR (500 MHz, DMSO-$d_6$) δ 8.18 (t, J=2.4 Hz, 1H), 7.96 (dd, J=8.2, 2.6 Hz, 1H), 7.12 (t, J=8.0 Hz, 1H), 6.91-6.82 (m, 2H), 3.81-3.60 (m, 10H), 1.92 (tt, J=8.3, 4.9 Hz, 1H), 1.01-0.91 (m, 2H), 0.74-0.62 (m, 2H). $^{13}$C NMR (126 MHz, DMSO) δ 168.73, 164.29, 164.28, 162.23, 160.30, 156.03, 154.63, 154.09, 145.71, 145.64, 140.86, 140.77, 131.96, 131.92, 131.57, 131.36, 121.68, 121.65, 120.14, 120.01, 112.17, 112.00, 106.14, 105.93, 45.60, 45.28, 44.76, 33.16, 15.21, 15.19, 10.17, 10.11. ESI-MS (M+1): 399.23 iv.

PZ-4357

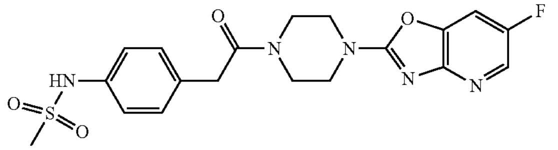

PZ-4357 was prepared from 2-(piperazin-1-yl)oxazolo[4,5-b]pyridine and 2-(4-(methylsulfonamido)phenyl)acetic acid as explained for PZ-4350 in step-4. $^1$H NMR (500 MHz, DMSO-$d_6$) δ 9.67 (s, 1H), 8.18 (t, J=2.3 Hz, 1H), 7.95 (dd, J=8.3, 2.6 Hz, 1H), 7.28-7.09 (m, 3H), 3.75 (s, 2H), 3.72-3.58 (m, 8H), 2.97 (s, 3H). $^{13}$C NMR (126 MHz, DMSO) δ 169.68, 164.29, 164.28, 162.79, 156.02, 154.62, 154.08, 140.84, 140.76, 137.16, 131.74, 131.57, 131.36, 130.45, 120.49, 106.13, 105.92, 45.61, 45.27, 44.98. ESI-MS (M+1): 434.17 v.

PZ-4359

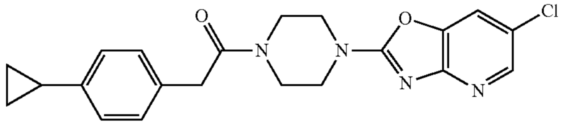

$^1$H NMR (500 MHz, DMSO-$d_6$) δ 8.19 (d, J=2.2 Hz, 1H), 8.02 (d, J=2.2 Hz, 1H), 7.12 (d, J=8.2 Hz, 2H), 7.02 (d, J=8.1 Hz, 2H), 3.77-3.55 (m, 10H), 1.88 (tt, J=8.4, 5.1 Hz, 1H), 0.97-0.88 (m, 2H), 0.68-0.58 (m, 2H). $^{13}$C NMR (126 MHz, DMSO) δ 169.82, 164.11, 157.07, 142.90, 142.21, 141.38, 132.86, 129.36, 125.81, 122.61, 116.52, 45.61, 45.29, 44.99, 15.20, 9.73. ESI-MS (M+1): 397.25 vi.

PZ-4360

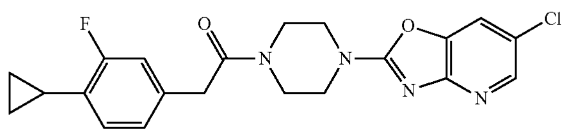

$^1$H NMR (500 MHz, DMSO-$d_6$) δ 8.19 (dd, J=4.7, 2.2 Hz, 1H), 8.03 (dd, J=5.3, 2.2 Hz, 1H), 7.06-6.87 (m, 3H), 3.71 (d, J=55.8 Hz, 7H), 2.04-1.94 (m, 1H), 0.98-0.91 (m, 2H), 0.74-0.64 (m, 2H). ESI-MS (M+1): 415.16

PZ-4359 v

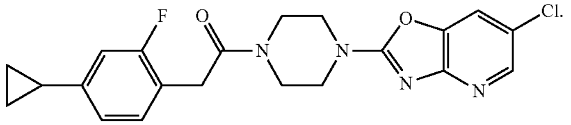

$^1$H NMR (500 MHz, DMSO-$d_6$) δ 8.19 (d, J=2.2 Hz, 1H), 8.03 (d, J=2.2 Hz, 1H), 7.12 (t, J=8.0 Hz, 1H), 6.92-6.79 (m, 2H), 3.83-3.55 (m, 10H), 1.92 (tt, J=8.4, 5.0 Hz, 1H), 1.03-0.88 (m, 2H), 0.75-0.60 (m, 2H). $^{13}$C NMR (126 MHz, DMSO) δ 168.73, 164.12, 162.24, 160.30, 157.09, 145.71, 145.65, 142.92, 141.39, 131.96, 131.92, 122.62, 121.68, 121.66, 120.14, 120.01, 116.53, 112.17, 112.00, 45.61, 45.30, 44.74, 15.21, 15.19, 10.11. ESI-MS (M+1): 415.25

PZ-4363 viii

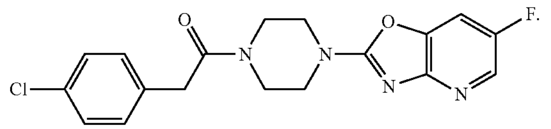

$^1$H NMR (500 MHz, DMSO-d6) δ 8.18 (t, J=2.3 Hz, 1H), 7.95 (dd, J=8.2, 2.6 Hz, 1H), 7.38 (d, J=8.4 Hz, 2H), 7.27 (d, J=8.5 Hz, 2H), 3.80 (s, 2H), 3.73-3.58 (m, 8H). $^{13}$C NMR (126 MHz, DMSO) δ 169.38, 164.29, 164.28, 156.03, 154.61, 154.09, 140.84, 140.76, 135.28, 131.63, 131.57, 131.37, 128.65, 106.14, 105.93, 45.60, 45.26, 44.91. ESI-MS (M+1): 375.42

PZ-4467 ix

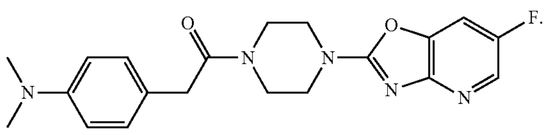

$^1$H NMR (500 MHz, Chloroform-d) δ 8.15 (t, J=2.3 Hz, 1H), 7.33-7.26 (m, 1H), 7.13 (d, J=8.7 Hz, 2H), 6.71 (d, J=8.7 Hz, 2H), 3.79 (dd, J=6.6, 3.9 Hz, 2H), 3.76-3.67 (m, 4H), 3.61 (dd, J=6.5, 3.9 Hz, 2H), 3.48 (dd, J=6.5, 3.9 Hz, 2H), 2.94 (s, 6H). ESI-MS (M+1): 384.32 pz-4364 x

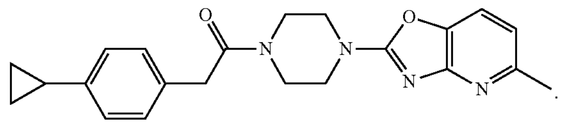

$^1$H NMR (400 MHz, DMSO-$d_6$) δ 7.62 (d, J=7.9 Hz, 1H), 7.12 (d, J=8.2 Hz, 2H), 7.02 (d, J=8.2 Hz, 2H), 6.86 (dd, J=8.0, 0.6 Hz, 1H), 3.72 (s, 2H), 3.70-3.51 (m, 8H), 2.43 (s, 3H), 1.88 (tt, J=8.4, 5.1 Hz, 1H), 0.96-0.87 (m, 2H), 0.67-0.58 (m, 2H). $^{13}$C NMR (101 MHz, DMSO) δ 169.30, 163.12, 156.98, 152.62, 141.69, 138.97, 132.39, 128.84, 125.31, 115.54, 114.81, 45.03, 44.68, 44.56, 23.73, 14.69, 9.20. ESI-MS (M+1): 377.22

PZ-4386 xi

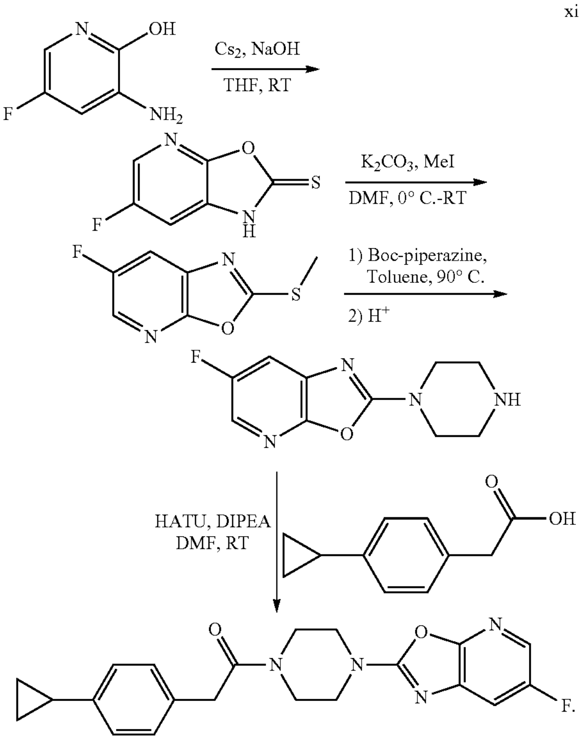

To 3-amino-5-fluoropyridin-2-ol (1.0 g, 7.81 mmol) in THF (30 mL) at room temperature thiophosgene (0.714 ml, 9.37 mmol) was added slowly dropwise and the mixture was stirred for 1 h. The reaction mixture then neutralized to pH 5 with 2N. NaOH and THF was removed under reduced pressure followed by dilution with water (15 mL). The solids were collected by filtration, washed with water and dried under vacuum to afford product 6-fluorooxazolo[5,4-b]pyridine-2(1H)-thione, which was then used in further steps as explained for PZ-4350 to synthesize PZ-4386. $^1$H NMR (500 MHz, DMSO-$d_6$) δ 7.88 (dd, J=2.7, 1.9 Hz, 1H), 7.66 (dd, J=8.9, 2.7 Hz, 1H), 7.12 (d, J=8.2 Hz, 2H), 7.02 (d, J=8.2 Hz, 2H), 3.81-3.50 (m, 10H), 1.88 (tt, J=8.4, 5.1 Hz, 1H), 0.99-0.84 (m, 2H), 0.69-0.53 (m, 2H). 13C NMR (126 MHz, DMSO) δ 169.81, 162.64, 157.50, 154.47, 142.20, 132.87, 129.35, 125.81, 111.44, 111.24, 45.39, 45.12, 45.01, 15.20, 9.73. ESI-MS (M+1): 381.52

PZ-4432 xii

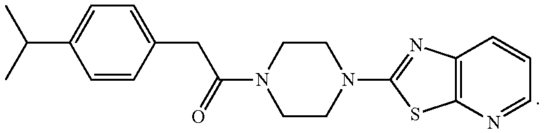

$^1$H NMR (500 MHz, DMSO-$d_6$) δ 8.17 (dd, J=4.7, 1.5 Hz, 1H), 7.77 (dd, J=8.1, 1.5 Hz, 1H), 7.33 (dd, J=8.1, 4.7 Hz, 1H), 7.26-7.07 (m, 4H), 3.87-3.51 (m, 10H), 2.86 (p, J=6.9 Hz, 1H), 1.19 (d, J=6.9 Hz, 6H). $^{13}$C NMR (126 MHz, DMSO) δ 169.81, 166.97, 155.23, 146.89, 146.80, 142.70, 133.40, 129.43, 126.72, 125.12, 122.13, 48.10, 47.84, 45.11, 33.52, 24.39. ESI-MS (M+1): 381.12

PZ-4433 xiii

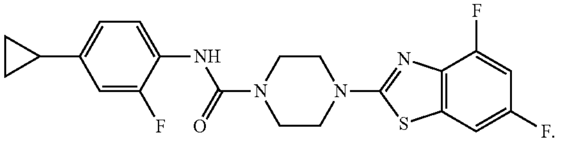

$^1$H NMR (500 MHz, DMSO-$d_6$) δ 8.38 (s, 1H), 7.65 (ddd, J=8.3, 2.5, 1.0 Hz, 1H), 7.31-7.17 (m, 2H), 6.96-6.81 (m, 2H), 3.75-3.52 (m, 8H), 1.91 (tt, J=8.4, 5.0 Hz, 1H), 1.02-0.89 (m, 2H), 0.74-0.61 (m, 2H). $^{13}$C NMR (126 MHz, DMSO) δ 168.69, 157.17, 155.64, 142.35, 142.29, 137.75, 137.73, 137.65, 137.63, 133.65, 133.60, 133.55, 133.50, 126.91, 126.89, 124.80, 124.70, 121.45, 121.42, 112.71, 112.55, 105.00, 104.97, 104.79, 104.76, 102.37, 102.19, 102.15, 101.97, 48.30, 43.60, 15.06, 9.97. ESI-MS (M+1): 433.33

PZ-4434 xiv

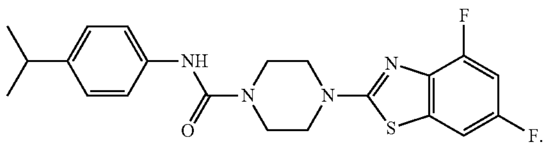

$^1$H NMR (500 MHz, DMSO-$d_6$) δ 8.60 (s, 1H), 7.74-7.60 (m, 1H), 7.36 (d, J=8.6 Hz, 2H), 7.24 (ddd, J=11.1, 9.7, 2.5 Hz, 1H), 7.12 (d, J=8.7 Hz, 2H), 3.63 (s, 8H), 2.82 (p, J=6.9 Hz, 1H), 1.18 (d, J=6.9 Hz, 6H). $^{13}$C NMR (126 MHz, DMSO) δ 168.69, 155.99, 155.90, 155.52, 150.89, 142.43, 138.46, 137.76, 137.74, 137.66, 137.64, 133.64, 133.59, 133.54, 133.49, 126.53, 120.39, 105.00, 104.96, 104.78, 104.75, 102.37, 102.19, 102.14, 101.97, 48.35, 43.57, 33.24, 24.51. ESI-MS (M+1): 417.52

PZ-4435 xv

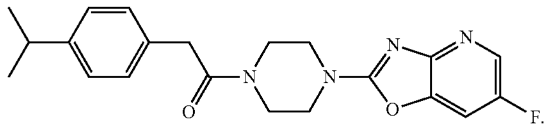

$^1$H NMR (500 MHz, DMSO-$d_6$) δ 8.18 (t, J=2.4 Hz, 1H), 7.95 (dd, J=8.2, 2.6 Hz, 1H), 7.28-7.05 (m, 4H), 3.80-3.56 (m, 10H), 2.86 (p, J=6.9 Hz, 1H), 1.19 (d, J=6.9 Hz, 6H). $^{13}$C NMR (126 MHz, DMSO) δ 169.83, 164.29, 164.27, 156.02, 154.62, 154.08, 146.89, 140.84, 140.76, 133.40, 131.56, 131.35, 129.44, 126.71, 106.13, 105.92, 45.61, 45.28, 45.03, 33.51, 24.39. ESI-MS (M+1): 383.22

PZ-4436 xvi

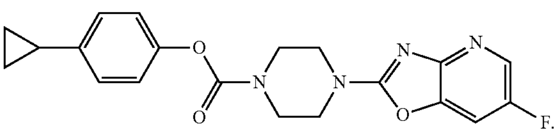

$^1$H NMR (500 MHz, DMSO-$d_6$) δ 8.19 (t, J=2.4 Hz, 1H), 7.97 (dd, J=8.2, 2.7 Hz, 1H), 7.17-6.94 (m, 4H), 3.69 (d, J=74.7 Hz, 8H), 1.93 (tt, J=8.4, 5.1 Hz, 1H), 0.99-0.88 (m, 2H), 0.70-0.60 (m, 2H). $^{13}$C NMR (126 MHz, DMSO) δ 164.30, 164.29, 156.05, 154.62, 154.11, 153.58, 149.22, 141.18, 140.86, 140.78, 131.61, 131.40, 126.53, 122.08, 106.16, 105.95, 45.21, 43.87, 43.20, 15.01, 9.81. ESI-MS (M+1): 384.52

PZ-4462 xvii

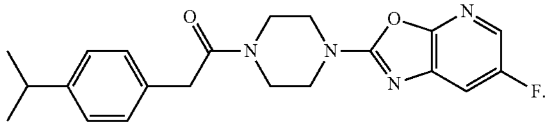

$^1$H NMR (500 MHz, DMSO-$d_6$) δ 7.88 (dd, J=2.6, 1.9 Hz, 1H), 7.66 (dd, J=9.0, 2.6 Hz, 1H), 7.27-7.09 (m, 4H), 3.80-3.54 (m, 10H), 2.95-2.79 (m, 1H), 1.19 (d, J=6.9 Hz, 6H). $^{13}$C NMR (126 MHz, DMSO) δ 169.83, 162.64, 159.44, 157.50, 154.47, 146.89, 137.20, 137.11, 133.40, 129.44, 126.71, 125.45, 125.21, 111.44, 111.24, 45.40, 45.12, 45.03, 33.52, 24.39. ESI-MS (M+1): 383.22

PZ-4463 xviii

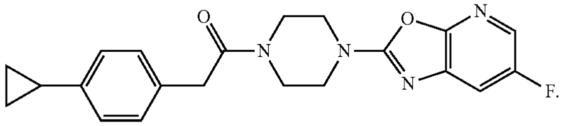

$^1$H NMR (500 MHz, DMSO-$d_6$) δ 7.90 (t, J=2.3 Hz, 1H), 7.68 (dd, J=8.9, 2.6 Hz, 1H), 7.13-6.94 (m, 4H), 3.69 (d,

J=74.1 Hz, 8H), 1.93 (tt, J=8.6, 5.1 Hz, 1H), 1.03-0.85 (m, 2H), 0.65 (dd, J=5.0, 1.9 Hz, 2H). $^{13}C$ NMR (126 MHz, DMSO) δ 162.65, 154.49, 153.57, 149.22, 141.18, 126.52, 122.08, 111.49, 111.30, 45.03, 43.87, 43.19, 15.01, 9.81. ESI-MS (M+1): 383.12

PZ-4470 xix

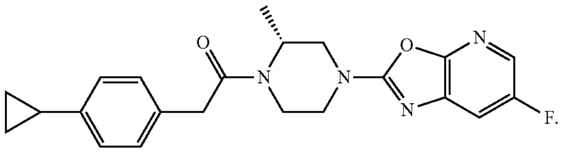

$^{1}H$ NMR (500 MHz, DMSO-$d_6$) δ 7.87 (t, J=2.3 Hz, 1H), 7.64 (dd, J=9.0, 2.6 Hz, 1H), 7.16-7.06 (m, 2H), 7.01 (dd, J=8.1, 2.0 Hz, 2H), 4.75 (s, 1H), 4.49-4.30 (m, 1H), 4.19-3.85 (m, 3H), 3.79-3.61 (m, 3H), 3.49 (s, 2H), 3.20-2.93 (m, 2H), 1.89 (dtt, J=13.4, 8.8, 3.8 Hz, 1H), 1.09 (d, J=6.8 Hz, 3H), 0.94-0.88 (m, 2H), 0.63 (dd, J=4.9, 2.3 Hz, 2H). ESI-MS (M+1): 395.32

PZ-4471 xx

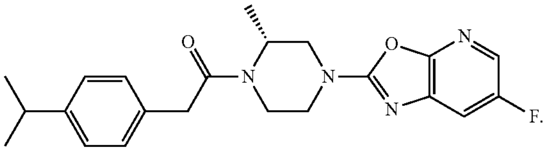

$^{1}H$ NMR (500 MHz, DMSO-$d_6$) δ 7.87 (t, J=2.3 Hz, 1H), 7.65 (dd, J=9.0, 2.6 Hz, 1H), 7.26-7.07 (m, 4H), 4.76 (s, 1H), 4.52-4.29 (m, 1H), 4.20-4.00 (m, 1H), 4.00-3.86 (m, 2H), 3.73 (t, J=9.7 Hz, 2H), 3.51 (s, 2H), 3.23-2.95 (m, 1H), 2.93-2.78 (m, 2H), 1.19 (dd, J=7.0, 1.7 Hz, 6H), 1.10 (d, J=6.8 Hz, 3H). ESI-MS (M+1): 397.22

PZ-4474 xxi

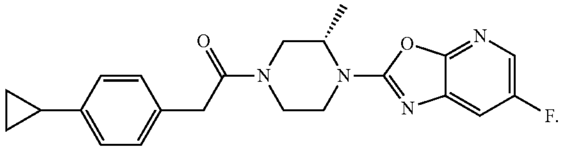

$^{1}H$ NMR (500 MHz, DMSO-$d_6$) δ 7.87 (q, J=2.0 Hz, 1H), 7.65 (dt, J=8.9, 3.2 Hz, 1H), 7.14 (d, J=7.8 Hz, 2H), 7.05-6.95 (m, 2H), 4.55-4.24 (m, 2H), 4.15-3.88 (m, 2H), 3.84-3.54 (m, 2H), 3.35 (s, 5H), 3.09-2.81 (m, 1H), 1.88 (ddq, J=8.5, 5.5, 2.8 Hz, 1H), 0.95-0.87 (m, 2H), 0.69-0.54 (m, 2H). $^{13}C$ NMR (126 MHz, DMSO) δ 170.40, 162.20, 159.43, 157.50, 154.40, 142.27, 137.15, 137.06, 132.93, 132.87, 129.44, 129.28, 125.82, 125.76, 111.39, 111.20, 49.46, 49.29, 49.04, 45.05, 44.90, 15.20, 9.76, 9.74, 9.72. ESI-MS (M+1): 395.42

PZ-4475 xxii

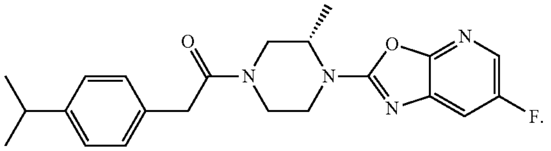

$^{1}H$ NMR (500 MHz, DMSO-$d_6$) δ 7.96 (s, 1H), 7.87 (d, J=2.3 Hz, 1H), 7.65 (dt, J=9.0, 2.1 Hz, 1H), 7.19 (s, 4H), 4.50-4.35 (m, 2H), 4.28 (dt, J=13.2, 2.0 Hz, 1H), 4.08 (dt, J=11.2, 2.8 Hz, 1H), 4.03-3.87 (m, 2H), 3.84-3.58 (m, 2H), 3.54-3.18 (m, 2H), 3.10-2.88 (m, 2H), 1.19 (dd, J=6.9, 2.1 Hz, 6H), 1.14 (dd, J=6.8, 4.0 Hz, 3H). ESI-MS (M+1): 397.52 v. Synthesis of PZ-4469

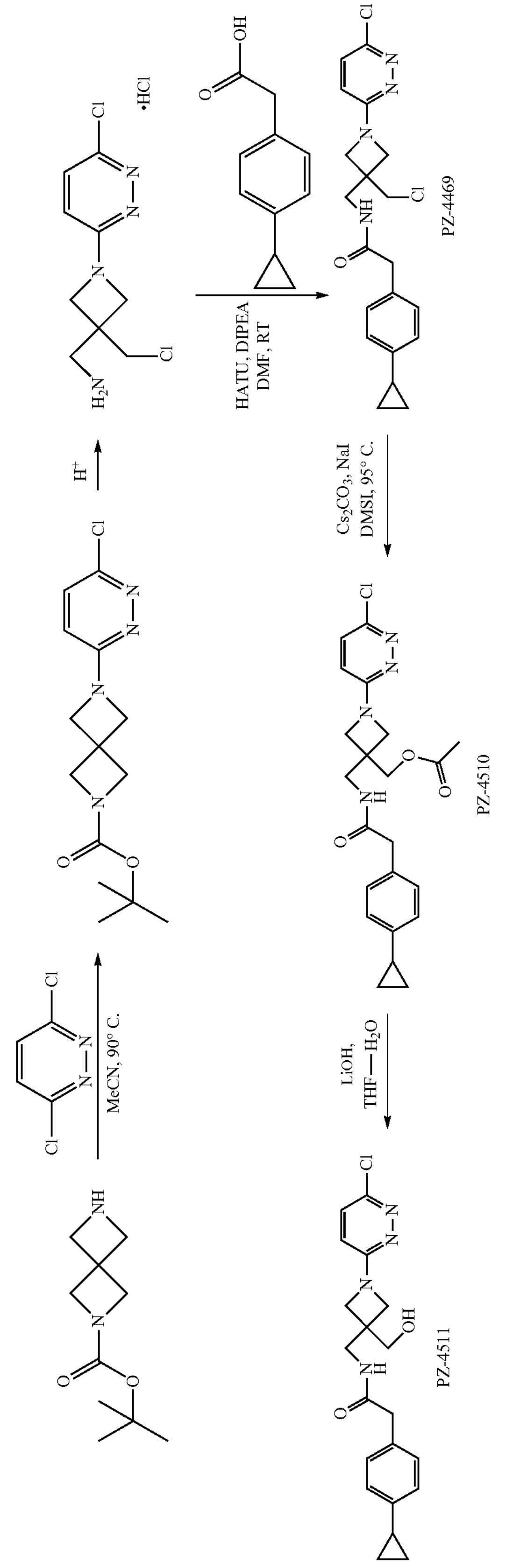
MeCN, 90° C.
H+
•HCl
HATU, DIPEA
DMF, RT
PZ-4469
$Cs_2CO_3$, NaI
DMSI, 95° C.
PZ-4510
LiOH,
THF—$H_2O$
PZ-4511

Step 1: In a sealed tube the mixture of 3,6-dichloropyridazine (0.750 g, 5.03 mmol), tert-butyl 2,6-diazaspiro[3.3]heptane-2-carboxylate, HCl (1.182 g, 5.03 mmol) and DIPEA (2 ml, 11.45 mmol) in acetonitrile (10 mL) was subjected to heat at 150° C. under microwave condition for 30 minutes. The reaction mixture was cooled to room temperature and diluted with water (20 mL). The solid product tert-butyl 6-(6-chloropyridazin-3-yl)-2,6-diazaspiro[3.3]heptane-2-carboxylate (1.5 g) was collected by filtration, washed with water and dried under vacuum. ESI-MS (M+1): 311.32

Step 2: The intermediate tert-butyl 6-(6-chloropyridazin-3-yl)-2,6-diazaspiro[3.3]heptane-2-carboxylate (1.5 g, 4.83 mmol) was taken in DCM (10 ml) and added 4 N. HCl in dioxane (6.03 ml, 24.13 mmol) at 0° C. and then slowly warmed to room temperature. The reaction mixture was allowed to stir for 3 h then evaporated under reduced pressure to get the product (3-(chloromethyl)-1-(6-chloropyridazin-3-yl)azetidin-3-yl)methanamine, HCl. ESI-MS (M+1): 247.31

Step 3: To a mixture of 2-(4-cyclopropylphenyl)acetic acid (441 mg, 2.504 mmol) and DMF (5 mL) HATU (1047 mg, 2.75 mmol) was added followed by DIPEA (1312 µl, 7.51 mmol) and allowed to stir for 10 minutes. Then (3-(chloromethyl)-1-(6-chloropyridazin-3-yl)azetidin-3-yl)methanamine, HCl (710 mg, 2.504 mmol) was added to the mixture and allowed to stir at room temperature for 3 h. The reaction mixture was diluted with water, collected the solid product N-((3-(chloromethyl)-1-(6-chloropyridazin-3-yl)azetidin-3-yl)methyl)-2-(4-cyclopropylphenyl)acetamide (PZ-4469) by filtration and washed with water. $^1$H NMR (500 MHz, DMSO-$d_6$) δ 8.35 (t, J=6.2 Hz, 1H), 7.51 (d, J=9.3 Hz, 1H), 7.05 (d, J=7.8 Hz, 2H), 6.87 (dd, J=8.8, 7.5 Hz, 3H), 3.94 (s, 2H), 3.90-3.73 (m, 4H), 3.45 (d, J=6.2 Hz, 2H), 3.37 (s, 4H), 1.83 (tt, J=8.5, 5.1 Hz, 1H), 0.99-0.85 (m, 2H), 0.69-0.53 (m, 2H). $^{13}$C NMR (126 MHz, DMSO) δ 171.73, 160.08, 146.52, 142.05, 133.62, 129.24, 129.08, 125.60, 115.96, 55.98, 49.46, 42.50, 41.68, 41.36, 15.17, 9.67. ESI-MS (M+1): 405.42

PZ-4510

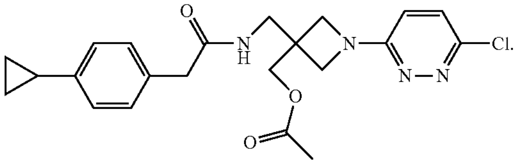

i

Step 4: The mixture of N-((3-(chloromethyl)-1-(6-chloropyridazin-3-yl)azetidin-3-yl)methyl)-2-(4-cyclopropylphenyl)acetamide (239 mg, 0.590 mmol) cesium carbonate (1153 mg, 3.54 mmol) sodium iodide (177 mg, 1.179 mmol) in DMSO (10 mL) stirred at 90 C for 3 h. The reaction mixture was diluted with water (50 mL) and extracted with ethyl acetate (30 mL×2). The combined ethyl acetate was washed with brine (50 mL), dried over $Na_2SO_4$ and evaporated to get product. $^1$H NMR (400 MHz, Chloroform-d) δ 7.10 (d, J=9.2 Hz, 1H), 7.04-6.85 (m, 4H), 6.36 (d, J=9.3 Hz, 1H), 5.78 (s, 1H), 4.12 (s, 2H), 3.88-3.69 (m, 4H), 3.45 (t, J=3.2 Hz, 4H), 1.77 (tt, J=8.4, 5.1 Hz, 1H), 0.97-0.80 (m, 2H), 0.66-0.49 (m, 2H). $^{13}$C NMR (126 MHz, DMSO) δ 171.61, 170.93, 160.19, 146.45, 142.05, 133.61, 129.23, 129.09, 125.60, 115.90, 66.56, 55.52, 42.48, 41.67, 21.11, 15.17, 9.67. ESI-MS (M+1): 429.25

PZ-4511

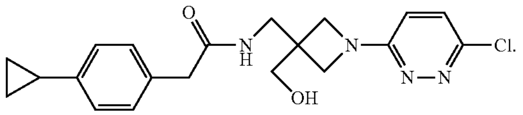

ii

Step 5: The mix of (1-(6-chloropyridazin-3-yl)-3-((2-(4-cyclopropylphenyl)acetamido)methyl)azetidin-3-yl)methyl acetate (200 mg, 0.466 mmol) and lithium hydroxide (33.5 mg, 1.399 mmol) in MeOH—$H_2O$ (6 mL, 3:1) for 1 h. The RM volume was reduced to 2 mL by blowing nitrogen and then diluted with more water to crash out the product, which was collected by filtration, washed with water and dried to get the pure product N-((1-(6-chloropyridazin-3-yl)-3-(hydroxymethyl)azetidin-3-yl)methyl)-2-(4-cyclopropylphenyl)acetamide (PZ-4511). $^1$H NMR (400 MHz, Chloroform-d) δ 7.09 (d, J=9.2 Hz, 1H), 7.06-6.93 (m, 4H), 6.40 (d, J=9.2 Hz, 1H), 6.10 (s, 1H), 3.75-3.61 (m, 5H), 3.60-3.47 (m, 6H), 1.80 (tt, J=8.4, 5.1 Hz, 1H), 0.97-0.84 (m, 2H), 0.66-0.54 (m, 2H). ESI-MS (M+1): 487.24

PZ-4468

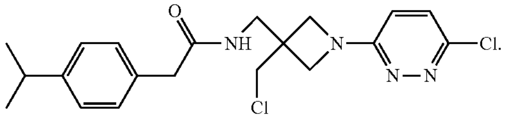

iii $^1$H NMR (500 MHz, DMSO-$d_6$) δ 8.37 (t, J=6.2 Hz, 1H), 7.51 (d, J=9.3 Hz, 1H), 7.12-7.00 (m, 4H), 6.91 (d, J=9.3 Hz, 1H), 3.95 (s, 2H), 3.85 (dd, J=44.5, 8.7 Hz, 4H), 3.46 (d, J=6.2 Hz, 2H), 3.39 (s, 2H), 2.81 (p, J=6.9 Hz, 1H), 1.16 (d, J=6.9 Hz, 6H). 13C NMR (126 MHz, DMSO) δ 171.71, 160.10, 146.78, 146.53, 134.10, 129.25, 129.14, 126.51, 115.99, 56.01, 49.46, 42.51, 41.74, 41.35, 33.49, 24.36. ESI-MS (M+1): 407.42

PZ-4472 w

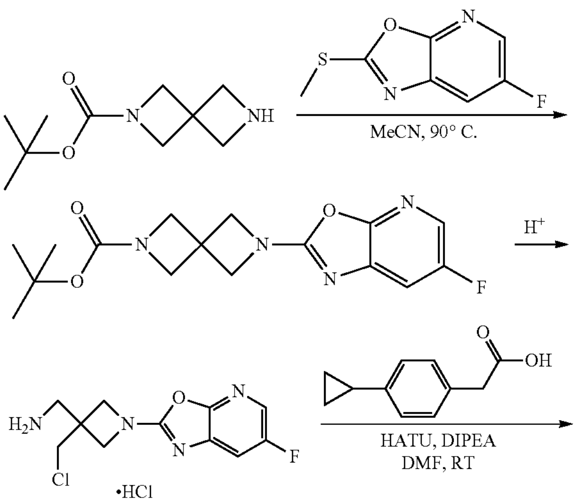

-continued

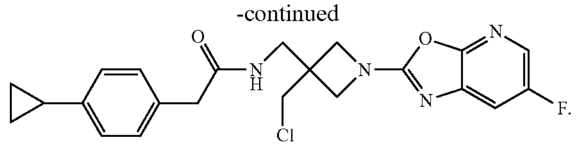

PZ-4472

$^1$H NMR (500 MHz, DMSO-$d_6$) δ 8.41 (t, J=6.3 Hz, 1H), 7.96 (s, 1H), 7.90 (t, J=2.2 Hz, 1H), 7.68 (dd, J=8.9, 2.7 Hz, 1H), 7.07 (d, J=8.2 Hz, 2H), 6.84 (d, J=8.2 Hz, 2H), 4.11-3.92 (m, 6H), 3.47 (d, J=6.2 Hz, 2H), 3.38 (s, 2H), 1.75 (tt, J=8.3, 5.0 Hz, 1H), 0.88-0.80 (m, 2H), 0.57-0.44 (m, 2H). $^{13}$C NMR (126 MHz, DMSO) δ 171.94, 162.92, 162.78, 159.40, 157.46, 154.80, 142.08, 137.25, 137.17, 133.58, 129.67, 129.07, 125.68, 125.58, 125.36, 111.64, 111.45, 56.14, 48.82, 42.52, 41.99, 41.52, 15.12, 9.59. ESI-MS (M+1): 429.43

PZ-4473 i

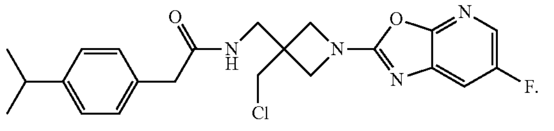

$^1$H NMR (500 MHz, DMSO-d6) δ 8.43 (t, J=6.2 Hz, 1H), 7.96 (s, 1H), 7.90 (dd, J=2.7, 1.8 Hz, 1H), 7.69 (dd, J=9.0, 2.6 Hz, 1H), 7.06 (dd, J=54.4, 8.1 Hz, 4H), 4.04 (dd, J=45.4, 8.8 Hz, 4H), 3.97 (s, 2H), 3.48 (d, J=6.2 Hz, 2H), 3.40 (s, 2H), 1.11 (d, J=6.9 Hz, 6H). $^{13}$C NMR (126 MHz, DMSO) δ 171.93, 162.93, 162.78, 159.41, 157.47, 154.80, 146.81, 137.27, 137.18, 134.07, 129.13, 126.48, 125.58, 125.35, 111.64, 111.45, 56.15, 48.83, 42.54, 41.98, 41.56, 33.44, 24.27. ESI-MS (M+1): 431.43 x. Synthesis of PC-4478 and PZ-4479

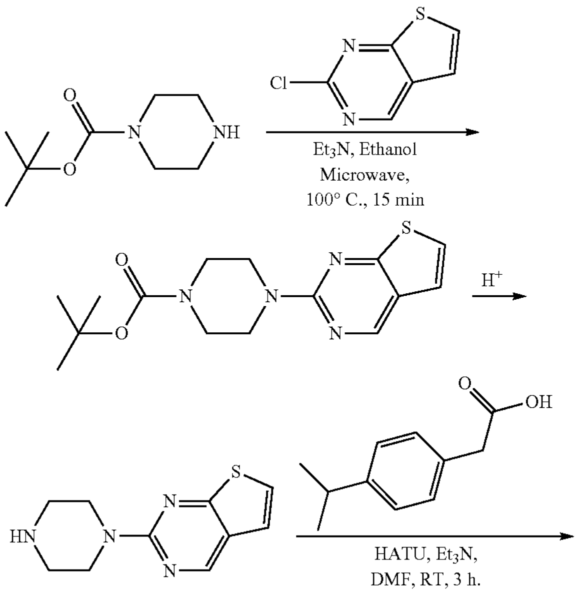

-continued

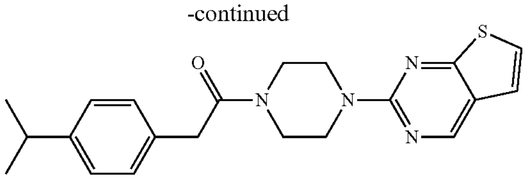

A mixture of 2-chlorothieno[2,3-d]pyrimidine (200 mg, 1.165 mmol), tert-butyl piperazine-1-carboxylate (260 mg, 1.399 mmol) and triethylamine (0.325 mL) in ethanol (1 mL) was heated to 100° C. for 15 min under microwave condition. The reaction mixture was cooled to room temperature, diluted with water (2 mL) and the resulting solid product tert-butyl 4-(thieno[2,3-d]pyrimidin-2-yl)piperazine-1-carboxylate was collected by filtration. ESI-MS ($M^+$-$^t$Bu): 265.31. This intermediate was carried out in further steps as explained in previous methods to synthesize PZ-4478 and PZ-4479.

PZ-4478 i

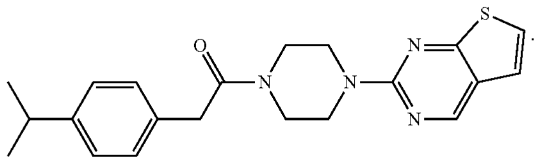

$^1$H NMR (500 MHz, DMSO-$d_6$) δ 8.90 (s, 1H), 7.32 (dd, J=42.0, 5.9 Hz, 2H), 7.17 (s, 4H), 3.84-3.69 (m, 6H), 3.60 (ddd, J=14.7, 7.0, 4.3 Hz, 4H), 2.86 (dq, J=13.8, 7.3 Hz, 1H), 1.18 (d, J=6.9 Hz, 6H). $^{13}$C NMR (126 MHz, DMSO) δ 170.89, 169.77, 158.94, 153.63, 146.85, 133.53, 129.41, 126.70, 122.77, 121.93, 121.06, 45.58, 44.46, 44.12, 41.45, 33.51, 24.38. ESI-MS (M+1): 381.22

PZ-4479 ii

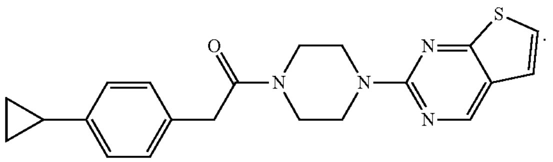

$^1$H NMR (500 MHz, DMSO-$d_6$) δ 8.90 (s, 1H), 7.32 (dd, J=43.7, 5.9 Hz, 2H), 7.07 (dd, J=57.9, 7.9 Hz, 4H), 3.84-3.68 (m, 6H), 3.59 (ddd, J=10.5, 6.5, 3.5 Hz, 4H), 1.87 (tt, J=8.4, 5.0 Hz, 1H), 0.96-0.87 (m, 2H), 0.67-0.59 (m, 2H). $^{13}$C NMR (126 MHz, DMSO) δ 170.89, 169.72, 158.94, 153.63, 142.14, 133.03, 129.33, 125.80, 122.77, 121.94, 121.05, 45.57, 44.45, 44.12, 41.45, 15.20, 9.72. ESI-MS (M+1): 379.42

2. Biological Assays

The PanK activity and Surface Plasmon Resonance assays were conducted as explained in the literature. See, e.g., "A therapeutic approach to pantothenate kinase associated neurodegeneration" *Nature Communications*, volume 9, Article number: 4399 (2018).

a. PANK Activity Assays

PANK activity assay was performed in the presence of 0-10 μM compound in a reaction mixture that contained 100 mM Tris-HCl, pH 7.5, 10 mM $MgCl_2$, 2.5 mM ATP, 45 μM D-[1-14C]pantothenate (specific activity, 22.5 mCi/mmol) and 5 nM of human PANK3. PANK3 concentrations were calculated using the extinction coefficient at 280 nm of 39,225M-1 $cm^{-1}$. The assay was linear with time and after 10 min at 37° C. the reaction was stopped by the addition of 4 μl of 10% (v/v) acetic acid. The mixture was spotted onto a DE81 disk, washed with three successive changes of 1% acetic acid in 95% ethanol and product formation determined by scintillation counting of the dried disc. If the $IC^{50}$ was determined to be in the nM range then the assay was repeated in the presence of 0-1 μM or 0-0.1 μM compound to more precisely determine the $IC^{50}$. All the experiments were repeated twice in duplicate and the data were an average ±data range. For the kinetic experiments, the assay was done either varying the pantothenate from 0-180 μM or ATP from 0-125 μM at a given concentration of test compound.

The experiments mimicking the mixture of ligands present in vivo were performed under different conditions. The reaction mix for the determination of the acetyl-CoA $IC^{51}$ contained 100 mM Tris-HCl (pH 7.5), 10 mM $MgCl_2$, 1 mM ATP, 45 μM D-[1-14C]pantothenate (specific activity 22.5 mCi/mmol), 2.5 μM test compound and 1 μg of PANK3. In the time-course experiments, the reaction mixtures contained 100 mM Tris-HCl (pH 7.5), 10 mM $MgCl_2$, 1 mM ATP, 45 μM or 90 μM D-[1-14C]pantothenate (specific activity, 22.5 mCi/mmol), 100 μM acetyl CoA±2.5 μM test compound, and 1 μg of PANK3. The $IC^{50}$ values for the structure-activity study were calculated by fitting the inhibition data to a one-site model of the Michaelis-Menten equation. Although this method was appropriate to measure the $IC^{50}$ with most of the test compounds, it underestimates ligand binding affinity if the concentration of protein in the assay alters the free ligand concentration. Thus, the data were fit to Morrison's quadratic equation (GraphPad software) that accounts for the impact of enzyme inhibitor binding on the free concentration of inhibitor.

b. Cell Culture Cellular and Tissue CoA Determinations.

Human C3A [HepG2/C3A, derivative of HepG2] cells (ATCC #CRL-10741) were purchased from ATCC® and maintained in Eagle's minimum Essential medium (ATCC) supplemented with 2 mM glutamine, 10% fetal bovine serum (FCS, Altanta Biologicals), 50 U/ml penicillin and 50 mg/ml streptomycin. The C3A cell line was confirmed to be mycoplasma-free. Test compounds or vehicle control (DMSO) was added and after 24 hrs of treatment the cells were washed with PBS and harvested and subjected to total CoA determination.

Cultured cells were resuspended in 2 ml cold water to which 500 μl of 0.25M KOH was added, derivatized with monobromobimane (mBBr, Life technologies) and quantified by HPLC. 30 mg of frozen tissue is homogenized in 2 ml of 1 mM KOH and then derivatized with mBBr. The mBBr derivatized samples were fractionated by reverse-phase HPLC using a Gemini C18 3 μm column (150×4.60 mm) from Phenomenex. The chromatography system was a Waters e2695 separation module with a UV/Vis and fluorescence detector and controlled by Empower 3 software. Solvent A was 50 mM potassium phosphate pH 4.6, and solvent B was 100% acetonitrile. Twenty microliters of sample was injected onto the column, and the flow rate was 0.5 ml/min. The HPLC program was the following: starting solvent mixture of 90% A/10% B, 0-2 min isocratic with 10% B, 2-6 min linear gradient from 10% B to 15% B, 6-18 min concave gradient from 15% B to 40% B, 18-23 min isocratic with 40% B, 23-25 min linear gradient from 40 to 10%, and 25-30 min isocratic with 10% B. The UV/vis detector was set at 393 nm, and the fluorescence detector was set with excitation at 393 nm and emission at 470 nm. The elution position of the mBBr-CoA, was determined by comparison with mBBr-CoA prepared from commercial CoA (Avanti Polar Lipids). The areas under the mBBr-derivatized CoA was integrated and compared to known concentrations of the mBBr-CoA standard.

3. Characterization of Exemplary Compounds

The compounds below in Table 2 were synthesized with methods identical or analogous to those described herein. The requisite starting materials were commercially available, described in the literature, or readily synthesized by one skilled in the art of organic synthesis.

TABLE 2

| PZ | Structure | IC50 (nM) | C3A CoA% elevation |
|---|---|---|---|
| PZ-3022 | 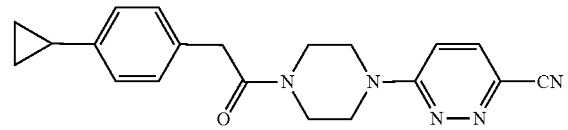 [SMILES: N#Cc1ccc(N2CCN(C(=O)Cc3ccc(C4CC4)cc3)CC2)nn1] | 6.8 ± 1.2 | |
| PZ-4060 | 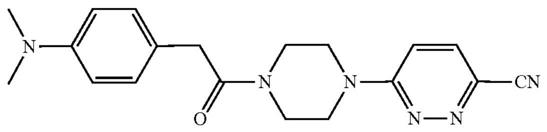 | 64 ± 7.7 | 230.5 |
| PZ-4061 | 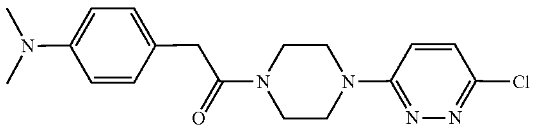 | 16.8 ± 1.7 | 418.7 |

TABLE 2-continued
| PZ | Structure | IC50 (nM) | C3A CoA% elevation |
|---|---|---|---|
| PZ-4069 | 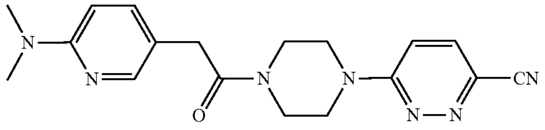 [SMILES: CN(C)c1ccc(CC(=O)N2CCN(c3ccc(C#N)nn3)CC2)cc1] | 440 ± 45 | |
| PZ-4070 | 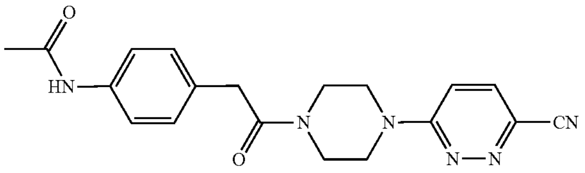 [SMILES: CC(=O)Nc1ccc(CC(=O)N2CCN(c3ccc(C#N)nn3)CC2)cc1] | 65 ± 9.8 | |
| PZ-4071 | 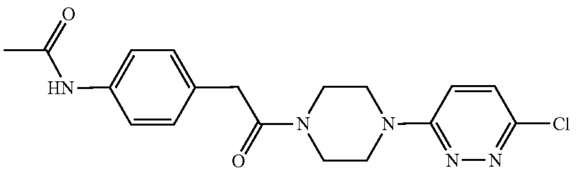 [SMILES: CC(=O)Nc1ccc(CC(=O)N2CCN(c3ccc(Cl)nn3)CC2)cc1] | 17 ± 1.5 | 185.3 |
| PZ-4109 | 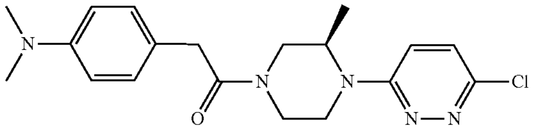 [SMILES: C[C@@H]1CN(C(=O)Cc2ccc(N(C)C)cc2)CCN1c1ccc(Cl)nn1] | 10.6 ± 1 | |
| PZ-4110 | 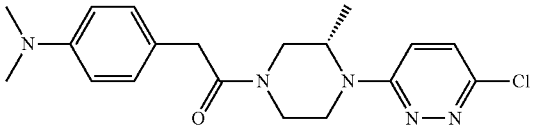 | 10.7 ± 0.6 | |
| PZ-4111 | 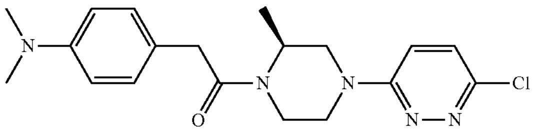 [SMILES: C[C@H]1CN(c2ccc(Cl)nn2)CCN1C(=O)Cc1ccc(N(C)C)cc1] | 11.1 ± 0.7 | |
| PZ-4112 | 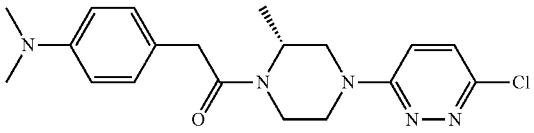 [SMILES: C[C@@H]1CN(c2ccc(Cl)nn2)CCN1C(=O)Cc1ccc(N(C)C)cc1] | 39.7 ± 4.7 | |
| PZ-4127 | 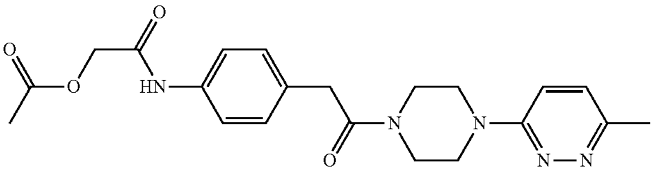 [SMILES: CC(=O)OCC(=O)Nc1ccc(CC(=O)N2CCN(c3ccc(C)nn3)CC2)cc1] | >1000 | |
| PZ-4128 | 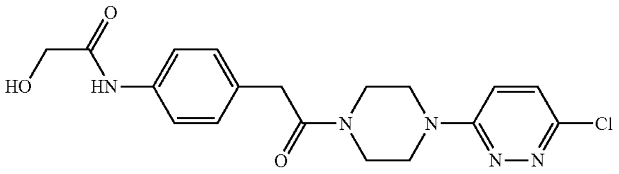 [SMILES: O=C(CO)Nc1ccc(CC(=O)N2CCN(c3ccc(Cl)nn3)CC2)cc1] | 150 ± 30 | |

TABLE 2-continued
| PZ | Structure | IC50 (nM) | C3A CoA% elevation |
|---|---|---|---|
| PZ-4140 | 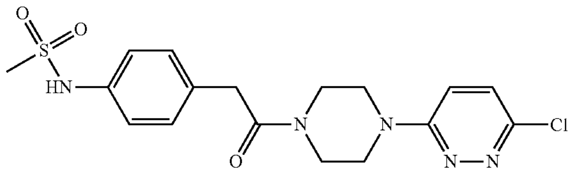 [SMILES: CS(=O)(=O)Nc1ccc(CC(=O)N2CCN(c3ccc(Cl)nn3)CC2)cc1] | 3.8 ± 0.1 | 64.4 |
| PZ-4200 | 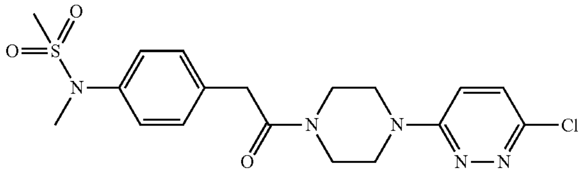 [SMILES: CN(c1ccc(CC(=O)N2CCN(c3ccc(Cl)nn3)CC2)cc1)S(C)(=O)=O] | 120 ± 11.2 | |
| PZ-4202 | 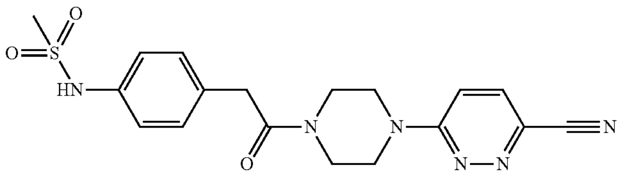 [SMILES: CS(=O)(=O)Nc1ccc(CC(=O)N2CCN(c3ccc(C#N)nn3)CC2)cc1] | 3.9 ± 0.4 | 183.3 |
| PZ-4215 | 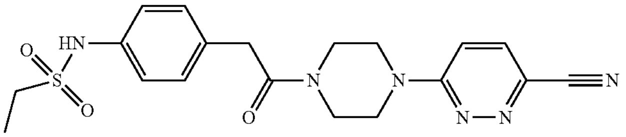 [SMILES: CCS(=O)(=O)Nc1ccc(CC(=O)N2CCN(c3ccc(C#N)nn3)CC2)cc1] | 4.0 ± 0.3 | 160.9 |
| PZ-4216 | 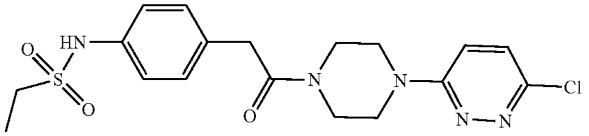 [SMILES: CCS(=O)(=O)Nc1ccc(CC(=O)N2CCN(c3ccc(Cl)nn3)CC2)cc1] | 2.4 ± 0.1 | 54.9 |
| PZ-4283 | 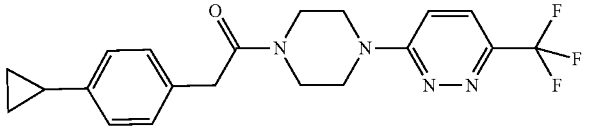 [SMILES: O=C(Cc1ccc(C2CC2)cc1)N1CCN(c2ccc(C(F)(F)F)nn2)CC1] | 34 ± 4 | 218.2 |
| PZ-4284 | 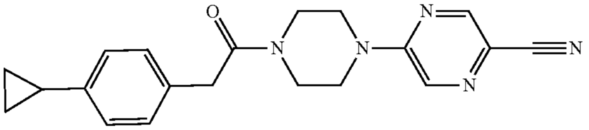 [SMILES: N#Cc1cnc(N2CCN(C(=O)Cc3ccc(C4CC4)cc3)CC2)cn1] | 27 ± 4 | 448.2 |
| PZ-4285 | 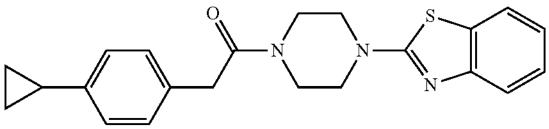 [SMILES: O=C(Cc1ccc(C2CC2)cc1)N1CCN(c2nc3ccccc3s2)CC1] | 26 ± 3 | 223.7 |
| PZ-4290 | 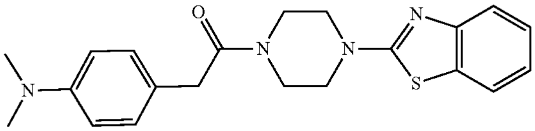 [SMILES: CN(C)c1ccc(CC(=O)N2CCN(c3nc4ccccc4s3)CC2)cc1] | 370 ± 47 | |

TABLE 2-continued
| PZ | Structure | IC50 (nM) | C3A CoA% elevation |
|---|---|---|---|
| PZ-4291 | 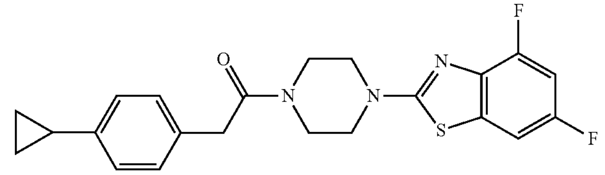 [SMILES: O=C(Cc1ccc(C2CC2)cc1)N1CCN(c2nc3c(F)cc(F)cc3s2)CC1] | 2.1 ± 0.1 | 238.4 |
| PZ-4294 | 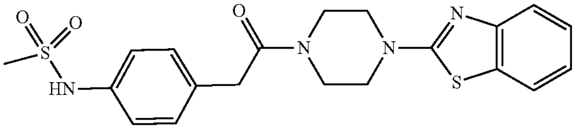 [SMILES: CS(=O)(=O)Nc1ccc(CC(=O)N2CCN(c3nc4ccccc4s3)CC2)cc1] | 13 ± 1.3 | 102.23 |
| PZ-4295 | 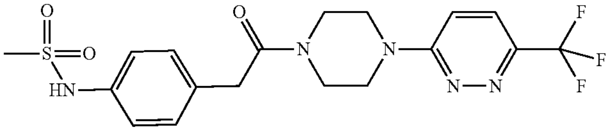 [SMILES: CS(=O)(=O)Nc1ccc(CC(=O)N2CCN(c3ccc(C(F)(F)F)nn3)CC2)cc1] | 8.2 ± 0.6 | 140.8 |
| Lee-4296 | 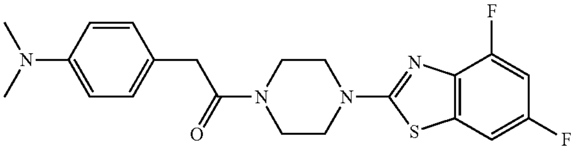 [SMILES: CN(C)c1ccc(CC(=O)N2CCN(c3nc4c(F)cc(F)cc4s3)CC2)cc1] | 25 ± 1.6 | 198.6 |
| PZ-4298 | 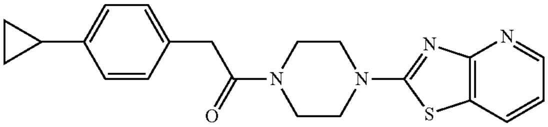 | 1.0 ± 0.1 | 60.1 |
| PZ-4299 | 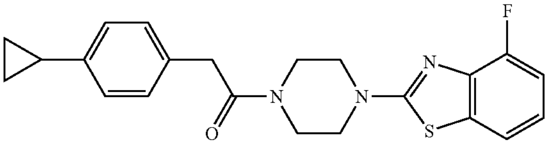 [SMILES: O=C(Cc1ccc(C2CC2)cc1)N1CCN(c2nc3c(F)cccc3s2)CC1] | 7.2 ± 1.3 | 228.4 |
| PZ-4300 | 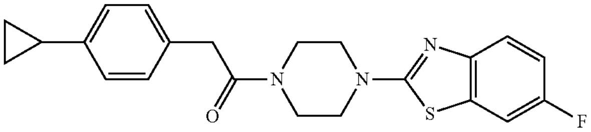 | 3.9 ± 0.3 | 242.5 |
| PZ-4301 | 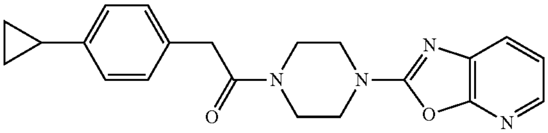 [SMILES: O=C(Cc1ccc(C2CC2)cc1)N1CCN(c2nc3cccnc3o2)CC1] | 52.9 ± 6.4 | 268.3 |
| PZ-4303 | 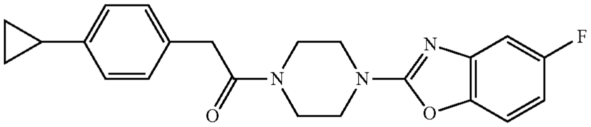 [SMILES: O=C(Cc1ccc(C2CC2)cc1)N1CCN(c2nc3cc(F)ccc3o2)CC1] | 54 ± 6.4 | |
| PZ-4304 | 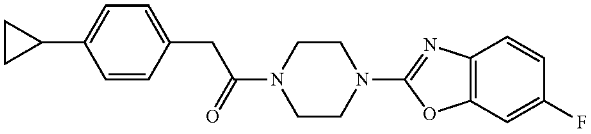 | 14.3 ± 0.6 | 167 |

TABLE 2-continued
| PZ | Structure | IC50 (nM) | C3A CoA% elevation |
|---|---|---|---|
| PZ-4305 | 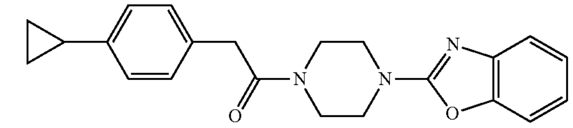 | 173 ± 48.5 | |
| PZ-4306 | 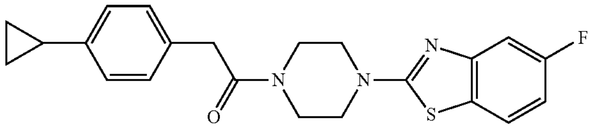 [SMILES: O=C(Cc1ccc(C2CC2)cc1)N1CCN(c2nc3cc(F)ccc3s2)CC1] | 5.4 ± 0.4 | 238.6 |
| PZ-4312 | 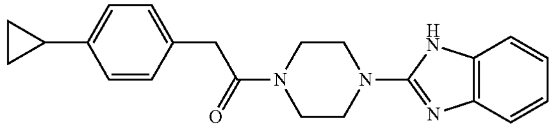 | 987 ± 476 | |
| PZ-4313 | 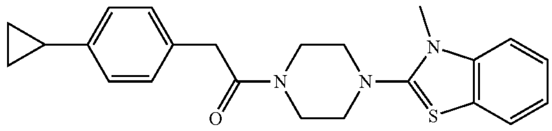 | 848 ± 638 | |
| PZ-4314 | 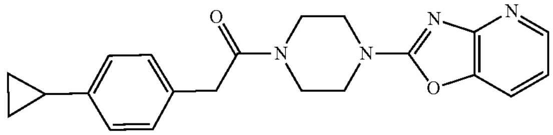 [SMILES: O=C(Cc1ccc(C2CC2)cc1)N1CCN(c2nc3ncccc3o2)CC1] | 2.9 ± 0.1 | 275 |
| PZ-4316 | 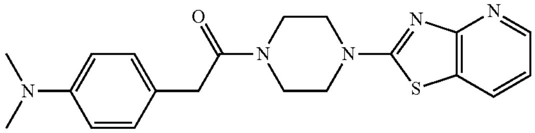 | 5 ± 0.5 | 183.4 |
| PZ-4317 | 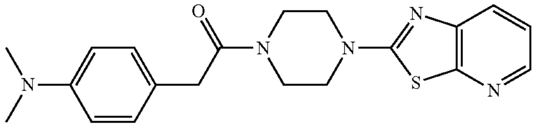 | 391 ± 129 | |
| PZ-4318 | 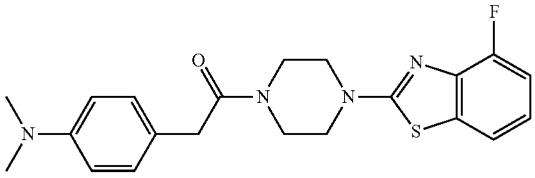 | 183 ± 71 | |
| PZ-4319 | 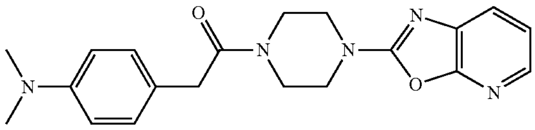 [SMILES: CN(C)c1ccc(CC(=O)N2CCN(c3nc4cccnc4s3)CC2)cc1] | 346 ± 100 | |
| PZ-4320 | 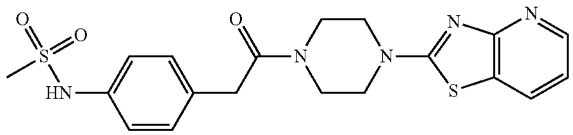 [SMILES: CS(=O)(=O)Nc1ccc(CC(=O)N2CCN(c3nc4ncccc4s3)CC2)cc1] | 1.4 ± 0.16 | 58 |

TABLE 2-continued
| PZ | Structure | IC50 (nM) | C3A CoA% elevation |
|---|---|---|---|
| PZ-4321 | 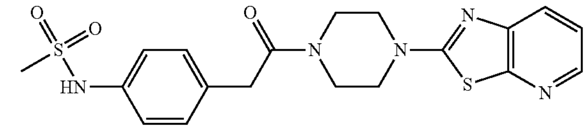 | 5.67 ± 0.39 | |
| PZ-4322 | 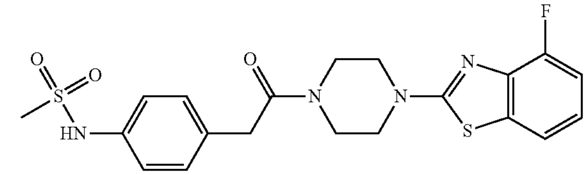 | 4.1 ± 0.49 | 171.6 |
| PZ-4323 | 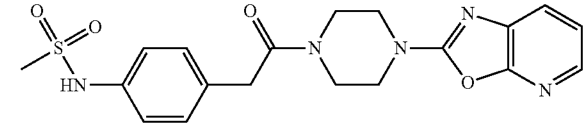 [SMILES: CS(=O)(=O)Nc1ccc(CC(=O)N2CCN(c3nc4cccnc4s3)CC2)cc1] | 9.9 ± 1.6 | |
| PZ-4324 | 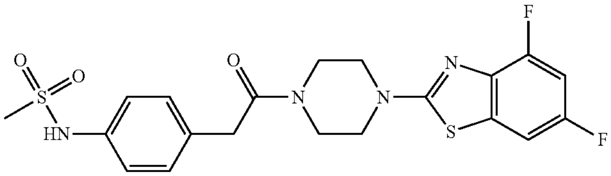 [SMILES: CS(=O)(=O)Nc1ccc(CC(=O)N2CCN(c3nc4c(F)cc(F)cc4s3)CC2)cc1] | 1.3 ± 0.06 | 104.3 |
| PZ-4343 | 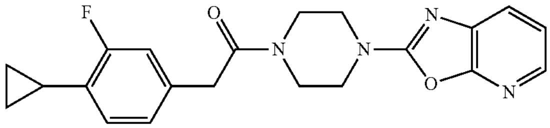 [SMILES: O=C(Cc1ccc(C2CC2)c(F)c1)N1CCN(c2nc3cccnc3o2)CC1] | 49 ± 3 | |
| PZ-4344 | 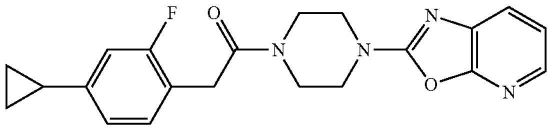 [SMILES: O=C(Cc1ccc(C2CC2)cc1F)N1CCN(c2nc3cccnc3o2)CC1] | 7.6 ± 0.48 | |
| PZ-4348 | 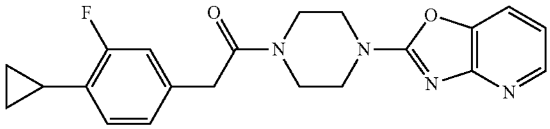 [SMILES: O=C(Cc1ccc(C2CC2)c(F)c1)N1CCN(c2nc3ncccc3o2)CC1] | 5.7 ± 0.49 | |
| PZ-4349 | 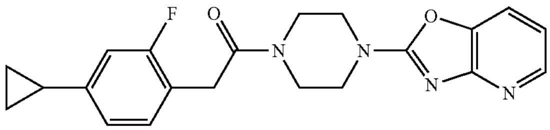 [SMILES: O=C(Cc1ccc(C2CC2)cc1F)N1CCN(c2nc3ncccc3o2)CC1] | 2.1 ± 0.26 | |
| PZ-4350 | 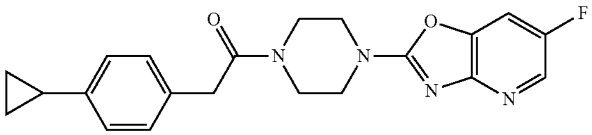 | 1.1 ± 0.12 | |
| PZ-4351 | 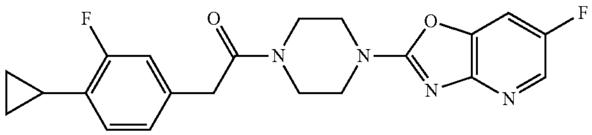 | 1.23 ± 0.15 | |

TABLE 2-continued
| PZ | Structure | IC50 (nM) | C3A CoA% elevation |
|---|---|---|---|
| PZ-4352 | 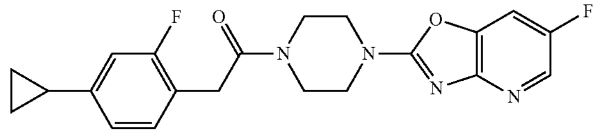 [SMILES: O=C(Cc1ccc(C2CC2)cc1F)N1CCN(c2nc3ncc(F)cc3o2)CC1] | 0.86 ± 0.078 | |
| PZ-4357 | 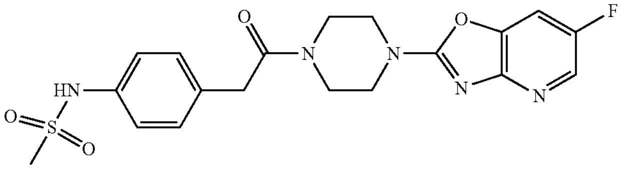 [SMILES: CS(=O)(=O)Nc1ccc(CC(=O)N2CCN(c3nc4ncc(F)cc4o3)CC2)cc1] | 1.95 ± 0.25 | |
| PZ-4359 | 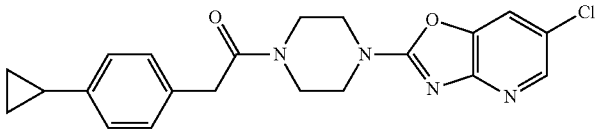 [SMILES: O=C(Cc1ccc(C2CC2)cc1)N1CCN(c2nc3ncc(Cl)cc3o2)CC1] | 1.23 ± 0.17 | |
| PZ-4360 | 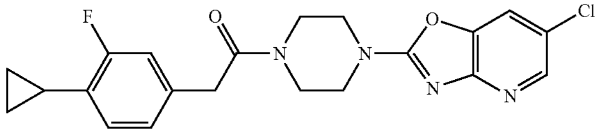 | 5.6 ± 0.88 | |
| PZ-4361 | 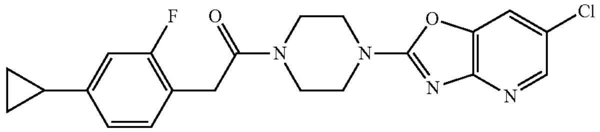 [SMILES: O=C(Cc1ccc(C2CC2)cc1F)N1CCN(c2nc3ncc(Cl)cc3o2)CC1] | 0.81 ± 0.15 | |
| PZ-4363 | 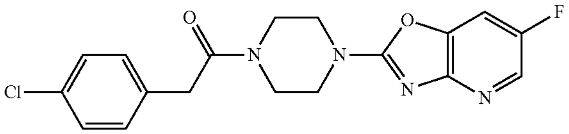 [SMILES: O=C(Cc1ccc(Cl)cc1)N1CCN(c2nc3ncc(F)cc3o2)CC1] | 37.5 ± 2.4 | |
| PZ-4364 | 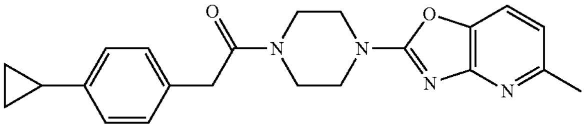 [SMILES: Cc1ccc2oc(N3CCN(C(=O)Cc4ccc(C5CC5)cc4)CC3)nc2n1] | 77.3 ± 8.2 | |
| PZ-4383 | 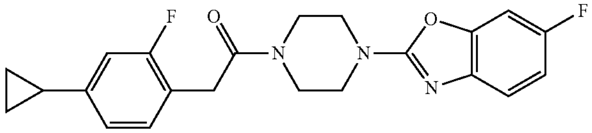 | 3.4 ± 0.33 | |
| PZ-4386 | 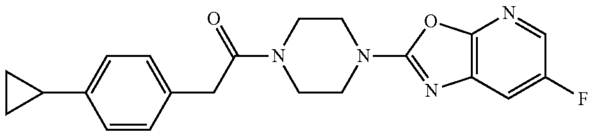 [SMILES: O=C(Cc1ccc(C2CC2)cc1)N1CCN(c2nc3cc(F)cnc3o2)CC1] | 2.1 ± 0.21 | |
| PZ-4392 | 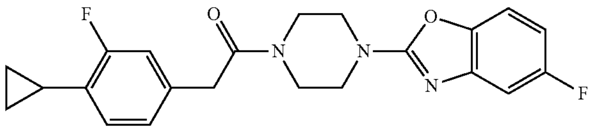 [SMILES: O=C(Cc1ccc(C2CC2)c(F)c1)N1CCN(c2nc3cc(F)ccc3o2)CC1] | 20.1 ± 1.9 | |

TABLE 2-continued
| PZ | Structure | IC50 (nM) | C3A CoA% elevation |
|---|---|---|---|
| PZ-4467 | 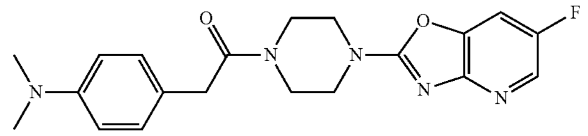 [SMILES: CN(C)c1ccc(CC(=O)N2CCN(c3nc4ncc(F)cc4o3)CC2)cc1] | 2.62 ± 0.18 | |
| PZ-4432 | 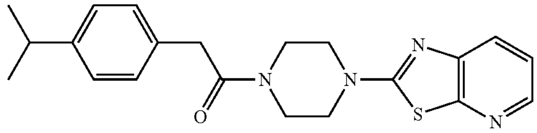 [SMILES: CC(C)c1ccc(CC(=O)N2CCN(c3nc4cccnc4s3)CC2)cc1] | 3.95 ± 0.26 | |
| PZ-4433 | 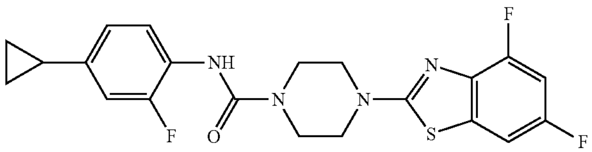 [SMILES: O=C(Nc1ccc(C2CC2)cc1F)N1CCN(c2nc3c(F)cc(F)cc3s2)CC1] | 1.79 ± 0.09 | |
| PZ-4434 | 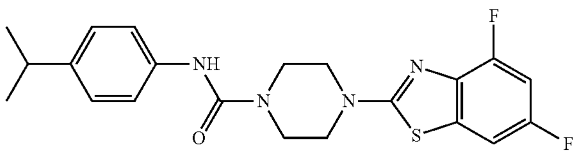 [SMILES: CC(C)c1ccc(NC(=O)N2CCN(c3nc4c(F)cc(F)cc4s3)CC2)cc1] | 1.04 ± 0.06 | |
| PZ-4435 | 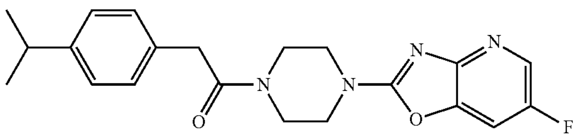 [SMILES: CC(C)c1ccc(CC(=O)N2CCN(c3nc4ncc(F)cc4o3)CC2)cc1] | 0.33 ± 0.02 | |
| PZ-4436 | 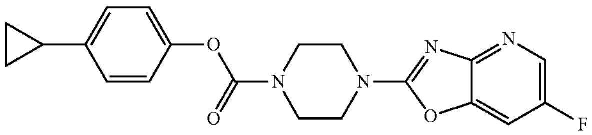 [SMILES: O=C(Oc1ccc(C2CC2)cc1)N1CCN(c2nc3ncc(F)cc3o2)CC1] | 2.0 ± 0.18 | |
| PZ-4462 | 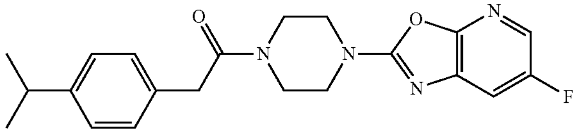 [SMILES: CC(C)c1ccc(CC(=O)N2CCN(c3nc4cc(F)cnc4o3)CC2)cc1] | 1.37 ± 0.16 | |
| PZ-4463 | 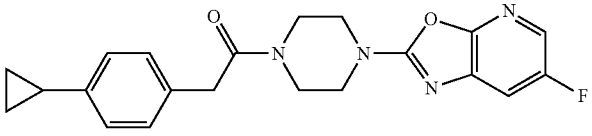 [SMILES: O=C(Cc1ccc(C2CC2)cc1)N1CCN(c2nc3cc(F)cnc3o2)CC1] | 10.3 ± 0.55 | |
| PZ-4468 | 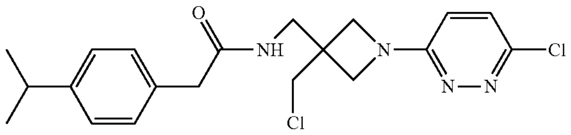 [SMILES: CC(C)c1ccc(CC(=O)NCC2(CCl)CN(c3ccc(Cl)nn3)C2)cc1] | 1.2 ± 0.13 | |
| PZ-4469 | 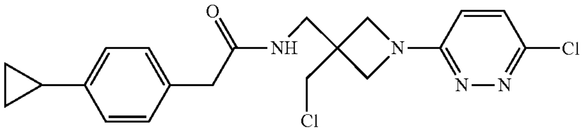 [SMILES: O=C(Cc1ccc(C2CC2)cc1)NCC1(CCl)CN(c2ccc(Cl)nn2)C1] | 5.4 ± 0.42 | |

TABLE 2-continued
| PZ | Structure | IC50 (nM) | C3A CoA% elevation |
|---|---|---|---|
| PZ-4470 | 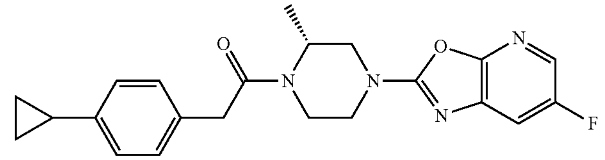 [SMILES: C[C@@H]1CN(c2nc3cc(F)cnc3o2)CCN1C(=O)Cc1ccc(C2CC2)cc1] | 3.88 ± 0.24 | |
| PZ-4471 | 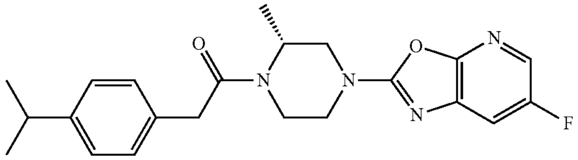 [SMILES: CC(C)c1ccc(CC(=O)N2CCN(c3nc4cc(F)cnc4o3)C[C@H]2C)cc1] | 0.88 ± 0.09 | |
| PZ-4472 | 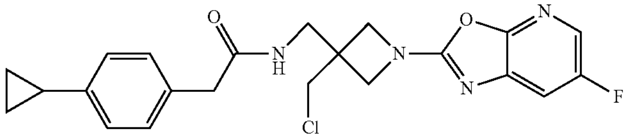 [SMILES: O=C(Cc1ccc(C2CC2)cc1)NCC1(CCl)CN(c2nc3cc(F)cnc3o2)C1] | 21.8 ± 1.78 | |
| PZ-4473 | 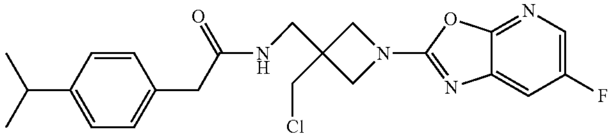 [SMILES: CC(C)c1ccc(CC(=O)NCC2(CCl)CN(c3nc4cc(F)cnc4o3)C2)cc1] | 7.51 ± 0.62 | |
| PZ-4474 | 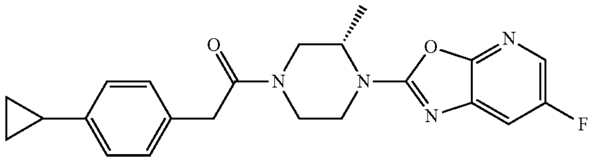 [SMILES: C[C@H]1CN(C(=O)Cc2ccc(C3CC3)cc2)CCN1c1nc2cc(F)cnc2o1] | 1.37 ± 0.14 | |
| PZ-4475 | 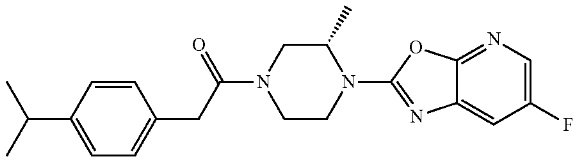 [SMILES: CC(C)c1ccc(CC(=O)N2CCN(c3nc4cc(F)cnc4o3)[C@@H](C)C2)cc1] | 0.76 ± 0.05 | |
| PZ-4478 | 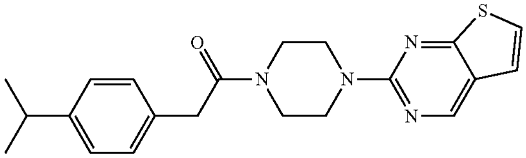 [SMILES: CC(C)c1ccc(CC(=O)N2CCN(c3ncc4ccsc4n3)CC2)cc1] | 125.3 ± 19.2 | |
| PZ-4479 | 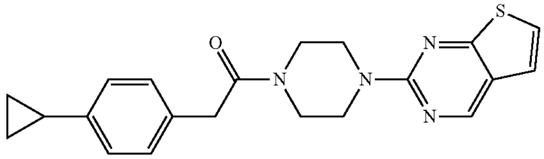 [SMILES: O=C(Cc1ccc(C2CC2)cc1)N1CCN(c2ncc3ccsc3n2)CC1] | 713.4 ± 294 | |
| PZ-4510 | 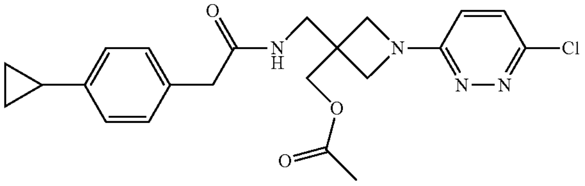 [SMILES: CC(=O)OCC1(CNC(=O)Cc2ccc(C3CC3)cc2)CN(c2ccc(Cl)nn2)C1] | 1114 ± 852 | |

TABLE 2-continued

| PZ | Structure | IC50 (nM) | C3A CoA% elevation |
|---|---|---|---|
| PZ-4511 | 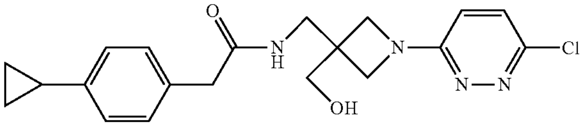 [SMILES: O=C(Cc1ccc(C2CC2)cc1)NCC1(CO)CN(c2ccc(Cl)nn2)C1] | 606 ± 237 | |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound selected from the group consisting of:

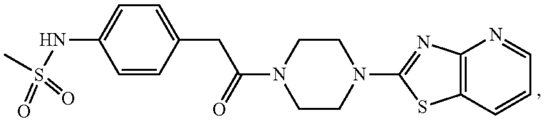,

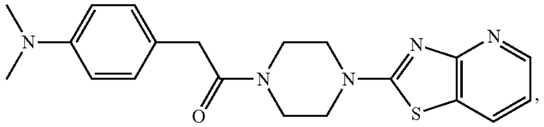,

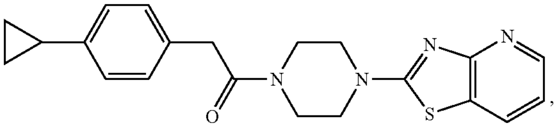,

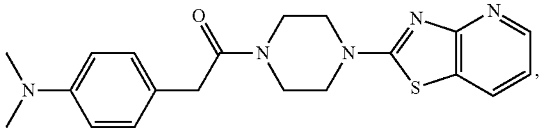,

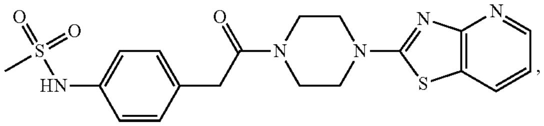,

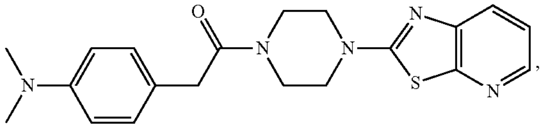,

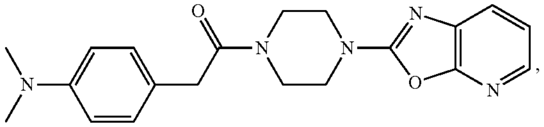,

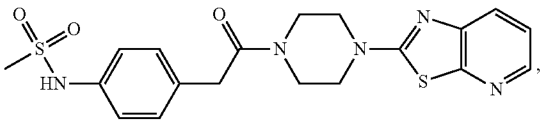,

-continued

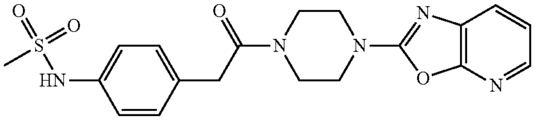,

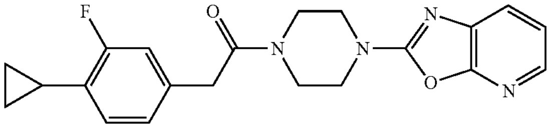,

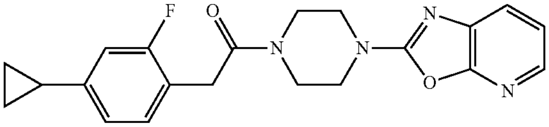,

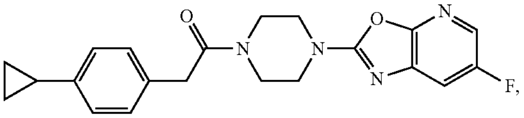

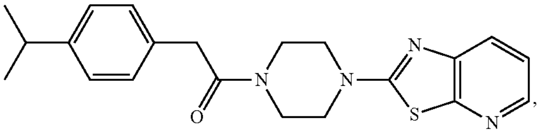,

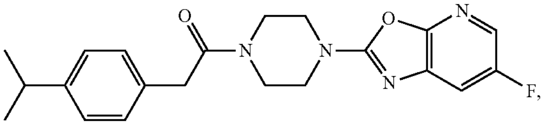

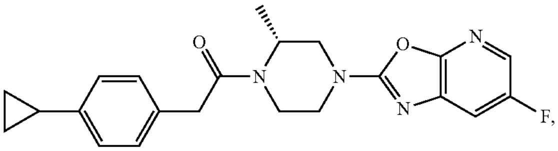

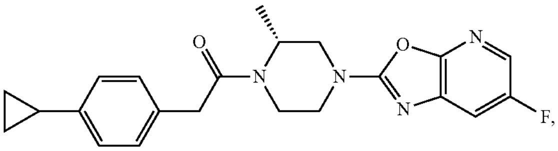

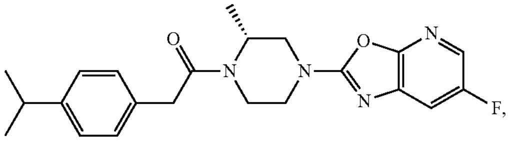

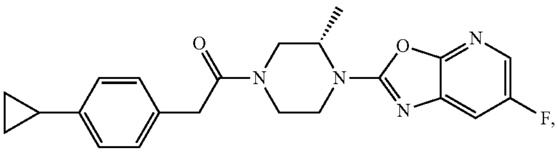

-continued

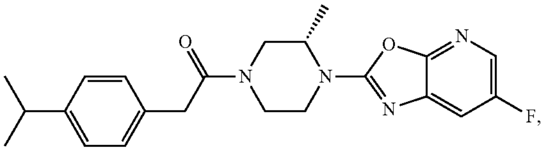,

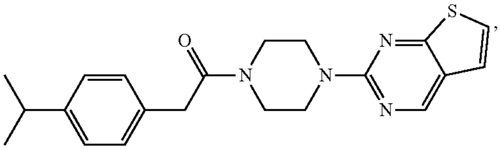, and

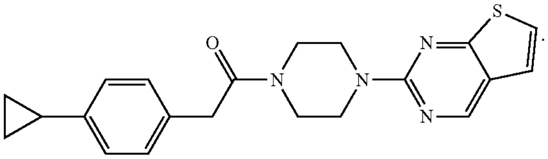.

2. A pharmaceutical composition comprising a therapeutically effective amount of at least one compound of claim 1 and a pharmaceutically acceptable carrier.

3. The compound of claim 1, wherein the compound is selected from the group consisting of:

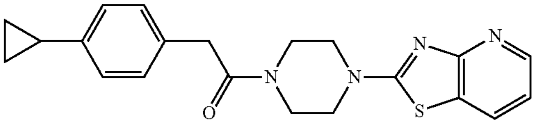 and

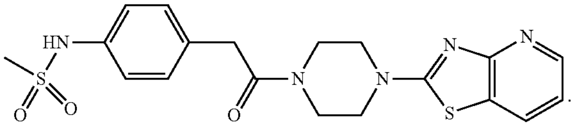.

4. The compound of claim 1, wherein the compound is:

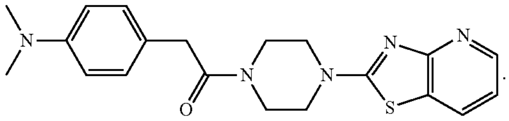 [SMILES: CN(C)c1ccc(CC(=O)N2CCN(c3nc4ncccc4s3)CC2)cc1].

5. The compound of claim 1, wherein the compound is selected from the group consisting of:

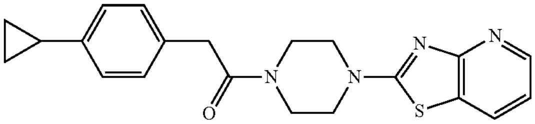 and

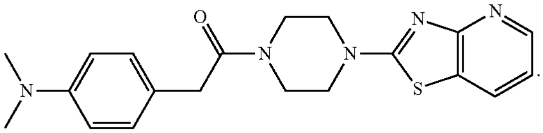.

6. The compound of claim 1, wherein the compound is selected from the group consisting of:

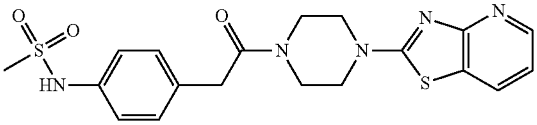 and

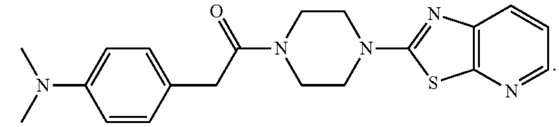.

7. The compound of claim 1, wherein the compound is selected from the group consisting of:

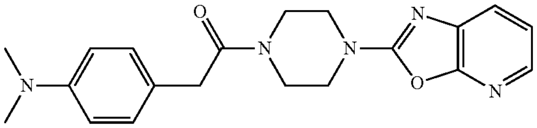 and

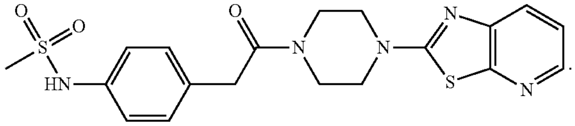.

8. The compound of claim 1, wherein the compound is selected from the group consisting of:

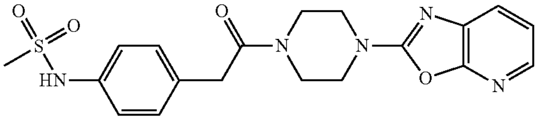 and

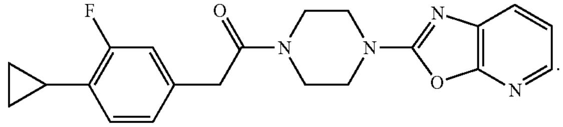.

9. The compound of claim 1, wherein the compound is selected from the group consisting of:

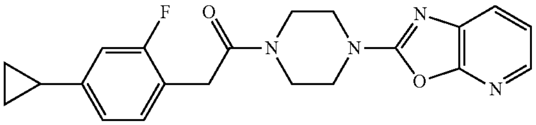 and

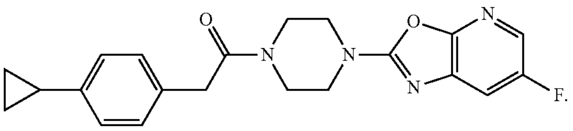.

10. The compound of claim 1, wherein the compound is:

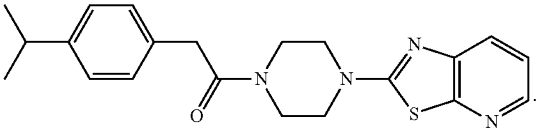 [SMILES: CC(C)c1ccc(CC(=O)N2CCN(c3nc4cccnc4s3)CC2)cc1]

11. The compound of claim 1, wherein the compound is:

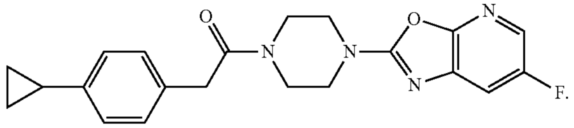 [SMILES: O=C(Cc1ccc(C2CC2)cc1)N1CCN(c2nc3cc(F)cnc3o2)CC1]

12. The compound of claim 1, wherein the compound is:

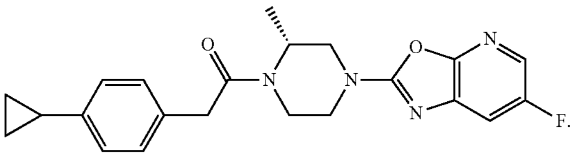 [SMILES: C[C@@H]1CN(c2nc3cc(F)cnc3o2)CCN1C(=O)Cc1ccc(C2CC2)cc1]

13. The compound of claim 1, wherein the compound is:

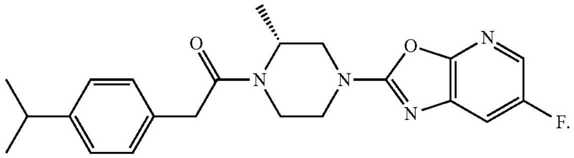 [SMILES: CC(C)c1ccc(CC(=O)N2CCN(c3nc4cc(F)cnc4o3)C[C@H]2C)cc1]

14. The compound of claim 1, wherein the compound is:

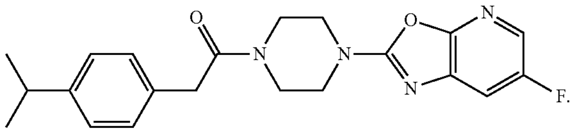 [SMILES: CC(C)c1ccc(CC(=O)N2CCN(c3nc4cc(F)cnc4o3)CC2)cc1]

15. The compound of claim 1, wherein the compound is:

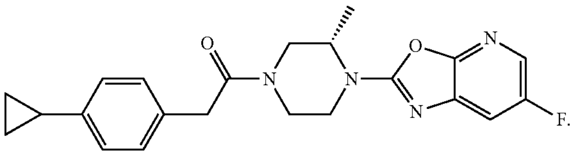 [SMILES: C[C@H]1CN(C(=O)Cc2ccc(C3CC3)cc2)CCN1c1nc2cc(F)cnc2o1]

16. The compound of claim 1, wherein the compound is:

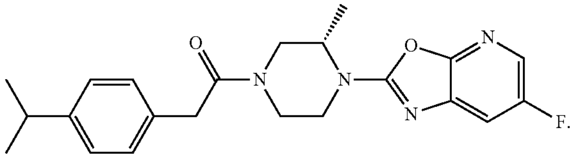 [SMILES: CC(C)c1ccc(CC(=O)N2CCN(c3nc4cc(F)cnc4o3)[C@@H](C)C2)cc1]

17. The compound of claim 1, wherein the compound is:

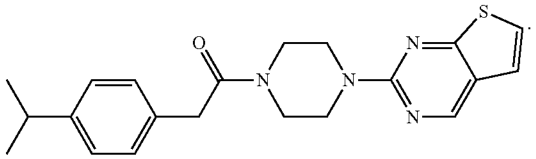 [SMILES: CC(C)c1ccc(CC(=O)N2CCN(c3ncc4ccsc4n3)CC2)cc1]

18. The compound of claim 1, wherein the compound is:

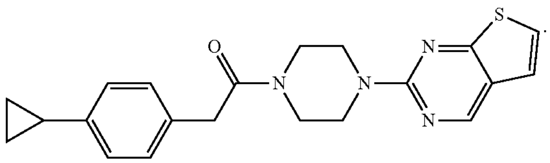 [SMILES: O=C(Cc1ccc(C2CC2)cc1)N1CCN(c2ncc3ccsc3n2)CC1]

* * * * *